(12) United States Patent
Bachmann et al.

(10) Patent No.: US 8,449,874 B2
(45) Date of Patent: May 28, 2013

(54) INTERLEUKIN-1 MUTEINS LINKED TO VIRUS-LIKE PARTICLES TO TREAT IL-1 ASSOCIATED DISEASES

(75) Inventors: Martin F. Bachmann, Seuzach (CH); Gunther Spohn, Zürich (CH); Alain Tissot, Zürich (CH)

(73) Assignee: Cytos Biotechnology AG, Zurich-Schlieren (CH)

(*) Notice: Subject to any disclaimer, the term of this patent is extended or adjusted under 35 U.S.C. 154(b) by 343 days.

(21) Appl. No.: 12/443,344

(22) PCT Filed: Mar. 29, 2007

(86) PCT No.: PCT/EP2007/053007
§ 371 (c)(1),
(2), (4) Date: May 3, 2010

(87) PCT Pub. No.: WO2008/037504
PCT Pub. Date: Apr. 3, 2008

(65) Prior Publication Data
US 2011/0091411 A1    Apr. 21, 2011

(30) Foreign Application Priority Data

Sep. 28, 2006    (WO) ................. PCT/EP2006/066866

(51) Int. Cl.
*A61K 38/20* (2006.01)
*A61K 39/12* (2006.01)

(52) U.S. Cl.
USPC .......................................... 424/85.2; 424/93.1

(58) Field of Classification Search
None
See application file for complete search history.

(56) References Cited

U.S. PATENT DOCUMENTS 5,286,847 A    2/1994    Gehrke et al.

FOREIGN PATENT DOCUMENTS

WO    WO 01/39803 A2    6/2001
WO    WO 2004/007538 A2    1/2004

OTHER PUBLICATIONS

Chackerian, B., et al., "Conjugation of a Self-antigen to Papillomavirus-like Particles Allows for Efficient Induction of Protective Autoantibodies," *J. Clin. Invest.* 108:415-423, American Society for Clinical Investigation (2001).

Chi, H., et al., "Interleukin-1 Receptor Signaling Mediates Atherosclerosis Associated with Bacterial Exposure and/or a High-Fat Diet in a Murine Apolipoprotein E Heterozygote Model-Pharmacotherapeutic Implications," *Circulation* 110:1678-1685, American Heart Association, Inc. (2004).

Dinarello, C.A., "Therapeutic Strategies to Reduce IL-1 Activity in Treating Local and Systemic Inflammation," *Curr. Opin. Pharmacol.* 4:378-385, Elsevier Ltd. (2004).

Dinarello, C.A., "Blocking IL-1 in Systemic Inflammation," *J. Exp. Med.* 201:1355-1359, The Rockefeller University Press (2005).

Dinarello, C.A., and Wolff, S.M., "The Role of Interleukin-1 in Disease," *N. Engl. J. Med.* 328:106-113, Massachusetts Medical Society (1993).

Jegerlehner, A., et al., "A Molecular Assembly System that Renders Antigens of Choice Highly Repetitive for Induction of Protective B Cell Responses," *Vaccine* 20:3104-3112, Elsevier Science Ltd. (2002).

Lechner, F., et al., "Virus-Like Particles as a Modular System for Novel Vaccines," *Intervirology* 45:212-217, S. Karger AG (2002).

Svenson, M., et al., "Cytokine Vaccination: Neutralising IL-1α Autoantibodies Induced by Immunisation with Homologous IL-1α," *J. Immunol. Methods* 236:1-8, Elsevier Science B.V. (2000).

NCBI Database, GenBank Accession No. AAR15433, Patent No. JP03197433-A, 1 page, entry date Feb. 1992.

International Search Report for International Application No. PCT/EP2007/053007, European Patent Office, Netherlands, 8 pages, mailed on Jan. 21, 2008.

*Primary Examiner* — Prema Mertz
(74) *Attorney, Agent, or Firm* — Sterne, Kessler, Goldstein & Fox P.L.L.C.

(57) ABSTRACT

The present invention is related to the fields of molecular biology, virology, immunology and medicine. The invention provides a composition comprising an ordered and repetitive antigen array, wherein the antigen is an IL-1 mutein. More specifically, the invention provides a composition comprising a virus-like particle, and at least one IL-1 mutein linked thereto. The invention also provides a process for producing the composition. The compositions of the invention are useful in the production of vaccines for the treatment of inflammatory diseases, and chronic autoimmune diseases, genetic diseases and cardiovascular diseases. The composition of the invention efficiently induces immune responses, in particular antibody responses. Furthermore, the compositions of the invention are particularly useful to efficiently induce self-specific immune responses within the indicated context.

20 Claims, 2 Drawing Sheets

Figure 1:
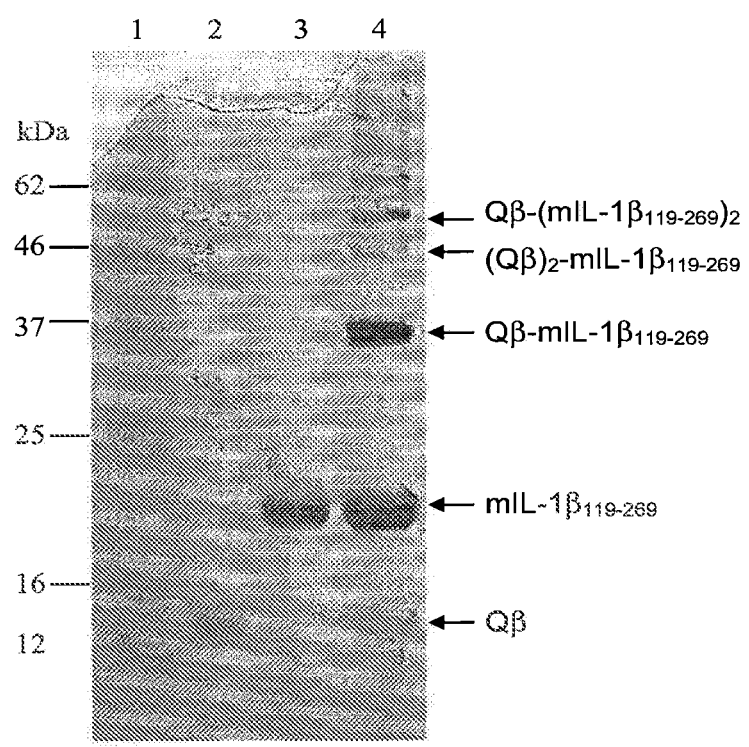

INTERLEUKIN-1 MUTEINS LINKED TO VIRUS-LIKE PARTICLES TO TREAT IL-1 ASSOCIATED DISEASES

REFERENCE TO SEQUENCE LISTING SUBMITTED ELECTRONICALLY

The content of the electronically submitted substitute sequence listing, file name: corrsequencelisting17000770 ascii.txt; Size 195,257 bytes; and Date of Creation: Nov. 12, 2010, filed herewith, is incorporated herein by reference in its entirety.

FIELD OF THE INVENTION

The present invention is in the fields of medicine, public health, immunology, molecular biology and virology. The invention provides compositions comprising a virus-like particle (VLP) or a virus particle and at least one antigen, wherein said antigen is an Interleukin-1 (IL-1) protein, an IL-1 fragment or peptide or an IL-1 mutein covalently linked to the VLP or the virus particle, wherein most preferably the antigen is an IL-1 mutein, preferably mutein of IL-1 beta or IL-1 alpha. The invention also provides a process for producing the compositions. The compositions of this invention are useful in the production of vaccines for the treatment of various human disorders, including rheumatoid arthritis osteoarthritis and others. The compositions of the invention hereby induce efficient immune responses, in particular antibody responses.

RELATED ART

IL-1 is a potent proinflammatory cytokine produced by various cell types, including macrophages, dendritic cells, B-cells and T-cells (Dinarello C. A., 1991. Blood 77(8):1627-1652). It consists of two molecular species, IL-1α and IL-β, which share only limited sequence identity but exert similar biological activities through binding to IL-1 receptor type I (IL-1RI) (Dinarello C. A. et al., 1997, Cytokine & Growth Factor Rev. 8:253). Both IL-1 molecules also bind to a second IL-1 receptor (IL-1RII), which lacks the intracellular signalling domain, and is believed to play a regulatory role as a decoy receptor (Dinarello C. A. et al., 1997, Cytokine & Growth Factor Rev. 8:253). In addition, a third member of the IL-1 family, the IL-1 receptor antagonist (IL-1ra), binds to both receptors without exerting any agonistic activity. IL-1ra together with IL-1RII and the shed forms of IL-1RI and IL-1RII counteract the activity of IL-1α and IL-1β and ensure a tight regulation of the inflammatory response.

A dysregulation of the IL-1-mediated inflammatory response is observed in many human disorders, including rheumatoid arthritis, inflammatory bowel disease, kidney diseases, osteoporosis and others. In each of these diseases either overproduction of IL-1 and/or underproduction of IL-1ra predisposes to the development of disease (Arend W. P., 2002, Cytokine & Growth Factor Reviews 13:323-340). A recombinant version of IL-1ra (anakinra, Kineret®) is efficacious in reducing inflammation and preventing tissue damage in several inflammatory disorders, but the need for high systemic concentrations and the short half life of the drug require frequent (daily) administrations of high doses (~100 mg), resulting in high cost of goods and potential patient compliance problems (Kineret® prescribing information, Amgen; Granowitz E. V. et al. 1992, Cytokine 4:353). In addition, a large proportion of patients develop antibodies against Kineret®, which potentially neutralize the biological activity of the drug (Fleischmann R M., et al., 2003, Arthritis Rheum 46:2287).

New therapeutic techniques therefore focus on active immunization strategies, which induce the production of IL-1-neutralizing antibodies by the immune system of the patient. Svenson and co-workers (2000, J. Immunol. Methods 236:1-8) immunized mice with recombinant IL-1α chemically crosslinked to purified protein derivative of tuberculin (PPD), and observed the induction of antibodies which neutralized the biological activity of IL-1α. This strategy relies on the delivery of T-cell help to autoreactive B-cells by physical linkage of the self-antigen to a foreign antigen.

U.S. Pat. No. 6,093,405 discloses a method of reducing the level of a circulating cytokine by immunization with an immunogenic composition containing the chemically or physically inactivated cytokine itself. Whereas in this method native cytokines are rendered immunogenic by physical or chemical treatment, the present invention discloses a method for making native cytokines immunogenic by presenting them in a highly repetitive fashion on the surface of VLPs. WO2003/084979 furthermore describes the use of immunogenic compounds containing cytokine-derived peptides of 5-40 amino acids length for the treatment of diseases associated with an overproduction of cytokines.

SUMMARY OF THE INVENTION

We have, now, surprisingly found that the inventive compositions and vaccines, respectively, comprising at least one IL-1 molecule, preferably a IL-1 mutein, are not only capable of inducing immune responses against IL-1, and hereby in particular antibody responses, but are, furthermore, capable of neutralizing the pro-inflammatory activity of IL-1 in vivo. In addition, we have surprisingly found that IL-1 molecule, when covalently linked to the VLP in accordance with the invention, can protect from inflammation and from clinical signs of arthritis in a mouse model of rheumatoid arthritis. Moreover, we have found that the inventive compositions protected mice better from the development of arthritis symptoms than the recombinant IL-1 receptor antagonist Kineret®, which is approved for the treatment of human rheumatoid arthritis (Example 7). We surprisingly found that compositions of the invention were able to inhibit the development of atherosclerotic symptoms, when injected into genetically susceptible mice (Example 4) and therefore are an efficient treatment for atherosclerosis. We also demonstrated that IL-1 α is involved in the pathogenesis of atherosclerosis. It was found that muteins of IL-1 beta and IL-1 alpha showing reduced biological activity can be obtained (Examples 11 and 16), and that such muteins of IL-1 beta are capable of inducing antibodies with neutralizing activity in vitro (Example 12D). Furthermore, structurally similar regions of IL-1 beta and IL-1 alpha have been identified where mutations, especially amino acid exchanges or deletions, result in muteins which are useful in the context of the invention.

Thus, in one aspect, the present invention provides a composition which comprises (a) a virus-like particle (VLP) with at least one first attachment site; and (b) at least one antigen with at least one second attachment site, wherein said at least one antigen an IL-1 molecule, preferably selected from the group consisting of IL-1 protein, IL-1 mature fragment, IL-1 peptide and IL-1 mutein, wherein (a) and (b) are linked through said at least one first and said at least one second attachment site, preferably to form an ordered and repetitive antigen array. In preferred embodiments of the invention, the virus-like particles suitable for use in the present invention comprises recombinant protein, preferably recombinant coat protein, mutants or fragments thereof, of a virus, preferably of an RNA bacteriophage. In one preferred embodiment, the inventive composition comprises at least one IL-1 mature fragment, preferably comprising the biological activity of IL-1. Thus, the present invention uses the presentation of the self-antigen in a highly repetitive fashion on virus-like particles to stimulate autoreactive B-cells.

In a further aspect the invention provides a composition comprising (a) a virus-like particle (VLP) with at least one first attachment site; and (b) at least one, preferably one, antigen with at least one, preferably one, second attachment site; wherein said at least one antigen is an IL-1 mutein, and wherein said IL-1 mutein comprises at least one, preferably one, mutated amino acid sequence derived from a wild type amino acid sequence, wherein said wild type amino acid sequence is an IL-1 beta amino acid sequence selected from the group consisting of: (1) position 3 to 11 of SEQ ID NO:64; (2) position 46 to 56 of SEQ ID NO:64; (3) position 88 to 109 of SEQ ID NO:64; and (4) position 143 to 153 of SEQ ID NO:64; or wherein said wild type amino acid sequence is an IL-1 alpha amino acid sequence selected from the group consisting of: (5) position 9 to 20 of SEQ ID NO:63; (6) position 52 to 62 of SEQ ID NO:63; (7) position 94 to 113 of SEQ ID NO:63; and (8) position 143 to 153 of SEQ ID NO:63; and wherein said at least one mutated amino acid sequence is characterized by an amino acid exchange in one, two or three positions as compared to said wild type amino acid sequence it is derived from; or wherein said at least one mutated amino acid sequence is characterized by a deletion of one to four consecutive amino acids of said wild type amino acid sequence it is derived from; and wherein (a) and (b) are linked through said at least one first and said at least one second attachment site. In a preferred embodiment said IL-1 mutein is an IL-1 beta mutein, wherein said IL-1 beta mutein comprise or preferably consist of a polypeptide having the amino acid sequence of SEQ ID NO:136. In a further preferred embodiment said IL-1 mutein is an IL-1 alpha mutein, wherein said IL-1 alpha mutein comprise or preferably consist of a polypeptide having the amino acid sequence of SEQ ID NO:210.

In another aspect, the present invention provides a vaccine composition.

Furthermore, the present invention provides a method to administering the vaccine composition to a human or an animal, preferably a mammal. The inventive vaccine composition is capable of inducing strong immune response, in particular antibody response, typically and preferably without the presence of at least one adjuvant. Thus, in one preferred embodiment, the vaccine is devoid of an adjuvant. The avoidance of using adjuvant may reduce a possible occurrence of unwanted inflammatory T cell responses.

In one preferred embodiment, the VLP is a VLP of an RNA bacteriophage. In a further preferred embodiment said RNA bacteriophage is an RNA bacteriophage selected from the group consisting of: Qβ, fr, GA and AP205. In a further preferred embodiment said VLP of an RNA bacteriophage comprised by the composition and the vaccine composition, respectively, is recombinantly produced in a host and the VLP of an RNA bacteriophage is essentially free of host RNA, preferably host nucleic acid. It is advantageous to reduce, or preferably to eliminate, the amount of host RNA to avoid unwanted T cell responses as well as other unwanted side effects, such as fever.

In one aspect, the present invention provides a method of treating a disease selected from the group consisting of: (a) vascular diseases; (b) inherited IL-1-dependent inflammatory diseases; (c) chronic autoimmune inflammatory diseases; (d) bone and cartilage degenerative diseases; (e) allergic diseases; and (f) neurological disease; in which diseases IL-1 protein mediates, or contributes to the condition, wherein the method comprises administering the inventive composition or the invention vaccine composition, respectively, to an animal, preferably human. Diseases, in which IL-1 protein mediates, or contributes to the condition, are, for example, atherosclerosis, familial Mediterranean fever, rheumatoid arthritis, osteoarthritis, and allergy.

In a further aspect, the present invention provides a pharmaceutical composition comprising the inventive composition and an acceptable pharmaceutical carrier.

In again a further aspect, the present invention provides for a method of producing the composition of the invention comprising (a) providing a VLP with at least one first attachment site; (b) providing at least one antigen, wherein said antigen is an IL-1 molecule, an IL-1 protein, an IL-1 mature fragment, an IL-1 peptide or an IL-1 mutein, with at least one second attachment site; and (c) combining said VLP and said at least one antigen to produce said composition, wherein said at least one antigen and said VLP are linked through said at least one first and said at least one second attachment sites.

BRIEF DESCRIPTION OF THE DRAWINGS

FIG. 1: Coupling of mIL-1$\beta_{119-269}$ Protein to Qβ Capsid Protein

Proteins were analyzed on a 12% SDS-polyacrylamide gel under reducing conditions. The gel was stained with Coomassie Brilliant Blue. Molecular weights of marker proteins are given in kDa on the left margin, identities of protein bands are indicated on the right margin. Lane 1: Pre stained protein marker (New England Biolabs). Lane 2: derivatized Qβ capsid protein. Lane 3: free reduced mIL-1$\beta_{119-269}$ protein. Lane 4: Qβ-mIL-1$\beta_{119-269}$ coupling reaction.

FIG. 2: Coupling of mIL-1$\alpha_{117-270}$ Protein to Qβ Capsid Protein

Proteins were analyzed on a 12% SDS-polyacrylamide gel under reducing conditions. The gel was stained with Coomassie Brilliant Blue. Molecular weights of marker proteins are given in kDa on the left margin, identities of protein bands are indicated on the right margin. Lane 1: Prestained protein marker (New England Biolabs). Lane 2: derivatized Qβ capsid protein. Lane 3: free reduced mIL-1$\alpha_{117-270}$ protein. Lane 4: Qβ-mIL-1$\alpha_{117-270}$ coupling reaction.

DETAILED DESCRIPTION OF THE INVENTION

Unless defined otherwise, all technical and scientific terms used herein have the same meanings as commonly understood by one of ordinary skill in the art to which this invention belongs.

Adjuvant: The term "adjuvant" as used herein refers to non-specific stimulators of the immune response or substances that allow generation of a depot in the host which when combined with the vaccine and pharmaceutical composition, respectively, of the present invention may provide for an even more enhanced immune response. Preferred adjuvants are complete and incomplete Freund's adjuvant, aluminum containing adjuvant, preferably aluminium hydroxide, and modified muramyldipeptide. Further preferred adjuvants are mineral gels such as aluminum hydroxide, surface active substances such as lysolecithin, pluronic polyols, polyanions, peptides, oil emulsions, keyhole limpet hemocyanins, dinitrophenol, and human adjuvants such as BCG (bacille Calmette Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants can also comprise a mixture of these substances. VLP have been generally described as an adjuvant. However, the term "adjuvant", as used within the context of this application, refers to an adjuvant not being the VLP used for the inventive compositions, rather it relates to an additional, distinct component.

Antigen: As used herein, the term "antigen" refers to a molecule capable of being bound by an antibody or a T-cell receptor (TCR) if presented by MHC molecules. The term "antigen", as used herein, also refers to T-cell epitopes. An antigen is additionally capable of being recognized by the immune system and/or being capable of inducing a humoral immune response and/or cellular immune response leading to the activation of B- and/or T-lymphocytes. This may, however, require that, at least in certain cases, the antigen contains or is linked to a Th cell epitope and is given in adjuvant. An antigen can have one or more epitopes (B- and T-epitopes). The specific reaction referred to above is meant to indicate that the antigen will preferably react, typically in a highly selective manner, with its corresponding antibody or TCR and not with the multitude of other antibodies or TCRs which may be evoked by other antigens. Antigens as used herein may also be mixtures of several individual antigens. The term "antigen" as used herein preferably refers to the IL-1 molecule, the IL-1 protein, IL-1 mature fragment, the IL-1 fragment, the IL-1 peptide and the IL-1 mutein, most preferably "antigen" refers to the IL-1 mutein. If not indicated otherwise, the term "antigen" as used herein does not refer to the virus-like particle.

epitope: The term epitope refers to continuous or discontinuous portions of an antigen, preferably a polypeptide, wherein said portions can be specifically bound by an antibody or by a T-cell receptor within the context of an MHC molecule. With respect to antibodies, specific binding excludes non-specific binding but does not necessarily exclude cross-reactivity. An epitope typically comprise 5-10 amino acids in a spatial conformation which is unique to the antigenic site.

Specific binding (antibody/antigen): Within this application, antibodies are defined to be specifically binding if they bind to the antigen with a binding affinity (Ka) of $10^6$ $M^{-1}$ or $10^9$ $M^{-1}$ or greater. The affinity of an antibody can be readily determined by one of ordinary skill in the art (for example by Scatchard analysis, by ELISA or by Biacore analysis).

Specific binding (IL-1/IL-1 receptor): The interaction between a receptor and a receptor ligand can be characterized by biophysical methods generally known in the art, including, for example, ELISA or Biacore analysis. An IL-1 molecule is regarded as capable of specifically binding an IL-1 receptor, when the binding affinity (Ka) of said IL-1 to said IL-1 receptor is at least $10^5$ $M^{-1}$, preferably at least $10^6$ $M^{-1}$, more preferably at least $10^7$ $M^{-1}$, still more preferably at least $10^8$ $M^{-1}$, and most preferably at least $10^9$ $M^{-1}$; wherein preferably said IL-1 receptor is an IL-1 receptor from mouse or human, most preferably human. Further preferably, said IL-1 receptor comprises or more preferably consists of any one of the sequences SEQ ID NO:166 to SEQ ID NO:169, most preferably said IL-1 receptor comprises or preferably consists of any one of the sequences SEQ ID NO:166 and SEQ ID NO:167.

Associated: The terms "associated" or "association" as used herein refer to all possible ways, preferably chemical interactions, by which two molecules are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds.

Attachment Site, First: As used herein, the phrase "first attachment site" refers to an element which is naturally occurring with the VLP or which is artificially added to the VLP, and to which the second attachment site may be linked. The first attachment site preferably is a protein, a polypeptide, an amino acid, a peptide, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the first attachment site is the amino group of an amino acid, preferably of lysine. The first attachment site is located, typically on the surface, and preferably on the outer surface of the VLP. Multiple first attachment sites are present on the surface, preferably on the outer surface of virus-like particle, typically in a repetitive configuration. In a preferred embodiment the first attachment site is associated with the VLP, through at least one covalent bond, preferably through at least one peptide bond. In a further preferred embodiment the first attachment site is naturally occurring with the VLP. Alternatively, in a preferred embodiment the first attachment site is artificially added to the VLP.

Attachment Site, Second: As used herein, the phrase "second attachment site" refers to an element which is naturally occurring with or which is artificially added to the IL-1 molecule and to which the first attachment site may be linked. The second attachment site of the IL-1 molecule preferably is a protein, a polypeptide, a peptide, an amino acid, a sugar, a polynucleotide, a natural or synthetic polymer, a secondary metabolite or compound (biotin, fluorescein, retinol, digoxigenin, metal ions, phenylmethylsulfonylfluoride), or a chemically reactive group such as an amino group, a carboxyl group, a sulfhydryl group, a hydroxyl group, a guanidinyl group, histidinyl group, or a combination thereof. A preferred embodiment of a chemically reactive group being the second attachment site is the sulfhydryl group, preferably of an amino acid cysteine. The term "IL-1 molecule with at least one second attachment site" refers, therefore, to a construct comprising the IL-1 molecule and at least one second attachment site. However, in particular for a second attachment site, which is not naturally occurring within the IL-1 molecule, such a construct typically and preferably further comprises a "linker". In another preferred embodiment the second attachment site is associated with the IL-1 molecule through at least one covalent bond, preferably through at least one peptide bond. In a further embodiment, the second attachment site is naturally occurring within the IL-1 molecule. In another further preferred embodiment, the second attachment site is artificially added to the IL-1 molecule through a linker, wherein said linker comprises or alternatively consists of a cysteine. Preferably the linker is fused to the IL-1 molecule by a peptide bond.

Coat protein: The term "coat protein" and the interchangeably used term "capsid protein" within this application, refers to a viral protein, preferably a subunit of a natural capsid of a virus, preferably of a RNA-phage, which is capable of being incorporated into a virus capsid or a VLP.

IL-1 molecule: The term "IL-1 molecule" or shortly "IL-1", as used herein, refers to any polypeptide having an amino acid sequence having at least 80%, preferably at least 90%, more preferably at least 95%, even more preferably at least 99% and most preferably 100% sequence identity with any one of the sequences selected from the group consisting of SEQ ID NO:36 to SEQ ID NO:116, SEQ ID NO:130 to SEQ ID NO:140 and SEQ ID NO:163 to SEQ ID NO:165. The term "IL-1-molecule", as used herein, preferably refers to any IL-1 protein, IL-1 fragment, IL-1 mature fragment, IL-1 peptide or IL-1 mutein comprising or alternatively consisting of a polypeptide having an amino acid sequence having at least 80%, preferably at least 90%, more preferably at least 95%, even more preferably at least 99% and most preferably 100% sequence identity with any one of the sequences selected from the group consisting of SEQ ID NO:36 to SEQ ID NO:116, SEQ ID NO:130 to SEQ ID NO:140 and SEQ ID NO:163 to SEQ ID NO:165. The term IL-1 molecule, as used herein, also typically and preferably refers to orthologs of IL-1 proteins of any animal species. An IL-1 molecule is preferably, but not necessarily, capable of binding to the IL-1 receptor and further preferably comprises biological activity.

IL-1 alpha molecule: The term "IL-1 alpha molecule" or shortly "IL-1 alpha", as used herein, refers to an IL-1 alpha protein, IL-1 alpha fragment, IL-1 alpha mature fragment, IL-1 alpha peptide or IL-1 alpha mutein comprising or alternatively consisting of an polypeptide having an amino acid sequence having at least 80%, preferably at least 90%, more preferably at least 95%, even more preferably at least 99% and most preferably 100% sequence identity with any one of the sequences selected from the group consisting of SEQ ID NO:36 to 48, SEQ ID NO:63, SEQ ID NO:65, SEQ ID NO:67 to SEQ ID NO:88, and SEQ ID NO:163. A specifically preferred embodiment of IL-1 alpha is human IL-1 alpha 119-271 (SEQ ID NO:63).

IL-1 beta molecule: The term "IL-1 beta molecule" or shortly "IL-1 beta", as used herein, refers to an IL-1 beta protein, IL-1 beta fragment, IL-1 beta mature fragment, IL-1 beta peptide or IL-1 beta mutein comprising or alternatively consisting of an polypeptide having an amino acid sequence having at least 80%, preferably at least 90%, more preferably at least 95%, even more preferably at least 99% and most preferably 100% sequence identity with any one of the sequences selected from the group consisting of SEQ ID NO:49 to SEQ ID NO:62, SEQ ID NO:64, SEQ ID NO:66, SEQ ID NO:89 to SEQ ID NO:116, SEQ ID NO:130 to SEQ ID NO:140, SEQ ID NO:164, and SEQ ID NO:165. A specifically preferred embodiment of IL-1 beta is human IL-1 beta 117-269 (SEQ ID NO:64).

IL-1 protein: The term "IL-1 protein", as used herein, refers to a naturally occurring protein, wherein said naturally occurring protein has an amino acid sequence having at least 80%, preferably at least 90%, more preferably at least 95%, even more preferably at least 99% and most preferably 100% sequence identity with any one of SEQ ID NO:36 to SEQ ID NO:62; or wherein said naturally occurring protein is capable of binding the IL-1 receptor and preferably comprises biological activity. The term "IL-1 protein", as used herein, preferably refers to a naturally occurring protein, wherein said naturally occurring protein has an amino acid sequence having at least 80%, preferably at least 90%, more preferably at least 95%, even more preferably at least 99% and most preferably 100% sequence identity with any one of SEQ ID NO:36 to SEQ ID NO:62; and wherein said naturally occurring protein is capable of binding the IL-1 receptor and preferably comprises biological activity. Typically and preferably, the term "IL-1 protein", as used herein, refers to at least one naturally occurring protein, wherein said protein is capable of binding the IL-1 receptor and comprises biological activity, and wherein further said protein comprises or alternatively consists of a polypeptide having an amino acid sequence having at least 80%, preferably at least 90%, more preferably at least 95%, even more preferably at least 99% and most preferably 100% sequence identity with any one of SEQ ID NO:36 to SEQ ID NO:62. Accordingly, the term "IL-1 alpha protein" relates to an IL-1 protein comprising or alternatively consisting of a polypeptide having an amino acid sequence having at least 80%, preferably at least 90%, more preferably at least 95%, even more preferably at least 99% and most preferably 100% sequence identity with any one of SEQ ID NO:36 to SEQ ID NO:48, whereas the term "IL-1 beta protein" relates to an IL-1 protein comprising or alternatively consisting of a polypeptide having an amino acid sequence having at least 80%, preferably at least 90%, more preferably at least 95%, even more preferably at least 99% and most preferably 100% sequence identity with any one of SEQ ID NO:49 to SEQ ID NO:62.

IL-1 fragment: The term "IL-1 fragment", as used herein, relates to a polypeptide comprising a consecutive stretch of an IL-1 protein, wherein said polypeptide is at least 50, preferably at least 100, most preferably at least 150 amino acids in length. Typically and preferably said IL-1 fragment is at most 300, more preferably at most 250, and most preferably at most 200 amino acids in length. Typically and preferably, IL-1 fragments are capable of binding the IL-1 receptor and further preferably comprises biological activity. Accordingly, the terms "IL-1 alpha fragment" and "IL-1 beta fragment" relate to an IL-1 fragment as defined, wherein said IL-1 protein is an IL-1 alpha protein or an IL-1 beta protein, respectively.

IL-1 mature fragment: The term "IL-1 mature fragment", as used herein, relates to a IL-1 fragment, wherein said IL-1 fragment is a naturally occurring maturation product of an IL-1 protein. Accordingly, the terms "IL-1 alpha mature fragment" and "IL-1 beta mature fragment", as used herein relate to IL-1 mature fragments as defined, wherein said IL-1 protein is an IL-1 alpha protein or an IL-1 beta protein, respectively. Preferred embodiments of IL-1 alpha mature fragments are SEQ ID NO:63, SEQ ID NO:65 and SEQ ID NO:163. Preferred embodiments of IL-1 beta mature fragments are SEQ ID NO:64, SEQ ID NO:66, SEQ ID NO:130, SEQ ID NO:164, and SEQ ID NO:165.

Preferred IL-1 alpha mature fragments comprise or preferably consist of an amino acid sequence selected from the group consisting of: (a) human IL-1 alpha 119-271 (SEQ ID NO:63); (b) mouse IL-1 alpha 117-270 (SEQ ID NO:65); (c) mouse IL-1 alpha 117-270s (SEQ ID NO:163); and (e) an amino acid sequence which is at least 80%, or preferably at least 90%, more preferably at least 95%, or most preferably at least 99% identical with any one of SEQ ID NO:63, SEQ ID NO:65 and SEQ ID NO:163.

Preferred IL-1 beta mature fragments comprise or preferably consist of an amino acid sequence selected from the group consisting of: (a) human IL-1 beta 117-269 (SEQ ID NO:64); (b) human IL-1 beta 116-269 (SEQ ID NO:165); (c) mouse IL-1 beta 119-269 (SEQ ID NO:66); (d) mouse IL-1 beta 119-269s (SEQ ID NO:164); and (e) an amino acid sequence which is at least 80%, or preferably at least 90%, more preferably at least 95%, or most preferably at least 99% identical with any one of SEQ ID NO:64, SEQ ID NO:66, SEQ ID NO:164 and SEQ ID NO:165.

IL-1 peptide: The term "IL-1 peptide", as used herein, relates to a polypeptide comprising a consecutive stretch of a naturally occurring protein, wherein said protein is capable of binding the IL-1 receptor and preferably comprises biological activity, wherein said polypeptide is 4 to 49, preferably 6 to 35, most preferably 10 to 25 amino acids in length. The IL-1 peptide may be, but typically is not, capable of binding the IL-1 receptor and typically has no biological activity. Accordingly, the terms "IL-1 alpha peptide" and "IL-1 beta peptide", as used herein relate to IL-1 peptides as defined, wherein said naturally occurring protein is an IL-1 alpha protein or an IL-1 beta protein, respectively. Preferred IL-1 peptides are SEQ ID NO:82 to SEQ ID NO:116.

IL-1 mutein: The term "IL-1 mutein" as used herein comprise or preferably consist of any polypeptide derived from an IL-1 molecule, preferably from an IL-1 alpha or an IL-1 beta protein, an IL-1 alpha or an IL-1 beta fragment, an IL-1 alpha or an IL-1 beta mature fragment or an IL-1 alpha or an IL-1 beta peptide, wherein preferably said polypeptide exhibits reduced biological activity as compared to the IL-1 molecule it is derived from. Accordingly, IL-1 alpha muteins and IL-1 beta muteins are IL-1 muteins as defined, wherein said polypeptide is derived from an IL-1 alpha molecule or an IL-1 beta molecule, respectively. Very preferred IL-1 beta muteins are IL-1 beta muteins derived from IL-1 beta mature fragments, preferably from human IL-1$\beta_{117-269}$ (SEQ ID NO:64). Very preferred IL-1 alpha muteins are derived from IL-1 alpha mature fragments, preferably from human IL-1 $\alpha_{119-271}$ (SEQ ID NO:63).

In preferred IL-1 muteins, said biological activity is less than 80%, more preferably less than 60%, still more preferably less than 40%, still more preferably less than 20% of the biological activity of the IL-1 molecule it is derived from, wherein further preferably said biological activity is determined by the capacity of said IL-1 mutein to induce IL-6 in human PBMCs, wherein most preferably said biological activity is determined essentially as described in Example 11B.

In preferred IL-1 beta muteins, said biological activity is less than 80%, more preferably less than 60%, still more preferably less than 40%, still more preferably less than 20% of the biological activity of the IL-1 beta molecule it is derived from, wherein preferably said IL-1 beta molecule is an IL-1 beta mature fragment, preferably human IL-1$\beta_{117-269}$ (SEQ ID NO:64), and wherein further preferably said biological activity is determined by the capacity of said IL-1 beta mutein to induce IL-6 in human PBMCs, wherein most preferably said biological activity is determined essentially as described in Example 11B.

In preferred IL-1 alpha muteins, said biological activity is less than 80%, more preferably less than 60%, still more preferably less than 40%, still more preferably less than 20% of the biological activity of the IL-1 alpha molecule it is derived from, wherein preferably said IL-1 alpha molecule is an IL-1 alpha mature fragment, preferably human human IL-1 $\alpha_{119-271}$ (SEQ ID NO:63), and wherein further preferably said biological activity is determined by the capacity of said IL-1 alpha mutein to induce IL-6 in human PBMCs, wherein most preferably said biological activity is determined essentially as described in Example 16.

Further preferred IL-1 muteins are derived from an IL-1 mature fragment, wherein the biological activity of said IL-1 mutein is less than 80%, more preferably less than 60%, still more preferably less than 40%, still more preferably less than 20% of the biological activity of the IL-1 mature fragment said IL-1 mutein is derived from. Very preferred IL-1 muteins do not exhibit biological activity.

Further preferably, but not necessarily, IL-1 muteins are capable of specifically binding an IL-1 receptor.

When introduced into an animal, compositions of the invention comprising a preferred IL-1 mutein as the sole antigen induce a titer of antibodies capable of specifically binding the IL-1 molecule said IL-1 mutein is derived from, wherein said titer is at least 20%, preferably at least 40%, still more preferably at least 60%, still more preferably at least 80% and most preferably at least 100% of the titer obtained with a composition comprising the IL-1 molecule said IL-1 mutein is derived from as the sole antigen, wherein preferably said titer is determined essentially as described in Example 12D.

When introduced into an animal, compositions of the invention comprising a preferred IL-1 beta mutein as the sole antigen induce a titer of antibodies capable of specifically binding the IL-1 beta molecule said IL-1 beta mutein is derived from, wherein preferably said IL-1 beta molecule is an IL-1 beta mature fragment, most preferably human IL-1$\beta_{117-269}$ (SEQ ID NO:64), wherein said titer is at least 20%, preferably at least 40%, still more preferably at least 60%, still more preferably at least 80% and most preferably at least 100% of the titer obtained with a composition comprising the IL-1 beta molecule said IL-1 beta mutein is derived from, preferably said IL-1 beta mature fragment, most preferably said human IL-1$\beta_{117-269}$ (SEQ ID NO:64) as the sole antigen, wherein further preferably said titer is determined essentially as described in Example 12D.

When introduced into an animal, compositions of the invention comprising a preferred IL-1 alpha mutein as the sole antigen induce a titer of antibodies capable of specifically binding the IL-1 alpha molecule said IL-1 alpha mutein is derived from, wherein preferably said IL-1 alpha molecule is an IL-1 alpha mature fragment, most preferably human IL-1 $\alpha_{119-271}$ (SEQ ID NO:63), wherein said titer is at least 20%, preferably at least 40%, still more preferably at least 60%, still more preferably at least 80% and most preferably at least 100% of the titer obtained with a composition comprising the IL-1 alpha molecule said IL-1 alpha mutein is derived from, preferably said IL-1 alpha mature fragment, most preferably said human IL-1 $\alpha_{119-271}$ (SEQ ID NO:63) as the sole antigen, wherein further preferably said titer is determined essentially as described in Example 12D.

A very preferred are IL-1 mutein is an IL-1 mutein, wherein said biological activity is less than 80%, more preferably less than 60%, still more preferably less than 40%, still more preferably less than 20% of the biological activity of the IL-1 molecule it is derived from, wherein further preferably said biological activity is determined by the capacity of said IL-1 mutein to induce IL-6 in human PBMCs, wherein most preferably said biological activity is determined essentially as described in Example 11B, and wherein additionally compositions of the invention comprising said very preferred IL-1 mutein as the sole antigen induce a titer of antibodies capable of specifically binding the IL-1 molecule said very preferred IL-1 mutein is derived from, wherein said titer is at least 20%, preferably at least 40%, still more preferably at least 60%, still more preferably at least 80% and most preferably at least 100% of the titer obtained with a composition comprising the IL-1 molecule said very preferred IL-1 mutein is derived from as the sole antigen, wherein preferably said titer is determined essentially as described in Example 12D.

Very preferred are IL-1 muteins derived from (i) an IL-1 protein, preferably from SEQ ID NO:36 to SEQ ID NO:62; or (ii) more preferably of an IL-1 mature fragment, preferably from any one of SEQ ID NO:63 to SEQ ID NO:66, SEQ ID NO:130, and SEQ ID NO:163 to SEQ ID NO:165.

IL-1 muteins useful in the context have been described in Kamogashira et al. (1988) J. Biochem. 104:837-840; Gehrke et al. (1990) The Journal of Biological Chemistry 265(11): 5922-5925; Conca et al. (1991) The Journal of Biological Chemistry 266(25):16265-16268; Ju et al. (1991) PNAS 88:2658-2662; Auron et al. (1992) Biochemistry 31:6632-6638; Guinet et al. (1993) Eur. J. Biochem 211:583-590; Camacho (1993) Biochemistry 32:8749-8757; Baumann (1993) Journal of Recepror Research 13(1-4):245-262; Simon (1993) The Journal of Biological Chemistry 268(13): 9771-9779; and Simoncsits (1994) Cytokine 6(2):206-214, the disclosure of which is incorporated herein by reference.

Preferred IL-1 muteins comprise or preferably consist of a polypeptide having an amino acid sequence which differs from the amino acid sequence of an IL-1 protein, an IL-1 fragment, an IL-1 mature fragment or an IL-1 peptide in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). In a preferred embodiment, said amino acid residues are in one consecutive stretch. Further preferred IL-1 muteins comprise or preferably consist of a polypeptide having an amino acid sequence which differs from the amino acid sequence of an IL-1 protein, an IL-1 fragment, or an IL-1 mature fragment, preferably of an IL-1 mature fragment, in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii).

Further preferred IL-1 muteins comprise or more preferably consist of a polypeptide having an amino acid sequence which differs from the amino acid sequence of any one of SEQ ID NO:36 to SEQ ID NO:48 or SEQ ID NO:49 to SEQ ID NO:62 in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Further preferred IL-1 muteins comprise or preferably consist of a polypeptide having an amino acid sequence which differs from the amino acid sequence selected from the group consisting of (i) any one of SEQ ID NO:63, SEQ ID NO:65, and SEQ ID NO:163, most preferably SEQ ID NO:63; or (ii) of any one selected from the group consisting of SEQ ID NO:64, SEQ ID NO:66, SEQ ID NO:130, SEQ ID NO:164, and SEQ ID NO:165, most preferably SEQ ID NO:64 in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii).

Further preferred IL-1 muteins are IL-1 alpha muteins, wherein said IL-1 alpha muteins comprise or more preferably consist of a polypeptide having an amino acid sequence which differs from the amino acid sequence of any one of SEQ ID NO:36 to SEQ ID NO:48 in 1 to 6, preferably 1 to 5, more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Further preferred IL-1 alpha muteins comprise or preferably consist of a polypeptide having an amino acid sequence which differs from the amino acid sequence selected from the group consisting of (i) any one of SEQ ID NO:63, SEQ ID NO:65, and SEQ ID NO:163, most preferably SEQ ID NO:63, in 1 to 6, preferably 1 to 5, more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Very preferred IL-1 alpha muteins comprise or preferably consist of a polypeptide having an amino acid sequence which differs from the amino acid sequence of SEQ ID NO:63 in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Still more preferred IL-1 alpha muteins comprise or preferably consist of a polypeptide having an amino acid sequence selected from any one of the group consisting of SEQ ID NO:210 to SEQ ID NO:218.

Further preferred IL-1 muteins are IL-1 beta muteins, wherein said IL-1 beta muteins comprise or more preferably consist of a polypeptide having an amino acid sequence which differs from the amino acid sequence of any one of SEQ ID NO:49 to SEQ ID NO:62 in 1 to 6, preferably 1 to 5, more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Further preferred IL-1 beta muteins comprise or preferably consist of a polypeptide having an amino acid sequence which differs from the amino acid sequence selected from the group consisting of SEQ ID NO:64, SEQ ID NO:66, SEQ ID NO:130, SEQ ID NO:164, and SEQ ID NO:165, most preferably SEQ ID NO:64, in 1 to 6, preferably 1 to 5, more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Very preferred IL-1 beta muteins comprise or preferably consist of a polypeptide having an amino acid sequence which differs from the amino acid sequence of SEQ ID NO:64 in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) deleted from said polypeptide, (ii) inserted into said polypeptide, (iii) exchanged by another amino acid residue, or (iv) any combination of (i) to (iii). Still more preferred IL-1 beta muteins comprise or preferably consist of a polypeptide having an amino acid sequence selected from any one of the group consisting of SEQ ID NO:131 to SEQ ID NO:140 and SEQ ID NO:205 to SEQ ID NO:209.

"derived from": in the context of the invention the expression an amino acid sequence which is derived from another amino acid sequence means that said amino acid sequence is essentially identical with the amino acid sequence it is derived from, with the exception of certain mutations, wherein said mutations are selected from the group consisting of (i) amino acid exchanges, (ii) deletions, (iii) insertions, and (iv) any combination of (i) to (iii), wherein preferably said mutations are selected from (i) amino acid exchanges and (ii) deletions. In particular, a mutated amino acid sequence derived from a wild type amino acid sequence preferably differs from said wild type amino acid sequence in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) exchanged by another amino acid, (ii) deleted from said wild type amino acid, (iii) inserted into said wild type sequence, and (iv) any combination of (i) to (iii), wherein most preferably said amino acid residue(s) are (i) exchanged by another amino acid, or (ii) deleted from said wild type amino acid. Deletions of more than one amino acid residue preferably occur as a deletion of a consecutive stretch of amino acid residues of said wild type amino acid sequence. A mutated amino acid sequence which is derived from a wild type amino acid sequence preferably has at least 90%, 91%, 92%, 93%, 94%, 95%, 96%, 97%, 98%, and most preferably at least 99% sequence identity with said wild type amino acid sequence.

Similarly, the expression "mutein derived from a IL-1 molecule" refers to a mutein, wherein said mutein comprises or preferably consists of a polypeptide having an amino acid sequence which is essentially identical to that of the IL-1 molecule it is derived from, with the exception of certain mutations, wherein said mutations are selected from the group consisting of (i) amino acid exchanges, (ii) deletions, (iii) insertions, and (iv) any combination of (i) to (iii), wherein preferably said mutations are selected from (i) amino acid exchanges and (ii) deletions. In particular, an IL-1 mutein derived from an IL-1 molecule differs from said IL-1 molecule in 1 to 10, preferably 1 to 6, more preferably 1 to 5, still more preferably 1 to 4, still more preferably 1 to 3, still more preferably 1 to 2, and most preferably in exactly 1 amino acid residue(s), wherein preferably said amino acid residue(s) are (i) exchanged by another amino acid, (ii) deleted from said wild type amino acid, (iii) inserted into said wild type sequence, and (iv) any combination of (i) to (iii), wherein most preferably said amino acid residue(s) are (i) exchanged by another amino acid, or (ii) deleted from said wild type amino acid. Deletions of more than one amino acid residue preferably occur as a deletion of a consecutive stretch of amino acid residues of the IL-1 molecule said IL-1 mutein is derived from. A mutein derived from a wild type amino acid sequence preferably has at least 90%, 91%, 92%, 93%, 94%, 95%, 96%, 97%, 98%, and most preferably at least 99% sequence identity with the IL-1 molecule said IL-1 mutein is derived from.

Amino acid exchange: the expression amino acid exchange refers to the exchange of an amino acid residue in a certain position of an amino acid sequence by any other amino acid residue.

Agonistic effect/biological activity of the IL-1: The terms "biological activity" or "biologically active" as used herein with respect to IL-1 refer to the ability of the IL-1 molecule to induce the production of IL-6 after systemical administration into animals, preferably as outlined in Example 2E. and in Example 3E. By biological activity of the IL-1 molecule is also meant the ability to induce the proliferation of thymocytes (Epps et al., Cytokine 9(3):149-156 (1997), D10.G4.1 T helper cells (Orencole and Dinarello, Cytokine 1(1):14-22 (1989), or the ability to induce the production of IL-6 from MG64 or HaCaT cells (Boraschi et al., J. Immunol. 155:4719-4725 (1995) or fibroblasts (Dinarello et al., Current Protocols in Immunology 6.2.1-6-2-7 (2000)), or the production of IL-2 from EL-4 thymoma cells (Simon et al., J. Immunol. Methods 84(1-2):85-94 (1985)), or the ability to inhibit the growth of the human melanoma cell line A375 (Nakai et al., Biochem. Biophys. Res. Commun. 154:1189-1196 (1988)). Very preferably, the term biological activity of an IL-1 molecule or an IL-1 mutein refers to the capacity of a composition of the invention comprising said IL-1 molecule or said IL-1 mutein to induce IL-6 in human PBMCs, wherein preferably said IL-1 molecule or said IL-1 mutein is the sole antigen in said composition, and wherein most preferably said biological activity is determined essentially as described in Example 11B.

Linked: The terms "linked" or "linkage" as used herein, refer to all possible ways, preferably chemical interactions, by which the at least one first attachment site and the at least one second attachment site are joined together. Chemical interactions include covalent and non-covalent interactions. Typical examples for non-covalent interactions are ionic interactions, hydrophobic interactions or hydrogen bonds, whereas covalent interactions are based, by way of example, on covalent bonds such as ester, ether, phosphoester, amide, peptide, carbon-phosphorus bonds, carbon-sulfur bonds such as thioether, or imide bonds. In certain preferred embodiments the first attachment site and the second attachment site are linked through at least one covalent bond, preferably through at least one non-peptide bond, and even more preferably through exclusively non-peptide bond(s). The term "linked" as used herein, however, shall not only refer to a direct linkage of the at least one first attachment site and the at least one second attachment site but also, alternatively and preferably, an indirect linkage of the at least one first attachment site and the at least one second attachment site through intermediate molecule(s), and hereby typically and preferably by using at least one, preferably one, heterobifunctional cross-linker. In other preferred embodiments the first attachment site and the second attachment site are linked through at least one covalent bond, preferably through at least one peptide bond, and even more preferably through exclusively peptide bond(s). In a very preferred embodiment the first attachment site and the second attachment site are linked exclusively by peptide bounds, preferably by genetic fusion, either directly, or, preferably, via an amino acid linker. In a further preferred embodiment the second attachment site is linked to the C-terminus of said first attachment site exclusively by peptide bounds, preferably by genetic fusion.

Linker: A "linker", as used herein, either associates the second attachment site with the IL-1 molecule or already comprises, essentially consists of, or consists of the second attachment site. Preferably, a "linker", as used herein, already comprises the second attachment site, typically and preferably—but not necessarily—as one amino acid residue, preferably as a cysteine residue. A "linker" as used herein is also termed "amino acid linker", in particular when a linker according to the invention contains at least one amino acid residue. Thus, the terms "linker" and "amino acid linker" are interchangeably used herein. However, this does not imply that such a linker consists exclusively of amino acid residues, even if a linker consisting of amino acid residues is a preferred embodiment of the present invention. The amino acid residues of the linker are, preferably, composed of naturally occurring amino acids or unnatural amino acids known in the art, all-L or all-D or mixtures thereof. Further preferred embodiments of a linker in accordance with this invention are molecules comprising a sulfhydryl group or a cysteine residue and such molecules are, therefore, also encompassed within this invention. Further linkers useful for the present invention are molecules comprising a C1-C6 alkyl-, a cycloalkyl such as a cyclopentyl or cyclohexyl, a cycloalkenyl, aryl or heteroaryl moiety. Moreover, linkers comprising preferably a C1-C6 alkyl-, cycloalkyl- (C5, C6), aryl- or heteroaryl-moiety and additional amino acid(s) can also be used as linkers for the present invention and shall be encompassed within the scope of the invention. Association of the linker with the IL-1 molecule is preferably by way of at least one covalent bond, more preferably by way of at least one peptide bond. In the context of linkage by genetic fusion, a linker may be absent or preferably is an amino acid linker, more preferably an amino acid linker consisting exclusively of amino acid residues. Very preferred linkers for genetic fusion are flexible amino acid linkers. In the context of linkage by genetic fusion linkers preferred consist of 1 to 20, more preferably of 2 to 15, still more preferably of 2 to 10, still more preferably of 2 to 5, and most preferably of 3 amino acids. Very preferred linkers for genetic fusion comprise or preferably consist of GSG (SEQ ID NO:189).

Ordered and repetitive antigen array: As used herein, the term "ordered and repetitive antigen array" generally refers to a repeating pattern of antigen or, characterized by a typically and preferably high order of uniformity in spacial arrangement of the antigens with respect to virus-like particle, respectively. In one embodiment of the invention, the repeating pattern may be a geometric pattern. Certain embodiments of the invention, such as antigens coupled to the VLP of RNA bacteriophages, are typical and preferred examples of suitable ordered and repetitive antigen arrays which, moreover, possess strictly repetitive paracrystalline orders of antigens, preferably with spacing of 1 to 30 nanometers, preferably 2 to 15 nanometers, even more preferably 2 to 10 nanometers, even again more preferably 2 to 8 nanometers, and further more preferably 1.6 to 7 nanometers.

Packaged: The term "packaged" as used herein refers to the state of a polyanionic macromolecule or immunostimulatory substances in relation to the VLP. The term "packaged" as used herein includes binding that may be covalent, e.g., by chemically coupling, or non-covalent, e.g., ionic interactions, hydrophobic interactions, hydrogen bonds, etc. The term also includes the enclosement, or partial enclosement, of a polyanionic macromolecule. Thus, the polyanionic macromolecule or immunostimulatory substances can be enclosed by the VLP without the existence of an actual binding, in particular of a covalent binding. In preferred embodiments, the at least one polyanionic macromolecule or immunostimulatory substances is packaged inside the VLP, most preferably in a non-covalent manner. In case said immunostimulatory substances is nucleic acid, preferably a DNA, the term packaged implies that said nucleic acid is not accessible to nucleases hydrolysis, preferably not accessible to DNAse hydrolysis (e.g. DNaseI or Benzonase), wherein preferably said accessibility is assayed as described in Examples 11-17 of WO2003/024481A2.

Polypeptide: The term "polypeptide" as used herein refers to a molecule composed of monomers (amino acids) linearly linked by amide bonds (also known as peptide bonds). It indicates a molecular chain of amino acids and does not refer to a specific length of the product. Thus, peptides, dipeptides, tripeptides, oligopeptides and proteins are included within the definition of polypeptide. Post-translational modifications of the polypeptide, for example, glycosylations, acetylations, phosphorylations, and the like are also encompassed.

Recombinant VLP: The term "recombinant VLP", as used herein, refers to a VLP that is obtained by a process which comprises at least one step of recombinant DNA technology. The term "VLP recombinantly produced", as used herein, refers to a VLP that is obtained by a process which comprises at least one step of recombinant DNA technology. Thus, the terms "recombinant VLP" and "VLP recombinantly produced" are interchangeably used herein and should have the identical meaning.

Virus particle: The term "virus particle" as used herein refers to the morphological form of a virus. In some virus types it comprises a genome surrounded by a protein capsid; others have additional structures (e.g., envelopes, tails, etc.).

Virus-like particle (VLP), as used herein, refers to a non-replicative or non-infectious, preferably a non-replicative and non-infectious virus particle, or refers to a non-replicative or non-infectious, preferably a non-replicative and non-infectious structure resembling a virus particle, preferably a capsid of a virus. The term "non-replicative", as used herein, refers to being incapable of replicating the genome comprised by the VLP. The term "non-infectious", as used herein, refers to being incapable of entering the host cell. Preferably a virus-like particle in accordance with the invention is non-replicative and/or non-infectious since it lacks all or part of the viral genome or genome function. In one embodiment, a virus-like particle is a virus particle, in which the viral genome has been physically or chemically inactivated. Typically and more preferably a virus-like particle lacks all or part of the replicative and infectious components of the viral genome. A virus-like particle in accordance with the invention may contain nucleic acid distinct from their genome. A typical and preferred embodiment of a virus-like particle in accordance with the present invention is a viral capsid such as the viral capsid of the corresponding virus, bacteriophage, preferably RNA bacteriophage. The terms "viral capsid" or "capsid", refer to a macromolecular assembly composed of viral protein subunits. Typically, there are 60, 120, 180, 240, 300, 360 and more than 360 viral protein subunits. Typically and preferably, the interactions of these subunits lead to the formation of viral capsid or viral-capsid like structure with an inherent repetitive organization, wherein said structure is, typically, spherical or tubular. For example, the capsids of RNA bacteriophages or HBcAgs have a spherical form of icosahedral symmetry. The term "capsid-like structure" as used herein, refers to a macromolecular assembly composed of viral protein subunits resembling the capsid morphology in the above defined sense but deviating from the typical symmetrical assembly while maintaining a sufficient degree of order and repetitiveness. One common feature of virus particle and virus-like particle is its highly ordered and repetitive arrangement of its subunits.

Virus-like particle of an RNA bacteriophage: As used herein, the term "virus-like particle of an RNA bacteriophage" refers to a virus-like particle comprising, or preferably consisting essentially of or consisting of coat proteins, mutants or fragments thereof, of an RNA bacteriophage. In addition, virus-like particle of an RNA bacteriophage resembling the structure of an RNA bacteriophage, being non replicative and/or non-infectious, and lacking at least the gene or genes encoding for the replication machinery of the RNA bacteriophage, and typically also lacking the gene or genes encoding the protein or proteins responsible for viral attachment to or entry into the host. This definition should, however, also encompass virus-like particles of RNA bacteriophages, in which the aforementioned gene or genes are still present but inactive, and, therefore, also leading to non-replicative and/or non-infectious virus-like particles of an RNA bacteriophage. Preferred VLPs derived from RNA bacteriophages exhibit icosahedral symmetry and consist of 180 subunits (monomers). Preferred methods to render a virus-like particle of an RNA bacteriophage non replicative and/or non-infectious is by physical, chemical inactivation, such as UV irradiation, formaldehyde treatment, typically and preferably by genetic manipulation.

One, a, or an: when the terms "one", "a", or "an" are used in this disclosure, they mean "at least one" or "one or more" unless otherwise indicated.

The amino acid sequence identity of polypeptides can be determined conventionally using known computer programs such as the Bestfit program. When using Bestfit or any other sequence alignment program, preferably using Bestfit, to determine whether a particular sequence is, for instance, 95% identical to a reference amino acid sequence, the parameters are set such that the percentage of identity is calculated over the full length of the reference amino acid sequence and that gaps in homology of up to 5% of the total number of amino acid residues in the reference sequence are allowed. This aforementioned method in determining the percentage of identity between polypeptides is applicable to all proteins, polypeptides or a fragment thereof disclosed in this invention.

This invention provides compositions and methods for enhancing immune responses against IL-1 in an animal or in human. Compositions of the invention comprise: (a) a core particle with at least one first attachment site, wherein said core particle is a virus-like particle (VLP) or a virus particle; and (b) at least one antigen with at least one second attachment site, wherein the at least one antigen is an IL-1 molecule, preferably selected from the group consisting of IL-1 protein, IL-1 mature fragment, IL-1 peptide and IL-1 mutein, wherein (a) and (b) are covalently linked through the at least one first and the at least one second attachment site. Preferably, said IL-1 molecule is linked to the core particle, so as to form an ordered and repetitive antigen-VLP array. In preferred embodiments of the invention, at least 20, preferably at least 30, more preferably at least 60, again more preferably at least 120 and further more preferably at least 180 IL-1 molecules are linked to the core particle.

Any virus known in the art having an ordered and repetitive structure may be selected as a VLP or a virus particle of the invention. Illustrative DNA or RNA viruses, the coat or capsid protein of which can be used for the preparation of VLPs have been disclosed in WO 2004/009124 on page 25, line 10-21, on page 26, line 11-28, and on page 28, line 4 to page 31, line 4. These disclosures are incorporated herein by way of reference.

Virus or virus-like particle can be produced and purified from virus-infected cell cultures. The resulting virus or virus-like particle for vaccine purpose should be preferably non-replicative or non-infectious, more preferably non-replicative and non-infectious. UV irradiation, chemical treatment, such as with formaldehyde or chloroform, are the general methods known to skilled person in the art to inactivate virus.

In one preferred embodiment, the core particle is a virus particle, and wherein preferably said virus particle is a bacteriophage, and wherein further preferably said bacteriophage is an RNA bacteriophage, and wherein even further preferably said RNA bacteriophage is an RNA bacteriophage selected from Qβ, fr, GA or AP205.

In one preferred embodiment, the core particle is a VLP. In a further preferred embodiment, the VLP is a recombinant VLP. Almost all commonly known viruses have been sequenced and are readily available to the public. The gene encoding the coat protein can be easily identified by a skilled artisan. The preparation of VLPs by recombinantly expressing the coat protein in a host is within the common knowledge of a skilled artisan.

In one preferred embodiment, the virus-like particle comprises, or alternatively consists of, recombinant proteins, mutants or fragments thereof, of a virus selected form the group consisting of: a) RNA bacteriophages; b) bacteriophages; c) Hepatitis B virus, preferably its capsid protein (Ulrich, et al., Virus Res. 50:141-182 (1998)) or its surface protein (WO 92/11291); d) measles virus (Warnes, et al., Gene 160:173-178 (1995)); e) Sindbis virus; f) rotavirus (U.S. Pat. No. 5,071,651 and U.S. Pat. No. 5,374,426); g) foot-and-mouth-disease virus (Twomey, et al., Vaccine 13:1603 1610, (1995)); h) Norwalk virus (Jiang, X., et al., Science 250:1580 1583 (1990); Matsui, S. M., et al., J. Clin. Invest. 87:1456 1461 (1991)); i) Alphavirus; j) retrovirus, preferably its GAG protein (WO 96/30523); k) retrotransposon Ty, preferably the protein p1; l) human Papilloma virus (WO 98/15631); m) Polyoma virus; n) Tobacco mosaic virus; and o) Flock House Virus.

VLP comprising more than one different recombinant proteins is generally referred, in this application, as mosaic VLP. In one embodiment, the VLP is a mosaic VLP, wherein said mosaic VLP comprises, or consists of, more than one recombinant protein, preferably of two recombinant proteins, most preferably of two recombinant capsid proteins, mutants or fragments thereof.

The term "fragment of a recombinant protein" or the term "fragment of a coat protein", as used herein, is defined as a polypeptide, which is of at least 70%, preferably at least 80%, more preferably at least 90%, even more preferably at least 95% the length of the wild-type recombinant protein, or coat protein, respectively and which preferably retains the capability of forming VLP. Preferably, the fragment is obtained by at least one internal deletion, at least one truncation or at least one combination thereof. Further preferably, the fragment is obtained by at most 5, 4, 3 or 2 internal deletions, by at most 2 truncations or by exactly one combination thereof.

The term "fragment of a recombinant protein" or "fragment of a coat protein" shall further refer to a polypeptide, which has at least 80%, preferably 90%, even more preferably 95% amino acid sequence identity with the "fragment of a recombinant protein" or "fragment of a coat protein", respectively, as defined above and which is preferably capable of assembling into a virus-like particle.

The term "mutant coat protein" refers to a polypeptide having an amino acid sequence derived from the wild type recombinant protein, or coat protein, respectively, wherein the amino acid sequence is at least 80%, preferably at least 85%, 90%, 95%, 97%, or 99% identical to the wild type sequence and preferably retains the ability to assemble into a VLP.

In one preferred embodiment, the virus-like particle of the invention is of Hepatitis B virus. The preparation of Hepatitis B virus-like particles has been disclosed, inter alia, in WO 00/32227, WO 01/85208 and in WO 01/056905. All three documents are explicitly incorporated herein by way of reference. Other variants of HBcAg suitable for use in the practice of the present invention have been disclosed in page 34-39 of WO 01/056905.

In one further preferred embodiment of the invention, a lysine residue is introduced into the HBcAg polypeptide, to mediate the linking of IL-1 molecule to the VLP of HBcAg. In preferred embodiments, VLPs and compositions of the invention are prepared using a HBcAg comprising, or alternatively consisting of, amino acids 1-144, or 1-149, 1-185 of SEQ ID NO:1, which is modified so that the amino acids at positions 79 and 80 are replaced with a peptide having the amino acid sequence of Gly-Gly-Lys-Gly-Gly (SEQ ID NO:170). This modification changes the SEQ ID NO:1 to SEQ ID NO:2. In further preferred embodiments, the cysteine residues at positions 48 and 110 of SEQ ID NO:2, or its corresponding fragments, preferably 1-144 or 1-149, are mutated to serine. The invention further includes compositions comprising Hepatitis B core protein mutants having above noted corresponding amino acid alterations. The invention further includes compositions and vaccines, respectively, comprising HBcAg polypeptides which comprise, or alternatively consist of, amino acid sequences which are at least 80%, 85%, 90%, 95%, 97% or 99% identical to SEQ ID NO:2.

In one preferred embodiment of the invention, the virus-like particle of the invention comprises, consists essentially of, or alternatively consists of, recombinant coat proteins, mutants or fragments thereof, of an RNA bacteriophage. Preferably, the RNA bacteriophage is selected from the group consisting of a) bacteriophage Qβ; b) bacteriophage R17; c) bacteriophage fr; d) bacteriophage GA; e) bacteriophage SP; f) bacteriophage MS2; g) bacteriophage M11; h) bacteriophage MX1; i) bacteriophage NL95; k) bacteriophage f2; l) bacteriophage PP7 and m) bacteriophage AP205.

In one preferred embodiment of the invention, the composition comprises coat protein, mutants or fragments thereof, of RNA bacteriophages, wherein the coat protein has amino acid sequence selected from the group consisting of: (a) SEQ ID NO:3 referring to P CP; (b) a mixture of SEQ ID NO:3 and SEQ ID NO:4 (Qβ A1 protein); (c) SEQ ID NO:5 (R17 capsid protein); (d) SEQ ID NO:6 (fr capsid protein); (e) SEQ ID NO:7 (GA capsid protein); (f) SEQ ID NO:8 (SP capsid protein); (g) a mixture of SEQ ID NO:8 and SEQ ID NO:9; (h) SEQ ID NO:10 (MS2 capsid protein); (i) SEQ ID NO:11 (M11 capsid protein); (j) SEQ ID NO:12 (MX1 capsid protein); (k) SEQ ID NO:13 (NL95 capsid protein); (l) SEQ ID NO:14 (f2 capsid protein); (m) SEQ ID NO:15 (PP7 capsid protein); and (n) SEQ ID NO:21 (AP205 capsid protein).

In one preferred embodiment of the invention, the VLP is a mosaic VLP comprising or alternatively consisting of more than one amino acid sequence, preferably two amino acid sequences, of coat proteins, mutants or fragments thereof, of an RNA bacteriophage.

In one very preferred embodiment, the VLP comprises or alternatively consists of two different coat proteins of an RNA bacteriophage, said two coat proteins have an amino acid sequence of CP Qβ (SEQ ID NO: 3) and CP Qβ A1 (SEQ ID NO:4), or of CP SP (SEQ ID NO:8) and CP SP A1 (SEQ ID NO:9).

In preferred embodiments of the present invention, the virus-like particle of the invention comprises, or alternatively consists essentially of, or alternatively consists of recombinant coat proteins, mutants or fragments thereof, of the RNA-bacteriophage Qβ, fr, AP205 or GA.

In one preferred embodiment, the VLP of the invention is a VLP of RNA bacteriophage Qβ. The capsid or virus-like particle of Qβ showed an icosahedral phage-like capsid structure with a diameter of 25 nm and T=3 quasi symmetry. The capsid contains 180 copies of the coat protein, which are linked in covalent pentamers and hexamers by disulfide bridges (Golmohammadi, R. et al., Structure 4:543-5554 (1996)), leading to a remarkable stability of the Qβ capsid. Capsids or VLPs made from recombinant Qβ coat protein may contain, however, subunits not linked via disulfide bonds to other subunits within the capsid, or incompletely linked. The capsid or VLP of Qβ shows unusual resistance to organic solvents and denaturing agents. Surprisingly, we have observed that DMSO and acetonitrile concentrations as high as 30%, and guanidinium concentrations as high as 1 M do not affect the stability of the capsid. The high stability of the capsid or VLP of Qβ is an advantageous feature, in particular, for its use in immunization and vaccination of mammals and humans in accordance of the present invention.

Further preferred virus-like particles of RNA bacteriophages, in particular of Qβ and fr in accordance of this invention are disclosed in WO 02/056905, the disclosure of which is herewith incorporated by reference in its entirety. Particular example 18 of WO 02/056905 gave detailed description of preparation of VLP particles from Qβ.

In another preferred embodiment, the VLP of the invention is a VLP of RNA bacteriophage AP205. Assembly-competent mutant forms of AP205 VLPs, including AP205 coat protein with the substitution of proline at amino acid 5 to threonine, may also be used in the practice of the invention and leads to other preferred embodiments of the invention. WO 2004/007538 describes, in particular in Example 1 and Example 2, how to obtain VLP comprising AP205 coat proteins, and hereby in particular the expression and the purification thereto. WO 2004/007538 is incorporated herein by way of reference. AP205 VLPs are highly immunogenic, and can be linked with IL-1 molecule to typically and preferably generate vaccine constructs displaying the IL-1 molecule oriented in a repetitive manner.

In one preferred embodiment, the VLP of the invention comprises or consists of a mutant coat protein of a virus, preferably an RNA bacteriophage, wherein the mutant coat protein has been modified by removal of at least one lysine residue by way of substitution and/or by way of deletion. In another preferred embodiment, the VLP of the invention comprises or consists of a mutant coat protein of a virus, preferably an RNA bacteriophage, wherein the mutant coat protein has been modified by addition of at least one lysine residue by way of substitution and/or by way of insertion. The deletion, substitution or addition of at least one lysine residue allows varying the degree of coupling, i.e. the amount of IL-1 molecule per subunits of the VLP of a virus, preferably of an RNA bacteriophages, in particular, to match and tailor the requirements of the vaccine.

In one preferred embodiment, the compositions and vaccines of the invention have an antigen density being from 0.5 to 4.0. The term "antigen density", as used herein, refers to the average number of IL-1 molecules which is linked per subunit, preferably per coat protein, of the VLP, and hereby preferably of the VLP of an RNA bacteriophage. Thus, this value is calculated as an average over all the subunits of the VLP, preferably of the VLP of the RNA bacteriophage, in the composition or vaccines of the invention.

VLPs or capsids of Qβ coat protein display a defined number of lysine residues on their surface, with a defined topology with three lysine residues pointing towards the interior of the capsid and interacting with the RNA, and four other lysine residues exposed to the exterior of the capsid. Preferably, the at least one first attachment site is a lysine residue, pointing to or being on the exterior of the VLP.

Qβ mutants, of which exposed lysine residues are replaced by arginines can be used for the present invention. Thus, in another preferred embodiment of the present invention, the virus-like particle comprises, consists essentially of or alternatively consists of mutant Qβ coat proteins. Preferably these mutant coat proteins comprise or alternatively consist of an amino acid sequence selected from the group of a) Qβ-240 (SEQ ID NO:16, Lys13-Arg of SEQ ID NO: 3) b) Qβ-243 (SEQ ID NO:17, Asn10-Lys of SEQ ID NO:3); c) Qβ-250 (SEQ ID NO:18, Lys2-Arg of SEQ ID NO:3) d) Qβ-251 (SEQ ID NO:19, Lys16-Arg of SEQ ID NO:3); and e) Qβ-259 (SEQ ID NO:20, Lys2-Arg, Lys16-Arg of SEQ ID NO:3). The construction, expression and purification of the above indicated Qβ mutant coat proteins, mutant Qβ coat protein VLPs and capsids, respectively, are described in WO 02/056905. In particular is hereby referred to Example 18 of above mentioned application.

In another preferred embodiment of the present invention, the virus-like particle comprises, or alternatively consists essentially of, or alternatively consists of mutant coat protein of Qβ, or mutants or fragments thereof, and the corresponding A1 protein. In a further preferred embodiment, the virus-like particle comprises, or alternatively consists essentially of, or alternatively consists of mutant coat protein with amino acid sequence SEQ ID NO:16, 17, 18, 19, or 20 and the corresponding A1 protein.

Further RNA bacteriophage coat proteins have also been shown to self-assemble upon expression in a bacterial host (Kastelein, R A. et al., Gene 23:245-254 (1983), Kozlovskaya, T M. et al., Dokl. Akad. Nauk SSSR 287:452-455 (1986), Adhin, M R. et al., Virology 170:238-242 (1989), Priano, C. et al., J. Mol. Biol. 249:283-297 (1995)). In particular the biological and biochemical properties of GA (Ni, C Z., et al., Protein Sci. 5:2485-2493 (1996), Tars, K et al., J. Mol. Biol. 271:759-773 (1997)) and of fr (Pushko P. et al., Prot. Eng. 6:883-891 (1993), Liljas, L et al. J. Mol. Biol. 244:279-290, (1994)) have been disclosed. The crystal structure of several RNA bacteriophages has been determined (Golmohammadi, R. et al., Structure 4:543-554 (1996)). Using such information, surface exposed residues can be identified and, thus, RNA bacteriophage coat proteins can be modified such that one or more reactive amino acid residues can be inserted by way of insertion or substitution. Another advantage of the VLPs derived from RNA bacteriophages is their high expression yield in bacteria that allows production of large quantities of material at affordable cost.

In one preferred embodiment, the composition of the invention comprises at least one antigen, preferably one to four, more preferably one to three, still more preferably one to two and most preferably exactly one antigen, wherein said antigen is an IL-1 molecule, preferably an IL-1 protein, an IL-1 fragment, an IL-1 mature fragment, an IL-1 peptide or an IL-1 mutein, wherein said IL-1 molecule preferably comprises or even more preferably consists of a polypeptide having an amino acid sequence having at least 80%, preferably at least 90%, more preferably at least 95%, even more preferably at least 99% and most preferably 100% sequence identity with any one of SEQ ID NO:36 to SEQ ID NO:116, SEQ ID NO:130 to SEQ ID NO:140 and SEQ ID NO:163 to SEQ ID NO:165.

In a further preferred embodiment said antigen is an IL-1 molecule derived from an organism selected from the group consisting of: (a) humans; (b) primates; (c) rodents; (d) horses; (e) sheep; (f) cat; (g) cattle; (h) pig; (i) rabbit; (j) dog; (k) mouse; and (l) rat. Most preferably said IL-1 molecule is derived from humans, preferably comprising or even more preferably consisting of a polypeptide having at least 80%, preferably at least 90%, more preferably at least 95%, even more preferably at least 99% and most preferably 100% sequence identity with any one of the sequences selected from the group consisting of SEQ ID NO:36, SEQ ID NO:49, SEQ ID NO:63, SEQ ID NO:64, any one of SEQ ID NO:67 to 110, and one of SEQ ID NO:130-140, and SEQ ID NO:165.

In a further preferred embodiment said IL-1 molecule derived from rat or mouse, preferably mouse, wherein said IL-1 molecule preferably comprises or even more preferably consists of a polypeptide having an amino acid sequence having at least 80%, preferably at least 90%, more preferably at least 95%, even more preferably at least 99% and most preferably 100% sequence identity with any one of SEQ ID NO:45, SEQ ID NO:46, SEQ ID NO:53, SEQ ID NO:54, SEQ ID NO:65, SEQ ID NO:66, any one of SEQ ID NO:111 to SEQ ID NO:116, SEQ ID NO:163, and SEQ ID NO:164.

In a further preferred embodiment IL-1 molecule is an IL-1 alpha molecule, preferably an IL-1 alpha protein, an IL-1 alpha fragment, an IL-1 alpha mature fragment, an IL-1 alpha peptide or an IL-1 alpha mutein, wherein said IL-1 alpha molecule preferably comprises or even more preferably consists of a polypeptide having an amino acid sequence having at least 80%, preferably at least 90%, more preferably at least 95%, even more preferably at least 99% and most preferably 100% sequence identity with any one of the sequences selected from the group consisting of SEQ ID NO:36 to 48, SEQ ID NO:63, SEQ ID NO:65, SEQ ID NO:67 to 88, and SEQ ID NO:165. Specifically preferred embodiments of IL-1 alpha molecules are human IL-1 alpha molecules, preferably human IL-1 alpha proteins, human IL-1 alpha fragments or human IL-1 alpha mature fragments, wherein said IL-1 alpha molecules preferably comprise or even more preferably consist of a polypeptide having an amino acid sequence having at least 80%, preferably at least 90%, more preferably at least 95%, even more preferably at least 99% and most preferably 100% sequence identity with any one of SEQ ID NO:36, SEQ ID NO:63, and SEQ ID NO:163, most preferably SEQ ID NO:63.

In a further preferred embodiment said IL-1 molecule is an IL-1 beta molecule, preferably an IL-1 beta protein, an IL-1 beta fragment, an IL-1 beta mature fragment, an IL-1 beta peptide or an IL-1 beta mutein, wherein said IL-1 beta molecule preferably comprises or even more preferably consists of a polypeptide having an amino acid sequence having at least 80%, preferably at least 90%, more preferably at least 95%, even more preferably at least 99% and most preferably 100% sequence identity with any one of the sequences selected from the group consisting of SEQ ID NO:49 to 62, SEQ ID NO:64, SEQ ID NO:66, SEQ ID NO:89 to 116, SEQ ID NO:130 to SEQ ID NO:140, SEQ ID NO:164, and SEQ ID NO:165. Specifically preferred embodiments of IL-1 beta molecules are human IL-1 beta molecules, preferably human IL-1 beta proteins, human IL-1 beta fragments or human IL-1 beta mature fragments, wherein said IL-1 beta molecules preferably comprises or even more preferably consists of a polypeptide having an amino acid sequence having at least 80%, preferably at least 90%, more preferably at least 95%, even more preferably at least 99% and most preferably 100% sequence identity with any one of SEQ ID NO:49, SEQ ID NO:64, SEQ ID NO:130 to SEQ ID NO:140 and SEQ ID NO:165, most preferably SEQ ID NO:64.

In a further preferred embodiment said IL-1 molecule is an IL-1 protein, an IL-1 fragment or, preferably, an IL-1 mature fragment, wherein said IL-1 protein, IL-1 fragment or IL-1 mature fragment preferably are capable of binding to the IL-1 receptor and, still more preferably, additionally also comprise biological activity.

In a further preferred embodiment said IL-1 molecule is an IL-1 protein, wherein said IL-1 protein preferably comprises or even more preferably consists of a polypeptide having an amino acid sequence having at least 80%, preferably at least 90%, more preferably at least 95%, even more preferably at least 99% and most preferably 100% sequence identity with any one of SEQ ID NO:36 to SEQ ID NO:62.

In a further preferred embodiment said IL-1 protein is an IL-1 alpha protein, wherein said IL-1 alpha protein preferably comprises or even more preferably consists of a polypeptide having an amino acid sequence having at least 80%, preferably at least 90%, more preferably at least 95%, even more preferably at least 99% and most preferably 100% sequence identity with any one of the sequences selected from the group consisting of SEQ ID NO:36 to SEQ ID NO:48. Most preferably said IL-1 alpha protein is a human IL-1 alpha protein, wherein said human IL-1 alpha protein preferably comprises or even more preferably consists of a polypeptide having least 80%, preferably at least 90%, more preferably at least 95%, even more preferably at least 99% and most preferably 100% sequence identity with SEQ ID NO:36.

In a further preferred embodiment said IL-1 protein is an is an IL-1 beta protein, wherein said IL-1 beta protein preferably comprises or even more preferably consists of a polypeptide having an amino acid sequence having at least 80%, preferably at least 90%, more preferably at least 95%, even more preferably at least 99% and most preferably 100% sequence identity with any one of the sequences selected from the group consisting of SEQ ID NO:49 to SEQ ID NO:62. Most preferably said IL-1 beta protein is a human IL-1 beta protein, wherein said human IL-1 beta protein preferably comprises or even more preferably consists of a polypeptide having least 80%, preferably at least 90%, more preferably at least 95%, even more preferably at least 99% and most preferably 100% sequence identity with SEQ ID NO:49.

In a further preferred embodiment said IL-1 molecule is an IL-1 fragment, preferably an IL-1 mature fragment, and wherein said IL-1 fragment or said IL-1 mature fragment preferably is derived from mouse or human, most preferably human. Preferably said IL-1 fragment or said IL-1 mature fragment comprises or even more preferably consists of a polypeptide having an amino acid sequence having at least 80%, preferably at least 90%, more preferably at least 95%, even more preferably at least 99% and most preferably 100% sequence identity with any one of SEQ ID NO:63 to SEQ ID NO:66, SEQ ID NO:130, and SEQ ID NO:163 to SEQ ID NO:165.

In a further preferred embodiment said IL-1 mature fragment is an IL-1 alpha mature fragment, wherein said IL-1 alpha mature fragment preferably comprises biological activity and wherein further said IL-1 alpha mature fragment preferably comprises or even more preferably consists of a polypeptide having an amino acid sequence having at least 80%, preferably at least 90%, more preferably at least 95%, even more preferably at least 99% and most preferably 100% sequence identity with any one of SEQ ID NO:63 or SEQ ID NO:65, most preferably SEQ ID NO:63.

In a further preferred embodiment said IL-1 mature fragment is an IL-1 beta mature fragment, wherein said IL-1 beta mature fragment preferably comprises biological activity and wherein further said IL-1 beta mature fragment preferably comprises or even more preferably consists of a polypeptide having an amino acid sequence having at least 80%, preferably at least 90%, more preferably at least 95%, even more preferably at least 99% and most preferably 100% sequence identity with any one of SEQ ID NO:64, SEQ ID NO:66, and SEQ ID NO:130, most preferably SEQ ID NO:64.

In a further preferred embodiment said IL-1 molecule is an IL-1 peptide, wherein said IL-1 peptide is derived from mouse, rat or human, most preferably human. Preferably said IL-1 peptide comprises or even more preferably consists of a polypeptide having an amino acid sequence having at least 80%, preferably at least 90%, more preferably at least 95%, even more preferably at least 99% and most preferably 100% sequence identity with any one of SEQ ID NO:67 to SEQ ID NO:116.

In a further preferred embodiment said IL-1 molecule is an IL-1 mutein, wherein preferably said IL-1 mutein comprises reduced or more preferably no biological activity, and wherein further said IL-1 mutein is capable of binding the IL-1 receptor. In a further preferred embodiment said IL-1 mutein comprises or preferably consists of a polypeptide having an amino acid sequence which differs from the amino acid sequence of an IL-1 mature fragment in 1 to 3, more preferably in 1 to 2, and most preferably in exactly 1 amino acid residue.

In one preferred embodiment, said IL-1 mutein comprises at least one, preferably one, mutated amino acid sequence derived from a wild type amino acid sequence, wherein said wild type amino acid sequence is an IL-1 beta amino acid sequence selected from the group consisting of: (1) position 3 to 11 of SEQ ID NO:64; (2) position 46 to 56 of SEQ ID NO:64; (3) position 88 to 109 of SEQ ID NO:64; and (4) position 143 to 153 of SEQ ID NO:64; or wherein said wild type amino acid sequence is an IL-1 alpha amino acid sequence selected from the group consisting of: (5) position 9 to 20 of SEQ ID NO:63; (6) position 52 to 62 of SEQ ID NO:63; (7) position 94 to 113 of SEQ ID NO:63; and (8) position 143 to 153 of SEQ ID NO:63; and wherein said at least one mutated amino acid sequence is characterized by an amino acid exchange in one to four positions, preferably in one, two or three positions, more preferably in one or two positions, as compared to said wild type amino acid sequence it is derived from; or wherein said at least one mutated amino acid sequence is characterized by a deletion of one to four consecutive amino acids of said wild type amino acid sequence it is derived from.

In a further preferred embodiment said IL-1 mutein comprises at most one mutated amino acid sequence derived from each of said L-1 beta amino acid sequences (1) to (4); or wherein said IL-1 mutein comprises at most one mutated amino acid sequence derived from each of said IL-1 alpha amino acid sequences (5) to (8).

In a very preferred embodiment said IL-1 mutein comprises exactly one of said at least one mutated amino acid sequence, wherein preferably said exactly one mutated amino acid sequence is derived from a wild type amino acid sequence, wherein said wild type amino acid sequence is position 143 to 153 of SEQ ID NO:64 or position 143 to 153 of SEQ ID NO:63.

In a further preferred embodiment said at least one mutated amino acid sequence is characterized by a deletion of one to three, preferably of one to two, consecutive amino acids of said wild type amino acid sequence it is derived from.

In a further preferred embodiment said at least one mutated amino acid sequence is characterized by a deletion of exactly one amino acid of said wild type amino acid sequence it is derived from.

In a further preferred embodiment said at least one mutated amino acid sequence is derived from a wild type amino acid sequence, wherein said wild type amino acid sequence is position 143 to 153 of SEQ ID NO:64 or position 143 to 153 of SEQ ID NO:63. Most preferably said at least one mutated amino acid sequence is derived from position 143 to 153 of SEQ ID NO:64.

In a further preferred embodiment said at least one mutated amino acid sequence is derived from a wild type amino acid sequence, wherein said wild type amino acid sequence is position 46 to 56 of SEQ ID NO:64 or position 52 to 62 of SEQ ID NO:63, wherein preferably said at least one mutated amino acid sequence is characterized by a deletion of one to four, preferably of two to three, consecutive amino acids of said wild type amino acid sequence it is derived from. In a very preferred embodiment said IL-1 mutein comprises or preferably consists of a polypeptide having the amino acid sequence of SEQ ID NO:137 or SEQ ID NO:138.

In a further preferred embodiment said at least one mutated amino acid sequence is derived from a wild type amino acid sequence, wherein said wild type amino acid sequence is position 88 to 109 of SEQ ID NO:64 or position 94-113 of SEQ ID NO:63, wherein said at least one mutated amino acid sequence is characterized by the deletion of one to four, preferably of one to three, more preferably of one to two consecutive amino acids of said wild type amino acid sequence it is derived from.

In a further preferred embodiment said at least one mutated amino acid sequence is characterized by an amino acid exchange in one or two positions, preferably in exactly one position, as compared to said wild type amino acid sequence it is derived from.

In a further preferred embodiment said wild type amino acid sequence is position 143 to 153 of SEQ ID NO:64 or position 143 to 153 of SEQ ID NO:63 and said at least one mutated amino acid sequence is characterized by an amino acid exchange in one or two positions, preferably in exactly one position, as compared to said wild type amino acid sequence, wherein further preferably said exactly one position is position 145 of SEQ ID NO:64 or position 145 of SEQ ID NO:63, wherein still further preferably said amino acid exchange is an exchange of aspartic acid (D) to an amino acid selected from the group consisting of lysine (K), tyrosine (Y), phenylalanine (F), asparagine (N) and arginine (R).

In a very preferred embodiment said amino acid exchange is an exchange of aspartic acid (D) to lysine (K).

In a further preferred embodiment said wild type amino acid sequence is position 143 to 153 of SEQ ID NO:64 or position 143 to 153 of SEQ ID NO:63 and said at least one mutated amino acid sequence is characterized by an amino acid exchange in exactly one position as compared to said wild type amino acid sequence, wherein further preferably said exactly one position is position 146 of SEQ ID NO:64 or position 146 of SEQ ID NO:63, wherein still further preferably said amino acid exchange is an exchange of phenylalanine (F) to an amino acid selected from the group consisting of asparagine (N), glutamine (Q), and serine (S).

In a further preferred embodiment said IL-1 mutein is an IL-1 beta mutein, preferably a human IL-1 beta mutein, most preferably a human IL-1 beta mutein selected from SEQ ID NO:131 to SEQ ID NO:140.

In a further preferred embodiment said IL-1 mutein is an IL-1 beta mutein, wherein preferably said IL-1 beta mutein comprises or preferably consists of a polypeptide having an amino acid sequence, wherein said amino acid sequence differs from the amino acid sequence of SEQ ID NO:64 in 1 to 10, 1 to 9, 1 to 8, 1 to 7, 1 to 6, 1 to 5, 1 to 4, 1 to 3, or 1 to 2 amino acid residues. Most preferably said amino acid sequence differs from the amino acid sequence of SEQ ID NO:64 in exactly 1 amino acid residue. In a very preferred embodiment said IL-1 beta mutein comprises or preferably consists of a polypeptide having an amino acid sequence selected from the group consisting of SEQ ID NO:131 to SEQ ID NO:140 and SEQ ID NO:205 to SEQ ID NO:209, wherein most preferably said IL-1 beta mutein comprises or preferably consists of a polypeptide having the amino acid sequence of SEQ ID NO:136.

In a further preferred embodiment said IL-1 mutein is an IL-1 alpha mutein, wherein preferably said IL-1 alpha mutein comprises or preferably consists of a polypeptide having an amino acid sequence, wherein said amino acid sequence differs from the amino acid sequence of SEQ ID NO:63 in 1 to 10, 1 to 9, 1 to 8, 1 to 7, 1 to 6, 1 to 5, 1 to 4, 1 to 3, or 1 to 2 amino acid residues. Most preferably said amino acid sequence differs from the amino acid sequence of SEQ ID NO:63 in exactly 1 amino acid residue. In a very preferred embodiment said IL-1 alpha mutein comprise or preferably consist of a polypeptide having an amino acid sequence selected from the group consisting of SEQ ID NO:210 to SEQ ID NO:218, wherein most preferably said IL-1 alpha mutein comprises or preferably consists of a polypeptide having the amino acid sequence of SEQ ID NO:210.

The present invention provides for a method of producing the composition of the invention comprising (a) providing a VLP with at least one first attachment site; (b) providing at least one antigen, wherein said antigen is an IL-1 molecule, an IL-1 protein, an IL-1 fragment, preferably an IL-1 mature fragment, an IL-1 peptide or an IL-1 mutein, with at least one second attachment site; and (c) combining said VLP and said at least one antigen to produce said composition, wherein said at least one antigen and said VLP are linked through the first and the second attachment sites. In a preferred embodiment, the provision of the at least one antigen, i.e. IL-1 molecule, an IL-1 protein, an IL-1 fragment, preferably an IL-1 mature fragment, an IL-1 peptide or an IL-1 mutein, with the at least one second attachment site is by way of expression, preferably by way of expression in a bacterial system, preferably in *E. coli*. Usually a purification tag, such as His tag, Myc tag, Fc tag or HA tag is added to facilitate the purification process. In another approach particularly the IL-1 peptides or IL-1 muteins with no longer than 50 amino acids are chemically synthesized.

In one preferred embodiment of the invention, the VLP with at least one first attachment site is linked to the IL-1 molecule with at least one second attachment site via at least one peptide bond. A gene encoding an IL-1 molecule, preferably an IL-1 mature fragment, is in-frame ligated, either internally or preferably to the N— or the C-terminus to the gene encoding the coat protein of the VLP. Fusion may also be effected by inserting sequences of the IL-1 into a mutant coat protein where part of the coat protein sequence has been deleted, that are further referred to as truncation mutants. Truncation mutants may have N- or C-terminal, or internal deletions of part of the sequence of the coat protein. For example for the specific VLP HBcAg, amino acids 79-80 are replaced with a foreign epitope. The fusion protein shall preferably retain the ability of assembly into a VLP upon expression which can be examined by electromicroscopy.

Flanking amino acid residues may be added to increase the distance between the coat protein and foreign epitope. Glycine and serine residues are particularly favored amino acids to be used in the flanking sequences. Such a flanking sequence confers additional flexibility, which may diminish the potential destabilizing effect of fusing a foreign sequence into the sequence of a VLP subunit and diminish the interference with the assembly by the presence of the foreign epitope.

In other embodiments, the at least one IL-1 molecule, preferably the IL-1 mature fragment can be fused to a number of other viral coat protein, as way of examples, to the C-terminus of a truncated form of the A1 protein of Qβ (Kozlovska, T. M., et al., Intervirology 39:9-15 (1996)), or being inserted between position 72 and 73 of the CP extension. As another example, the IL-1 can be inserted between amino acid 2 and 3 of the fr CP, leading to a IL-1-fr CP fusion protein (Pushko P. et al., Prot. Eng. 6:883-891 (1993)). Furthermore, IL-1 can be fused to the N-terminal protuberant β-hairpin of the coat protein of RNA bacteriophage MS-2 (WO 92/13081). Alternatively, the IL-1 can be fused to a capsid protein of papillomavirus, preferably to the major capsid protein L1 of bovine papillomavirus type 1 (BPV-1) (Chackerian, B. et al., Proc. Natl. Acad. Sci. USA 96:2373-2378 (1999), WO 00/23955). Substitution of amino acids 130-136 of BPV-1 L1 with an IL-1 is also an embodiment of the invention. Further embodiments of fusing an IL-1 molecule to coat protein, mutants or fragments thereof, to a coat protein of a virus have been disclosed in WO 2004/009124 page 62 line 20 to page 68 line 17 and herein are incorporated by way of reference.

U.S. Pat. No. 5,698,424 describes a modified coat protein of bacteriophage MS-2 capable of forming a capsid, wherein the coat protein is modified by an insertion of a cysteine residue into the N-terminal hairpin region, and by replacement of each of the cysteine residues located external to the N-terminal hairpin region by a non-cysteine amino acid residue. The inserted cysteine may then be linked directly to a desired molecular species to be presented such as an epitope or an antigenic protein.

We note, however, that the presence of an exposed free cysteine residue in the capsid may lead to oligomerization of capsids by way of disulfide bridge formation. Moreover, attachment between capsids and antigenic proteins by way of disulfide bonds are labile, in particular, to sulfhydryl-moiety containing molecules, and are, furthermore, less stable in serum than, for example, thioether attachments (Martin F J. and Papahadjopoulos D. (1982) Irreversible Coupling of Immunoglobulin Fragments to Preformed Vesicles. J. Biol. Chem. 257: 286-288).

Therefore, in a further very preferred embodiment of the present invention, the association or linkage of the VLP and the at least one antigen, i.e. IL-1 molecule, does not comprise a disulfide bond. Further preferred hereby, the at least one second attachment comprise, or preferably is, a sulfhydryl group. Moreover, in again a very preferred embodiment of the present invention, the association or linkage of the VLP and the at least one IL-1 molecule does not comprise a sulphur-sulphur bond. Further preferred hereby, the at least one second attachment comprise, or preferably is, a sulfhydryl group. In a further very preferred embodiment, said at least one first attachment site is not or does not comprise a sulfhydryl group. In again a further very preferred embodiment, said at least one first attachment site is not or does not comprise a sulfhydryl group of a cysteine.

In a further preferred embodiment said at least one first attachment comprises an amino group and said second attachment comprises a sulfhydryl group.

In a further preferred embodiment only one of said second attachment sites associates with said first attachment site through at least one non-peptide covalent bond leading to a single and uniform type of binding of said IL-1 molecule to said core particle, wherein said only one second attachment site that associates with said first attachment site is a sulfhydryl group, and wherein said IL-1 molecule and said core particle interact through said association to form an ordered and repetitive antigen array.

In another preferred embodiment, an IL-1 molecule, preferably an IL-1 protein, more preferably an IL-1 mature fragment, still more preferably an IL-1 mature fragment comprising or consisting of amino acid sequenced SEQ ID NO:63 to SEQ ID NO:66, most preferably SEQ ID NO:63 or SEQ ID NO:64, is fused to either the N- or the C-terminus, preferably the C-terminus, of a coat protein, mutants or fragments thereof, of RNA bacteriophage AP205. VLPs comprising fusion proteins of coat protein of bacteriophage AP205 with an antigen are generally disclosed in WO2006/032674A1 which is incorporated herein by reference. In one further preferred embodiment, the fusion protein further comprises a linker, wherein said linker is fused to the coat protein, fragments or mutants thereof, of AP205 and the IL-1 molecule. In a further preferred embodiment said IL-1 molecule is fused to the C-terminus of said coat protein, fragments or mutants thereof, of AP205 via said linker.

It has been found that IL-1 molecules, in particular IL-1 proteins and IL-1 fragments comprising at least 100 and up to 300 amino acids, typically and preferably about 140 to 160 amino acids, and most preferably about 155 amino acids, can be fused to coat protein of bacteriophages, preferably to coat protein of AP205, while maintaining the ability of the coat protein to self assemble into a VLP.

Given the large size of IL-1 proteins, IL-1 fragments and IL-1 mature fragments and also for steric reasons, an expression system producing mosaic VLPs comprising AP205 coat proteins fused to an IL-1 molecule as well as wt coat protein subunits was constructed. In this system, suppression of the stop codon yields the AP205-IL-1 coat protein fusion, while proper termination yields the wt AP205 coat protein. Both proteins are produced simultaneously in the cell and assemble into a mosaic VLP. The advantage of such a system is that large proteins can be displayed without interfering with the assembly of the VLP. As the level of incorporation of AP205-IL-1 fusion protein into the mosaic VLP is depending on the level of suppression, AP205-IL-1 is expressed in *E. coli* cells already containing a plasmid overexpressing a suppressor t-RNA. For opal suppression, plasmid pISM3001 (Smiley, B. K., Minion, F. C. (1993) Enhanced readthrough of opal (UGA) stop codons and production of *Mycoplasma pneumoniae* P1 epitopes in *Escherichia coli*. *Gene* 134, 33-40), which encodes a suppressor t-RNA recognizing the opal stop codon and introducing Trp is used. Suppression of amber termination can be increased by use of plasmid pISM579, which overexpresses a suppressor t-RNA recognizing the amber stop codon and introducing Trp as well. Plasmid pISM579 was generated by excising the trpT176 gene from pISM3001 with restriction endonuclease EcoRI and replacing it by an EcoRI fragment from plasmid pMY579 (gift of Michael Yarus) containing an amber t-RNA suppressor gene. This t-RNA suppressor gene is a mutant of trpT175 (Raftery L A. Et al. (1984) J. Bacteriol. 158:849-859), and differs from trpT at three positions: G33, A24 and T35. Expression of the AP205-interleukin-1alpha fusion protein in an *E. coli* strain with amber suppression (supE or glnV) such as *E. coli* JM109 may generate a proportion of AP205-IL-1 fusion proteins with a Gln instead of Trp introduced at the amber stop codon, in addition to AP205-IL-1 fusion proteins with a Trp introduced at the amber stop codon. The identity of the amino acid translated at the stop codon may therefore depend on the combination of suppressor t-RNA overexpressed, and strain phenotype. As described by Miller J H et al. ((1983) J. Mol. Biol. 164: 59-71) and as is well known in the art, the efficiency of suppression is context dependent. In particular, the codon 3' of the stop codon and the first base 3' from the stop codon are particularly important. For example, stop codons followed by a purine base are in general well suppressed.

Thus, in a preferred embodiment said VLP is a mosaic VLP, wherein said mosaic VLP comprises or preferably consists of at least one, preferably one, first polypeptide and of at least one, preferably one, second polypeptide, wherein said first polypeptide is a recombinant capsid protein, mutant or fragments thereof; and wherein said second polypeptide is a genetic fusion product of a recombinant capsid protein, mutant or fragments thereof, preferably of said first polypeptide, with an IL-1 molecule. In a further preferred embodiment said first polypeptide is a recombinant capsid protein of bacteriophage AP205 or a mutant or fragment thereof. In a further preferred embodiment said first polypeptide is selected from SEQ ID NO:21, SEQ ID NO:22, SEQ ID NO:23. In a very preferred embodiment said first polypeptide is SEQ ID NO:21. Mosaic VLPs of bacteriophage AP205 comprising an antigen are generally disclosed in WO2006/

032674A1, in particular in paragraph 107 of said publication. In a further preferred embodiment said second polypeptide is a genetic fusion product of a recombinant capsid protein, mutant or fragments thereof, preferably of said first polypeptide, with an IL-1 molecule, wherein said IL-1 molecule is fused to the C-terminus of said recombinant capsid protein, mutant or fragments thereof, preferably via an amino acid linker. In a further preferred embodiment said IL-1 molecule comprises or preferably consists of 100 to 300 amino acids, typically and preferably about 140 to 160 amino acids, and most preferably about 155 amino acids. In a very preferred embodiment, the molar ratio of said first polypeptide and said second polypeptide in said mosaic VLP is 10:1 to 5:1, preferably 8:1 to 6:1, most preferably about 7:1.

In one preferred embodiment of the present invention, the composition comprises or alternatively consists essentially of a virus-like particle with at least one first attachment site linked to at least one antigen, i.e. an IL-1 molecule, with at least one second attachment site via at least one covalent bond, wherein preferably the covalent bond is a non-peptide bond. In a preferred embodiment of the present invention, the first attachment site comprises, or preferably is, an amino group, preferably the amino group of a lysine residue. In another preferred embodiment of the present invention, the second attachment site comprises, or preferably is, a sulfhydryl group, preferably a sulfhydryl group of a cysteine.

In a very preferred embodiment of the invention, the at least one first attachment site is an amino group, preferably an amino group of a lysine residue and the at least one second attachment site is a sulfhydryl group, preferably a sulfhydryl group of a cysteine.

In one preferred embodiment of the invention, the IL-1 molecule is linked to the VLP by way of chemical cross-linking, typically and preferably by using a heterobifunctional cross-linker. In preferred embodiments, the hetero-bifunctional cross-linker contains a functional group which can react with the preferred first attachment sites, preferably with the amino group, more preferably with the amino groups of lysine residue(s) of the VLP, and a further functional group which can react with the preferred second attachment site, i.e. a sulfhydryl group, preferably of cysteine(s) residue inherent of, or artificially added to the IL-1 molecule, and optionally also made available for reaction by reduction. Several hetero-bifunctional cross-linkers are known to the art. These include the preferred cross-linkers SMPH (Pierce), Sulfo-MBS, Sulfo-EMCS, Sulfo-GMBS, Sulfo-SIAB, Sulfo-SMPB, Sulfo-SMCC, SVSB, SIA and other cross-linkers available for example from the Pierce Chemical Company, and having one functional group reactive towards amino groups and one functional group reactive towards sulfhydryl groups. The above mentioned cross-linkers all lead to formation of an amide bond after reaction with the amino group and a thioether linkage with the sulfhydryl groups. Another class of cross-linkers suitable in the practice of the invention is characterized by the introduction of a disulfide linkage between the IL-1 molecule and the VLP upon coupling. Preferred cross-linkers belonging to this class include, for example, SPDP and Sulfo-LC-SPDP (Pierce).

In a preferred embodiment, the composition of the invention further comprises a linker. Engineering of a second attachment site onto the IL-1 molecule is achieved by the association of a linker, preferably containing at least one amino acid suitable as second attachment site according to the disclosures of this invention. Therefore, in a preferred embodiment of the present invention, a linker is associated to the IL-1 molecule by way of at least one covalent bond, preferably, by at least one, preferably one peptide bond. Preferably, the linker comprises, or alternatively consists of, the second attachment site. In a further preferred embodiment, the linker comprises a sulfhydryl group, preferably of a cysteine residue. In another preferred embodiment, the amino acid linker is a cysteine residue.

The selection of a linker will be dependent on the nature of the IL-1 molecule, on its biochemical properties, such as pI, charge distribution and glycosylation. In general, flexible amino acid linkers are favored. In a further preferred embodiment of the present invention, the linker consists of amino acids, wherein further preferably the linker consists of at least one and at most 25, preferably at most 20, more preferably at most 15 amino acids. In an again preferred embodiment of the invention, the amino acid linker contains 1 to 10 amino acids. Preferred embodiments of the linker are selected from the group consisting of: (a) CGG (SEQ ID NO:171); (b) N-terminal gamma 1-linker, preferably CGDKTHTSPP (SEQ ID NO:172); (c) N-terminal gamma 3-linker, preferably CGGPKPSTPPGSSGGAP (SEQ ID NO:173); (d) Ig hinge regions; (e) N-terminal glycine linkers, preferably GCGGGG (SEQ ID NO:174); (f) (G)kC(G)n with n=0-12 and k=0-5 (SEQ ID NO:175); (g) N-terminal glycine-serine linkers, preferably (GGGGS)n, n=1-3 (SEQ ID NO:176) with one further cysteine; (h) (G)kC(G)m(S)l(GGGGS)n with n=0-3, k=0-5, m=0-10, l=0-2 (SEQ ID NO:177); (i) GGC (SEQ ID NO:178); (k) GGC-NH2 (SEQ ID NO:179); (l) C-terminal gamma 1-linker, preferably DKTHTSPPCG (SEQ ID NO:180); (m) C-terminal gamma 3-linker, preferably PKPSTPPGSSGGAPGGCG (SEQ ID NO:181); (n) C-terminal glycine linkers, preferably GGGGCG (SEQ ID NO:182)); (o) (G)nC(G)k with n=0-12 and k=0-5 (SEQ ID NO:183); (p) C-terminal glycine-serine linkers, preferably (SGGGG)n n=1-3 (SEQ ID NO:184) with one further cysteine; (q) (G)m (S)l(GGGGS)n(G)oC(G)k with n=0-3, k=0-5, m=0-10, l=0-2, and o=0-8 (SEQ ID NO:185). In a further preferred embodiment the linker is added to the N-terminus of the IL-1 molecule. In another preferred embodiment of the invention, the linker is added to the C-terminus of IL-1 molecule.

Preferred linkers according to this invention are glycine linkers (G)n further containing a cysteine residue as second attachment site, such as N-terminal glycine linker (GCGGGG, SEQ ID NO:174) and C-terminal glycine linker (GGGGCG, SEQ ID NO:182). Further preferred embodiments are C-terminal glycine-lysine linker (GGKKGC, SEQ ID NO:186) and N-terminal glycine-lysine linker (CGKKGG, SEQ ID NO:187), GGCG (SEQ ID NO:188) and GGC (SEQ ID NO:178) or GGC-NH2 (SEQ ID NO:179, "NH2" stands for amidation) linkers at the C-terminus of the peptide or CGG (SEQ ID NO:171) at its N-terminus. In general, glycine residues will be inserted between bulky amino acids and the cysteine to be used as second attachment site, to avoid potential steric hindrance of the bulkier amino acid in the coupling reaction.

Linking of the IL-1 molecule to the VLP by using a hetero-bifunctional cross-linker according to the preferred methods described above, allows coupling of the IL-1 molecule to the VLP in an oriented fashion. Other methods of linking the IL-1 molecule to the VLP include methods wherein the IL-1 molecule is cross-linked to the VLP, using the carbodiimide EDC, and NHS. The IL-1 molecule may also be first thiolated through reaction, for example with SATA, SATP or iminothiolane. The IL-1 molecule, after deprotection if required, may then be coupled to the VLP as follows. After separation of the excess thiolation reagent, the IL-1 molecule is reacted with the VLP, previously activated with a hetero-bifunctional cross-linker comprising a cysteine reactive moiety, and therefore displaying at least one or several functional groups reactive towards cysteine residues, to which the thiolated IL-1 molecule can react, such as described above. Optionally, low amounts of a reducing agent are included in the reaction mixture. In further methods, the IL-1 molecule is attached to the VLP, using a homo-bifunctional cross-linker such as glutaraldehyde, DSG, BM[PEO]4, BS3, (Pierce) or other known homo-bifunctional cross-linkers with functional groups reactive towards amine groups or carboxyl groups of the VLP.

In other embodiments of the present invention, the composition comprises or alternatively consists essentially of a virus-like particle linked to IL-1 molecule via chemical interactions, wherein at least one of these interactions is not a covalent bond.

Linking of the VLP to the IL-1 molecule can be effected by biotinylating the VLP and expressing the IL-1 molecule as a streptavidin-fusion protein.

One or several antigen molecules, i.e. IL-1 molecules, can be attached to one subunit of the VLP, preferably of RNA bacteriophage coat proteins, preferably through the exposed lysine residues of the coat proteins of RNA bacteriophage VLP, if sterically allowable. A specific feature of the VLPs of RNA bacteriophage and in particular of the Qβ coat protein VLP is thus the possibility to couple several antigens per subunit. This allows for the generation of a dense antigen array.

In very preferred embodiments of the invention, the IL-1 molecule is linked via a cysteine residue, having been added to either the N-terminus or the C-terminus of, or a natural cysteine residue within an IL-1 molecule, to lysine residues of coat proteins of the VLPs of RNA bacteriophage, and in particular to the coat protein of Qβ.

As described above, four lysine residues are exposed on the surface of the VLP of Qβ coat protein. Typically and preferably these residues are derivatized upon reaction with a cross-linker molecule. In the instance where not all of the exposed lysine residues can be coupled to an antigen, the lysine residues which have reacted with the cross-linker are left with a cross-linker molecule attached to the ϵ-amino group after the derivatization step. This leads to disappearance of one or several positive charges, which may be detrimental to the solubility and stability of the VLP. By replacing some of the lysine residues with arginines, as in the disclosed Qβ coat protein mutants, we prevent the excessive disappearance of positive charges since the arginine residues do not react with the preferred cross-linkers. Moreover, replacement of lysine residues by arginine residues may lead to more defined antigen arrays, as fewer sites are available for reaction to the antigen.

Accordingly, exposed lysine residues were replaced by arginines in the following Qβ coat protein mutants: Qβ-240 (Lys13-Arg; SEQ ID NO:16), Qβ-250 (Lys 2-Arg, Lys13-Arg; SEQ ID NO:18), Qβ-259 (Lys 2-Arg, Lys16-Arg; SEQ ID NO:20) and Qβ-251; (Lys16-Arg, SEQ ID NO:19). In a further embodiment, we disclose a Qβ mutant coat protein with one additional lysine residue Qβ-243 (Asn 10-Lys; SEQ ID NO:17), suitable for obtaining even higher density arrays of antigens.

In one preferred embodiment of the invention, the VLP of an RNA bacteriophage is recombinantly produced by a host and wherein said VLP is essentially free of host RNA, preferably host nucleic acids. In one further preferred embodiment, the composition further comprises at least one polyanionic macromolecule bound to, preferably packaged in or enclosed in, the VLP. In a still further preferred embodiment, the polyanionic macromolecule is polyglutamic acid and/or polyaspartic acid.

In another preferred embodiment, the composition further comprises at least one immunostimulatory substance bound to, preferably packaged in or enclosed in, the VLP. In a still further preferred embodiment, the immunostimulatory substance is a nucleic acid, preferably DNA, most preferably an unmethylated CpG containing oligonucleotide.

Essentially free of host RNA, preferably host nucleic acids: The term "essentially free of host RNA, preferably host nucleic acids" as used herein, refers to the amount of host RNA, preferably host nucleic acids, comprised by the VLP, which amount typically and preferably is less than 30 μg, preferably less than 20 μg, more preferably less than 10 μg, even more preferably less than 8 μg, even more preferably less than 6 μg, even more preferably less than 4 μg, most preferably less than 2 μg, per mg of the VLP. Host, as used within the afore-mentioned context, refers to the host in which the VLP is recombinantly produced. Conventional methods of determining the amount of RNA, preferably nucleic acids, are known to the skilled person in the art. The typical and preferred method to determine the amount of RNA, preferably nucleic acids, in accordance with the present invention is described in Example 17 of WO2006/037787A2. Identical, similar or analogous conditions are, typically and preferably, used for the determination of the amount of RNA, preferably nucleic acids, for inventive compositions comprising VLPs other than Qβ. The modifications of the conditions eventually needed are within the knowledge of the skilled person in the art. The numeric value of the amounts determined should typically and preferably be understood as comprising values having a deviation of ±10%, preferably having a deviation of ±5%, of the indicated numeric value.

Polyanionic macromolecule: The term "polyanionic macromolecule", as used herein, refers to a molecule of high relative molecular mass which comprises repetitive groups of negative charge, the structure of which essentially comprises the multiple repetition of units derived, actually or conceptually, from molecules of low relative molecular mass. A polyanionic macromolecule should have a molecular weight of at least 2000 Dalton, more preferably of at least 3000 Dalton and even more preferably of at least 5000 Dalton. The term "polyanionic macromolecule" as used herein, typically and preferably refers to a molecule that is not capable of activating toll-like receptors. Thus, the term "polyanionic macromolecule" typically and preferably excludes Toll-like receptors ligands, and even more preferably furthermore excludes immunostimulatory substances such as Toll-like receptors ligands, immunostimulatory nucleic acids, and lipopolysacchrides (LPS). More preferably the term "polyanionic macromolecule" as used herein, refers to a molecule that is not capable of inducing cytokine production. Even more preferably the term "polyanionic macromolecule" excludes immunostimulatory substances. The term "immunostimulatory substance", as used herein, refers to a molecule that is capable of inducing and/or enhancing immune response specifically against the antigen comprised in the present invention.

Host RNA, preferably host nucleic acids: The term "host RNA, preferably host nucleic acids" or the term "host RNA, preferably host nucleic acids, with secondary structure", as used herein, refers to the RNA, or preferably nucleic acids, that are originally synthesized by the host. The RNA, preferably nucleic acids, may, however, undergo chemical and/or physical changes during the procedure of reducing or eliminating the amount of RNA, preferably nucleic acids, typically and preferably by way of the inventive methods, for example, the size of the RNA, preferably nucleic acids, may be shortened or the secondary structure thereof may be altered. However, even such resulting RNA or nucleic acids is still considered as host RNA, or host nucleic acids.

Methods to determine the amount of RNA and to reduce the amount of RNA comprised by the VLP have disclosed in US provisional application filed by the same assignee on Oct. 5, 2004 and thus the entire application is incorporated herein by way of reference. Reducing or eliminating the amount of host RNA, preferably host nucleic, minimizes or reduces unwanted T cell responses, such as inflammatory T cell response and cytotoxic T cell response, and other unwanted side effects, such as fever, while maintaining strong antibody response specifically against IL-1.

In one preferred embodiment, this invention provides a method of preparing the inventive compositions and VLP of an RNA-bacteriophage the invention, wherein said VLP is recombinantly produced by a host and wherein said VLP is essentially free of host RNA, preferably host nucleic acids, comprising the steps of: a) recombinantly producing a virus-like particle (VLP) with at least one first attachment site by a host, wherein said VLP comprises coat proteins, variants or fragments thereof, of a RNA-bacteriophage; b) disassembling said virus-like particle to said coat proteins, variants or fragments thereof, of said RNA-bacteriophage; c) purifying said coat proteins, variants or fragments thereof; d) reassembling said purified coat proteins, variants or fragments thereof, of said RNA-bacteriophage to a virus-like particle, wherein said virus-like particle is essentially free of host RNA, preferably host nucleic acids; and e) linking at least one antigen of the invention with at least one second attachment site to said VLP obtained from step d). In a further preferred embodiment, the reassembling of said purified coat proteins, variants or fragments thereof, is effected in the presence of at least one polyanionic macromolecule.

In one aspect, the invention provides a vaccine comprising the composition of the invention. In one preferred embodiment, the IL-1 molecule which is linked to the VLP in the vaccine composition may be of animal, preferably mammal or human origin. In preferred embodiments, the IL-1 of the invention is of human, bovine, dog, cat, mouse, rat, pig or horse origin.

In one preferred embodiment, the vaccine composition further comprises at least one adjuvant. The administration of the at least one adjuvant may hereby occur prior to, contemporaneously or after the administration of the inventive composition. The term "adjuvant" as used herein refers to non-specific stimulators of the immune response or substances that allow generation of a depot in the host which when combined with the vaccine and pharmaceutical composition, respectively, of the present invention may provide for an even more enhanced immune response.

In another preferred embodiment, the vaccine composition is devoid of adjuvant.

An advantageous feature of the present invention is the high immunogenicity of the composition, even in the absence of adjuvants. The absence of an adjuvant, furthermore, minimizes the occurrence of unwanted inflammatory T-cell responses representing a safety concern in the vaccination against self antigens. Thus, the administration of the vaccine of the invention to a patient will preferably occur without administering at least one adjuvant to the same patient prior to, contemporaneously or after the administration of the vaccine.

The invention further discloses a method of immunization comprising administering the vaccine of the present invention to an animal or a human. The animal is preferably a mammal, such as cat, sheep, pig, horse, bovine, dog, rat, mouse and particularly human. The vaccine may be administered to an animal or a human by various methods known in the art, but will normally be administered by injection, infusion, inhalation, oral administration, or other suitable physical methods. The conjugates may alternatively be administered intramuscularly, intravenously, transmucosally, transdermally, intranasally, intraperitoneally or subcutaneously. Components of conjugates for administration include sterile aqueous (e.g., physiological saline) or non-aqueous solutions and suspensions. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption.

Vaccines of the invention are said to be "pharmacologically acceptable" if their administration can be tolerated by a recipient individual. Further, the vaccines of the invention will be administered in a "therapeutically effective amount" (i.e., an amount that produces a desired physiological effect). The nature or type of immune response is not a limiting factor of this disclosure. Without the intention to limit the present invention by the following mechanistic explanation, the inventive vaccine might induce antibodies which bind to IL-1 and thus reducing its concentration and/or interfering with its physiological or pathological function.

In one aspect, the invention provides a pharmaceutical composition comprising the composition as taught in the present invention and an acceptable pharmaceutical carrier. When vaccine of the invention is administered to an individual, it may be in a form which contains salts, buffers, adjuvants, or other substances which are desirable for improving the efficacy of the conjugate. Examples of materials suitable for use in preparation of pharmaceutical compositions are provided in numerous sources including Remington's Pharmaceutical Sciences (Osol, A, ed., Mack Publishing Co., (1990)).

The invention teaches a process for producing the composition of the invention comprising the steps of: (a) providing a VLP with at least one first attachment site; (b) providing a IL-1 molecule with at least one second attachment site, and (c) combining said VLP and said IL-1 molecule to produce a composition, wherein said IL-1 molecule and said VLP are linked through the first and the second attachment sites.

In a further preferred embodiment, the step of providing a VLP with at least one first attachment site comprises further steps: (a) disassembling said virus-like particle to said coat proteins, mutants or fragments thereof, of said RNA-bacteriophage; (b) purifying said coat proteins, mutants or fragments thereof; (c) reassembling said purified coat proteins, mutants or fragments thereof, of said RNA-bacteriophage to a virus-like particle, wherein said virus-like particle is essentially free of host RNA, preferably host nucleic acids. In a still further preferred embodiment, the reassembling of said purified coat proteins is effected in the presence of at least one polyanionic macromolecule.

The invention provides a method of using the compositions of the invention for treating and/or attenuating diseases or conditions in which IL-1 exerts an important pathological function in an animal or in human.

The invention further provides for use of the compositions of the invention or the vaccine of the invention or the pharmaceutical composition of the invention for the manufacture of a medicament for treatment of a disease in an animal, preferably dog, cat horse or human, most preferably human, wherein said disease is preferably selected from the group consisting of: (a) vascular diseases, preferably coronary artery disease, atherosclerosis and vasculitis, most preferably atherosclerosis; (b) inherited IL-1-dependent inflammatory diseases, preferably Familial Mediterranean Fever (FMF), Familial Cold Autoinflammatory Syndrome (FCAS) Neonatal Onset Multisystem Inflammatory Disease (NOMID) and Muckle Wells Syndrome, most preferably Familial Mediterranean Fever (FMF); (c) chronic autoimmune inflammatory diseases, preferably rheumatoid arthritis, systemic onset juvenile idiopathic arthritis, adult onset Still's disease, psoriasis, Crohn's disease and ulcerative colitis, most preferably rheumatoid arthritis; (d) bone and cartilage degenerative diseases, preferably gout, osteoporosis and osteoarthritis, most preferably osteoarthritis; (e) allergic diseases, preferably contact hypersensitivity, type 1 hypersensitivity and allergy, most preferably allergy; and (f) neurological diseases, preferably Alzheimer's disease, epilepsy, Parkinson's disease and multiple sclerosis, most preferably multiple sclerosis.

The invention further provides for use of the compositions of the invention or the vaccine of the invention or the pharmaceutical composition of the invention for the manufacture of a medicament for treatment of a disease in an animal, preferably dog, cat horse or human, most preferably human, wherein said disease is a vascular disease, preferably coronary artery disease, atherosclerosis and vasculitis, most preferably atherosclerosis, and wherein said at least one antigen comprised by said composition, said vaccine or said pharmaceutical composition is an IL-1 alpha molecule of the invention, preferably an IL-1 alpha mature fragment, most preferably SEQ ID NO:63 or a mutein thereof.

The invention further provides for use of the compositions of the invention or the vaccine of the invention or the pharmaceutical composition of the invention for the manufacture of a medicament for treatment of a disease in an animal, preferably dog, cat horse or human, most preferably human, wherein said disease is selected from the group consisting of: (a) inherited IL-1-dependent inflammatory diseases, preferably Familial Mediterranean Fever (FMF), Familial Cold Autoinflammatory Syndrome (FCAS) Neonatal Onset Multisystem Inflammatory Disease (NOMID) and Muckle Wells Syndrome, most preferably Familial Mediterranean Fever (FMF); (b) chronic autoimmune inflammatory diseases, preferably rheumatoid arthritis, systemic onset juvenile idiopathic arthritis, adult onset Still's disease, psoriasis, Crohn's disease and ulcerative colitis, most preferably rheumatoid arthritis; (c) bone and cartilage degenerative diseases, preferably gout, osteoporosis and osteoarthritis, most preferably osteoarthritis; (d) allergic diseases, preferably contact hypersensitivity, type 1 hypersensitivity and allergy, most preferably allergy; and (e) neurological diseases, preferably Alzheimer's disease, epilepsy, Parkinson's disease and multiple sclerosis, most preferably multiple sclerosis, and wherein said at least one antigen comprised by said composition, said vaccine or said pharmaceutical composition is an IL-1 beta molecule, preferably an IL-1 beta mature fragment, most preferably SEQ ID NO:64 or a mutein thereof.

The invention further provides for use of the compositions of the invention or the vaccine of the invention or the pharmaceutical composition of the invention for the manufacture of a medicament for treatment of a disease in an animal, preferably dog, cat horse or human, most preferably human, wherein said disease is an inherited IL-1-dependent inflammatory diseases, preferably Familial Mediterranean Fever (FMF); and wherein said at least one antigen comprised by said composition, said vaccine or said pharmaceutical composition is an IL-1 beta molecule, preferably an IL-1 beta mature fragment, most preferably SEQ ID NO:64 or a mutein thereof.

The invention further provides for use of the compositions of the invention or the vaccine of the invention or the pharmaceutical composition of the invention for the manufacture of a medicament for treatment of a disease in an animal, preferably human, wherein said disease is a vascular disease, preferably atherosclerosis.

The invention further provides for use of the compositions of the invention or the vaccine of the invention or the pharmaceutical composition of the invention for the manufacture of a medicament for treatment of a disease in an animal, preferably human, wherein said disease is an inherited IL-1-dependent inflammatory diseases, preferably familial Mediterranean fever (FMF).

The invention further provides for use of the compositions of the invention or the vaccine of the invention or the pharmaceutical composition of the invention for the manufacture of a medicament for treatment of a disease in an animal, preferably human, wherein said disease is a chronic autoimmune inflammatory diseases, preferably rheumatoid arthritis.

The invention further provides for use of the compositions of the invention or the vaccine of the invention or the pharmaceutical composition of the invention for the manufacture of a medicament for treatment of a disease in an animal, preferably human, wherein said disease is a bone and cartilage degenerative diseases, preferably osteoarthritis.

The invention further provides for use of the compositions of the invention or the vaccine of the invention or the pharmaceutical composition of the invention for the manufacture of a medicament for treatment of a disease in an animal, preferably human, wherein said disease is a neurological disease, preferably multiple sclerosis.

The invention further provides a method of treating a disease, the method comprising administering the composition of the invention, the vaccine of the invention or the pharmaceutical composition of the invention to an animal, preferably dog, cat horse or human, most preferably human, wherein said disease is preferably selected from the group consisting of: (a) vascular diseases, preferably coronary artery disease, atherosclerosis and vasculitis, most preferably atherosclerosis; (b) inherited IL-1-dependent inflammatory diseases, preferably Familial Mediterranean Fever (FMF), Familial Cold Autoinflammatory Syndrome (FCAS) Neonatal Onset Multisystem Inflammatory Disease (NOMID) and Muckle Wells Syndrome, most preferably Familial Mediterranean Fever (FMF); (c) chronic autoimmune inflammatory diseases, preferably rheumatoid arthritis, systemic onset juvenile idiopathic arthritis, adult onset Still's disease, psoriasis, Crohn's disease and ulcerative colitis, most preferably rheumatoid arthritis; (d) bone and cartilage degenerative diseases, preferably gout, osteoporosis and osteoarthritis, most preferably osteoarthritis; (e) allergic diseases, preferably contact hypersensitivity, type 1 hypersensitivity and allergy, most preferably allergy; and (f) neurological diseases, preferably Alzheimer's disease, epilepsy, Parkinson's disease and multiple sclerosis, preferably multiple sclerosis.

The invention further provides a method of treating a disease, the method comprising administering the composition of the invention, the vaccine of the invention or the pharmaceutical composition of the invention to an animal, preferably dog, cat horse or human, most preferably human, wherein said disease is a vascular diseases, preferably coronary artery disease, atherosclerosis and vasculitis, most preferably atherosclerosis, and wherein said at least one antigen comprised by said composition, said vaccine or said pharmaceutical composition is an IL-1 alpha molecule, preferably an IL-1 alpha mature fragment, most preferably SEQ ID NO:63 or a mutein thereof.

The invention further provides a method of treating a disease, the method comprising administering the composition of the invention, the vaccine of the invention or the pharmaceutical composition of the invention to an animal, preferably dog, cat horse or human, most preferably human, wherein said disease is preferably selected from the group consisting of: (a) inherited IL-1-dependent inflammatory diseases, preferably Familial Mediterranean Fever (FMF), Familial Cold Autoinflammatory Syndrome (FCAS) Neonatal Onset Multisystem Inflammatory Disease (NOMID) and Muckle Wells Syndrome, most preferably Familial Mediterranean Fever (FMF); (b) chronic autoimmune inflammatory diseases, preferably rheumatoid arthritis, systemic onset juvenile idiopathic arthritis, adult onset Still's disease, psoriasis, Crohn's disease and ulcerative colitis, most preferably rheumatoid arthritis; (c) bone and cartilage degenerative diseases, preferably gout, osteoporosis and osteoarthritis, most preferably osteoarthritis; (d) allergic diseases, preferably contact hypersensitivity, type 1 hypersensitivity and allergy, most preferably allergy; and (e) neurological diseases, preferably Alzheimer's disease, epilepsy, Parkinson's disease and multiple sclerosis, most preferably multiple sclerosis, and wherein said at least one antigen comprised by said composition, said vaccine or said pharmaceutical composition is an IL-1 beta molecule, preferably an IL-1 beta mature fragment, most preferably SEQ ID NO:64 or a mutein thereof.

The invention further provides a method of treating a disease, the method comprising administering the composition of the invention, the vaccine of the invention or the pharmaceutical composition of the invention to an animal, preferably dog, cat horse or human, most preferably human, wherein said disease is an inherited IL-1-dependent inflammatory diseases, preferably Familial Mediterranean Fever (FMF); and wherein said at least one antigen comprised by said composition, said vaccine or said pharmaceutical composition is an IL-1 beta molecule, preferably an IL-1 beta mature fragment, most preferably SEQ ID NO:64 or a mutein thereof.

The invention further provides a method of treating a disease, the method comprising administering the composition of the invention, the vaccine of the invention or the pharmaceutical composition of the invention to an animal, preferably human, wherein said disease is a vascular disease, preferably atherosclerosis.

The invention further provides a method of treating a disease, the method comprising administering the composition of the invention, the vaccine of the invention or the pharmaceutical composition of the invention to an animal, preferably human, wherein said disease is an inherited IL-1-dependent inflammatory diseases, preferably familial Mediterranean fever (FMF).

The invention further provides a method of treating a disease, the method comprising administering the composition of the invention, the vaccine of the invention or the pharmaceutical composition of the invention to an animal, preferably human, wherein said disease is a chronic autoimmune inflammatory diseases, preferably rheumatoid arthritis.

The invention further provides a method of treating a disease, the method comprising administering the composition of the invention, the vaccine of the invention or the pharmaceutical composition of the invention to an animal, preferably human, wherein said disease is a bone and cartilage degenerative diseases, preferably osteoarthritis.

All references cited herein are incorporated entirely by reference.

EXAMPLES

Example 1

Cloning, Expression and Purification of Murine IL1$\alpha_{117-270}$ and IL-1$\beta_{119-269}$ The nucleotide sequence encoding amino acids 117-270 of murine IL-1α was amplified by PCR from a cDNA library of TNFα-activated murine macrophages using oligonucleotides IL1α1 (5'-ATATATGCTAGCCCCTTACACCTACCA-GAGTGATTTG-3'; SEQ ID NO:24) and IL1α2 (5'-ATATATCTCGAGTGATATCTGGAAGTCTGTCATA GAG-3'; SEQ ID NO:25). Using the same cDNA library, the nucleotide sequence encoding amino acids 119-269 of the murine IL-1β precursor was amplified with oligonucleotides IL1β1 (5'-ATATATGCTAGCCCCCATTAGACAGCTG-CACTACAGG-3'; SEQ ID NO:26) and IL1β2 (5'-ATATATCTCGAGGGAAGACACAGATTC-CATGGTGAAG-3'; SEQ ID NO: 27). Both DNA fragments were digested with NheI and XhoI, and cloned into the expression vector pModEC1 (SEQ ID NO:29)

The vector pModEC1 (SEQ ID NO:29) is a derivative of pET22b(+) (Novagen Inc.), and was constructed in two steps. In a first step the multiple cloning site of pET22b(+) was changed by replacing the original sequence between the NdeI and XhoI sites with the annealed oligos primerMCS-1F (5'-TATGGATCCGGCTAGCGCTCGAGGGTTTA AACG-GCGGCCGCAT-3'; SEQ ID NO:30) and primerMCS-1R (5'-TCGAATGCGGCCG CCGTTTAAACCCTCGAGCGCTAGCCGGATCCA-3'; SEQ ID NO:31) (annealing in 15 mM TrisHCl pH 8 buffer). The resulting plasmid was termed pMod00, and had NdeI, BamHI, NheI, XhoI, PmeI and NotI restriction sites in its multiple cloning site. The annealed pair of oligos Bamhis6-EK-Nhe-F (5'-GATCCACACCACCACCACCACCACGG TTCTGGTGACGACGATGACAAAGCGCTAGCC-3'; SEQ ID NO:32) and Bamhis6-EKNhe-R (5'-TC-GAGGGCTAGCGCTTTGTCATCGTCGT-CACCAGAACCGTGGT GGTGGTGGTGGTGTG-3'; SEQ ID NO:33) and the annealed pair of oligoIF-C-glycine-linker (5'-TCGAGGGTGGTGGTGGTGGTTGCGGT-TAATAAGTTTAAACGC-3'; SEQ ID NO:34) and oligoIR-C-glycine-linker (5'-GGCCGCGTTTAAACTTATTA ACCGCAACCACCACCACCACCC-3'; SEQ ID NO:35) were ligated together into the BamHI-NotI digested pMod00 plasmid to obtain pModEC1, which encodes an N-terminal hexahistidine tag, an enterokinase cleavage site and a C-terminal glycine linker containing one cysteine residue.

The cloning of the above mentioned fragments into pModEC1 gave rise to plasmids pModEC1-His-EK-mIL1$\alpha_{117-270}$ and pModEC1-His-EK-mIL1$\beta_{119-269}$, respectively. These plasmids encode fusion proteins consisting of an N-terminal His-tag, an enterokinase cleavage site, the mature murine IL-1α or IL-1β, respectively, and a C-terminal cysteine-containing linker (GGGGGCG, SEQ ID NO:28). For expression, *Escherichia coli* BL21 cells harbouring either plasmid were grown at 37° C. to an OD at 600 nm of 1.0 and then induced by addition of isopropyl-β-D-thiogalactopyranoside at a concentration of 1 mM. Bacteria were grown for 4 more hours at 37° C., harvested by centrifugation and resuspended in 80 ml lysis buffer (10 mM $Na_2HPO_4$, 30 mM NaCl, pH 7.0). Cells were then disrupted by sonication and cellular DNA and RNA were digested by 30 min incubation at room temperature with 64 µl 2 M $MgCl_2$ and 10 µl Benzonase. Cellular debris was removed by centrifugation (SS34 rotor, 20000 rpm, 4° C., 60 min), and the cleared lysate was applied to a $Ni^{2+}$-NTA agarose column (Qiagen, Hilden, Germany). After extensive washing of the column with washing buffer (50 mM $NaH_2PO_4$, 300 mM NaCl, 20 mM Imidazol, pH 8.0) the proteins were eluted with elution buffer (50 mM $NaH_2PO_4$, 300 mM NaCl, 200 mM Imidazol, pH 8.0). Purified proteins were dialysed against PBS pH 7.2, flash-frozen in liquid nitrogen and stored at −80° C. until further use.

Example 2

A. Coupling of Mouse IL-1$\beta_{119-269}$ to Q$\beta$ Virus-Like Particles

A solution containing 1.3 mg/ml of the purified murine IL-1$\beta_{119-269}$ protein from EXAMPLE 1 (SEQ ID NO:66) in PBS pH 7.2 was incubated for 60 min at room temperature with an equimolar amount of TCEP for reduction of the C-terminal cysteine residue.

A solution of 6 ml of 2 mg/ml Q$\beta$ capsid protein in PBS pH 7.2 was then reacted for 60 min at room temperature with 131 µl of a SMPH solution (65 mM in DMSO). The reaction solution was dialysed at 4° C. against three 3 l changes of 20 mM HEPES, 150 mM NaCl pH 7.2 over 24 hours. Seventy-five µl of the derivatized and dialyzed Q$\beta$ solution was mixed with 117 µl H$_2$O and 308 µl of the purified and pre-reduced mouse IL-1$\beta_{119-269}$ protein and incubated over night at 15° C. for chemical crosslinking Uncoupled protein was removed by tangential flow filtration against PBS using cellulose ester membranes with a molecular weight cutoff of 300.000 Da.

Coupled products were analyzed on a 12% SDS-polyacrylamide gel under reducing conditions. The Coomassie stained gel is shown in FIG. 1. Several bands of increased molecular weight with respect to the Q$\beta$ capsid monomer are visible, clearly demonstrating the successful cross-linking of the mouse IL-1$\beta_{119-269}$ protein to the Q$\beta$ capsid.

B. Immunization of Mice with Mouse IL-1$\beta_{119-269}$ Protein Coupled to Q$\beta$ capsid (Q$\beta$-mIL-1$\beta_{119-269}$)

Five female balb/c mice were immunized with Q$\beta$-mIL-1$\beta_{119-269}$ (SEQ ID NO:66). Fifty µg of total protein were diluted in PBS to 200 µl and injected subcutaneously (100 µl on two ventral sides) on day 0 and day 21. Mice were bled retroorbitally on day 0, 21, and 35, and sera were analyzed using mouse IL-1$\beta_{119-269}$-specific ELISA.

C. ELISA

ELISA plates were coated with mouse IL-1$\beta_{119-269}$ protein at a concentration of 1 µg/ml. The plates were blocked and then incubated with serially diluted mouse sera from day 0, 21, and 35. Bound antibodies were detected with enzymatically labeled anti-mouse IgG antibody. Antibody titers of mouse sera were calculated as the average of those dilutions which led to half maximal optical density at 450 nm. The average anti-mouse IL-1$\beta_{119-269}$ titer was 1:22262 at day 21 and 1:309276 at day 35. This demonstrates that immunization with Q$\beta$ coupled to the mouse IL-1$\beta_{119-269}$ protein could overcome immunological tolerance and produce high titer antibodies which recognize specifically IL-1$\beta_{119-269}$

D. In Vitro Neutralization of IL-1$\beta$

Sera of mice immunized with Q$\beta$-mIL-1$\beta_{119-269}$ (SEQ ID NO:66) were then tested for their ability to inhibit the binding of mouse IL-1$\beta$ protein to its receptor. ELISA plates were therefore coated with a recombinant mIL-1receptorI-hFc fusion protein at a concentration of 1 µg/ml, and co-incubated with serial dilutions of sera from mice which had been immunized either with mouse IL-1$\beta_{119-269}$ coupled to Q$\beta$ capsid or mouse IL-1$\alpha_{117}$-270 coupled to Q$\beta$ capsid and 100 ng/ml of mouse IL-1$\beta_{119-269}$. Binding of IL-1$\beta_{119-269}$ to the immobilized mIL-1receptorI-hFc fusion protein was detected with a biotinylated anti-mouse IL-1$\beta$ antibody and horse radish peroxidase conjugated streptavidin. All sera from mice immunized against murine IL-1$\beta_{119-269}$ inhibited completely the binding of mouse IL-1$\beta_{119-269}$ to its receptor at concentrations of $\geqq$0.4%, whereas sera from mice immunized against mouse IL-1$\alpha_{117-270}$ did not show any inhibitory effect even at the highest concentration used (3.3%). These data demonstrate that immunization with mouse IL-1$\beta_{119-269}$ coupled to Q$\beta$ capsid can yield antibodies which are able to neutralize the interaction of mouse IL-1$\beta_{119-269}$ and its receptor.

E. In Vivo Neutralization of IL-1$\beta$

The in vivo neutralizing capacity of the antibodies raised by immunization with Q$\beta$-mIL-1$\beta_{119-269}$ was investigated next. Four female balb/c mice were therefore immunized twice at days 0 and 14 with Q$\beta$-mIL-1$\beta_{119-269}$ and four mice were immunized at the same time with Q$\beta$ capsid alone. At day 21 all mice were injected intravenously with 1 µg free IL-1$\beta_{119-269}$. As readout of the inflammatory activity of the injected IL-1$\beta_{119-269}$, serum samples were analysed 3 h after injection for the relative increase in the concentration of the pro-inflammatory cytokine IL-6. Q$\beta$-immunized mice showed an average increase in the serum IL-6 concentration of 1.01±0.61 ng/ml, whereas mice immunized with Q$\beta$-mIL-1$\beta_{119-269}$ showed an average increase of only 0.11±0.30 ng/ml (p=0.04). As a control on day 28 all mice were injected with 1 µg mIL-1$\alpha$. Three hours after injection mice immunized with Q$\beta$ carrier alone showed an average increase in serum IL-6 concentrations of 40.24±8.06 ng/ml, while mice immunized with Q$\beta$-mIL-1$\beta_{119-269}$ showed an increase of 57.98±29.92 ng/ml (p=0.30). These data indicate that the antibodies produced by immunization with Q$\beta$-mIL-1$\beta_{119-269}$ were able to neutralize specifically and efficiently the pro-inflammatory activity of IL-1$\beta$.

F. Efficacy of Q$\beta$-mIL-1$\beta_{119-269}$ in a Mouse Model of Rheumatoid Arthritis The efficacy of Q$\beta$-mIL-1$\beta_{119-269}$ immunization was tested in the murine collagen-induced arthritis model (CIA). This model reflects most of the immunological and histological aspects of human rheumatoid arthritis and is therefore routinely used to assay the efficacy of anti-inflammatory agents. Male DBA/1 mice were immunized subcutaneously three times (days 0, 14 and 28) with 50 µg of either Q$\beta$-mIL-1$\beta_{119-269}$ (n=8) or Q$\beta$ alone (n=8), and then injected intradermally at day 42 with 200 µg bovine type II collagen mixed with complete Freund's adjuvant. After a booster injection of 200 µg bovine type II collagen mixed with incomplete Freund's adjuvant at day 63 mice were examined on a daily basis for the development of arthritis symptoms.

A clinical score ranging from 0 to 3 was assigned to each limb according to the degree of reddening and swelling observed, and ankle thickness of all hind limbs was measured. The clinical score was assigned over 3 consecutive weeks to each limb according to the following definitions: 0 normal, 1 mild erythema and/or swelling of digits/paw, 2 erythema and swelling extending over whole paw/joint, 3 strong swelling, deformation of paw/joint, stiffness. Cumulative clinical scores of individual mice were calculated as the sum of clinical scores of all four limbs, resulting in a possible maximal cumulative score per mouse of 12.

Two weeks after the second collagen injection Q$\beta$-immunized mice showed an average cumulative clinical score of 4.44, while Q$\beta$-mIL-1$\beta_{119-269}$-immunized mice showed an average score of only 1.06. Moreover, the average increase in hind ankle thickness was 18% for Q$\beta$-immunized mice and only 1% for mice which had been immunized with Qβ-mIL-1β$_{119-269}$. As an additional readout of the inflammatory reaction, serum levels of IL-6 were determined 1 week after the second collagen injection. Qβ-immunized mice had an average IL-6 serum concentration of 1.92±0.36 while Qβ-mIL-1β$_{119-269}$-immunized mice had an average IL-6 concentration of only 0.79±0.16 (p=0.01). Taken together, these data show that immunization with Qβ-mIL-1β$_{119-269}$ strongly protects mice from inflammation and clinical signs of arthritis in the CIA model.

Example 3

A. Coupling of Mouse IL-1α$_{117-270}$ to Qβ Virus-Like Particles

A solution containing 1.8 mg/ml of the purified IL-1α$_{117-270}$ protein from EXAMPLE 1 (SEQ ID NO:65) in PBS pH 7.2 was incubated for 60 min at room temperature with an equimolar amount of TCEP for reduction of the C-terminal cysteine residue.

A solution of 6 ml of 2 mg/ml Qβ capsid protein in PBS pH 7.2 was then reacted for 60 minutes at room temperature with 131 μl of a SMPH solution (65 mM in DMSO). The reaction solution was dialyzed at 4° C. against three 3 l changes of 20 mM HEPES, 150 mM NaCl pH 7.2 over 24 hours. Seventy-five μl of the derivatized and dialyzed Qβ solution was mixed with 192 μl H$_2$O and 233 μl of the purified and pre-reduced mouse IL-1α$_{117-270}$ protein and incubated over night at 15° C. for chemical crosslinking Uncoupled protein was removed by tangential flow filtration against PBS using cellulose ester membranes with a molecular weight cutoff of 300.000 Da.

Figure 2:
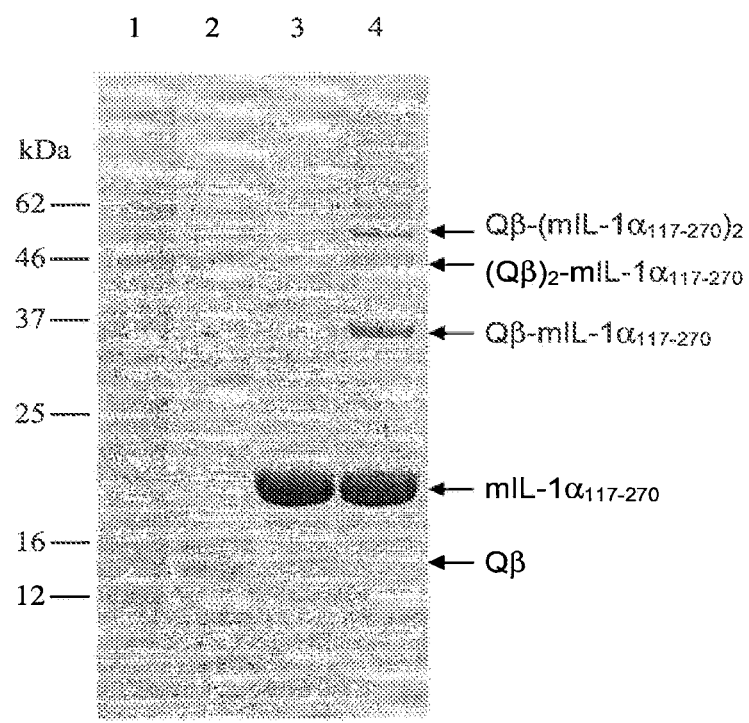

Coupled products were analyzed on a 12% SDS-polyacrylamide gel under reducing conditions. The Coomassie stained gel is shown in FIG. 2. Several bands of increased molecular weight with respect to the Qβ capsid monomer are visible, clearly demonstrating the successful cross-linking of the mouse IL-1α$_{117-270}$ protein to the Qβ capsid.

B. Immunization of Mice with Mouse IL-1α$_{117-270}$ Protein Coupled To Qβ Capsid (Qβ-mIL-1α$_{117-270}$)

Five female balb/c mice were immunized with Qβ-mIL-1α$_{117-270}$ Fifty μg of total protein were diluted in PBS to 200 μl and injected subcutaneously (100 μl on two ventral sides) on day 0 and day 21. Mice were bled retroorbitally on day 0, 21, and 35, and sera were analyzed using mouse IL-1α$_{117-270}$-specific ELISA.

C. ELISA

ELISA plates were coated with mouse IL-1α$_{117-270}$ protein at a concentration of 1 μg/ml. The plates were blocked and then incubated with serially diluted mouse sera from day 0, 21, and 35. Bound antibodies were detected with enzymatically labeled anti-mouse IgG antibody. Antibody titers of mouse sera were calculated as the average of those dilutions which led to half maximal optical density at 450 nm. The average anti-mouse IL-1α$_{117-270}$ titer was 1:9252 at day 21 and 1:736912 at day 35. This demonstrates that immunization with Qβ coupled to the mouse IL-1α$_{117-270}$ protein could overcome immunological tolerance and produce high titer antibodies which recognize specifically IL-1α$_{117-270}$ D. In Vitro Neutralization of IL-1α

Sera of mice immunized with Qβ-mIL-1α$_{117-270}$ were then tested for their ability to inhibit the binding of mouse IL-1α protein to its receptor. ELISA plates were therefore coated with a recombinant mIL-1receptorI-hFc fusion protein at a concentration of 1 μg/ml, and co-incubated with serial dilutions of sera from mice which had been immunized either with mouse IL-1α$_{117-270}$ coupled to Qβ capsid or with mouse IL-1β$_{119-269}$ coupled to Qβ capsid and 5 ng/ml of mouse IL-1α$_{117-270}$. Binding of IL-1α$_{117-270}$ to the immobilized mIL-1receptorI-hFc fusion protein was detected with a biotinylated anti-mouse IL-1α antibody and horse radish peroxidase conjugated streptavidin. All sera from mice immunized against murine IL-1α$_{117-270}$ inhibited completely the binding of mouse IL-1α$_{117-270}$ to its receptor at concentrations of ≧0.4%, whereas sera from mice immunized against mouse IL-1β$_{119-269}$ did not show a significant inhibitory effect even at the highest concentration used (3.3%). These data demonstrate that immunization with mouse IL-1α$_{117-270}$ coupled to Qβ capsid can yield antibodies which are able to neutralize specifically the interaction of mouse IL-1α$_{117-270}$ and its receptor.

E. In Vivo Neutralization of IL-1α

The in vivo neutralizing capacity of the antibodies raised by immunization with Qβ-mIL-1α$_{117-270}$ was investigated next. Four female balb/c mice were therefore immunized twice at days 0 and 14 with Qβ-mIL-1α$_{117-270}$ and four mice were immunized at the same time with Qβ capsid alone. At day 21 all mice were injected intravenously with 1 μg free IL-1α$_{117-270}$. As readout of the inflammatory activity of the injected IL-1α$_{117-270}$, serum samples were analysed 3 h after injection for the relative increase in the concentration of the pro-inflammatory cytokine IL-6. Qβ-immunized mice showed an average increase in the serum IL-6 concentration of 8.16±2.33 ng/ml, whereas mice immunized with Qβ-mIL-1α$_{117-270}$ showed an average increase of only 0.15±0.27 ng/ml (p=0.0005). As a control on day 28 all mice were injected with 1 μg mIL-1β. Three hours after injection mice immunized with Qβ carrier alone showed an average increase in serum IL-6 concentrations of 9.52±7.33 ng/ml, while mice immunized with Qβ-mIL-1α$_{117-270}$ showed an increase of 21.46±27.36 ng/ml (p=0.43). These data indicate that the antibodies produced by immunization with Qβ-mIL-1α$_{117-270}$ were able to neutralize specifically and efficiently the pro-inflammatory activity of IL-1α.

F. Efficacy of Qβ-mIL-1α$_{117-270}$ in a Mouse Model of Rheumatoid Arthritis

The efficacy of Qβ-mIL-1α$_{117-270}$ immunization was tested in the murine collagen-induced arthritis model (CIA). This model reflects most of the immunological and histological aspects of human rheumatoid arthritis and is therefore routinely used to assay the efficacy of anti-inflammatory agents. Male DBA/1 mice were immunized subcutaneously three times (days 0, 14 and 28) with 50 μg of either Qβ-mIL-1α$_{117-270}$ (n=8) or Qβ alone (n=8), and then injected intradermally at day 42 with 200 μg bovine type II collagen mixed with complete Freund's adjuvant. After a booster injection of 200 μg bovine type II collagen mixed with incomplete Freund's adjuvant at day 63 mice were examined on a daily basis for the development of arthritis symptoms. A clinical score as defined in EXAMPLE 2F was assigned to each limb according to the degree of reddening and swelling observed, and ankle thickness of all hind limbs was measured. Two weeks after the second collagen injection Qβ-immunized mice showed an average cumulative clinical score of 4.44, while Qβ-mIL-1α$_{117-270}$-immunized mice showed an average score of only 2.31. Moreover, the average increase in hind ankle thickness was 18% for Qβ-immunized mice and only 7% for mice which had been immunized with Qβ-mIL-1α$_{117-270}$. As an additional readout of the inflammatory reaction, serum levels of IL-6 were determined 1 week after the second collagen injection. Qβ-immunized mice had an average IL-6 serum concentration of 1.92±0.36 while Qβ-mIL-1α$_{117-270}$-immunized mice had an average IL-6 concentration of only 0.94±0.48. Taken together, these data show that immunization with Qβ-mIL-1α$_{117-270}$ protects mice from inflammation and clinical signs of arthritis in the CIA model.

Example 4

Efficacy of Qβ-mIL-1α$_{117-270}$ in a Mouse Model of Atherosclerosis

Seven to eight weeks old male Apoe$^{-/-}$ mice (The Jackson Laboratory, Bar Harbor Me.) were injected subcutaneously with either 50 μg Qβ-mIL-1α$_{117-270}$ vaccine (n=13) or with 50 μg Qβ (n=12) on day 0, 14, 28, 56, 105 and 133 (5 animals, 3 in the Qβ-mIL-1α$_{117-270}$ and 2 in the Qβ groups were received their second boost on day 33). The mice were fed initially with a normal chow diet, which was replaced on day 21 by a western diet (20% fat, 0.15% cholesterol, Provimi Kliba AG, Switzerland). Mice were bled at regular intervals throughout the experiment and the antibody response against IL-1 alpha was measured in the sera. Sacrifice was on day 159, and the aorta were isolated and prepared essentially as described (Tangirala R. K. et al. (1995) *J. Lipid. Res.* 36: 2320-2328). In addition, hearts were removed and snap-frozen in liquid nitrogen for subsequent histologic preparation essentially as described by Paigen B. et al. (*Atherosclerosis* 1987; 68:231-240) and Zhou X. et al. (*Arterioscler Thromb Vasc Biol* 2001; 21:108-114). The animals were bled by cardiac puncture and perfused with cold PBS. The aorta was then exposed, as much as possible of the adventitia removed in situ, and the aorta finally sectioned 2 mm from the heart. The heart was sectioned in the middle, and the upper part was immediately frozen in Hank's balanced salt solution in a plastic tube in liquid nitrogen. Serial sections (7 μm thickness) were cut in a cryostat through the origin of the aorta and harvested upon appearance of at least two valve cusps, until disappearance of the last valve cusps. Sections were fixed in formalin, stained with oil red 0, and plaque load was evaluated in 4-7 sections (3 sections in one animal of the Qβ group) per mouse by quantitative image analysis. An average plaque area was computed for each animal from the plaque area of each section used for the evaluation. An average group plaque area was computed for the Qβ-mIL-1α$_{117-270}$ and Qβ group respectively. Statistical analysis was performed with a Student t-test. P<0.05 was considered statistically significant.

For the evaluation of atherosclerosis in the whole aorta, these were further cleaned from residual adventitia on a glass petri dish filled with cold PBS, and the arch was sectioned 5 mm down from the left sub-clavian artery. The aorta were cut longitudinally, pinned out on a black wax surface and fixed overnight in 4% formalin. They were then stained overnight in oil red O. The plaques were quantified with an imaging software (Motic Image Plus 2.0) on digital photographs. The plaque load was expressed as the sum of the surface of all plaques of the aorta taken up to the iliac bifurcation, divided by the total surface of the aorta measured up to the iliac bifurcation, in percentage. The difference in mean or median of the plaque load between the Qβ-mIL-1α$_{117-270}$ and Qβ group was analyzed.

The antibody response was measured in a classical ELISA, with recombinant IL-1alpha coated on the ELISA plate. Binding of specific antibodies was detected using a goat anti-mouse HRP conjugate. The titers against IL-1alpha were calculated as the reciprocal of the serum dilution giving half-maximal binding in the assay. Specificity of the response was assessed by measuring pre-immune serum. The pre-immune titer was below the lowest serum dilution used in the assay, and was assigned this lowest-serum dilution value. The results of the measurement of the antibody response in the Qβ-mIL-1α$_{117-270}$ immunized animals are shown in Table 1, and clearly demonstrate that immunization against murine IL-1alpha coupled to Qβ led to a strong and sustained specific antibody response against IL-1alpha, since nearly no titer was detectable in the preimmune (d0) sera. Furthermore, induction of an antibody response specific for IL-1alpha led to a reduction of 37% in plaque area at the aortic origin in the Qβ-mIL-1α$_{117-270}$ group compared to the Qβ group (292803±21272 μm$^2$ vs. 464694±36545 μm$^2$, p=0.0005). In addition, a reduction of 31% in median plaque load in whole aortas prepared "en face" (5.7 vs. 8.3, p=0.06) was observed.

These data demonstrate that induction of anti-IL 1alpha antibodies by the Qβ-mIL-1α$_{117-270}$ vaccine inhibited the development of atherosclerosis and therefore that the Qβ-mIL-1α$_{117-270}$ vaccine is an effective treatment for atherosclerosis. Furthermore, these data demonstrate that IL-1alpha is involved in the pathogenesis of atherosclerosis.

TABLE 1

Geometric mean anti-IL1alpha antibody titer in Apoe$^{-/-}$ mice immunized with Qb-IL1alpha (geometric mean titer ± standard error of the mean)

| | d0 | d21 | d28* | d56 | d84 | d105 | d159 |
|---|---|---|---|---|---|---|---|
| Geomean ± SEM | <10000 | 225400 ± 93385 | 167867 ± 121345 | 522864 ± 106887 | 712061 ± 144922 | 621687 ± 184389 | 805370 ± 155764 |

*For 5 animals, the values are from day 33.

Example 5

Protection from TNBS-Induced Inflammatory Bowel Disease by Immunization with Qβ-mIL-1α$_{117-270}$ and/or Qβ-mIL-1β$_{119-269}$ Eight weeks old male SJL mice (5 per group) are injected subcutaneously three times at two week intervals with either 50 μg of Qβ-mIL-1α$_{117-270}$ or 50 μg Qβ-mIL-1β$_{119-269}$, or a mixture of 50 μg each of Qβ-mIL-1α$_{117-270}$ and Qβ-mIL-1β$_{119-269}$. As a control 5 mice are injected at the same regimen with Qβ VLPs alone. Two weeks after the last immunization, all mice are slightly anesthetized with Isofluran, and 1 mg of trinitrobenzesulfonic acid (TNBS) in 100 μl 50% ethanol is administered intrarectally via a polyethylene catheter at a distance of 4 cm of the anus. Body weight is recorded daily as readout of disease progression, and 7 days after TNBS administration all mice are sacrificed. The colon of each mouse is removed, a specimen of colon located 2 cm proximal to the anus is fixed in PBS-buffered formalin, and the degree of inflammation is graded semi-quantitatively on hematoxylin- and eosin-stained colonic cross-sections according to Neurath M. F. et al. (JEM (1995), 182:1281-1290).

Immunization with either Qβ-mIL-1$\alpha_{117-270}$ or Qβ-mIL-1$\beta_{119-269}$ alone, or with a combination of Qβ-mIL-1$\alpha_{117-270}$ and Qβ-mIL-1$\beta_{119-269}$ reduces the TNBS-induced weight loss, as compared to Qβ-immunized mice. Furthermore, histological examination of colonic cross-sections reveals, that Qβ-mIL-1$\alpha_{117-270}$ and/or Qβ-mIL-1$\beta_{119-269}$-immunized mice display a markedly reduced infiltration of inflammatory cells into the colonic tissue when compared to Qβ-immunized mice.

Example 6

Amelioration of Endotoxin-Hypersensitivity in Mice Carrying a Truncated Version of the MEFV Gene by Immunization with Qβ-mIL-1$\beta_{119-269}$ Familial Mediterranean Fever is a recessively inherited inflammatory disorder characterized by recurrent fever as well as peritonitis, serositis, arthritis and skin rashes. Affected individuals carry a missense mutation in the MEFV gene, leading to expression of a truncated pyrin protein. Mice carrying a similar mutation in the MEFV gene show an increased caspase-1 activity, leading to overproduction of mature IL-1β and increased hypothermia and lethality after LPS administration. Eight weeks old homozygote pyrin-truncation mice (5 per group) are immunized three times at two weeks intervals with 50 μg of Qβ-mIL-1$\beta_{119-269}$ or 50 μg of Qβ VLPs alone. Two weeks after the last immunization all mice are injected intraperitoneally with a mixture 20 mg D-Galactosamine and 0.01 μg/g LPS. mIL-1$\beta_{119-269}$-immunized mice show a markedly reduced hypothermia and a reduced lethality in response to LPS administration, when compared to Qβ-immunized controls.

Example 7

Comparison of Qβ-mIL-1$\alpha_{117-270}$ and Qβ-mIL-1$\beta_{119-269}$ Immunization to Kineret® Treatment in a Mouse Model of Rheumatoid Arthritis Kineret® (Anakinra, Amgen) is a recombinant version of the human IL-1 receptor antagonist, which is approved for the treatment of human rheumatoid arthritis. In order to reach a clinical benefit, relatively high amounts (100 mg) have to be applied via subcutaneous injection on a daily basis. The collagen-induced arthritis model was used to compare the efficacy of Qβ-mIL-1$\alpha_{117-270}$ and Qβ-mIL-1$\beta_{119-269}$ immunization with daily applications of different doses of Kineret®. Male DBA/1 mice were immunized subcutaneously three times (days 0, 14 and 28) with 50 μg of either Qβ-mIL-1$\alpha_{117-270}$ (n=8), Qβ-mIL-1$\beta_{119-269}$ (n=8) or Qβ alone (n=32), and then injected intradermally on day 42 with 200 μg bovine type II collagen mixed with complete Freund's adjuvant. From day 42 on, mice immunized with Qβ-mIL-1$\alpha_{117-270}$ and Qβ-mIL-1$\beta_{119-269}$, and one group of Qβ-immunized mice (n=8) received daily intraperitoneal injections of 200 μl PBS, while three additional Qβ-immunized groups received daily intraperitoneal injections of either 37.5 μg (n=8), 375 μg (n=8), or 3.75 mg (n=8) Kineret®. A daily injection of 37.5 μg Kineret® per mouse corresponds roughly to a dose of 1.5 mg/kg, which is in the range of the recommended efficacious amount for humans (100 mg). All mice were boosted on day 63 by intradermal injection of 200 μg bovine type II collagen mixed with incomplete Freund's adjuvant, and examined on a daily basis for the development of arthritis symptoms.

Four weeks after the second collagen injection, Qβ-immunized control mice showed an average cumulative clinical score (as defined in EXAMPLE 2F) of 3.75, while Qβ-mIL-1$\alpha_{117-270}$- and Qβ-mIL-1$\beta_{119-269}$-immunized mice showed average scores of only 0.81 and 1.44, respectively (see Table 2). Mice treated with 37.5 μg or 375 μg Kineret® reached an average score of 2.44 and 2.63, respectively, while mice treated with 3.75 mg Kineret® remained largely asymptomatic, reaching a maximal score of only 0.19.

As an additional readout of the inflammatory reaction, the hind ankle thickness of all animals was measured on a regular basis. Four weeks after the second collagen injection Qβ-immunized control mice showed an average increase in hind ankle thickness of 16%, while Qβ-mIL-1$\alpha_{117-270}$-immunized mice showed an increase of 2% and Qβ-mIL-1$\beta_{119-269}$-immunized mice showed an increase of 6%. Mice treated with either 37.5 μg or 375 μg Kineret® showed an average increase of 13% and 10%, respectively, while mice treated with 3.75 mg Kineret® showed no increase in hind ankle thickness at all.

In conclusion we surprisingly found that three injections of either Qβ-mIL-1$\alpha_{117-270}$ or Qβ-mIL-1$\beta_{119-269}$ protected mice better from the development of arthritis symptoms than daily injections of Kineret® in amounts corresponding to the human dose or even the ten-fold human dose. Only application of the 100-fold human dose of Kineret® showed an increased benefit with respect to Qβ-mIL-1$\alpha_{117-270}$ or Qβ-mIL-1$\beta_{119-269}$ vaccination.

TABLE 2 clinical disease symptoms in collagen-induced arthritis model.

| Treatment | average clinical score day 91 | Average increase in hind ankle thickness (%) day 63-91 |
| --- | --- | --- |
| 3x Qβ s.c. + PBS i.p. (200 (μl/day) | 3.75 | 16 |
| 3x Qβ-mIL-1$\alpha_{117-270}$ s.c. + PBS i.p. (200 (μl/day) | 0.81 | 2 |
| 3x Qβ-mIL-1$\beta_{119-269}$ s.c. + PBS i.p. (200 μl/day) | 1.44 | 6 |
| 3x Qβ s.c. + Kineret ® i.p. (37.5 μg/day) | 2.44 | 13 |
| 3x Qβ s.c. + Kineret ® i.p. (375 μg/day) | 2.63 | 10 |
| 3x Qβ s.c. + Kineret ® i.p. (3.75 mg/day) | 0.19 | 0 |

Example 8

A. Cloning, Expression, and Purification of Virus-Like Particles Consisting of AP205 Coat Protein Genetically Fused to Mouse IL-1$\alpha_{117-270}$ (AP205_mIL-1$\alpha_{117-270}$)

Given the large size of interleukin-1 alpha and for steric reasons, an expression system producing so called mosaic particles, comprising AP205 coat proteins fused to interleukin-1alpha as well as wt coat protein subunits was constructed. In this system, suppression of the stop codon yields the AP205-interleukin-1alpha coat protein fusion, while proper termination yields the wt AP205 coat protein. Both proteins are produced simultaneously in the cell and assemble into a mosaic virus-like particle. Two intermediary plasmids, pAP590 and pAP592, encoding the AP205 coat protein gene terminated by the suppressor codons TAG (amber, pAP590) or TGA (opal, pAP592) were made. A linker sequence encoding the tripeptide Gly-Ser-Gly (SEQ ID NO:189) was added downstream and in frame of the coat protein gene. Kpn2I and HindIII sites were added for cloning sequences encoding foreign amino acid sequences at the C-terminus of the Gly-Ser-Gly amino acid linker, C-terminal to the AP205 coat protein. The resulting constructs were: AP590 (SEQ ID NO:117): AP205 coat protein gene—amber codon—GSG (Kpn2I—HindIII); and AP592 (SEQ ID NO:118): AP205 coat protein gene—opal codon—GSG(Kpn2I—HindIII). For construction of plasmid pAP590, a PCR fragment obtained with oligonucleotides p1.44 (5'-NNCCATG-GCAAATAAGCCAATGCAACCG-3'; SEQ ID NO:119) and pINC-36 (5'-GTAAGCTTAGATGCATTATCCGGA TCCCTAAGCAGTAGTATCAGACGATACG-3'; SEQ ID NO:120) was digested with NcoI and HindIII, and cloned into vector pQb185, which had been digested with the same restriction enzymes. pQb185 is a vector derived from pGEM vector. Expression of the cloned genes in this vector is controlled by the trp promoter (Kozlovska, T. M. et al., *Gene* 137:133-37 (1993)). Similarly, plasmid pAP592 was constructed by cloning a NcoI/HindIII-digested PCR fragment obtained with oligonucleotides p1.44 and pINC-40 (5'-GTAAGCTTAGATGCATTATCCGGATCCT-CAAGCAGTAGTA TCAGACGATACG-3'; SEQ ID NO:121) into the same vector.

The sequence encoding amino acids 117-270 of murine IL-1α was amplified by PCR from plasmid pModEC1-His-EK-mIL1α$_{117-270}$ (see EXAMPLE 1), using primers pINC-34 (5'-GGTCCGGAGCGCTAGCCCCTTACAC-3'; SEQ ID NO:122) and pINC-35 (5'-GTAAGCTTATGCATTAT-GATATCTGGAAGTCTGTCATAGA-3'; SEQ ID NO:123), which added Kpn2I and HindIII restriction sites to the 5' and 3' ends, respectively. The obtained DNA fragment was digested with Kpn2I and HindIII and cloned into both vector pAP590, creating plasmid pAP594 (amber suppression), and into vector pAP592, creating plasmid pAP596 (opal suppression), respectively.

For expression of mosaic AP205 VLPs displaying murine IL-1α on their surface, *E. coli* JM109 cells containing plasmid pISM 579 or pISM 3001 were transformed with plasmid pAP594 or pAP596, respectively. Plasmid pISM579 was generated by excising the trpT176 gene from pISM3001 with restriction endonuclease EcoRI and replacing it by an EcoRI fragment from plasmid pMY579 (gift of Michael Yarus) containing an amber t-RNA suppressor gene. This t-RNA suppressor gene is a mutant of trpT175 (Raftery L A. Et al. (1984) *J. Bacteriol.* 158:849-859), and differs from trpT at three positions: G33, A24 and T35. Five milliliters of LB liquid medium containing 20 µg/ml ampicillin and 10 µg/ml kanamycin were inoculated with a single colony, and incubated at 37° C. for 16-24 h without shaking The prepared inoculum was diluted 50× with M9 medium containing 20 µg/ml ampicillin and 10 µg/ml Kanamycin and incubated at 37° C. overnight on a shaker Cells were harvested by centrifugation.

Cells (1 g, transformed with plasmid pAP594 and containing pISM579) were lysed by ultrasonication in lysis buffer (20 mM Tris-HCl, 5 mM EDTA, 150 mM NaCl, pH 7.8, 0.1% Tween 20). The lysate was cleared by centrifugation, and the cell debris were washed with lysis buffer. Pooled supernatant were loaded on a Sepharose CL-4B column eluted in TEN buffer (20 mM Tris-HCl, 5 mM EDTA, 150 mM NaCl, pH 7.8). The presence of capsids in the cleared lysate and wash supernatant was confirmed by agarose gel electrophoresis (1% TAE, ethidium bromide stained gel and UV detection).

Two peaks eluted from the column as determined by SDS-PAGE or UV-spectrometric analysis of light scattering at 310 nm. Fractions of the second peak, containing the capsids, were pooled and loaded on a Sepharose CL-6B column. Peak fractions from the CL-6B columne were pooled and concentrated using a centrifugal filter unit (Amicon Ultra 15 MWCO 30000, Millipore). The protein was purified further by one additional round of gel filtration on a CL-4B column, and the resulting peak fractions were pooled and concentrated on a centrifugal filter unit as above. The buffer was exchanged to 10 mM Hepes, pH 7.5, and glycerol was added to a final concentration of 50%.

Purification of AP205_mIL-1α$_{117-270}$ from plasmid pAP596 was performed essentially as described for pAP594 above, with the inclusion of an additional sucrose gradient purification step after the last CL-4B column. The protein was layered on a gradient prepared with the following sucrose solutions: 9 ml 36%, 3 ml 30%, 6 ml 25%, 8 ml 20%, 6 ml 15%, 6 ml 10% and 3 ml 5% sucrose. Fractions were identified by UV spectroscopy, and pooled fractions containing the capsids were concentrated on a centrifugal filter unit as above, and the buffer exchanged to 10 mM Hepes, pH 7.5. Glycerol was finally added to a final concentration of 50%.

B. Immunization of Mice with AP205_mIL-1α$_{117-270}$

Four female balb/c mice were immunized with AP205_mIL-1α$_{117-270}$. Twentyfive µg of total protein were diluted in PBS to 200 µl and injected subcutaneously (100 µl on two ventral sides) on day 0, day 14, and day 28. Mice were bled retroorbitally on days 0, 14, 28 and 35, and sera were analyzed using mouse IL-1α$_{117-270}$-specific ELISA.

C. ELISA

ELISA plates were coated with mouse IL-1α$_{117-270}$ protein at a concentration of 1 µg/ml. The plates were blocked and then incubated with serially diluted mouse sera from days 14, 28 and 35. Bound antibodies were detected with enzymatically labeled anti-mouse IgG antibody. Antibody titers of mouse sera were calculated as the average of those dilutions which led to half maximal optical density at 450 nm. The average anti-mouse IL-1α$_{117-270}$ titer was 1:4412 at day 14, 1:27955 on day 28 and 1:34824 on day 35. This demonstrates that immunization with AP205_mIL-1α$_{117-270}$ could overcome immunological tolerance and produce high titer antibodies which recognize specifically IL-1α$_{117-270}$.

D. In Vitro Neutralization of IL-1α

Sera of mice immunized with AP205_mIL-1α$_{117-270}$ were tested for their ability to inhibit the binding of mouse IL-1α protein to its receptor. ELISA plates were therefore coated with a recombinant mIL-1receptorI-hFc fusion protein at a concentration of 1 µg/ml, and co-incubated with serial dilutions of sera from mice which had been immunized either with AP205_mIL-1α$_{117-270}$ or with AP205 alone and 100 ng/ml of mouse IL-1α$_{117-270}$. Binding of mIL-1α$_{117-270}$ to the immobilized mIL-1receptorI-hFc fusion protein was detected with a biotinylated anti-mouse IL-1α antibody and horse radish peroxidase conjugated streptavidin. All sera from mice immunized AP205_mIL-1α$_{117-270}$ inhibited completely the binding of mouse IL-1α$_{117-270}$ to its receptor at concentrations of ≧3.3%, whereas sera from mice immunized with AP205 did not show a significant inhibitory effect at any concentration used. These data demonstrate that immunization with AP205_mIL-1α$_{117-270}$ can yield antibodies which are able to neutralize specifically the interaction of mouse IL-1α$_{117-270}$ with its receptor.

E. In Vivo Neutralization of IL-1α

The in vivo neutralizing capacity of the antibodies raised by immunization with AP205_mIL-1α$_{117-270}$ was investigated next. Four female balb/c mice were therefore immunized three times on days 0, 14, and 28 with AP205_mIL-1α$_{117-270}$ and four mice were immunized at the same time with AP205 alone. On day 42 all mice were injected intravenously with 1 µg of free murine IL-1α$_{117-270}$. As readout of the inflammatory activity of the injected IL-1α$_{117-270}$, serum samples were withdrawn before and 3 h after injection and analyzed for the relative increase in the concentration of the pro-inflammatory cytokine IL-6. AP205-immunized mice showed an average increase in the serum IL-6 concentration of 12.92±3.95 ng/ml, whereas mice immunized with AP205_mIL-1α$_{117-270}$ showed an average increase of only 0.06±0.05 ng/ml (p<0.01). These data indicate that the antibodies produced by immunization with AP205_mIL-1α$_{117-270}$ were able to neutralize specifically and efficiently the pro-inflammatory activity of IL-1α.

F. Efficacy of AP205_mIL-1α$_{117-270}$ in a Mouse Model of Rheumatoid Arthritis The efficacy of AP205_mIL-1α$_{117-270}$-immunization was tested in the murine collagen-induced arthritis model (CIA). Male DBA/1 mice were immunized subcutaneously three times (days 0, 14 and 28) with 50 µg of either AP205_mIL-1α$_{117-270}$ (n=8) or AP205 alone (n=8), and then injected intradermally on day 42 with 200 µg bovine type II collagen mixed with complete Freund's adjuvant. After a booster injection of 200 µg bovine type II collagen mixed with incomplete Freund's adjuvant on day 63, mice were examined on a daily basis for the development of arthritis symptoms. A clinical score ranging from 0 to 3 was assigned to each limb according to the degree of reddening and swelling observed, and ankle thickness of all hind limbs was measured. Four weeks after the second collagen injection Qβ -immunized mice showed an average cumulative clinical score of 5.81, while AP205_mIL-1α$_{117-270}$-immunized mice showed an average score of only 2.06. Moreover, the average increase in hind ankle thickness was 19% for AP205-immunized mice and only 9% for mice which had been immunized with AP205_mIL-1α$_{117-270}$. Taken together, these data show that immunization with AP205_mIL-1α$_{117-270}$ strongly protects mice from inflammation and clinical signs of arthritis in the CIA model.

Example 9

A. Cloning and Expression of Virus-Like Particles Consisting of AP205 Coat Protein Genetically Fused to Mouse IL-1β$_{119-269}$ (AP205_mIL-1β$_{119-269}$)

Cloning, expression and purification of virus-like particles consisting of AP205 coat protein genetically fused to mouse IL-1β$_{119-269}$ is carried out essentially as described for AP205_mIL-1α$_{117-270}$ in EXAMPLE 8. The sequence of murine interleukin 1 beta was amplified from plasmid pModEC1-His-EK-mIL1β$_{119-269}$ coding for murine interleukin 1 beta using primers pINC-75 (5'-GA TCCGGAGGTGGTGTCCCCATTAGACAGCT-3', SEQ ID NO:192) and pINC-77 (5'-GT AAGCTTAGGAAGACACAGATTCCAT-3', SEQ ID NO:193). These primers amplify a murine interleukin-1 beta gene with 5' Kpn2I and 3' Hind III sites, and encoding additionally the amino acid sequence Gly-Gly at the N-terminus of murine interleukin 1beta. The obtained mur-IL-1β fragment was digested with Kpn2I and HindIII and cloned in the same restriction sites into vector pAP590 (amber suppression) creating plasmid pAP630. E. coli JM109 containing plasmid pISM 579, providing amber suppression, was transformed with plasmid pAP630. 5 ml of LB liquid medium with 20 µg/ml ampicillin and 10 µg/ml kanamycin were inoculated with a single colony, and incubated at 37° C. for 16-24 h without shaking The prepared inoculum was diluted 50× with M9 medium containing 20 µg/ml ampicillin and 10 µg/ml kanamycin and incubated at 37° C. overnight on a shaker Cells were harvested by centrifugation.

B. Cloning and Expression of Virus-Like Particles Consisting of AP205 Coat Protein Genetically Fused to Human IL-1β$_{116-269}$ (AP205_hIL-1β$_{116-269}$)

The sequence of human interleukin 1 beta was amplified from plasmid pET42T-hIL-1β$_{116-269}$ coding for human interleukin 1 beta using primers pINC-74 (5'-GA TCCGGA GGT GGT GCC CCT GTA CGA TCA CTG AAC TG-3', SEQ ID NO:194) and pINC-76 (5'-GT ATGCATTAGGAAGACACAAATTGCATGGTGAAGTC-3, SEQ ID NO:195), introducing a 5' Kpn2I and 3' Mph1103I site, respectively. The obtained human-IL-1β fragment was digested with Kpn2I and Mph1103I and cloned in the same restriction sites into vector pAP590 (amber suppression) creating plasmid pAP649. E. coli JM109 containing plasmid pISM 579 (providing amber suppression), was transformed with plasmid pAP649. 5 ml of LB liquid medium with 20 µg/ml ampicillin and 10 µg/ml canamicin were inoculated with a single colony, and incubated at 37° C. for 16-24 h without shaking. The prepared inoculum was diluted 50× with M9 medium containing 20 µg/ml ampicillin and 10 µg/ml kanamycin and incubated at 37° C. overnight on a shaker. Cells were harvested by centrifugation.

C. Immunization of Mice with AP205_mIL-1β$_{119-269}$

Four female C3H/HeJ mice were immunized with AP205_mIL-1β$_{119-269}$ Twentyfive µg of total protein were diluted in PBS to 200 µl and injected subcutaneously (100 µl on two ventral sides) on day 0, day 14, and day 28. Mice were bled retroorbitally on days 0, 14, 28 and 35, and sera were analyzed using mIL-1β$_{119-269}$-specific ELISA.

D. ELISA

ELISA plates were coated with mouse IL-1β$_{119-269}$ protein at a concentration of 1 µg/ml. The plates were blocked and then incubated with serially diluted mouse sera from days 0, 14, 28, and 35. Bound antibodies were detected with enzymatically labeled anti-mouse IgG antibody. Antibody titers of mouse sera were calculated as the average of those dilutions which lead to half maximal optical density at 450 nm. The average anti-mouse IL-1β$_{119-269}$ titer was 1:19000 on day 14, 1:58200 on day 28 and 1:104700 on day 35. This demonstrates that immunization with AP205_mIL-1β$_{119-269}$ could overcome immunological tolerance and produce high titer antibodies which recognize specifically mouse IL-1β$_{119-269}$ E. In Vitro Neutralization of IL-1β

Sera of mice immunized with AP205_mIL-1β$_{119-269}$ are then tested for their ability to inhibit the binding of mouse IL-1β protein to its receptor. ELISA plates are therefore coated with a recombinant mIL-1receptorI-hFc fusion protein at a concentration of 1 μg/ml, and co-incubated with serial dilutions of sera from mice immunized either with AP205_mIL-1$\beta_{119-269}$ or with AP205 alone, and 100 ng/ml of mouse IL-1$\beta_{119-269}$. Binding of IL-1$\beta_{119-269}$ to the immobilized mIL-1receptorI-hFc fusion protein is detected with a biotinylated anti-mouse IL-1β antibody and horse radish peroxidase conjugated streptavidin. All sera from mice immunized with AP205_mIL-1$\beta_{119-269}$ strongly inhibit the binding of mouse IL-1$\beta_{119-269}$ to its receptor, whereas sera from mice immunized with AP205 alone do not show any inhibitory effect. These data demonstrate that immunization with AP205_mIL-1$\beta_{119-269}$ can yield antibodies which are able to neutralize the interaction of mouse IL-1$\beta_{119-269}$ and its receptor.

F. In Vivo Neutralization of IL-1β

The in vivo neutralizing capacity of the antibodies raised by immunization with AP205_mIL-1$\beta_{119-269}$ were investigated next. Four female C3H/HeJ mice were therefore immunized three times on days 0, 14, and 28 with AP205_mIL-1$\beta_{119-269}$ and four mice were immunized at the same time with AP205 alone. On day 42 all mice were injected intravenously with 1 μg of free mIL-1$\beta_{119-269}$. As readout of the inflammatory activity of the injected mIL-1$\beta_{119-269}$, serum samples were withdrawn before and 3 h after injection and analysed for the relative increase in the concentration of the pro-inflammatory cytokine IL-6. AP205-immunized mice showed an increase of 0.28 ng/ml in serum IL-6 concentrations, whereas mice immunized with AP205_mIL-1$\beta_{119-269}$ showed no increase at all. These data indicate that the antibodies produced by immunization with AP205_mIL-1$\beta_{119-269}$ were able to neutralize specifically and efficiently the pro-inflammatory activity of IL-1β.

G. Efficacy of AP205_mIL-1$\beta_{119-269}$ in a Mouse Model of Rheumatoid Arthritis The efficacy of AP205_mIL-1$\beta_{119-269}$-immunization was tested in the murine collagen-induced arthritis model (CIA). Male DBA/1 mice were immunized subcutaneously four times (days 0, 14, 28, and 42) with 25 μg of either AP205_mIL-1$\beta_{119-269}$ (n=8) or AP205 alone (n=8), and then injected intradermally on day 58 with 200 μg bovine type II collagen mixed with complete Freund's adjuvant. After a booster injection of 200 μg bovine type II collagen mixed with incomplete Freund's adjuvant on day 79 mice were examined on a daily basis for the development of arthritis symptoms. A clinical score as defined in EXAMPLE 2F was assigned to each limb according to the degree of reddening and swelling observed, and ankle thickness of all hind limbs was measured. Twenty days after the second collagen injection AP205-immunized mice showed an average cumulative clinical score of 2.69, while AP205_mIL-1$\beta_{119-269}$-immunized mice showed an average score of only 1.0. Moreover, the average increase in hind ankle thickness was 8.8% for AP205-immunized mice and only 0.6% for mice which had been immunized with AP205_mIL-1$\beta_{119-269}$. Taken together, these data show that immunization with AP205_mIL-1$\beta_{119-269}$ strongly protected mice from inflammation and clinical signs of arthritis in the CIA model.

H. Immunization of Mice with AP205_hIL-1$\beta_{116-269}$

Four female C3H/HeJ mice were immunized with AP205_hIL-1$\beta_{116-269}$. Twentyfive μg of total protein were diluted in PBS to 200 μl and injected subcutaneously (100 μl on two ventral sides) on days 0, 14, and 28. Mice were bled retroorbitally on days 0, 14, 28 and 35, and sera were analyzed using human IL-1$\beta_{116-269}$-specific ELISA.

I. ELISA

ELISA plates were coated with human IL-1$\beta_{116-269}$ protein at a concentration of 1 μg/ml. The plates were blocked and then incubated with serially diluted mouse sera from days 0, 14, 28, and 35. Bound antibodies were detected with enzymatically labeled anti-mouse IgG antibody. Antibody titers of mouse sera were calculated as the average of those dilutions which lead to half maximal optical density at 450 nm. The average anti-human IL-1$\beta_{116-269}$ titer was 1:39600 on day 14, 1:58300 on day 28 and 1:65600 on day 35. This demonstrates that AP205_hIL-1$\beta_{116-269}$ induces high titers of hIL-1$\beta_{116-269}$-specific antibodies in mice.

Example 10

A. Cloning, Expression and Purification of Human IL-1$\beta_{116-269}$

The nucleotide sequence encoding amino acids 116-269 of human IL-1β (hIL-1$\beta_{116-269}$) was amplified by PCR from a cDNA library of human liver tissue using oligonucleotides HIL-1 (5'-ATATATGATATCCCTGTACGATCACT-GAACTGCACG-3'; SEQ ID NO:124) and HIL-2 (5'-ATATATCTCGAGGGAAGACA CAAATTGCATGGT-GAAG-3'; SEQ ID NO:125), digested with XhoI and EcoRV and cloned into the expression vector pET42T(+).

Plasmid pET-42T(+) was constructed by replacing the whole region between the T7 promoter and the T7 terminator of pET-42a(+) (Novagen) in two steps by new linker sequences, which facilitate the expression of a protein of interest as a fusion with a C-terminal tag (SEQ ID NO:190) comprising a His-tag and a cysteine containing linker In a first step plasmid pET-42a(+) was digested with the restriction enzymes NdeI and AvrII, liberating a 958 by fragment between the T7 promoter and T7 terminator composed of a GST-tag, S-tag, two His-tags and the multiple cloning site. The residual 4972 by fragment containing the vector backbone of pET-42a(+) was isolated and ligated to the annealed complementary oligonucleotides 42-1 (5'-TATGGATATC-GAATTCAAGCTTCTGCAGCTGCTCGAGTAA TTGAT-TAC-3'; SEQ ID NO:126) and 42-2 (5'-CTAGGTAATCAAT-TACTCGA GCAGCTGCAGAAGCTTGAATTCGATATCCA-3'; SEQ ID NO:127), giving rise to plasmid pET-42S(+). In the second step plasmid pET-42S(+) was linearized by digestion with restriction enzymes XhoI and AvrII, and ligated to the complementary annealed oligonucleotides 42T-1 (5'-TC-GAGCACCACCACCACCACCACGGTGGTT GCTAATAATAATTGATTAATAC-3'; SEQ ID NO:128) and 42T-2 (5'-CTAGGTATTAATCAATTATTATTAG-CAACCACCGTGGTGGTGGTGGTGC-3'; SEQ ID NO:129), resulting in plasmid pET-42T(+).

The cloning of the above mentioned fragment hIL-1$\beta_{116-269}$ into pET-42T(+) gave rise to plasmid pET42T-hIL-1$\beta_{116-269}$. This plasmid encodes a fusion protein corresponding to the mature human IL-1β and a His-tag and a C-terminal cysteine-containing linker (GGC, SEQ ID NO:178). Thus, the fusion protein consists of SEQ ID NO:190 C-terminally fused to SEQ ID NO:165. The original alanine residue at position 117 of human IL-1β was changed to isoleucin in this fusion protein. Expression and purification of the human IL-1β$_{116-269}$ protein was performed essentially as described for the murine mIL1β$_{119-269}$ protein in EXAMPLE 1.

B Cloning, Expression and Purification of Human IL-1β$_{116-269}$ Muteins

By site directed mutagenesis of the plasmid pET42T-hIL-1β$_{116-269}$, expression vectors for ten different mutant human IL-1β$_{116-269}$ fusion proteins were constructed. To this aim the Quik-Change® Site directed mutagenesis kit (Stratagene) was used according to the manufacturer's instructions. The expression vectors for these mutant IL-1β$_{119-269}$ proteins are listed in Table 3 together with the oligonucleotide pairs used for their construction. Expression and purification of the different human IL-1β$_{116-269}$ muteins was performed as described in EXAMPLE 1.

Example 11

A. Biological Activity of Human IL-1β$_{116-269}$ and Human IL-1β$_{116-269}$ Muteins in Mice Three female C3H/HeJ mice per group were injected intravenously with 10 μg of either the wild type human IL-1β$_{119-269}$ protein or one of the human IL-1β$_{119-269}$ protein muteins of EXAMPLE 10. Serum samples were withdrawn before and 3 h after injection and analysed for the relative increase in the concentration of the pro-inflammatory cytokine IL-6. As shown in table 4, mice injected with the wild type human IL-1β$_{119-269}$ protein showed an increase of 2.38 ng/ml in serum IL-6 concentrations. With the exception of muteins hIL-1β$_{116-269}$ (D54R) and hIL-1β$_{116-269}$ (K63S/K65S), which induced similar serum IL-6 concentrations as wild type human IL-1β$_{119-269}$, all muteins tested induced lower amounts of IL-6, indicating reduced biological activity.

TABLE 3

Overview over IL-1 muteins, expression vectors and oligonucleotides used for their construction.

| Expression vector | mutein sequence (without purification tag) | Oligonucleotide pair |
|---|---|---|
| pET42T-hIL-1β$_{116-269}$ (R4D) | hIL-1β$_{116-269}$ (R4D) (SEQ ID NO: 131) | R4D-1 (5'-CATATGGATA TCCCTGTAGA CTCACTGAAC TGCACGCTC-3'; SEQ ID NO: 143); R4D-2 (5'-GAGCGTGCAG TTCAGTGAGT CTACAGGGAT ATCCATATG-3'; SEQ ID NO: 144) |
| pET42T-hIL-1β$_{116-269}$ (L6A) | hIL-1β$_{116-269}$ (L6A) (SEQID NO: 132) | L6A-1 (5'-GATATCCCTG TACGATCAGC TAACTGCACG CTCCGGGAC-3'; SEQ ID NO: 145); L6A-2 (5'-GTCCCGGAGC GTGCAGTTAG CTGATCGTAC AGGGATATC-3'; SEQ ID NO: 146) |
| pET42T-hIL-1β$_{116-269}$ (T9G) | hIL-1β$_{116-269}$ (T9G) (SEQ ID NO: 133) | T9G-1 (5'-GTACGATCAC TGAACTGCGG TCTCCGGGAC TCACAGC-3'; SEQ ID NO: 147) T9G-2 (5'-GCTGTGAGTC CCGGAGACCG CAGTTCAGTG ATCGTAC-3'; SEQ ID NO: 148) |
| pET42T-hIL-1β$_{116-269}$ (R11G) | hIL-1β$_{116-269}$ (R11G) (SEQ ID NO: 134) | R11G-1 (5'-GAACTGCACG CTCGGGGACT CACAGC-3'; SEQ ID NO: 149) R11G-2 (5'-GCTGTGAGTC CCGAGCGTG CAGTTC-3'; SEQ ID NO: 150) |
| pET42T-hIL-1β$_{116-269}$ (D54R) | hIL-1β$_{116-269}$ (D54R) (SEQ ID NO: 135) | D54R-1 (5'-CAAGGAGAAGAAAGTAATCGCAAAATACCTGTGGC CTTG-3'; SEQ ID NO: 151 D54R-2 (5'-CAAGGCCACAGGTATTTTGCGATTACTTTCTTCTCCT TG-3'; SEQ ID NO: 152) |
| pET42T-hIL-1β$_{116-269}$ (D145K) | hIL-1β$_{116-269}$ (D145K) (SEQ ID NO: 136) | D145K-1 (5'-GCGGCCAGGATATAACTAAATTCACCATGCAATTTG TGTC-3'; SEQ ID NO: 161) D145K-2 (5'-GACACAAATTGCATGGTGAATTTAGTTATATCCTGG CCGC-3'; SEQ ID NO: 162) |
| pET42T-hIL-1β$_{116-269}$ (ΔEE$^{50, 51}$) | hIL-1β$_{116-269}$ (ΔEE$^{50, 51}$) (SEQ ID NO: 137) | EE-1 (5'-CATGTCCTTTGTACAAGGAAGTAATGACAAAATACC TGTG-3'; SEQ ID NO: 153) EE-2 (5'-CACAGGTATTTTGTCATTACTTCCTTGTACAAAGGAC ATG-3'; SEQ ID NO: 154) |
| pET42T-hIL-1β$_{116-269}$ (ΔSND$^{52-54}$) | hIL-1β$_{116-269}$ (ΔSND$^{52-54}$) (SEQ ID NO: 138) | SND-1 (5'-CTTTGTACAAGGAGAAGAAAAAATACCTGTGGCCTT G-3'; SEQ ID NO: 155) SND-2 (5'-CAAGGCCACAGGTATTTTTTCTTCTCCTTGTACAAA G-3'; SEQ ID NO: 156) |
| pET42T-hIL-1β$_{116-269}$ (K63S/K65S) | hIL-1β$_{116-269}$ (K63S/K65S) (SEQ ID NO: 139) | K6365S-1 (5'-GTGGCCTTGGGCCTCAGCGAAAGCAATCTGTACCTG TCCTG-3'; SEQ ID NO: 157) K6365S-2 (5'-CAGGACAGGTACAGATTGCTTTCGCTGAGGCCCAAG GCCAC-3'; SEQ ID NO: 158) |
| pET42T-hIL-1β$_{116-269}$ (Q126A/E128A) | hIL-1β$_{116-269}$ (Q126A/E128A) (SEQ ID NO: 140) | QE-1 (5'-GTACATCAGCACCTCTGCAGCAGCAAACATGCCCGT CTTC-3'; SEQ ID NO: 159) QE-2 (5'-GAAGACGGGCATGTTTGCTGCTGCAGAGGTGCTGAT GTAC-3'; SEQ ID NO: 160) |

TABLE 4

Biological activity of human IL-1β$_{116-269}$
and human IL-1β$_{116-269}$ muteins in mice.

| Protein/mutein | Average increase in serum IL-6 concentrations 3 h after injection in ng/ml (±SD) |
|---|---|
| hIL-1β$_{116-269}$ | 2.38 ± 0.69 |
| hIL-1β$_{116-269}$ (R4D) | 0.16 ± 0.03 |
| hIL-1β$_{116-269}$ (L6A) | 1.03 ± 0.65 |
| hIL-1β$_{116-269}$ (T9G) | 0.82 ± 0.42 |
| hIL-1β$_{116-269}$ (R11G) | 0.34 ± 0.25 |
| hIL-1β$_{116-269}$ (D54R) | 3.25 ± 1.67 |
| hIL-1β$_{116-269}$ (ΔEE$^{50, 51}$) | 1.10 ± 0.27 |
| hIL-1β$_{116-269}$ (ΔSND$^{52-54}$) | 0.13 ± 0.08 |
| hIL-1β$_{116-269}$ (K63S/K65S) | 2.22 ± 1.38 |
| hIL-1β$_{116-269}$ (Q126A/E128A) | 0.77 ± 0.55 |
| hIL-1β$_{116-269}$ (D145K) | 1.39 ± 0.26 |

B. Biological Activity of Human IL-1β$_{116-269}$ and Human IL-1β$_{116-269}$ Muteins in Human PBMC Peripheral blood mononuclear cells (PBMCs) were isolated from heparinized blood of a healthy donor by Ficoll density gradient centrifugation. 5×10$^5$ cells per well were incubated with titrating amounts of either the wild type human IL-1β$_{119-269}$ protein or one of the human IL-1β$_{119-269}$ muteins of EXAMPLE 10. After over night incubation the amount of IL-6 in the cell culture supernatant was measured as readout of the biological activity. Table 5 shows that with the exception of muteins hIL-1β$_{116-269}$ (D54R) and hIL-1β$_{116-269}$ (K63S/K65S), much higher amounts of all mutants were necessary to induce the same IL-6 secretion as wild type human IL-1β$_{119-269}$, indicating a reduction in bioactivity. The factor by which biological activity was reduced ranged from 13 fold for mutein hIL-1β$_{116-269}$ (R11G) to 381 fold for mutein hIL-1β$_{116-269}$ (ΔSND$^{52-54}$).

TABLE 5

Biological activity of human hIL-1β$_{116-269}$ and
human hIL-1β$_{116-269}$ muteins in human PBMC.

| Protein/mutein | Protein/mutein concentration (in ng/ml) required to induce 600 pg/ml IL-6 from human PBMC | Fold reduction in bioactivity relative to wild type hIL-1β$_{116-269}$ |
|---|---|---|
| hIL-1β$_{116-269}$ | 2 | —/— |
| hIL-1β$_{116-269}$ (R4D) | 333 | 146 |
| hIL-1β$_{116-269}$ (L6A) | 31 | 14 |
| hIL-1β$_{116-269}$ (T9G) | 79 | 34 |
| hIL-1β$_{116-269}$ (R11G) | 30 | 13 |
| hIL-1β$_{116-269}$ (D54R) | 5 | 2 |
| hIL-1β$_{116-269}$ (ΔEE$^{50, 51}$) | 187 | 82 |
| hIL-1β$_{116-269}$ (ΔSND$^{52-54}$) | 872 | 381 |
| hIL-1β$_{116-269}$ (K63S/K65S) | 13 | 6 |
| hIL-1β$_{116-269}$ (Q126A/E128A) | 94 | 41 |
| hIL-1β$_{116-269}$ (D145K) | 386 | 169 |

Example 12

A. Coupling of Human IL-1β$_{116-269}$ and Human IL-1β$_{116-269}$ Muteins to Qβ Virus-Like Particles Chemical cross-linking of the wild type human IL-1β$_{119-269}$ protein and the human IL-1β$_{119-269}$ muteins of EXAMPLE 10 to Qβ virus-like particles was performed essentially as described in EXAMPLE 2A.

B. Immunization of Mice with Human IL-1β$_{116-269}$ and Human IL-1β$_{116-269}$ Muteins Coupled to Qβ Capsid Four female balb/c mice per group were immunized with Qβ coupled to either the wild type hIL-1β$_{116-269}$ protein or one of the hIL-1β$_{116-269}$ mutein proteins. Fifty μg of total protein were diluted in PBS to 200 μl and injected subcutaneously (100 μl on two ventral sides) on day 0, 14 and 28. Mice were bled retroorbitally on day 35, and sera were analyzed using ELISAs specific for either for the respective human IL-1β$_{116-269}$ mutein used as immunogen, or the wild type human IL-1β$_{116-269}$ protein.

C ELISA

ELISA plates were coated either with the wild type hIL-1β$_{116-269}$ protein or the respective hIL-1β$_{116-269}$ mutein at a concentration of 1 μg/ml. The plates were blocked and then incubated with serially diluted mouse sera from day 35. Bound antibodies were detected with enzymatically labeled anti-mouse IgG antibody. Antibody titers of mouse sera were calculated as the average of those dilutions which led to half maximal optical density at 450 nm, and are shown in Table 6.

TABLE 6

Anti- hIL-1β$_{116-269}$ (wild type and mutein)-specific IgG titers raised
by immunization with Qβ-hIL-1β$_{116-269}$ or Qβ-hIL-1β$_{116-269}$ mutein vaccines.

| Vaccine | Average anti-hIL-1β$_{116-269}$ wild type IgG titer (±SD) | Average anti-hIL-1β$_{116-269}$ mutein IgG titer (±SD) |
|---|---|---|
| Qβ-hIL-1β$_{116-269}$ | 253325 ± 184813 | —/— |
| Qβ-hIL-1β$_{116-269}$ (R4D) | 231879 ± 115475 | 160666 ± 79478 |
| Qβ-hIL-1β$_{116-269}$ (L6A) | 120224 ± 7658 | 89377 ± 17965 |
| Qβ-hIL-1β$_{116-269}$ (T9G) | 261249 ± 153716 | 224809 ± 131823 |
| Qβ-hIL-1β$_{116-269}$ (R11G) | 278342 ± 50296 | 279290 ± 47232 |
| Qβ-hIL-1β$_{116-269}$ (D54R) | 269807 ± 122351 | 206516 ± 90998 |
| Qβ-hIL-1β$_{116-269}$ (D145K) | 78365 ± 26983 | 93241 ± 28856 |
| Qβ-hIL-1β$_{116-269}$ (ΔEE$^{50, 51}$) | 287625 ± 143835 | 229862 ± 140169 |
| Qβ-hIL-1β$_{116-269}$ (ΔSND$^{52-54}$) | 68895 ± 14267 | 106116 ± 25295 |
| Qβ-hIL-1β$_{116-269}$ (K63S/K65S) | 403712 ± 402594 | 244552 ± 173597 |
| Qβ-hIL-1β$_{116-269}$ (Q126A/E128A) | 195165 ± 71436 | 170434 ± 86831 |

Qβ-hIL-1β$_{116-269}$-immunization induced high titers of IgG antibodies against hIL-1β$_{116-269}$. Moreover, vaccination with either of the Qβ-hIL-1β$_{116-269}$ mutein vaccines induced high IgG titers against both the respective hIL-1β$_{116-269}$ mutein used as immunogen, and the wild type hIL-1β$_{116-269}$ protein.

D. In Vitro Neutralization of Human IL-1β

Sera of mice immunized with Qβ coupled to either wild type hIL-1β$_{116-269}$ protein or to one of the hIL-1β$_{116-269}$ muteins were tested for their ability to inhibit the binding of human IL-1β protein to its receptor. ELISA plates were therefore coated with a recombinant human IL-1receptorI-hFc fusion protein at a concentration of 1 µg/ml, and co-incubated with serial dilutions of the above mentioned sera and 100 ng/ml of hIL-1β$_{116-269}$ protein. Binding of hIL-1β$_{116-269}$ to the immobilized human IL-1receptorI-hFc fusion protein was detected with a biotinylated anti-human IL-1β antibody and horse radish peroxidase conjugated streptavidin. All sera raised against Qβ-hIL-1β$_{116-269}$ mutein vaccines completely inhibited the binding of 100 ng/ml wild type hIL-1β$_{116-269}$ to hIL-1RI at serum concentrations 3.3%.

The same sera were also tested for their ability to inhibit the hIL-1β$_{116-269}$-induced secretion of IL-6 from human cells. Human PBMCs were therefore prepared as described in EXAMPLE 11B and incubated with 10 ng/ml wild type hIL-1β$_{116-269}$, which had been premixed with titrating concentrations of the sera described above. After over night incubation the cell culture supernatants were analyzed for the presence of IL-6. The neutralizing capacity of the sera was expressed as those dilutions which lead to half maximal inhibition of IL-6 secretion. In order to allow a direct comparison to the neutralizing capacity of the serum raised against wild type hIL-1β$_{116-269}$, the neutralizing titers of all sera raised against hIL-1β$_{116-269}$ muteins were corrected for the respective ELISA titers measured against wild type hIL-1β$_{116-269}$ (see Table 6). As shown in Table 7 all sera raised against hIL-1β$_{116-269}$ muteins were able to inhibit the secretion of IL-6 induced by wild type hIL-1β$_{116-269}$. The neutralizing titers ranged from 1:113 for sera raised against Qβ-hIL-1β$_{116-269}$ (R11G) to 1:4532 for sera raised against Qβ-hIL-1β$_{116-269}$ (D54R).

TABLE 7

Neutralizing titer determined in sera of mice immunized with various IL-1 beta muteins.

| Vaccine | Neutralizing titer (corrected for ELISA titer against wild type hIL-1β$_{116-269}$) |
| --- | --- |
| Qβ-hIL-1β$_{116-269}$ | 3333 |
| Qβ-hIL-1β$_{116-269}$ (R4D) | 2150 |
| Qβ-hIL-1β$_{116-269}$ (L6A) | 2062 |
| Qβ-hIL-1β$_{116-269}$ (T9G) | 1036 |
| Qβ-hIL-1β$_{116-269}$ (R11G) | 113 |
| Qβ-hIL-1β$_{116-269}$ (D54R) | 4532 |
| Qβ-hIL-1β$_{116-269}$ (AEE$^{50, 51}$) | 2871 |
| Qβ-hIL-1β$_{116-269}$ (ΔSND$^{52-54}$) | 1109 |
| Qβ-hIL-1β$_{116-269}$ (K63S/K65S) | 3432 |
| Qβ-hIL-1β$_{116-269}$ (Q126A/E128A) | 1237 |
| Qβ-hIL-1β$_{116-269}$ (D145K) | 2369 |

E. In Vivo Neutralization of IL-1β

The in vivo neutralizing capacity of the antibodies raised by immunization with Qβ coupled to either wild type hIL-1β$_{116-269}$ protein or to one of the hIL-1β$_{116-269}$ muteins is investigated. Three female C3H/HeJ mice per group are therefore immunized three times on days 0, 14, and 28 with 50 µg of either vaccine. On day 35 all immunized mice are injected intravenously with 1 µg of free wild type hIL-1β$_{116-269}$. As a control three naive mice are injected at the same time with the same amount of wild type hIL-1β$_{116-269}$. As readout of the inflammatory activity of the injected hIL-1β$_{116-269}$, serum samples are withdrawn immediately before and 3 h after injection and analysed for the relative increase in the concentration of the pro-inflammatory cytokine IL-6. Whereas naive mice show a strong increase in serum IL-6 concentrations 3 h after injection of hIL-1β$_{116-269}$, all mice immunized with Qβ coupled to the wild type hIL-1β$_{116-269}$ protein or to one of the hIL-1β$_{116-269}$ muteins do not show any increase in serum IL-6, indicating that the injected hIL-1β$_{116-269}$ is efficiently neutralized by the antibodies induced by the vaccines.

Example 13

Amelioration of MSU-Induced Inflammation by Immunization with Qβ-mIL-1β$_{119-269}$ Gout is a painful inflammatory disorder caused by the precipitation of monosodium urate (MSU) crystals in joints and periarticular tissues. MSU crystals have been shown to activate the so called NALP3 inflammasome, resulting in the production of active which is mainly responsible for initiating and promoting the inflammatory response characteristic of the disease. C57BL/6 mice (5 per group) are immunized subcutaneously three times at two weeks intervals with 50 µg Qβ-mIL-1β$_{119-269}$ or 50 µg of Qβ VLPs alone. One week after the last immunization all mice are challenged intraperitoneally with 1.5 mg MSU crystals. Six hours after the challenge mice are sacrificed and neutrophil numbers as well as the concentrations of the neutrophil chemoattractants KC and MIP-2 are measured in peritoneal exsudates. Qβ-mIL-1β$_{119-269}$-immunized mice show markedly reduced neutrophilia and MIP-2 and KC concentrations, when compared to Qβ-immunized controls.

Example 14

Amelioration of Experimental Autoimmune Encephalitis by Immunization with Qβ-mIL-1β$_{119-269}$ In a mouse model for multiple sclerosis, C57BL/6 mice (8 per group) are immunized subcutaneously three times at two weeks intervals with 50 µg Qβ-mIL-1β$_{119-269}$ or 50 µg of Qβ VLPs alone. One week after the last immunization all mice are injected subcutaneously with 100 µg MOG peptide (MEVGWYRSPFSRVVHLYRNGK, SEQ ID NO:191) mixed with complete Freund's adjuvant. On the same day and two days later all mice are injected intraperitoneally with 400 ng of pertussis toxin. Mice are scored on a daily basis for development of neurological symptoms according to the following scheme: 0, no clinical disease; 0.5, end of tail limp; 1, tail completely limp; 1.5, limp tail and hind limb weakness (unsteady gait and poor grip of hind legs); 2, unilateral partial hind limb paralysis; 2.5, bilateral partial hind limb paralysis; 3, complete bilateral hind limb paralysis; 3.5, complete bilateral hind limb paralysis and unilateral front limb paralysis; 4, total paralysis of hind and front limbs. Qβ-mIL-1β$_{119-269}$-immunized mice show clearly reduced clinical symptoms when compared to Qβ-immunized mice.

Example 15

A Cloning, Expression and Purification of Mouse IL-1α$_{115-270}$ and Mouse IL-1α$_{115-270 (D}$145K)

The Nucleotide Sequence Encoding Amino Acids 115-270 of Wild Type Murine IL-1α was amplified by PCR from a library of TNFα-activated murine macrophages using oligonucleotides IL 1α1C (5'-ATATATCATA TGTCTGCCCC TTACACCTAC CAGAGTG-3': SEQ ID NO:196) and IL1α2 (5'-ATATATCTCG AGTGATATCT GGAAGTCTGT CATAGAG-3'; SEQ ID NO:25). The DNA fragment was digested with NheI and XhoI, and cloned into the expression vector pET42T(+), giving rise to the expression plasmid pET42T-mIL-1α$_{115-270}$.

By site directed mutagenesis of the latter plasmid, an expression vector for the mutein mIL-1α$_{115-270}$ (D145K) was constructed. Using the oligonucleotide pair alphaD145K-1: (5'-GGACTGCCCTCTATGACAAAATTCCA-GATATCACTCGAG-3; SEQ ID NO:197) alphaD145K-2 (5'-CTCGAGTGATATCTGGAATTTTGTCATA-GAGGGCAGTCC-3'; SEQ ID NO:198) and the QuikChange® Site directed mutagenesis kit (Stratagene), the D 145K mutation was introduced. Expression and purification of wild type mouse IL-1α$_{115-270}$ and the mutein mouse IL-1α$_{115-270}$ (D145K) was performed as described in EXAMPLE 1.

B Cloning, Expression and Purification of Human IL-1α$_{119-271}$ and Human IL-1α$_{119-271 (D}$145K)

The Nucleotide Sequence Encoding Amino Acids 119-271 of Wild Type Human IL-1α was amplified by PCR from a LPS-activated human B cell cDNA library using oligonucleotides HIL-3 (5'-ATATATCATA TGCTGAGCAA TGTGAAATAC AACTTTATG-3'; SEQ ID NO:141) and HIL-4 (5'-ATATATCTCG AGCGCCTGGT TTTCCAGTAT CTGAAAG-3'; SEQ ID NO:142). The DNA fragment was digested with NheI and XhoI, and cloned into the expression vector pET42T(+), giving rise to the expression plasmid pET42T-hIL-1α$_{119-271}$.

By site directed mutagenesis of the latter plasmid, an expression vector for the mutein hIL-1α$_{119-271}$ (D145K) was constructed. Using the oligonucleotide pair halphaD145K-1 (5'-GGGCCACCCT CTATCACTAA ATTTCAGATA CTG-GAAAACC-3': SEQ ID NO:199) and halphaD145K-2 (5'-GGTTTTCCAG TATCTGAAAT TTAGTGATAG AGGGTGGCCC-3'; SEQ ID NO:200) and the QuikChange® Site directed mutagenesis kit (Stratagene), the D145K mutation was introduced. Expression and purification of wild type human IL-1α$_{119-271}$ and the human IL-1α$_{119-271}$ (D145K) mutein was performed as described in EXAMPLE 1.

Example 16

A. Biological Activity of Human IL-1α$_{119-271}$, Human IL-1α$_{119-271}$ (D145K), Mouse IL-1α$_{115-270}$, and mouse IL-1α$_{115-270}$ (D145K) in Human PBMC

PBMC from a healthy donor (5×10$^5$ cells per well) were incubated with titrating amounts of either the wild type human IL-1α$_{119-271}$ protein, the human IL-1α$_{119-271}$ (D145K) mutein, the wild type mouse IL-1α$_{115-270}$ protein, or the mouse IL-1α$_{115-270}$ (D145K) mutein. After over night incubation the amount of IL-6 in the cell culture supernatant was measured by Sandwich ELISA as readout of the biological activity of the different proteins. Table 8 shows that 21 fold higher amounts of the mouse IL-1α$_{115-270}$ (D145K) mutein were required to induce the same amount of IL-6 as the corresponding wild type mouse IL-1α$_{115-270}$ protein. In the case of the human IL-1α$_{119-271}$ (D145K) mutein 46-fold higher amounts than the wild type human IL-1α$_{119-271}$ protein were required. This demonstrates that both the human IL-1α$_{119-271}$ (D145K) mutein and the mouse IL-1α$_{115-270}$ (D145K) mutein have reduced bioactivity in human cells as compared to their wild type counterparts.

TABLE 8

Biological activity of IL-1α wild type proteins and muteins in human PBMC as determined by IL-6 induction.

| Protein/mutein (expressed with SEQ ID NO: 201 as C-terminal tag) | Protein/mutein concentration required to induce 600 pg/ml IL-6 from human PBMC (ng/ml) |
|---|---|
| mouse IL-1α$_{115-270}$ (SEQ ID NO: 202) | 4.7 |
| mouse IL-1α$_{115-270}$ (D145K) (SEQ ID NO: 204) | 100 |
| human IL-1α$_{119-271}$ (SEQ ID NO: 203) | 0.8 |
| human IL-1α$_{119-271}$ (D145K) (SEQ ID NO: 210) | 37 |

B. Biological Activity of Human IL-1α$_{119-271}$, Human IL-1α$_{119-271}$ (D145K), Mouse IL-1α$_{115-270}$ Protein, and Mouse IL-1α$_{115-270}$ (D145K) in Mice

Four female Balb/c mice per group were injected intravenously with 10 ng of either the wild type human IL-1α$_{119-271}$ protein, the human IL-1α$_{119-271}$ (D145K) mutein, the wild type mouse IL-1α$_{115-270}$ protein, or the mouse IL-1α$_{115-270}$ (D145K) mutein. Three hours after injection serum amyloid A (SAA) was measured in serum of injected mice as readout of the bioactivity of the respective protein. As shown in Table 9 the mouse IL-1α$_{115-270}$ (D145K) mutein induced 53% less SAA than the corresponding wild type mouse IL-1α$_{115-270}$ protein (p<0.05, Student t-test) and the human IL-1α$_{119-271}$ (D145K) mutein induced 67% less SAA than the corresponding wild type human IL-1α$_{119-271}$ protein (p<0.001 Student t-test). This demonstrates that both the human IL-1α$_{119-271}$ (D145K) mutein and the mouse IL-1α$_{115-270}$ (D145K) mutein have reduced bioactivity in mice when compared to their wild type counterparts.

TABLE 9

Biological activity of IL-1α wild type proteins and muteins in mice determined by SAA.

| Protein/mutein | Serum SAA concentration (μg/ml) 3 h after protein/mutein injection (±SD) |
|---|---|
| mouse IL-1α$_{115-270}$ (SEQ ID NO: 202) | 115 ± 32 |
| mouse IL-1α$_{115-270}$ (D145K) (SEQ ID NO: 204) | 55 ± 10 |
| human IL-1α$_{119-271}$ (SEQ ID NO: 203) | 92 ± 20 |
| human IL-1α$_{119-271}$ (D145K) (SEQ ID NO: 210) | 31 ± 2 |

Example 17

Efficacy of mIL-1β$_{119-269}$ and mIL-1 α$_{115-270}$ Muteins Coupled to Qβ in a Mouse Model of Rheumatoid Arthritis Mouse IL-1β$_{119-269}$ muteins and mouse IL-1 α$_{115-270}$ muteins carrying the mutations of the corresponding human muteins of SEQ ID NO:131 to 140 and SEQ ID NO:205 to 218 are created according to table 10 and coupled to Qβ. The efficacy of mIL-1β$_{119-269}$ and mIL-1 α$_{115-270}$ muteins coupled to Qβ is tested in the murine collagen-induced arthritis model (CIA). Male DBA/1 mice are immunized subcutaneously three times (days 0, 14 and 28) with 50 μg of either Qβ-mIL-1β$_{119-269}$ mutein, Qβ-mIL-1α$_{115-270}$ mutein or Qβ alone, and then injected intradermally at day 42 with 200 μg bovine type II collagen mixed with complete Freund's adjuvant. After a booster injection of 200 μg bovine type II collagen mixed with incomplete Freund's adjuvant at day 63 mice were examined on a daily basis for the development of arthritis symptoms.

A clinical score was assigned to each limb as defined in Example 2F. Two weeks after the second collagen injection Qβ-mIL-1β$_{119-269}$ mutein and Qβ-mIL-1α$_{115-270}$ mutein immunized mice show strongly reduced clinical scores as compared to Qβ-immunized mice.

TABLE 10

Mouse IL-1 beta and Mouse IL-1 alpha muteins corresponding to preferred human IL-1 beta muteins (SEQ ID NO: 131 to 140 and SEQ ID NO: 205 to 209) and human IL-1 alpha muteins (SEQ ID NO: 210 to 218) are created according to this table and tested in the mouse model of rheumatoid arthritis.

| Human hIL-1beta 116-269 muteins | Amino acid changes introduced in mouse IL-1beta 119-269 (SEQ ID NO: 164) in order to obtain the corresponding mutation |
|---|---|
| R4D (SEQ ID NO: 131) | Exchange arginine at position 3 to aspartate |
| L6A (SEQ ID NO: 132) | Exchange leucine at position 5 to alanine |
| T9G (SEQ ID NO: 133) | Exchange arginine at position 8 to glycine |
| R11G (SEQ ID NO: 134) | Exchange arginine at position 10 to glycine |
| D54R (SEQ ID NO: 135) | Exchange aspartate at position 53 to arginine |
| D145K (SEQ ID NO: 136) | Exchange aspartate at position 143 to lysine |
| ΔEE50, 51 (SEQ ID NO: 137) | Delete glutamate, proline at positions 49, 50 |
| ΔSND52-54 (SEQ ID NO: 138) | Delete serine, asparagine, aspartate at positions 51 to 53 |
| K63S/K65S (SEQ ID NO: 139) | Exchange lysines at positions 62 and 64 to serines |
| Q126A/E128A (SEQ ID NO: 140) | Exchange glutamine at position 125 to alanine and glutamate at position 127 to alanine |
| K88N (SEQ ID NO: 205) | Exchange lysine at position 87 to asparagine |
| R98Q (SEQ ID NO: 206) | Exchange arginine at position 97 to glutamine |
| K103L (SEQ ID NO: 207) | Exchange lysine at position 102 to leucine |
| ΔKKK92-94 (SEQ ID NO: 208) | Delete lysine, lysine, lysine at positions 91 to 93 |
| L10N (SEQ ID NO: 209) | Exchange leucine at position 9 to asparagine |
| Human hIL-1alpha 119-271 muteins | Amino acid changes introduced in mouse IL-1alpha 115-270 (SEQ ID NO: 202) in order to obtain corresponding mutation |
| D145K (SEQ ID NO: 210) | Exchange aspartate at position 153 to lysine |
| L18K (SEQ ID NO: 211) | Exchange methionine at position 25 to lysine |
| F146N (SEQ ID NO: 212) | Exchange phenylalanine at position 154 to asparagine |
| R10A (SEQ ID NO: 213) | Exchange lysine at position 17 to alanine |
| I62A (SEQ ID NO: 214) | Exchange tyrosine at position 70 to alanine |
| W107F (SEQ ID NO: 215) | Exchange tryptophane at position 115 to phenylalanine |
| D20V (SEQ ID NO: 216) | Exchange aspartate at position 27 to valine |
| ΔFIL16-18 (SEQ ID NO: 217) | Delete phenylalanine, valine, methionine at positions 23 to 25 |
| ΔITGS96-99 (SEQ ID NO: 218) | Delete isoleucine, threonine, glycine, serine at positions 104 to 107 |

---

What is claimed is:

1. A composition comprising:
   (a) a virus-like particle (VLP) with at least one first attachment site; and
   (b) at least one antigen with at least one second attachment site;
   wherein said at least one antigen is an IL-1 beta mutein comprising the amino acid sequence of SEQ ID NO:136, and wherein (a) and (b) are linked through said at least one first and said at least one second attachment site.

2. The composition of claim 1, wherein said IL-1 beta mutein consists of the amino acid sequence of SEQ ID NO:136.

3. The composition of claim 1, wherein said VLP comprises recombinant coat proteins of an RNA bacteriophage or mutants or fragments thereof.

4. The composition of claim 1, wherein said VLP is a VLP of an RNA bacteriophage.

5. The composition of claim 1, wherein said VLP is a VLP of RNA bacteriophage Qβ.

6. The composition of claim 1, wherein said first attachment site is linked to said second attachment site via at least one non-peptide covalent bond.

7. The composition of claims 1, wherein said first attachment site is an amino group of a lysine, and wherein said second attachment site is a sulfhydryl group of a cysteine.

8. The composition of claim 1, wherein only one of said second attachment sites associates with said first attachment site through at least one non-peptide covalent bond leading to a single and uniform type of binding of said IL-1 mutein to said virus-like particle, wherein said only one second attachment site that associates with said first attachment site is a sulfhydryl group, and wherein said IL-1 mutein and said core particle interact through said association to form an ordered and repetitive antigen array.

9. A pharmaceutical composition comprising:

(a) the composition of claim 1; and (b) pharmaceutically acceptable carrier.

10. The composition of claim 3, wherein said recombinant coat proteins consist of the amino acid sequence of SEQ ID NO:3.

11. A method of treating rheumatoid arthritis in an animal, said method comprising administering a therapeutically effective amount of the composition of claim 1 to said animal.

12. The method of claim 11, wherein said animal is a human.

13. The composition of claim 5, wherein said VLP of RNA bacteriophage Qβ comprises recombinant coat proteins consisting of the amino acid sequence of SEQ ID NO:3.

14. The composition of claim 13, wherein said first attachment site is linked to said second attachment site via at least one non-peptide covalent bond.

15. The composition of claim 14, wherein said first attachment site is an amino group of a lysine, and wherein said second attachment site is a sulfhydryl group of a cysteine.

16. The composition of claim 15 further comprising a heterobifunctional cross-linker.

17. The composition of claim 16, wherein said heterobifunctional cross-linker is succinimidyl-6-[β-maleimidopropionamido]hexanoate (SMPH).

18. The composition of claim 17, wherein said IL-1 beta mutein consists of the amino acid sequence of SEQ ID NO:136.

19. The composition of claim 18 further comprising a linker, wherein said linker comprises said second attachment site, and wherein said linker is associated to said IL-1 beta mutein via a peptide bond.

20. The composition of claim 19, wherein said linker is added to the C-terminus of said IL-1 beta mutein, and said linker consists of GGCG (SEQ ID NO:188).

* * * * *

SEQUENCE LISTING

<160> NUMBER OF SEQ ID NOS: 218

<210> SEQ ID NO 1
<211> LENGTH: 185
<212> TYPE: PRT
<213> ORGANISM: Hepatitis B virus

<400> SEQUENCE: 1

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

```
Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Thr Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Asn Ala Pro Ile Leu Ser Thr Leu Pro
    130                 135                 140

Glu Thr Thr Val Val Arg Arg Arg Asp Arg Gly Arg Ser Pro Arg Arg
145                 150                 155                 160

Arg Thr Pro Ser Pro Arg Arg Arg Arg Ser Gln Ser Pro Arg Arg Arg
                165                 170                 175

Arg Ser Gln Ser Arg Glu Ser Gln Cys
            180                 185

<210> SEQ ID NO 2
<211> LENGTH: 188
<212> TYPE: PRT
<213> ORGANISM: Hepatitis B virus

<400> SEQUENCE: 2

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ala Ala Leu Tyr Arg Asp Ala Leu Glu Ser Pro Glu His Cys
        35                  40                  45

Ser Pro His His Thr Ala Leu Arg Gln Ala Ile Leu Cys Trp Gly Asp
    50                  55                  60

Leu Met Thr Leu Ala Thr Trp Val Gly Thr Asn Leu Glu Asp Gly Gly
65                  70                  75                  80

Lys Gly Gly Ser Arg Asp Leu Val Val Ser Tyr Val Asn Thr Asn Val
                85                  90                  95

Gly Leu Lys Phe Arg Gln Leu Leu Trp Phe His Ile Ser Cys Leu Thr
            100                 105                 110

Phe Gly Arg Glu Thr Val Leu Glu Tyr Leu Val Ser Phe Gly Val Trp
        115                 120                 125

Ile Arg Thr Pro Pro Ala Tyr Arg Pro Pro Asn Ala Pro Ile Leu Ser
    130                 135                 140

Thr Leu Pro Glu Thr Thr Val Val Arg Arg Arg Asp Arg Gly Arg Ser
145                 150                 155                 160

Pro Arg Arg Arg Thr Pro Ser Pro Arg Arg Arg Arg Ser Gln Ser Pro
                165                 170                 175

Arg Arg Arg Arg Ser Gln Ser Arg Glu Ser Gln Cys
            180                 185

<210> SEQ ID NO 3
<211> LENGTH: 132
<212> TYPE: PRT
<213> ORGANISM: Bacteriophage Qbeta

<400> SEQUENCE: 3

Ala Lys Leu Glu Thr Val Thr Leu Gly Asn Ile Gly Lys Asp Gly Lys
```

```
                1               5                  10                 15
Gln Thr Leu Val Leu Asn Pro Arg Gly Val Asn Pro Thr Asn Gly Val
                    20                 25                 30

Ala Ser Leu Ser Gln Ala Gly Ala Val Pro Ala Leu Glu Lys Arg Val
                    35                 40                 45

Thr Val Ser Val Ser Gln Pro Ser Arg Asn Arg Lys Asn Tyr Lys Val
                    50                 55                 60

Gln Val Lys Ile Gln Asn Pro Thr Ala Cys Thr Ala Asn Gly Ser Cys
 65                     70                 75                 80

Asp Pro Ser Val Thr Arg Gln Ala Tyr Ala Asp Val Thr Phe Ser Phe
                    85                 90                 95

Thr Gln Tyr Ser Thr Asp Glu Glu Arg Ala Phe Val Arg Thr Glu Leu
                   100                105                110

Ala Ala Leu Leu Ala Ser Pro Leu Leu Ile Asp Ala Ile Asp Gln Leu
                   115                120                125

Asn Pro Ala Tyr
                   130

<210> SEQ ID NO 4
<211> LENGTH: 329
<212> TYPE: PRT
<213> ORGANISM: Bacteriophage Qbeta

<400> SEQUENCE: 4

Met Ala Lys Leu Glu Thr Val Thr Leu Gly Asn Ile Gly Lys Asp Gly
 1               5                  10                 15

Lys Gln Thr Leu Val Leu Asn Pro Arg Gly Val Asn Pro Thr Asn Gly
                    20                 25                 30

Val Ala Ser Leu Ser Gln Ala Gly Ala Val Pro Ala Leu Glu Lys Arg
                    35                 40                 45

Val Thr Val Ser Val Ser Gln Pro Ser Arg Asn Arg Lys Asn Tyr Lys
                    50                 55                 60

Val Gln Val Lys Ile Gln Asn Pro Thr Ala Cys Thr Ala Asn Gly Ser
 65                     70                 75                 80

Cys Asp Pro Ser Val Thr Arg Gln Ala Tyr Ala Asp Val Thr Phe Ser
                    85                 90                 95

Phe Thr Gln Tyr Ser Thr Asp Glu Glu Arg Ala Phe Val Arg Thr Glu
                   100                105                110

Leu Ala Ala Leu Leu Ala Ser Pro Leu Leu Ile Asp Ala Ile Asp Gln
                   115                120                125

Leu Asn Pro Ala Tyr Trp Thr Leu Leu Ile Ala Gly Gly Gly Ser Gly
                   130                135                140

Ser Lys Pro Asp Pro Val Ile Pro Asp Pro Pro Ile Asp Pro Pro Pro
145                    150                155                160

Gly Thr Gly Lys Tyr Thr Cys Pro Phe Ala Ile Trp Ser Leu Glu Glu
                   165                170                175

Val Tyr Glu Pro Pro Thr Lys Asn Arg Pro Trp Pro Ile Tyr Asn Ala
                   180                185                190

Val Glu Leu Gln Pro Arg Glu Phe Asp Val Ala Leu Lys Asp Leu Leu
                   195                200                205

Gly Asn Thr Lys Trp Arg Asp Trp Asp Ser Arg Leu Ser Tyr Thr Thr
                   210                215                220

Phe Arg Gly Cys Arg Gly Asn Gly Tyr Ile Asp Leu Asp Ala Thr Tyr
225                    230                235                240

Leu Ala Thr Asp Gln Ala Met Arg Asp Gln Lys Tyr Asp Ile Arg Glu
```

```
                        245                 250                 255
Gly Lys Lys Pro Gly Ala Phe Gly Asn Ile Glu Arg Phe Ile Tyr Leu
            260                 265                 270

Lys Ser Ile Asn Ala Tyr Cys Ser Leu Ser Asp Ile Ala Ala Tyr His
        275                 280                 285

Ala Asp Gly Val Ile Val Gly Phe Trp Arg Asp Pro Ser Ser Gly Gly
    290                 295                 300

Ala Ile Pro Phe Asp Phe Thr Lys Phe Asp Lys Thr Lys Cys Pro Ile
305                 310                 315                 320

Gln Ala Val Ile Val Val Pro Arg Ala
            325

<210> SEQ ID NO 5
<211> LENGTH: 129
<212> TYPE: PRT
<213> ORGANISM: Bacteriophage R17

<400> SEQUENCE: 5

Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr

<210> SEQ ID NO 6
<211> LENGTH: 130
<212> TYPE: PRT
<213> ORGANISM: Bacteriophage fr

<400> SEQUENCE: 6

Met Ala Ser Asn Phe Glu Glu Phe Val Leu Val Asp Asn Gly Gly Thr
1               5                   10                  15

Gly Asp Val Lys Val Ala Pro Ser Asn Phe Ala Asn Gly Val Ala Glu
            20                  25                  30

Trp Ile Ser Ser Asn Ser Arg Ser Gln Ala Tyr Lys Val Thr Cys Ser
        35                  40                  45

Val Arg Gln Ser Ser Ala Asn Asn Arg Lys Tyr Thr Val Lys Val Glu
    50                  55                  60

Val Pro Lys Val Ala Thr Gln Val Gln Gly Gly Val Glu Leu Pro Val
65                  70                  75                  80

Ala Ala Trp Arg Ser Tyr Met Asn Met Glu Leu Thr Ile Pro Val Phe
                85                  90                  95

Ala Thr Asn Asp Asp Cys Ala Leu Ile Val Lys Ala Leu Gln Gly Thr
            100                 105                 110
```

Phe Lys Thr Gly Asn Pro Ile Ala Thr Ala Ile Ala Ala Asn Ser Gly
            115                 120                 125

Ile Tyr
    130

<210> SEQ ID NO 7
<211> LENGTH: 130
<212> TYPE: PRT
<213> ORGANISM: Bacteriophage GA

<400> SEQUENCE: 7

Met Ala Thr Leu Arg Ser Phe Val Leu Val Asp Asn Gly Gly Thr Gly
1               5                   10                  15

Asn Val Thr Val Val Pro Val Ser Asn Ala Asn Gly Val Ala Glu Trp
            20                  25                  30

Leu Ser Asn Asn Ser Arg Ser Gln Ala Tyr Arg Val Thr Ala Ser Tyr
        35                  40                  45

Arg Ala Ser Gly Ala Asp Lys Arg Lys Tyr Ala Ile Lys Leu Glu Val
    50                  55                  60

Pro Lys Ile Val Thr Gln Val Val Asn Gly Val Glu Leu Pro Gly Ser
65                  70                  75                  80

Ala Trp Lys Ala Tyr Ala Ser Ile Asp Leu Thr Ile Pro Ile Phe Ala
                85                  90                  95

Ala Thr Asp Asp Val Thr Val Ile Ser Lys Ser Leu Ala Gly Leu Phe
            100                 105                 110

Lys Val Gly Asn Pro Ile Ala Glu Ala Ile Ser Ser Gln Ser Gly Phe
        115                 120                 125

Tyr Ala
    130

<210> SEQ ID NO 8
<211> LENGTH: 132
<212> TYPE: PRT
<213> ORGANISM: Bacteriophage SP

<400> SEQUENCE: 8

Met Ala Lys Leu Asn Gln Val Thr Leu Ser Lys Ile Gly Lys Asn Gly
1               5                   10                  15

Asp Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Phe Lys
    50                  55                  60

Val Gln Ile Lys Leu Gln Asn Pro Thr Ala Cys Thr Arg Asp Ala Cys
65                  70                  75                  80

Asp Pro Ser Val Thr Arg Ser Ala Phe Ala Asp Val Thr Leu Ser Phe
                85                  90                  95

Thr Ser Tyr Ser Thr Asp Glu Glu Arg Ala Leu Ile Arg Thr Glu Leu
            100                 105                 110

Ala Ala Leu Leu Ala Asp Pro Leu Ile Val Asp Ala Ile Asp Asn Leu
        115                 120                 125

Asn Pro Ala Tyr
    130

<210> SEQ ID NO 9
<211> LENGTH: 329
<212> TYPE: PRT

<213> ORGANISM: Bacteriophage SP

<400> SEQUENCE: 9

```
Ala Lys Leu Asn Gln Val Thr Leu Ser Lys Ile Gly Lys Asn Gly Asp
1               5                   10                  15
Gln Thr Leu Thr Leu Thr Pro Arg Gly Val Asn Pro Thr Asn Gly Val
            20                  25                  30
Ala Ser Leu Ser Glu Ala Gly Ala Val Pro Ala Leu Glu Lys Arg Val
        35                  40                  45
Thr Val Ser Val Ala Gln Pro Ser Arg Asn Arg Lys Asn Phe Lys Val
    50                  55                  60
Gln Ile Lys Leu Gln Asn Pro Thr Ala Cys Thr Arg Asp Ala Cys Asp
65                  70                  75                  80
Pro Ser Val Thr Arg Ser Ala Phe Ala Asp Val Thr Leu Ser Phe Thr
                85                  90                  95
Ser Tyr Ser Thr Asp Glu Glu Arg Ala Leu Ile Arg Thr Glu Leu Ala
            100                 105                 110
Ala Leu Leu Ala Asp Pro Leu Ile Val Asp Ala Ile Asp Asn Leu Asn
        115                 120                 125
Pro Ala Tyr Trp Ala Ala Leu Leu Val Ala Ser Ser Gly Gly Gly Asp
    130                 135                 140
Asn Pro Ser Asp Pro Asp Val Pro Val Val Pro Asp Val Lys Pro Pro
145                 150                 155                 160
Asp Gly Thr Gly Arg Tyr Lys Cys Pro Phe Ala Cys Tyr Arg Leu Gly
                165                 170                 175
Ser Ile Tyr Glu Val Gly Lys Glu Gly Ser Pro Asp Ile Tyr Glu Arg
            180                 185                 190
Gly Asp Glu Val Ser Val Thr Phe Asp Tyr Ala Leu Glu Asp Phe Leu
        195                 200                 205
Gly Asn Thr Asn Trp Arg Asn Trp Asp Gln Arg Leu Ser Asp Tyr Asp
    210                 215                 220
Ile Ala Asn Arg Arg Arg Cys Arg Gly Asn Gly Tyr Ile Asp Leu Asp
225                 230                 235                 240
Ala Thr Ala Met Gln Ser Asp Asp Phe Val Leu Ser Gly Arg Tyr Gly
                245                 250                 255
Val Arg Lys Val Lys Phe Pro Gly Ala Phe Gly Ser Ile Lys Tyr Leu
            260                 265                 270
Leu Asn Ile Gln Gly Asp Ala Trp Leu Asp Leu Ser Glu Val Thr Ala
        275                 280                 285
Tyr Arg Ser Tyr Gly Met Val Ile Gly Phe Trp Thr Asp Ser Lys Ser
    290                 295                 300
Pro Gln Leu Pro Thr Asp Phe Thr Gln Phe Asn Ser Ala Asn Cys Pro
305                 310                 315                 320
Val Gln Thr Val Ile Ile Pro Ser
                325
```

<210> SEQ ID NO 10
<211> LENGTH: 130
<212> TYPE: PRT
<213> ORGANISM: Bacteriophage MS2

<400> SEQUENCE: 10

```
Met Ala Ser Asn Phe Thr Gln Phe Val Leu Val Asp Asn Gly Gly Thr
1               5                   10                  15
Gly Asp Val Thr Val Ala Pro Ser Asn Phe Ala Asn Gly Val Ala Glu
            20                  25                  30
```

Trp Ile Ser Ser Asn Ser Arg Ser Gln Ala Tyr Lys Val Thr Cys Ser
            35                  40                  45

Val Arg Gln Ser Ser Ala Gln Asn Arg Lys Tyr Thr Ile Lys Val Glu
 50                  55                  60

Val Pro Lys Val Ala Thr Gln Thr Val Gly Gly Val Glu Leu Pro Val
 65                  70                  75                  80

Ala Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
            115                 120                 125

Ile Tyr
    130

<210> SEQ ID NO 11
<211> LENGTH: 133
<212> TYPE: PRT
<213> ORGANISM: Bacteriophage M11

<400> SEQUENCE: 11

Met Ala Lys Leu Gln Ala Ile Thr Leu Ser Gly Ile Gly Lys Lys Gly
  1               5                  10                  15

Asp Val Thr Leu Asp Leu Asn Pro Arg Gly Val Asn Pro Thr Asn Gly
             20                  25                  30

Val Ala Ala Leu Ser Glu Ala Gly Ala Val Pro Ala Leu Glu Lys Arg
            35                  40                  45

Val Thr Ile Ser Val Ser Gln Pro Ser Arg Asn Arg Lys Asn Tyr Lys
 50                  55                  60

Val Gln Val Lys Ile Gln Asn Pro Thr Ser Cys Thr Ala Ser Gly Thr
 65                  70                  75                  80

Cys Asp Pro Ser Val Thr Arg Ser Ala Tyr Ser Asp Val Thr Phe Ser
                85                  90                  95

Phe Thr Gln Tyr Ser Thr Val Glu Glu Arg Ala Leu Val Arg Thr Glu
            100                 105                 110

Leu Gln Ala Leu Leu Ala Asp Pro Met Leu Val Asn Ala Ile Asp Asn
            115                 120                 125

Leu Asn Pro Ala Tyr
            130

<210> SEQ ID NO 12
<211> LENGTH: 133
<212> TYPE: PRT
<213> ORGANISM: Bacteriophage MX1

<400> SEQUENCE: 12

Met Ala Lys Leu Gln Ala Ile Thr Leu Ser Gly Ile Gly Lys Asn Gly
  1               5                  10                  15

Asp Val Thr Leu Asn Leu Asn Pro Arg Gly Val Asn Pro Thr Asn Gly
             20                  25                  30

Val Ala Ala Leu Ser Glu Ala Gly Ala Val Pro Ala Leu Glu Lys Arg
            35                  40                  45

Val Thr Ile Ser Val Ser Gln Pro Ser Arg Asn Arg Lys Asn Tyr Lys
 50                  55                  60

Val Gln Val Lys Ile Gln Asn Pro Thr Ser Cys Thr Ala Ser Gly Thr
 65                  70                  75                  80

```
Cys Asp Pro Ser Val Thr Arg Ser Ala Tyr Ala Asp Val Thr Phe Ser
                85                  90                  95

Phe Thr Gln Tyr Ser Thr Asp Glu Glu Arg Ala Leu Val Arg Thr Glu
            100                 105                 110

Leu Lys Ala Leu Leu Ala Asp Pro Met Leu Ile Asp Ala Ile Asp Asn
        115                 120                 125

Leu Asn Pro Ala Tyr
    130

<210> SEQ ID NO 13
<211> LENGTH: 330
<212> TYPE: PRT
<213> ORGANISM: Bacteriophage NL95

<400> SEQUENCE: 13

Met Ala Lys Leu Asn Lys Val Thr Leu Thr Gly Ile Gly Lys Ala Gly
1               5                   10                  15

Asn Gln Thr Leu Thr Leu Thr Pro Arg Gly Val Asn Pro Thr Asn Gly
            20                  25                  30

Val Ala Ser Leu Ser Glu Ala Gly Ala Val Pro Ala Leu Glu Lys Arg
        35                  40                  45

Val Thr Val Ser Val Ala Gln Pro Ser Arg Asn Arg Lys Asn Tyr Lys
    50                  55                  60

Val Gln Ile Lys Leu Gln Asn Pro Thr Ala Cys Thr Lys Asp Ala Cys
65                  70                  75                  80

Asp Pro Ser Val Thr Arg Ser Gly Ser Arg Asp Val Thr Leu Ser Phe
                85                  90                  95

Thr Ser Tyr Ser Thr Glu Arg Glu Arg Ala Leu Ile Arg Thr Glu Leu
            100                 105                 110

Ala Ala Leu Leu Lys Asp Asp Leu Ile Val Asp Ala Ile Asp Asn Leu
        115                 120                 125

Asn Pro Ala Tyr Trp Ala Ala Leu Leu Ala Ala Ser Pro Gly Gly Gly
    130                 135                 140

Asn Asn Pro Tyr Pro Gly Val Pro Asp Ser Pro Asn Val Lys Pro Pro
145                 150                 155                 160

Gly Gly Thr Gly Thr Tyr Arg Cys Pro Phe Ala Cys Tyr Arg Arg Gly
                165                 170                 175

Glu Leu Ile Thr Glu Ala Lys Asp Gly Ala Cys Ala Leu Tyr Ala Cys
            180                 185                 190

Gly Ser Glu Ala Leu Val Glu Phe Glu Tyr Ala Leu Glu Asp Phe Leu
        195                 200                 205

Gly Asn Glu Phe Trp Arg Asn Trp Asp Gly Arg Leu Ser Lys Tyr Asp
    210                 215                 220

Ile Glu Thr His Arg Arg Cys Arg Gly Asn Gly Tyr Val Asp Leu Asp
225                 230                 235                 240

Ala Ser Val Met Gln Ser Asp Glu Tyr Val Leu Ser Gly Ala Tyr Asp
                245                 250                 255

Val Val Lys Met Gln Pro Pro Gly Thr Phe Asp Ser Pro Arg Tyr Tyr
            260                 265                 270

Leu His Leu Met Asp Gly Ile Tyr Val Asp Leu Ala Glu Val Thr Ala
        275                 280                 285

Tyr Arg Ser Tyr Gly Met Val Ile Gly Phe Trp Thr Asp Ser Lys Ser
    290                 295                 300

Pro Gln Leu Pro Thr Asp Phe Thr Arg Phe Asn Arg His Asn Cys Pro
305                 310                 315                 320
```

-continued

```
Val Gln Thr Val Ile Val Ile Pro Ser Leu
                325                 330
```

<210> SEQ ID NO 14
<211> LENGTH: 129
<212> TYPE: PRT
<213> ORGANISM: Bacteriophage f2

<400> SEQUENCE: 14

```
Ala Ser Asn Phe Thr Gln Phe Val Leu Val Asn Asp Gly Gly Thr Gly
1               5                   10                  15

Asn Val Thr Val Ala Pro Ser Asn Phe Ala Asn Gly Val Ala Glu Trp
                20                  25                  30

Ile Ser Ser Asn Ser Arg Ser Gln Ala Tyr Lys Val Thr Cys Ser Val
            35                  40                  45

Arg Gln Ser Ser Ala Gln Asn Arg Lys Tyr Thr Ile Lys Val Glu Val
        50                  55                  60

Pro Lys Val Ala Thr Gln Thr Val Gly Gly Val Glu Leu Pro Val Ala
65                  70                  75                  80

Ala Trp Arg Ser Tyr Leu Asn Leu Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr
```

<210> SEQ ID NO 15
<211> LENGTH: 128
<212> TYPE: PRT
<213> ORGANISM: Bacteriophage PP7

<400> SEQUENCE: 15

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
                20                  25                  30

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
        50                  55                  60

Val Val Asp Cys Ser Thr Ser Val Cys Gly Glu Leu Pro Lys Val Arg
65                  70                  75                  80

Tyr Thr Gln Val Trp Ser His Asp Val Thr Ile Val Ala Asn Ser Thr
                85                  90                  95

Glu Ala Ser Arg Lys Ser Leu Tyr Asp Leu Thr Lys Ser Leu Val Ala
            100                 105                 110

Thr Ser Gln Val Glu Asp Leu Val Val Asn Leu Val Pro Leu Gly Arg
        115                 120                 125
```

<210> SEQ ID NO 16
<211> LENGTH: 132
<212> TYPE: PRT
<213> ORGANISM: Bacteriophage Qbeta

<400> SEQUENCE: 16

```
Ala Lys Leu Glu Thr Val Thr Leu Gly Asn Ile Gly Arg Asp Gly Lys
1               5                   10                  15
```

```
Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 17
<211> LENGTH: 132
<212> TYPE: PRT
<213> ORGANISM: Bacteriophage Qbeta

<400> SEQUENCE: 17

Ala Lys Leu Glu Thr Val Thr Leu Gly Lys Ile Gly Lys Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
            115                 120                 125

Asn Pro Ala Tyr
        130

<210> SEQ ID NO 18
<211> LENGTH: 132
<212> TYPE: PRT
<213> ORGANISM: Bacteriophage Qbeta

<400> SEQUENCE: 18

Ala Arg Leu Glu Thr Val Thr Leu Gly Asn Ile Gly Arg Asp Gly Lys
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
            35                  40                  45

Thr Val Ser Val Ser Gln Pro Ser Arg Asn Arg Lys Asn Tyr Lys Val
        50                  55                  60

Gln Val Lys Ile Gln Asn Pro Thr Ala Cys Thr Ala Asn Gly Ser Cys
```

```
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 19
<211> LENGTH: 132
<212> TYPE: PRT
<213> ORGANISM: Bacteriophage Qbeta

<400> SEQUENCE: 19

Ala Lys Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125

Asn Pro Ala Tyr
        130

<210> SEQ ID NO 20
<211> LENGTH: 132
<212> TYPE: PRT
<213> ORGANISM: Bacteriophage Qbeta

<400> SEQUENCE: 20

Ala Arg Leu Glu Thr Val Thr Leu Gly Asn Ile Gly Lys Asp Gly Arg
1               5                   10                  15

Gln Thr Leu Val Leu Asn Pro Arg Gly Val Asn Pro Thr Asn Gly Val
            20                  25                  30

Ala Ser Leu Ser Gln Ala Gly Ala Val Pro Ala Leu Glu Lys Arg Val
        35                  40                  45

Thr Val Ser Val Ser Gln Pro Ser Arg Asn Arg Lys Asn Tyr Lys Val
    50                  55                  60

Gln Val Lys Ile Gln Asn Pro Thr Ala Cys Thr Ala Asn Gly Ser Cys
65                  70                  75                  80

Asp Pro Ser Val Thr Arg Gln Lys Tyr Ala Asp Val Thr Phe Ser Phe
                85                  90                  95

Thr Gln Tyr Ser Thr Asp Glu Glu Arg Ala Phe Val Arg Thr Glu Leu
            100                 105                 110

Ala Ala Leu Leu Ala Ser Pro Leu Leu Ile Asp Ala Ile Asp Gln Leu
        115                 120                 125
```

Asn Pro Ala Tyr
    130

<210> SEQ ID NO 21
<211> LENGTH: 131
<212> TYPE: PRT
<213> ORGANISM: Bacteriophage AP205

<400> SEQUENCE: 21

Met Ala Asn Lys Pro Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 22
<211> LENGTH: 131
<212> TYPE: PRT
<213> ORGANISM: Bacteriophage AP205

<400> SEQUENCE: 22

Met Ala Asn Lys Thr Met Gln Pro Ile Thr Ser Thr Ala Asn Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 23
<211> LENGTH: 131
<212> TYPE: PRT
<213> ORGANISM: Bacteriophage AP205

-continued

```
<400> SEQUENCE: 23

Met Ala Asn Lys Pro Met Gln Pro Ile Thr Ser Thr Ala Asp Lys Ile
1               5                   10                  15

Val Trp Ser Asp Pro Thr Arg Leu Ser Thr Thr Phe Ser Ala Ser Leu
            20                  25                  30

Leu Arg Gln Arg Val Lys Val Gly Ile Ala Glu Leu Asn Asn Val Ser
        35                  40                  45

Gly Gln Tyr Val Ser Val Tyr Lys Arg Pro Ala Pro Lys Pro Glu Gly
    50                  55                  60

Cys Ala Asp Ala Cys Val Ile Met Pro Asn Glu Asn Gln Ser Ile Arg
65                  70                  75                  80

Thr Val Ile Ser Gly Ser Ala Glu Asn Leu Ala Thr Leu Lys Ala Glu
                85                  90                  95

Trp Glu Thr His Lys Arg Asn Val Asp Thr Leu Phe Ala Ser Gly Asn
            100                 105                 110

Ala Gly Leu Gly Phe Leu Asp Pro Thr Ala Ala Ile Val Ser Ser Asp
        115                 120                 125

Thr Thr Ala
    130

<210> SEQ ID NO 24
<211> LENGTH: 37
<212> TYPE: DNA
<213> ORGANISM: Artificial sequence
<220> FEATURE:
<223> OTHER INFORMATION: PCR primer

<400> SEQUENCE: 24
atatatgcta gccccttaca cctaccagag tgatttg                       37

<210> SEQ ID NO 25
<211> LENGTH: 37
<212> TYPE: DNA
<213> ORGANISM: Artificial sequence
<220> FEATURE:
<223> OTHER INFORMATION: PCR primer

<400> SEQUENCE: 25
atatatctcg agtgatatct ggaagtctgt catagag                       37

<210> SEQ ID NO 26
<211> LENGTH: 37
<212> TYPE: DNA
<213> ORGANISM: Artificial sequence
<220> FEATURE:
<223> OTHER INFORMATION: PCR primer

<400> SEQUENCE: 26
atatatgcta gccccccatta gacagctgca ctacagg                      37

<210> SEQ ID NO 27
<211> LENGTH: 37
<212> TYPE: DNA
<213> ORGANISM: Artificial sequence
<220> FEATURE:
<223> OTHER INFORMATION: PCR primer

<400> SEQUENCE: 27
atatatctcg agggaagaca cagattccat ggtgaag                       37

<210> SEQ ID NO 28
<211> LENGTH: 7
```

```
<212> TYPE: PRT
<213> ORGANISM: Artificial sequence
<220> FEATURE:
<223> OTHER INFORMATION: synthesized sequence

<400> SEQUENCE: 28

Gly Gly Gly Gly Gly Cys Gly
1               5

<210> SEQ ID NO 29
<211> LENGTH: 5473
<212> TYPE: DNA
<213> ORGANISM: Artificial sequence
<220> FEATURE:
<223> OTHER INFORMATION: Cloning Vector

<400> SEQUENCE: 29
acatcgtata acgttactgg tttcacattc accaccctga attgactctc ttccgggcgc      60
tatcatgcca taccgcgaaa ggttttgcgc cattcgatgg tgtccgggat ctcgacgctc     120
tcccttatgc gactcctgca ttaggaagca gcccagtagt aggttgaggc cgttgagcac     180
cgccgccgca aggaatggtg catgcaagga gatggcgccc aacagtcccc ggccacggg      240 gcctgccacc atacccacgc cgaaacaagc gctcatgagc ccgaagtggc gagcccgatc     300
ttccccatcg gtgatgtcgg cgatataggc gccagcaacc gcacctgtgg cgccggtgat     360
gccggccacg atgcgtccgg cgtagaggat cgagatctcg atcccgcgaa attaatacga     420
ctcactatag ggaattgtg agcggataac aattccctc tagaaataat ttgtttaac       480 tttaagaagg agatatacat atggatccac accaccaca ccaccacggt tctggtgacg      540
acgatgacaa agcgctagcc ctcgagggtg gtggtggtgg ttgcggttaa taagtttaaa     600
cgcggccgca tgcaccacca ccaccaccac tgagatccgg ctgctaacaa agcccgaaag     660
gaagctgagt tggctgctgc caccgctgag caataactag cataaccct tgggccctct      720 aaacgggtct tgagggtttt tttgctgaaa ggaggaacta tatccggatt ggcgaatggg     780
acgcgccctg tagcggcgca ttaagcgcgg cgggtgtggt ggttacgcgc agcgtgaccg     840
ctacacttgc cagcgcccta gcgcccgctc ctttcgcttt cttcccttcc tttctcgcca     900
cgttcgccgg ctttccccgt caagctctaa atcgggggct ccctttaggg ttccgattta     960
gtgctttacg gcacctcgac cccaaaaaac ttgattaggg tgatggttca cgtagtgggc    1020
catcgccctg atagacggtt tttcgccctt tgacgttgga gtccacgttc tttaatagtg    1080
gactcttgtt ccaaactgga acaacactca accctatctc ggtctattct tttgatttat    1140
aagggatttt gccgatttcg gcctattggt taaaaaatga gctgatttaa caaaaattta    1200
acgcgaattt aacaaaaata ttaacgttta caatttcagg tggcacttt cggggaaatg     1260 tgcgcggaac ccctatttgt ttattttct aaatacattc aaatatgtat ccgctcatga     1320
gacaataacc ctgataaatg cttcaataat attgaaaaag gaagagtatg agtattcaac    1380
atttccgtgt cgcccttatt cccttttttg cggcattttg ccttcctgtt tttgctcacc    1440
cagaaacgct ggtgaaagta aaagatgctg aagatcagtt gggtgcacga gtgggttaca    1500
tcgaactgga tctcaacagc ggtaagatcc ttgagagttt cgccccgaa gaacgttttc     1560 caatgatgag cacttttaaa gttctgctat gtggcgcggt attatcccgt attgacgccg    1620
ggcaagagca actcggtcgc cgcatacact attctcagaa tgacttggtt gagtactcac    1680
cagtcacaga aaagcatctt acggatggca tgacagtaag agaattatgc agtgctgcca    1740
taaccatgag tgataacact gcggccaact tacttctgac aacgatcgga ggaccgaagg    1800
```

```
agctaaccgc tttttttgcac aacatggggg atcatgtaac tcgccttgat cgttgggaac   1860
cggagctgaa tgaagccata ccaaacgacg agcgtgacac cacgatgcct gcagcaatgg   1920
caacaacgtt gcgcaaacta ttaactggcg aactacttac tctagcttcc cggcaacaat   1980
taatagactg gatggaggcg gataaagttg caggaccact tctgcgctcg ccccttccgg   2040
ctggctggtt tattgctgat aaatctggag ccggtgagcg tgggtctcgc ggtatcattg   2100
cagcactggg gccagatggt aagccctccc gtatcgtagt tatctacacg acggggagtc   2160
aggcaactat ggatgaacga atagacaga tcgctgagat aggtgcctca ctgattaagc   2220
attggtaact gtcagaccaa gtttactcat atatacttta gattgattta aaacttcatt   2280
tttaatttaa aaggatctag gtgaagatcc ttttttgataa tctcatgacc aaaatccctt   2340
aacgtgagtt ttcgttccac tgagcgtcag accccgtaga aaagatcaaa ggatcttctt   2400
gagatccttt ttttctgcgc gtaatctgct gcttgcaaac aaaaaaacca ccgctaccag   2460
cggtggtttg tttgccggat caagagctac caactctttt tccgaaggta actggcttca   2520
gcagagcgca gataccaaat actgtccttc tagtgtagcc gtagttaggc caccacttca   2580
agaactctgt agcaccgcct acatacccg ctctgctaat cctgttacca gtggctgctg   2640
ccagtggcga taagtcgtgt cttaccgggt tggactcaag acgatagtta ccggataagg   2700
cgcagcggtc gggctgaacg gggggttcgt gcacacagcc cagcttggag cgaacgacct   2760
acaccgaact gagataccta cagcgtgagc tatgagaaag cgccacgctt cccgaaggga   2820
gaaaggcgga caggtatccg gtaagcggca gggtcggaac aggagagcgc acgagggagc   2880
ttccaggggg aaacgcctgg tatctttata gtcctgtcgg gtttcgccac ctctgacttg   2940
agcgtcgatt tttgtgatgc tcgtcagggg ggcggagcct atggaaaaac gccagcaacg   3000
cggcctttt acggttcctg gccttttgct ggccttttgc tcacatgttc tttcctgcgt   3060
tatcccctga ttctgtggat aaccgtatta ccgcctttga gtgagctgat accgctcgcc   3120
gcagccgaac gaccgagcgc agcgagtcag tgagcgagga agcggaagag cgcctgatgc   3180
ggtattttct ccttacgcat ctgtgcggta tttcacaccg catatatggt gcactctcag   3240
tacaatctgc tctgatgccg catagttaag ccagtataca ctccgctatc gctacgtgac   3300
tgggtcatgg ctgcgccccg acacccgcca cacccgctg acgcgccctg acgggcttgt   3360
ctgctcccgg catccgctta cagacaagct gtgaccgtct ccgggagctg catgtgtcag   3420
aggttttcac cgtcatcacc gaaacgcgcg aggcagctgc ggtaaagctc atcagcgtgg   3480
tcgtgaagcg attcacagat gtctgcctgt tcatccgcgt ccagctcgtt gagtttctcc   3540
agaagcgtta atgtctggct tctgataaag cgggccatgt taagggcggt ttttttcctgt   3600
ttggtcactg atgcctccgt gtaagggga tttctgttca tgggggtaat gataccgatg   3660
aaacgagaga ggatgctcac gatacgggtt actgatgatg aacatgcccg gttactggaa   3720
cgttgtgagg gtaaacaact ggcggtatgg atgcggcggg accagagaaa aatcactcag   3780
ggtcaatgcc agcgcttcgt taatacagat gtaggtgttc cacagggtag ccagcagcat   3840
cctgcgatgc agatccggaa cataatggtg cagggcgctg acttccgcgt ttccagactt   3900
tacgaaacac ggaaaccgaa gaccattcat gttgttgctc aggtcgcaga cgttttgcag   3960
cagcagtcgc ttcacgttcg ctcgcgtatc ggtgattcat tctgctaacc agtaaggcaa   4020
ccccgccagc ctagccgggt cctcaacgac aggagcacga tcatgcgcac ccgtggggcc   4080
gccatgccgg cgataatggc ctgcttctcg ccgaaacgtt tggtggcggg accagtgacg   4140
aaggcttgag cgagggcgtg caagattccg aataccgcaa gcgacaggcc gatcatcgtc   4200
```

```
gcgctccagc gaaagcggtc ctcgccgaaa atgacccaga gcgctgccgg cacctgtcct    4260
acgagttgca tgataaagaa gacagtcata agtgcggcga cgatagtcat gccccgcgcc    4320
caccggaagg agctgactgg gttgaaggct ctcaagggca tcggtcgaga tcccggtgcc    4380
taatgagtga gctaacttac attaattgcg ttgcgctcac tgcccgcttt ccagtcggga    4440
aacctgtcgt gccagctgca ttaatgaatc ggccaacgcg cggggagagg cggtttgcgt    4500
attgggcgcc agggtggttt ttcttttcac cagtgagacg ggcaacagct gattgccctt    4560
caccgcctgg ccctgagaga gttgcagcaa gcggtccacg ctggtttgcc ccagcaggcg    4620
aaaatcctgt ttgatggtgg ttaacggcgg gatataacat gagctgtctt cggtatcgtc    4680
gtatcccact accgagatat ccgcaccaac gcgcagcccg gactcggtaa tggcgcgcat    4740
tgcgcccagc gccatctgat cgttggcaac cagcatcgca gtgggaacga tgccctcatt    4800
cagcatttgc atggtttgtt gaaaaccgga catggcactc cagtcgcctt cccgttccgc    4860
tatcggctga atttgattgc gagtgagata tttatgccag ccagccagac gcagacgcgc    4920
cgagacagaa cttaatgggc ccgctaacag cgcgatttgc tggtgaccca atgcgaccag    4980
atgctccacg cccagtcgcg taccgtcttc atgggagaaa ataatactgt tgatgggtgt    5040
ctggtcagag acatcaagaa ataacgccgg aacattagtg caggcagctt ccacagcaat    5100
ggcatcctgg tcatccagcg gatagttaat gatcagccca ctgacgcgtt gcgcgagaag    5160
attgtgcacc gccgctttac aggcttcgac gccgcttcgt tctaccatcg acaccaccac    5220
gctggcaccc agttgatcgg cgcgagattt aatcgccgcg acaatttgcg acggcgcgtg    5280
cagggccaga ctggaggtgg caacgccaat cagcaacgac tgtttgcccg ccagttgttg    5340
tgccacgcgg ttgggaatgt aattcagctc cgccatcgcc gcttccactt tttcccgcgt    5400
tttcgcagaa acgtggctgg cctggttcac cacgcgggaa acggtctgat aagagacacc    5460
ggcatactct gcg                                                      5473

<210> SEQ ID NO 30
<211> LENGTH: 43
<212> TYPE: DNA
<213> ORGANISM: Artificial sequence
<220> FEATURE:
<223> OTHER INFORMATION: PCR primer

<400> SEQUENCE: 30
tatggatccg gctagcgctc gagggtttaa acggcggccg cat                     43

<210> SEQ ID NO 31
<211> LENGTH: 45
<212> TYPE: DNA
<213> ORGANISM: Artificial sequence
<220> FEATURE:
<223> OTHER INFORMATION: PCR primer

<400> SEQUENCE: 31
tcgaatgcgg ccgccgttta aaccctcgag cgctagccgg atcca                   45

<210> SEQ ID NO 32
<211> LENGTH: 58
<212> TYPE: DNA
<213> ORGANISM: Artificial sequence
<220> FEATURE:
<223> OTHER INFORMATION: PCR primer

<400> SEQUENCE: 32
gatccacacc accaccacca ccacggttct ggtgacgacg atgacaaagc gctagccc     58
```

<210> SEQ ID NO 33
<211> LENGTH: 58
<212> TYPE: DNA
<213> ORGANISM: Artificial sequence
<220> FEATURE:
<223> OTHER INFORMATION: PCR primer

<400> SEQUENCE: 33
tcgagggcta gcgctttgtc atcgtcgtca ccagaaccgt ggtggtggtg gtggtgtg    58

<210> SEQ ID NO 34
<211> LENGTH: 42
<212> TYPE: DNA
<213> ORGANISM: Artificial sequence
<220> FEATURE:
<223> OTHER INFORMATION: PCR primer

<400> SEQUENCE: 34
tcgagggtgg tggtggtggt tgcggttaat aagtttaaac gc    42

<210> SEQ ID NO 35
<211> LENGTH: 42
<212> TYPE: DNA
<213> ORGANISM: Artificial sequence
<220> FEATURE:
<223> OTHER INFORMATION: PCR primer

<400> SEQUENCE: 35
ggccgcgttt aaacttatta accgcaacca ccaccaccac cc    42

<210> SEQ ID NO 36
<211> LENGTH: 271
<212> TYPE: PRT
<213> ORGANISM: Homo sapiens

<400> SEQUENCE: 36

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr His Val Ser Tyr Gly Pro Leu His Glu Gly Cys Met
        35                  40                  45

Asp Gln Ser Val Ser Leu Ser Ile Ser Glu Thr Ser Lys Thr Ser Lys
    50                  55                  60

Leu Thr Phe Lys Glu Ser Met Val Val Ala Thr Asn Gly Lys Val
65                  70                  75                  80

Leu Lys Lys Arg Arg Leu Ser Leu Ser Gln Ser Ile Thr Asp Asp Asp
                85                  90                  95

Leu Glu Ala Ile Ala Asn Asp Ser Glu Glu Glu Ile Ile Lys Pro Arg
            100                 105                 110

Ser Ser Pro Phe Ser Phe Leu Ser Asn Val Lys Tyr Asn Phe Met Arg
        115                 120                 125

Ile Ile Lys Tyr Glu Phe Ile Leu Asn Asp Ala Leu Asn Gln Ser Ile
    130                 135                 140

Ile Arg Ala Asn Asp Gln Tyr Leu Thr Ala Ala Leu His Asn Leu
145                 150                 155                 160

Asp Glu Ala Val Lys Phe Asp Met Gly Ala Tyr Lys Ser Ser Lys Asp
                165                 170                 175

Asp Ala Lys Ile Thr Val Ile Leu Arg Ile Ser Lys Thr Gln Leu Tyr
            180                 185                 190

```
Val Thr Ala Gln Asp Glu Asp Gln Pro Val Leu Leu Lys Glu Met Pro
            195                 200                 205

Glu Ile Pro Lys Thr Ile Thr Gly Ser Glu Thr Asn Leu Leu Phe Phe
210                 215                 220

Trp Glu Thr His Gly Thr Lys Asn Tyr Phe Thr Ser Val Ala His Pro
225                 230                 235                 240

Asn Leu Phe Ile Ala Thr Lys Gln Asp Tyr Trp Val Cys Leu Ala Gly
            245                 250                 255

Gly Pro Pro Ser Ile Thr Asp Phe Gln Ile Leu Glu Asn Gln Ala
            260                 265                 270

<210> SEQ ID NO 37
<211> LENGTH: 271
<212> TYPE: PRT
<213> ORGANISM: Macaca mulatta

<400> SEQUENCE: 37

Met Ala Lys Val Pro Asp Met Phe Glu Asp Leu Lys Asn Cys Tyr Ser
1               5                   10                  15

Glu Asn Glu Glu Asp Ser Ser Ser Ile Asp His Leu Ser Leu Asn Gln
            20                  25                  30

Lys Ser Phe Tyr Asp Val Ser Tyr Gly Pro Leu His Glu Gly Cys Met
        35                  40                  45

Asp Gln Ser Val Ser Leu Ser Ile Ser Glu Ile Ser Lys Thr Ser Lys
    50                  55                  60

Leu Thr Phe Lys Gln Ser Met Val Val Ser Thr Asn Gly Lys Val
65                  70                  75                  80

Leu Lys Lys Arg Arg Leu Ser Leu Ser Gln Ser Ile Thr Asp Asn Asn
                85                  90                  95

Leu Glu Ala Ile Ala Asn Asp Ser Glu Glu Ile Ile Lys Pro Arg
            100                 105                 110

Ser Ala Pro Phe Ser Phe Leu Ser Asn Met Thr Tyr His Phe Ile Arg
        115                 120                 125

Ile Ile Lys His Glu Phe Ile Leu Asn Asp Thr Leu Asn Gln Thr Ile
    130                 135                 140

Ile Arg Ala Asn Asp Gln His Leu Thr Ala Ala Ile His Asn Leu
145                 150                 155                 160

Asp Glu Ala Val Lys Phe Asp Met Gly Ala Tyr Thr Ser Ser Lys Asp
                165                 170                 175

Asp Thr Lys Val Pro Val Ile Leu Arg Ile Ser Lys Thr Gln Leu Tyr
            180                 185                 190

Val Ser Ala Gln Asp Glu Asp Gln Pro Val Leu Leu Lys Glu Met Pro
        195                 200                 205

Glu Ile Asn Lys Thr Ile Thr Gly Ser Glu Thr Asn Phe Leu Phe Phe
    210                 215                 220

Trp Glu Thr His Gly Thr Lys Asn Tyr Phe Ile Ser Val Ala His Pro
225                 230                 235                 240

Asn Leu Phe Ile Ala Thr Lys His Asp Asn Trp Val Cys Leu Ala Lys
                245                 250                 255

Gly Leu Pro Ser Ile Thr Asp Phe Gln Ile Leu Glu Asn Gln Ala
            260                 265                 270

<210> SEQ ID NO 38
<211> LENGTH: 270
<212> TYPE: PRT
<213> ORGANISM: Equus caballus
```

```
<400> SEQUENCE: 38

Met Ala Lys Val Pro Asp Leu Phe Glu Asp Leu Lys Asn Cys Tyr Ser
1               5                   10                  15

Glu Asn Glu Asp Tyr Ser Ser Glu Ile Asp His Leu Ser Leu Thr Gln
            20                  25                  30

Lys Ser Phe Tyr Asp Ala Ser Tyr Asp Pro Leu Pro Glu Asp Cys Met
        35                  40                  45

Asp Thr Phe Met Ser Leu Ser Thr Ser Glu Thr Ser Lys Thr Ser Lys
    50                  55                  60

Leu Asn Phe Lys Glu Ser Val Val Leu Val Ala Ala Asn Gly Lys Thr
65                  70                  75                  80

Leu Lys Lys Arg Arg Leu Ser Leu Asn Gln Phe Ile Thr Asn Asp Asp
                85                  90                  95

Leu Glu Ala Ile Ala Asn Asp Pro Glu Glu Gly Ile Ile Arg Pro Arg
            100                 105                 110

Ser Val His Tyr Asn Phe Gln Ser Asn Thr Lys Tyr Asn Phe Met Arg
        115                 120                 125

Ile Val Asn His Gln Cys Thr Leu Asn Asp Ala Leu Asn Gln Ser Val
    130                 135                 140

Ile Arg Asp Thr Ser Gly Gln Tyr Leu Ala Thr Ala Ala Leu Asn Asn
145                 150                 155                 160

Leu Asp Asp Ala Val Lys Phe Asp Met Gly Ala Tyr Thr Ser Glu Glu
                165                 170                 175

Asp Ser Gln Leu Pro Val Thr Leu Arg Ile Ser Lys Thr Arg Leu Phe
            180                 185                 190

Val Ser Ala Gln Asn Glu Asp Glu Pro Val Leu Leu Lys Glu Met Pro
        195                 200                 205

Asp Thr Pro Lys Thr Ile Lys Asp Glu Thr Asn Leu Leu Phe Phe Trp
    210                 215                 220

Glu Arg His Gly Ser Lys Asn Tyr Phe Lys Ser Val Ala His Pro Lys
225                 230                 235                 240

Leu Phe Ile Ala Thr Lys Gln Gly Lys Leu Val His Met Ala Arg Gly
                245                 250                 255

Gln Pro Ser Ile Thr Asp Phe Gln Ile Leu Asp Asn Gln Phe
            260                 265                 270

<210> SEQ ID NO 39
<211> LENGTH: 268
<212> TYPE: PRT
<213> ORGANISM: Ovis aries

<400> SEQUENCE: 39

Met Ala Lys Val Pro Asp Leu Phe Glu Asp Leu Lys Asn Cys Tyr Ser
1               5                   10                  15

Glu Asn Glu Asp Tyr Ser Ser Glu Ile Asp His Leu Ser Leu Asn Gln
            20                  25                  30

Lys Ser Phe Tyr Asp Ala Ser Tyr Glu Pro Leu Arg Glu Asp His Met
        35                  40                  45

Asn Lys Phe Met Ser Leu Asp Thr Ser Glu Thr Ser Lys Thr Ser Arg
    50                  55                  60

Leu Ser Phe Lys Glu Asn Val Val Met Met Thr Ala Asn Gly Lys Ile
65                  70                  75                  80

Leu Lys Lys Arg Arg Leu Ser Leu Asn Gln Phe Ile Thr Asp Asp Asp
                85                  90                  95

Leu Glu Ala Ile Ala Asn Asp Thr Glu Glu Glu Ile Ile Lys Pro Arg
```

```
                            100                 105                 110
Ser Ala His Tyr Ser Phe Gln Ser Asn Val Lys Tyr Asn Phe Met Arg
                115                 120                 125

Val Ile His Gln Glu Cys Ile Leu Asn Asp Ala Leu Asn Gln Ser Ile
            130                 135                 140

Ile Arg Asp Met Ser Gly Pro Tyr Leu Thr Ala Ala Thr Leu Asn Asn
145                 150                 155                 160

Leu Glu Glu Ala Val Lys Phe Asp Met Val Ala Tyr Val Ser Glu Glu
                165                 170                 175

Asp Ser Gln Leu Pro Val Thr Leu Arg Ile Ser Lys Thr Gln Leu Phe
            180                 185                 190

Val Ser Ala Gln Asn Glu Asp Glu Pro Val Leu Leu Lys Glu Met Pro
        195                 200                 205

Glu Thr Pro Lys Ile Ile Lys Asp Glu Thr Asn Leu Leu Phe Phe Trp
    210                 215                 220

Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                245                 250                 255

Pro Pro Ser Ile Thr Asp Phe Gln Ile Leu Glu Lys
            260                 265

<210> SEQ ID NO 40
<211> LENGTH: 270
<212> TYPE: PRT
<213> ORGANISM: Felis catus

<400> SEQUENCE: 40

Met Ala Lys Val Pro Asp Leu Phe Glu Asp Leu Lys Asn Cys Tyr Ser
1               5                   10                  15

Glu Asn Glu Glu Tyr Ser Ser Glu Ile Asp His Leu Thr Leu Asn Gln
                20                  25                  30

Lys Ser Phe Tyr Asp Ala Ser Tyr Asp Pro Leu His Glu Asp Cys Thr
            35                  40                  45

Asp Lys Phe Met Ser Pro Ser Thr Glu Thr Ser Lys Thr Pro Gln
50                  55                  60

Leu Thr Leu Lys Lys Ser Val Val Met Val Ala Ala Asn Gly Lys Ile
65                  70                  75                  80

Leu Lys Lys Arg Arg Leu Ser Leu Asn Gln Phe Leu Thr Ala Asp Asp
                85                  90                  95

Leu Glu Ala Ile Ala Asn Glu Val Glu Glu Ile Met Lys Pro Arg
            100                 105                 110

Ser Val Ala Pro Asn Phe Tyr Ser Ser Glu Lys Tyr Asn Tyr Gln Lys
        115                 120                 125

Ile Ile Lys Ser Gln Phe Ile Leu Asn Asp Asn Leu Ser Gln Ser Val
    130                 135                 140

Ile Arg Lys Ala Gly Gly Lys Tyr Leu Ala Ala Ala Leu Gln Asn
145                 150                 155                 160

Leu Asp Asp Ala Val Lys Phe Asp Met Gly Ala Tyr Thr Ser Lys Glu
                165                 170                 175

Asp Ser Lys Leu Pro Val Thr Leu Arg Ile Ser Lys Thr Arg Leu Phe
            180                 185                 190

Val Ser Ala Gln Asn Glu Asp Glu Pro Val Leu Leu Lys Glu Met Pro
        195                 200                 205

Glu Thr Pro Lys Thr Ile Arg Asp Glu Thr Asn Leu Leu Phe Phe Trp
```

```
            210                 215                 220
Glu Arg His Gly Ser Lys Asn Tyr Phe Lys Ser Val Ala His Pro Lys
225                 230                 235                 240

Leu Phe Ile Ala Thr Gln Glu Gln Leu Val His Met Ala Arg Gly
                245                 250                 255

Leu Pro Ser Val Thr Asp Phe Gln Ile Leu Glu Thr Gln Ser
                260                 265                 270

<210> SEQ ID NO 41
<211> LENGTH: 268
<212> TYPE: PRT
<213> ORGANISM: Bos taurus

<400> SEQUENCE: 41

Met Ala Lys Val Pro Asp Leu Phe Glu Asp Leu Lys Asn Cys Tyr Ser
1               5                   10                  15

Glu Asn Glu Asp Tyr Ser Ser Glu Ile Asp His Leu Ser Leu Asn Gln
                20                  25                  30

Lys Ser Phe Tyr Asp Ala Ser Tyr Glu Pro Leu Arg Glu Asp Gln Met
            35                  40                  45

Asn Lys Phe Met Ser Leu Asp Thr Ser Glu Thr Ser Lys Thr Ser Lys
50                  55                  60

Leu Ser Phe Lys Glu Asn Val Val Met Val Ala Ala Ser Gly Lys Ile
65                  70                  75                  80

Leu Lys Lys Arg Arg Leu Ser Leu Asn Gln Phe Ile Thr Asp Asp
                85                  90                  95

Leu Glu Ala Ile Ala Asn Asn Thr Glu Glu Ile Ile Lys Pro Arg
            100                 105                 110

Ser Ala His Tyr Ser Phe Gln Ser Asn Val Lys Tyr Asn Phe Met Arg
            115                 120                 125

Val Ile His Gln Glu Cys Ile Leu Asn Asp Ala Leu Asn Gln Ser Ile
            130                 135                 140

Ile Arg Asp Met Ser Gly Pro Tyr Leu Thr Ala Thr Thr Leu Asn Asn
145                 150                 155                 160

Leu Glu Glu Ala Val Lys Phe Asp Met Val Ala Tyr Val Ser Glu Glu
                165                 170                 175

Asp Ser Gln Leu Pro Val Thr Leu Arg Ile Ser Lys Thr Gln Leu Phe
            180                 185                 190

Val Ser Ala Gln Asn Glu Asp Glu Pro Val Leu Leu Lys Glu Met Pro
        195                 200                 205

Glu Thr Pro Lys Ile Ile Lys Asp Glu Thr Asn Leu Leu Phe Phe Trp
210                 215                 220

Glu Lys His Gly Ser Met Asp Tyr Phe Lys Ser Val Ala His Pro Lys
225                 230                 235                 240

Leu Phe Ile Ala Thr Lys Gln Glu Lys Leu Val His Met Ala Ser Gly
                245                 250                 255

Pro Pro Ser Ile Thr Asp Phe Gln Ile Leu Glu Lys
            260                 265

<210> SEQ ID NO 42
<211> LENGTH: 270
<212> TYPE: PRT
<213> ORGANISM: Sus scrofa

<400> SEQUENCE: 42

Met Ala Lys Val Pro Asp Leu Phe Glu Asp Leu Lys Asn Cys Tyr Ser
1               5                   10                  15
```

Glu Asn Glu Glu Tyr Ser Ser Asp Ile Asp His Leu Ser Leu Asn Gln
            20                  25                  30

Lys Ser Phe Tyr Asp Ala Ser Tyr Glu Pro Leu Pro Gly Asp Gly Met
        35                  40                  45

Asp Lys Phe Met Pro Leu Ser Thr Ser Lys Thr Ser Lys Thr Ser Arg
50                  55                  60

Leu Asn Phe Lys Asp Ser Val Val Met Ala Ala Ala Asn Gly Lys Ile
65                  70                  75                  80

Leu Lys Lys Arg Arg Leu Ser Leu Asn Gln Phe Ile Thr Asp Asp
            85                  90                  95

Leu Glu Ala Ile Ala Asn Asp Thr Glu Glu Ile Ile Lys Pro Arg
                100                 105                 110

Ser Ala Thr Tyr Ser Phe Gln Ser Asn Met Lys Tyr Asn Phe Met Arg
            115                 120                 125

Val Ile Asn His Gln Cys Ile Leu Asn Asp Ala Arg Asn Gln Ser Ile
130                 135                 140

Ile Arg Asp Pro Ser Gly Gln Tyr Leu Met Ala Ala Val Leu Asn Asn
145                 150                 155                 160

Leu Asp Glu Ala Val Lys Phe Asp Met Ala Ala Tyr Thr Ser Asn Asp
                165                 170                 175

Asp Ser Gln Leu Pro Val Thr Leu Arg Ile Ser Glu Thr Arg Leu Phe
            180                 185                 190

Val Ser Ala Gln Asn Glu Asp Glu Pro Val Leu Leu Lys Glu Leu Pro
            195                 200                 205

Glu Thr Pro Lys Thr Ile Lys Asp Glu Thr Ser Leu Leu Phe Phe Trp
210                 215                 220

Glu Lys His Gly Asn Met Asp Tyr Phe Lys Ser Ala Ala His Pro Lys
225                 230                 235                 240

Leu Phe Ile Ala Thr Arg Gln Glu Lys Leu Val His Met Ala Pro Gly
                245                 250                 255

Leu Pro Ser Val Thr Asp Phe Gln Ile Leu Glu Asn Gln Ser
            260                 265                 270

<210> SEQ ID NO 43
<211> LENGTH: 268
<212> TYPE: PRT
<213> ORGANISM: Oryctolagus cuniculus

<400> SEQUENCE: 43

Met Ala Lys Val Pro Asp Leu Phe Glu Asp Leu Lys Asn Cys Phe Ser
1               5                   10                  15

Glu Asn Glu Glu Tyr Ser Ser Ala Ile Asp His Leu Ser Leu Asn Gln
            20                  25                  30

Lys Ser Phe Tyr Asp Ala Ser Tyr Glu Pro Leu His Glu Asp Cys Met
        35                  40                  45

Asn Lys Val Val Ser Leu Ser Thr Ser Glu Thr Ser Val Ser Pro Asn
50                  55                  60

Leu Thr Phe Gln Glu Asn Val Val Ala Val Thr Ala Ser Gly Lys Ile
65                  70                  75                  80

Leu Lys Lys Arg Arg Leu Ser Leu Asn Gln Pro Ile Thr Asp Val Asp
            85                  90                  95

Leu Glu Thr Asn Val Ser Asp Pro Glu Glu Gly Ile Ile Lys Pro Arg
                100                 105                 110

Ser Val Pro Tyr Thr Phe Gln Arg Asn Met Arg Tyr Lys Tyr Leu Arg
            115                 120                 125

```
Ile Ile Lys Gln Glu Phe Thr Leu Asn Asp Ala Leu Asn Gln Ser Leu
    130                 135                 140

Val Arg Asp Thr Ser Asp Gln Tyr Leu Arg Ala Ala Pro Leu Gln Asn
145                 150                 155                 160

Leu Gly Asp Ala Val Lys Phe Asp Met Gly Val Tyr Met Thr Ser Lys
                    165                 170                 175

Glu Asp Ser Ile Leu Pro Val Thr Leu Arg Ile Ser Gln Thr Pro Leu
                180                 185                 190

Phe Val Ser Ala Gln Asn Glu Asp Glu Pro Val Leu Leu Lys Glu Met
                195                 200                 205

Pro Glu Thr Pro Arg Ile Ile Thr Asp Ser Glu Ser Asp Ile Leu Phe
210                 215                 220

Phe Trp Glu Thr Gln Gly Asn Lys Asn Tyr Phe Lys Ser Ala Ala Asn
225                 230                 235                 240

Pro Gln Leu Phe Ile Ala Thr Lys Pro Glu His Leu Val His Met Ala
                245                 250                 255

Arg Gly Leu Pro Ser Met Thr Asp Phe Gln Ile Ser
                260                 265

<210> SEQ ID NO 44
<211> LENGTH: 265
<212> TYPE: PRT
<213> ORGANISM: Canis familiaris

<400> SEQUENCE: 44

Met Ala Lys Val Pro Asp Leu Phe Glu Asp Leu Lys Asn Cys Tyr Ser
1               5                   10                  15

Glu Asn Glu Glu Tyr Ser Ser Glu Ile Asp His Leu Ser Leu Asn Gln
                20                  25                  30

Lys Ser Phe Tyr Asp Met Ser Cys Asp Pro Leu His Glu Asp Cys Met
                35                  40                  45

Ser Leu Ser Thr Ser Glu Ile Ser Lys Thr Ser Gln Leu Thr Phe Lys
    50                  55                  60

Glu Asn Val Val Val Ala Ala Asn Gly Lys Ile Leu Lys Lys Arg
65                  70                  75                  80

Arg Leu Ser Leu Ser Gln Phe Ile Thr Asp Asp Leu Glu Gly Ile
                85                  90                  95

Ala Asn Asp Thr Glu Glu Val Ile Met Lys Pro Arg Ser Val Ala Tyr
                100                 105                 110

Asn Phe His Asn Asn Glu Lys Tyr Asn Tyr Ile Arg Ile Ile Lys Ser
                115                 120                 125

Gln Phe Ile Leu Asn Asp Asn Leu Asn Gln Ser Ile Val Arg Gln Thr
    130                 135                 140

Gly Gly Asn Tyr Leu Met Thr Ala Ala Leu Gln Asn Leu Asp Asp Ala
145                 150                 155                 160

Val Lys Phe Asp Met Gly Ala Tyr Thr Ser Glu Asp Ser Lys Leu Pro
                165                 170                 175

Val Thr Leu Arg Ile Ser Lys Thr Arg Leu Phe Val Ser Ala Gln Asn
                180                 185                 190

Glu Asp Glu Pro Val Leu Leu Lys Glu Met Pro Glu Thr Pro Lys Thr
                195                 200                 205

Ile Arg Asp Glu Thr Asn Leu Leu Phe Phe Trp Glu Arg His Gly Ser
    210                 215                 220

Lys His Tyr Phe Lys Ser Val Ala Gln Pro Lys Leu Phe Ile Ala Thr
225                 230                 235                 240
```

```
Gln Glu Arg Lys Leu Val His Met Ala Arg Gly Gln Pro Ser Ile Thr
                245                 250                 255

Asp Phe Arg Leu Leu Glu Thr Gln Pro
            260                 265

<210> SEQ ID NO 45
<211> LENGTH: 270
<212> TYPE: PRT
<213> ORGANISM: Mus musculus

<400> SEQUENCE: 45

Met Ala Lys Val Pro Asp Leu Phe Glu Asp Leu Lys Asn Cys Tyr Ser
1               5                   10                  15

Glu Asn Glu Asp Tyr Ser Ser Ala Ile Asp His Leu Ser Leu Asn Gln
            20                  25                  30

Lys Ser Phe Tyr Asp Ala Ser Tyr Gly Ser Leu His Glu Thr Cys Thr
        35                  40                  45

Asp Gln Phe Val Ser Leu Arg Thr Ser Glu Thr Ser Lys Met Ser Asn
    50                  55                  60

Phe Thr Phe Lys Glu Ser Arg Val Thr Val Ser Ala Thr Ser Ser Asn
65                  70                  75                  80

Gly Lys Ile Leu Lys Lys Arg Arg Leu Ser Phe Ser Glu Thr Phe Thr
                85                  90                  95

Glu Asp Asp Leu Gln Ser Ile Thr His Asp Leu Glu Glu Thr Ile Gln
            100                 105                 110

Pro Arg Ser Ala Pro Tyr Thr Tyr Gln Ser Asp Leu Arg Tyr Lys Leu
        115                 120                 125

Met Lys Leu Val Arg Gln Lys Phe Val Met Asn Asp Ser Leu Asn Gln
    130                 135                 140

Thr Ile Tyr Gln Asp Val Asp Lys His Tyr Leu Ser Thr Thr Trp Leu
145                 150                 155                 160

Asn Asp Leu Gln Gln Glu Val Lys Phe Asp Met Tyr Ala Tyr Ser Ser
                165                 170                 175

Gly Gly Asp Ser Lys Tyr Pro Val Thr Leu Lys Ile Ser Asp Ser
            180                 185                 190

Gln Leu Phe Val Ser Ala Gln Gly Glu Asp Gln Pro Val Leu Leu Lys
        195                 200                 205

Glu Leu Pro Glu Thr Pro Lys Leu Ile Thr Gly Ser Glu Thr Asp Leu
    210                 215                 220

Ile Phe Phe Trp Lys Ser Ile Asn Ser Lys Asn Tyr Phe Thr Ser Ala
225                 230                 235                 240

Ala Tyr Pro Glu Leu Phe Ile Ala Thr Lys Glu Gln Ser Arg Val His
                245                 250                 255

Leu Ala Arg Gly Leu Pro Ser Met Thr Asp Phe Gln Ile Ser
            260                 265                 270

<210> SEQ ID NO 46
<211> LENGTH: 270
<212> TYPE: PRT
<213> ORGANISM: Rattus norvegicus

<400> SEQUENCE: 46

Met Ala Lys Val Pro Asp Leu Phe Glu Asp Leu Lys Asn Cys Tyr Ser
1               5                   10                  15

Glu Asn Glu Glu Tyr Ser Ser Ala Ile Asp His Leu Ser Leu Asn Gln
            20                  25                  30
```

```
Lys Ser Phe Tyr Asp Ala Ser Tyr Gly Ser Leu His Glu Asn Cys Thr
            35                  40                  45

Asp Lys Phe Val Ser Leu Arg Thr Ser Glu Thr Ser Lys Met Ser Thr
 50                  55                  60

Phe Thr Phe Lys Glu Ser Arg Val Val Ser Ala Thr Ser Asn Lys
 65                  70                  75                  80

Gly Lys Ile Leu Lys Lys Arg Leu Ser Phe Asn Gln Pro Phe Thr
                85                  90                  95

Glu Asp Asp Leu Glu Ala Ile Ala His Asp Leu Glu Glu Thr Ile Gln
                100                 105                 110

Pro Arg Ser Ala Pro His Ser Phe Gln Asn Asn Leu Arg Tyr Lys Leu
            115                 120                 125

Ile Arg Ile Val Lys Gln Glu Phe Ile Met Asn Asp Ser Leu Asn Gln
130                 135                 140

Asn Ile Tyr Val Asp Met Asp Arg Ile His Leu Lys Ala Ala Ser Leu
145                 150                 155                 160

Asn Asp Leu Gln Leu Glu Val Lys Phe Asp Met Tyr Ala Tyr Ser Ser
                165                 170                 175

Gly Gly Asp Asp Ser Lys Tyr Pro Val Thr Leu Lys Val Ser Asn Thr
                180                 185                 190

Gln Leu Phe Val Ser Ala Gln Gly Glu Asp Lys Pro Val Leu Leu Lys
                195                 200                 205

Glu Ile Pro Glu Thr Pro Lys Leu Ile Thr Gly Ser Glu Thr Asp Leu
            210                 215                 220

Ile Phe Phe Trp Glu Lys Ile Asn Ser Lys Asn Tyr Phe Thr Ser Ala
225                 230                 235                 240

Ala Phe Pro Glu Leu Leu Ile Ala Thr Lys Glu Gln Ser Gln Val His
                245                 250                 255

Leu Ala Arg Gly Leu Pro Ser Met Ile Asp Phe Gln Ile Ser
            260                 265                 270

<210> SEQ ID NO 47
<211> LENGTH: 152
<212> TYPE: PRT
<213> ORGANISM: Gorilla gorilla

<400> SEQUENCE: 47

Lys Asn Cys Tyr Ser Glu Asn Glu Glu Asp Ser Ser Ile Asp His
 1               5                  10                  15

Leu Ser Leu Asn Gln Lys Ser Phe Tyr His Val Thr Tyr Gly Pro Leu
                20                  25                  30

His Glu Gly Cys Met Asp Gln Ser Val Ser Leu Ser Ile Ser Glu Thr
            35                  40                  45

Ser Lys Thr Ser Lys Leu Thr Phe Lys Glu Ser Met Val Val Ala
 50                  55                  60

Thr Asn Gly Lys Val Leu Lys Lys Arg Arg Leu Ser Leu Ser Gln Ser
 65                  70                  75                  80

Ile Thr Asp Asp Asp Leu Glu Ala Ile Ala Asn Asp Ser Glu Glu Glu
                85                  90                  95

Ile Ile Lys Pro Arg Ser Ala Pro Phe Ser Phe Leu Ser Asn Val Lys
                100                 105                 110

Tyr Asn Phe Met Arg Ile Ile Lys Asn Glu Phe Ile Leu Asn Asp Ala
                115                 120                 125

Leu Asn Gln Ser Ile Ile Arg Ala Asn Asp Gln Tyr Leu Thr Ala Ala
            130                 135                 140
```

Ala Leu His Asn Leu Asp Glu Ala
145                 150

<210> SEQ ID NO 48
<211> LENGTH: 204
<212> TYPE: PRT
<213> ORGANISM: Cavia porcellus

<400> SEQUENCE: 48

Phe Glu Asp Leu Lys Asn Cys Tyr Ser Glu Asn Glu Glu Tyr Ala Ser
1               5                   10                  15

Ala Ile Asp His Leu Ser Leu Asn Gln Lys Ser Phe Tyr Asp Thr Asn
            20                  25                  30

Tyr Asp Pro Leu His Glu Asn Arg Val Asp Glu Pro Val Ser Pro Asn
        35                  40                  45

Pro Tyr Glu Asn Ser Glu Glu Ser Asn Phe Thr Leu Glu Asp Ser Ser
    50                  55                  60

Asp Ser Ser Ala Val Val Leu Thr Ser Ala His Gly Glu Val Leu Lys
65                  70                  75                  80

Lys Arg Arg Leu Ser Leu Asn Gln Thr Met Ser Asn Glu Asp Leu Glu
                85                  90                  95

Ala Ile Ala Asn Asp Ser Glu Glu Ile Ile Glu Pro Trp Ser Val
            100                 105                 110

Pro Tyr Ser Phe Gln Ser Asn Leu Lys Phe Lys Tyr Gln Arg Ser Ile
            115                 120                 125

Lys Lys Gly Ala Val Ile Thr Asp Ala Met His Gln Ser Leu Ile Arg
    130                 135                 140

Glu Ser Asn Gly Gln His Leu Lys Ala Met His Val Val Asp Arg Lys
145                 150                 155                 160

His Glu Val Lys Phe Asp Ile Asp Gly Tyr Val Ser Thr Ala Thr Arg
                165                 170                 175

Ile Arg Pro Val Thr Leu Lys Ile Ser Lys Thr Gln Leu Tyr Val Cys
            180                 185                 190

Ala Gln Glu Glu Gly Gln Pro Val Leu Leu Lys Glu
        195                 200

<210> SEQ ID NO 49
<211> LENGTH: 269
<212> TYPE: PRT
<213> ORGANISM: Homo sapiens

<400> SEQUENCE: 49

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
            20                  25                  30

Lys Cys Ser Phe Gln Asp Leu Asp Leu Cys Pro Leu Asp Gly Gly Ile
        35                  40                  45

Gln Leu Arg Ile Ser Asp His His Tyr Ser Lys Gly Phe Arg Gln Ala
    50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
            100                 105                 110

Tyr Val His Asp Ala Pro Val Arg Ser Leu Asn Cys Thr Leu Arg Asp

```
                    115                 120                 125
Ser Gln Gln Lys Ser Leu Val Met Ser Gly Pro Tyr Glu Leu Lys Ala
            130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
                195                 200                 205

Lys Lys Met Glu Lys Arg Phe Val Phe Asn Lys Ile Glu Ile Asn Asn
            210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 50
<211> LENGTH: 193
<212> TYPE: PRT
<213> ORGANISM: Pan troglodytes

<400> SEQUENCE: 50

Met Leu Val Pro Cys Pro Gln Thr Phe Gln Glu Asn Asp Leu Ser Thr
1               5                   10                  15

Phe Phe Pro Phe Ile Phe Glu Glu Pro Ile Phe Phe Asp Thr Trp
                20                  25                  30

Glu Asn Glu Ala Tyr Val His Asp Ala Pro Val Arg Ser Leu Asn Cys
            35                  40                  45

Thr Leu Arg Asp Ser Gln Gln Lys Ser Leu Val Met Ser Gly Pro Tyr
50                  55                  60

Glu Leu Lys Ala Leu His Leu Gln Gly Gln Asp Met Glu Gln Gln Val
65                  70                  75                  80

Val Phe Ser Met Ser Phe Val Gln Gly Glu Glu Ser Asn Asp Lys Ile
                85                  90                  95

Pro Val Ala Leu Gly Leu Lys Glu Lys Asn Leu Tyr Leu Ser Cys Val
            100                 105                 110

Leu Lys Asp Asp Lys Pro Thr Leu Gln Leu Glu Ser Val Asp Pro Lys
        115                 120                 125

Asn Tyr Pro Lys Lys Lys Met Glu Lys Arg Phe Val Phe Asn Lys Ile
            130                 135                 140

Glu Ile Asn Asn Lys Leu Glu Phe Glu Ser Ala Gln Phe Pro Asn Trp
145                 150                 155                 160

Tyr Ile Ser Thr Ser Gln Ala Glu Asn Met Pro Val Phe Leu Gly Gly
                165                 170                 175

Thr Lys Gly Gly Gln Asp Ile Thr Asp Phe Thr Met Gln Phe Val Ser
            180                 185                 190

Ser

<210> SEQ ID NO 51
<211> LENGTH: 269
<212> TYPE: PRT
<213> ORGANISM: Macaca mulatta
```

<400> SEQUENCE: 51

Met Ala Glu Val Pro Glu Leu Ala Ser Glu Met Met Ala Tyr Tyr Ser
1               5                   10                  15

Gly Asn Glu Asp Asp Leu Phe Phe Asp Val Asp Gly Pro Lys Gln Met
            20                  25                  30

Lys Cys Ser Phe Gln Asp Leu Asp Leu Cys Pro Leu Gly Gly Gly Ile
        35                  40                  45

Gln Leu Gln Ile Ser His Glu His Tyr Asn Glu Gly Phe Arg Gln Ala
    50                  55                  60

Val Ser Val Val Val Ala Met Glu Lys Leu Arg Lys Met Leu Val Pro
65                  70                  75                  80

Cys Pro Gln Ile Phe Gln Asp Asn Asp Leu Ser Thr Leu Ile Pro Phe
                85                  90                  95

Ile Phe Glu Glu Glu Pro Val Phe Leu Asp Thr Arg Asn Asn Asp Ala
            100                 105                 110

Cys Val His Asp Ala Pro Val Arg Ser Leu His Cys Thr Leu Arg Asp
        115                 120                 125

Ala Gln Leu Lys Ser Leu Val Met Ser Gly Pro Tyr Glu Leu Lys Ala
    130                 135                 140

Leu His Leu Gln Gly Gln Asp Leu Glu Gln Gln Val Val Phe Ser Met
145                 150                 155                 160

Ser Phe Val Gln Gly Glu Ser Asn Asp Lys Ile Pro Val Ala Leu
                165                 170                 175

Gly Leu Lys Ala Lys Asn Leu Tyr Leu Ser Cys Val Leu Lys Asp Asp
            180                 185                 190

Lys Pro Thr Leu Gln Leu Glu Ser Val Asp Pro Lys Asn Tyr Pro Lys
        195                 200                 205

Lys Lys Met Glu Lys Arg Phe Val Phe Asn Lys Ile Glu Ile Asn Asn
    210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Arg Gly Gly
                245                 250                 255

Gln Asp Ile Thr Asp Phe Thr Met Gln Phe Val Ser Ser
            260                 265

<210> SEQ ID NO 52
<211> LENGTH: 268
<212> TYPE: PRT
<213> ORGANISM: Oryctolagus cunicullus

<400> SEQUENCE: 52

Met Ala Thr Val Pro Glu Leu Thr Ser Glu Met Met Ala Tyr His Ser
1               5                   10                  15

Gly Asn Glu Asn Asp Leu Phe Phe Glu Ala Asp Gly Pro Asn Tyr Met
            20                  25                  30

Lys Ser Cys Phe Gln Asp Leu Asp Leu Cys Pro Asp Glu Gly Ile
        35                  40                  45

Gln Leu Arg Ile Ser Cys Gln Pro Tyr Asn Lys Ser Phe Arg Gln Val
    50                  55                  60

Leu Ser Val Val Val Ala Leu Glu Lys Leu Arg Gln Lys Ala Val Pro
65                  70                  75                  80

Cys Pro Gln Ala Phe Gln Asp Asp Gly Leu Arg Thr Phe Phe Ser Leu
                85                  90                  95

```
Ile Phe Glu Glu Pro Val Leu Cys Asn Thr Trp Asp Asp Tyr Ser
            100                 105                 110
Leu Glu Cys Asp Ala Val Arg Ser Leu His Cys Arg Leu Gln Asp Ala
            115                 120                 125
Gln Gln Lys Ser Leu Val Leu Ser Gly Thr Tyr Glu Leu Lys Ala Leu
    130                 135                 140
His Leu Asn Ala Glu Asn Leu Asn Gln Gln Val Val Phe Ser Met Ser
145                 150                 155                 160
Phe Val Gln Gly Glu Ser Asn Asp Lys Ile Pro Val Ala Leu Gly
                165                 170                 175
Leu Arg Gly Lys Asn Leu Tyr Leu Ser Cys Val Met Lys Asp Asp Lys
            180                 185                 190
Pro Thr Leu Gln Leu Glu Ser Val Asp Pro Asn Arg Tyr Pro Lys Lys
            195                 200                 205
Lys Met Glu Lys Arg Phe Val Phe Asn Lys Ile Glu Ile Lys Asp Lys
    210                 215                 220
Leu Glu Phe Glu Ser Ala Gln Phe Pro Asn Trp Tyr Ile Ser Thr Ser
225                 230                 235                 240
Gln Thr Glu Tyr Met Pro Val Phe Leu Gly Asn Asn Ser Gly Gly Gln
                245                 250                 255
Asp Leu Ile Asp Phe Ser Met Glu Phe Val Ser Ser
            260                 265

<210> SEQ ID NO 53
<211> LENGTH: 269
<212> TYPE: PRT
<213> ORGANISM: Mus musculus

<400> SEQUENCE: 53

Met Ala Thr Val Pro Glu Leu Asn Cys Glu Met Pro Pro Phe Asp Ser
1               5                   10                  15
Asp Glu Asn Asp Leu Phe Phe Glu Val Asp Gly Pro Gln Lys Met Lys
            20                  25                  30
Gly Cys Phe Gln Thr Phe Asp Leu Gly Cys Pro Asp Glu Ser Ile Gln
        35                  40                  45
Leu Gln Ile Ser Gln Gln His Ile Asn Lys Ser Phe Arg Gln Ala Val
    50                  55                  60
Ser Leu Ile Val Ala Val Glu Lys Leu Trp Gln Leu Pro Val Ser Phe
65                  70                  75                  80
Pro Trp Thr Phe Gln Asp Glu Asp Met Ser Thr Phe Phe Ser Phe Ile
                85                  90                  95
Phe Glu Glu Glu Pro Ile Leu Cys Asp Ser Trp Asp Asp Asp Asn
            100                 105                 110
Leu Leu Val Cys Asp Val Pro Ile Arg Gln Leu His Tyr Arg Leu Arg
            115                 120                 125
Asp Glu Gln Gln Lys Ser Leu Val Leu Ser Asp Pro Tyr Glu Leu Lys
    130                 135                 140
Ala Leu His Leu Asn Gly Gln Asn Ile Asn Gln Gln Val Ile Phe Ser
145                 150                 155                 160
Met Ser Phe Val Gln Gly Glu Pro Ser Asn Asp Lys Ile Pro Val Ala
                165                 170                 175
Leu Gly Leu Lys Gly Lys Asn Leu Tyr Leu Ser Cys Val Met Lys Asp
            180                 185                 190
Gly Thr Pro Thr Leu Gln Leu Glu Ser Val Asp Pro Lys Gln Tyr Pro
            195                 200                 205
```

```
Lys Lys Lys Met Glu Lys Arg Phe Val Phe Asn Lys Ile Glu Val Lys
            210                 215                 220

Ser Lys Val Glu Phe Glu Ser Ala Glu Phe Pro Asn Trp Tyr Ile Ser
225                 230                 235                 240

Thr Ser Gln Ala Glu His Lys Pro Val Phe Leu Gly Asn Asn Ser Gly
                245                 250                 255

Gln Asp Ile Ile Asp Phe Thr Met Glu Ser Val Ser Ser
                260                 265
```

<210> SEQ ID NO 54
<211> LENGTH: 268
<212> TYPE: PRT
<213> ORGANISM: Rattus norvegicus

<400> SEQUENCE: 54

```
Met Ala Thr Val Pro Glu Leu Asn Cys Glu Ile Ala Ala Phe Asp Ser
1               5                   10                  15

Glu Glu Asn Asp Leu Phe Phe Glu Ala Asp Arg Pro Gln Lys Ile Lys
            20                  25                  30

Asp Cys Phe Gln Ala Leu Asp Leu Gly Cys Pro Asp Glu Ser Ile Gln
        35                  40                  45

Leu Gln Ile Ser Gln Gln His Leu Asp Lys Ser Phe Arg Lys Ala Val
50                  55                  60

Ser Leu Ile Val Ala Val Glu Lys Leu Trp Gln Leu Pro Met Ser Cys
65                  70                  75                  80

Pro Trp Ser Phe Gln Asp Glu Asp Pro Ser Thr Phe Phe Ser Phe Ile
                85                  90                  95

Phe Glu Glu Glu Pro Val Leu Cys Asp Ser Trp Asp Asp Asp Leu
            100                 105                 110

Leu Val Cys Asp Val Pro Ile Arg Gln Leu His Cys Arg Leu Arg Asp
        115                 120                 125

Glu Gln Gln Lys Cys Leu Val Leu Ser Asp Pro Cys Glu Leu Lys Ala
    130                 135                 140

Leu His Leu Asn Gly Gln Asn Ile Ser Gln Gln Val Val Phe Ser Met
145                 150                 155                 160

Ser Phe Val Gln Gly Glu Thr Ser Asn Asp Lys Ile Pro Val Ala Leu
                165                 170                 175

Gly Leu Lys Gly Leu Asn Leu Tyr Leu Ser Cys Val Met Lys Asp Gly
            180                 185                 190

Thr Pro Thr Leu Gln Leu Glu Ser Val Asp Pro Lys Gln Tyr Pro Lys
        195                 200                 205

Lys Lys Met Glu Lys Arg Phe Val Phe Asn Lys Ile Glu Val Lys Thr
    210                 215                 220

Lys Val Glu Phe Glu Ser Ala Gln Phe Pro Asn Trp Tyr Ile Ser Thr
225                 230                 235                 240

Ser Gln Ala Glu His Arg Pro Val Phe Leu Gly Asn Ser Asn Gly Arg
                245                 250                 255

Asp Ile Val Asp Phe Thr Met Glu Pro Val Ser Ser
            260                 265
```

<210> SEQ ID NO 55
<211> LENGTH: 268
<212> TYPE: PRT
<213> ORGANISM: Equus caballus

<400> SEQUENCE: 55

```
Met Ala Ala Val Pro Asp Thr Ser Asp Met Met Thr Tyr Cys Ser Gly
```

```
                1               5                  10                 15
Asn Glu Asn Asp Leu Phe Phe Glu Glu Asp Gly Pro Lys Gln Met Lys
            20                 25                 30

Gly Ser Phe Gln Asp Leu Asp Leu Ser Ser Met Gly Asn Gly Gly Ile
            35                 40                 45

Gln Leu Gln Phe Ser His Gln Leu Tyr Asn Lys Thr Phe Lys His Val
            50                 55                 60

Val Ser Ile Ile Val Ala Met Glu Lys Leu Lys Lys Ile Pro Val Pro
65                             70                 75                 80

Cys Ser Gln Ala Phe Gln Asp Asp Leu Arg Ser Leu Phe Ser Val
            85                 90                 95

Ile Phe Glu Glu Glu Pro Ile Ile Cys Asp Asn Trp Asp Asp Asp Tyr
            100                105                110

Val Cys Asp Ala Ala Val His Ser Val Asn Cys Arg Leu Arg Asp Ile
            115                120                125

Tyr His Lys Ser Leu Val Leu Ser Gly Ala Cys Glu Leu Gln Ala Val
            130                135                140

His Leu Asn Gly Glu Asn Thr Asn Gln Gln Val Val Phe Cys Met Ser
145                            150                155                160

Phe Val Gln Gly Glu Glu Thr Asp Lys Ile Pro Val Ala Leu Gly
            165                170                175

Leu Lys Glu Lys Asn Leu Tyr Leu Ser Cys Gly Met Lys Asp Gly Lys
            180                185                190

Pro Thr Leu Gln Leu Glu Thr Val Asp Pro Asn Thr Tyr Pro Lys Arg
            195                200                205

Lys Met Glu Lys Arg Phe Val Phe Asn Lys Met Glu Ile Lys Gly Asn
            210                215                220

Val Glu Phe Glu Ser Ala Met Tyr Pro Asn Trp Tyr Ile Ser Thr Ser
225                            230                235                240

Gln Ala Glu Lys Lys Pro Val Phe Leu Gly Asn Thr Arg Gly Arg
            245                250                255

Asp Ile Thr Asp Phe Ile Met Glu Ile Thr Ser Ala
            260                265

<210> SEQ ID NO 56
<211> LENGTH: 267
<212> TYPE: PRT
<213> ORGANISM: Felis catus

<400> SEQUENCE: 56

Met Ala Pro Val Pro Glu Leu Thr Ser Glu Met Met Ala Tyr Tyr Ser
1               5                  10                 15

Asp Glu Asn Asp Leu Phe Phe Glu Ala Asp Gly Pro Glu Lys Met Lys
            20                 25                 30

Gly Ser Leu Gln Asn Leu Ser His Ser Phe Leu Gly Asp Glu Gly Ile
            35                 40                 45

Gln Leu Gln Ile Ser His Gln Pro Asp Asn Lys Ser Leu Arg His Ala
            50                 55                 60

Val Ser Val Ile Val Ala Met Glu Lys Leu Lys Lys Ile Ser Phe Ala
65                             70                 75                 80

Cys Ser Gln Pro Leu Gln Asp Glu Asp Leu Lys Ser Leu Phe Cys Cys
            85                 90                 95

Ile Phe Glu Glu Glu Pro Ile Ile Cys Asp Thr Trp Asp Asp Gly Phe
            100                105                110

Val Cys Asp Ala Ala Ile Gln Ser Gln Asp Tyr Thr Phe Arg Asp Ile
```

```
                115                 120                 125
Ser Gln Lys Ser Leu Val Leu Ser Gly Ser Tyr Glu Leu Arg Ala Leu
        130                 135                 140

His Leu Asn Gly Gln Asn Met Asn Gln Gln Val Val Phe Arg Met Ser
145                 150                 155                 160

Phe Val His Gly Glu Glu Asn Ser Lys Lys Ile Pro Val Val Leu Cys
                165                 170                 175

Ile Lys Lys Asn Asn Leu Tyr Leu Ser Cys Val Met Lys Asp Gly Lys
            180                 185                 190

Pro Thr Leu Gln Leu Glu Met Leu Asp Pro Lys Val Tyr Pro Lys Lys
        195                 200                 205

Lys Met Glu Lys Arg Phe Val Phe Asn Lys Thr Glu Ile Lys Gly Asn
    210                 215                 220

Val Glu Phe Glu Ser Ser Gln Phe Pro Asn Trp Tyr Ile Ser Thr Ser
225                 230                 235                 240

Gln Ala Glu Glu Met Pro Val Phe Leu Gly Asn Thr Lys Gly Gly Gln
                245                 250                 255

Asp Ile Thr Asp Phe Ile Met Glu Ser Ala Ser
            260                 265

<210> SEQ ID NO 57
<211> LENGTH: 267
<212> TYPE: PRT
<213> ORGANISM: Sus scrofa

<400> SEQUENCE: 57

Met Ala Thr Val Pro Glu Pro Ala Lys Glu Val Met Ala Asn Asn Gly
1               5                   10                  15

Asp Asn Asn Asn Asp Leu Leu Phe Glu Ala Asp Gly Pro Lys Glu Met
            20                  25                  30

Lys Cys Arg Thr Gln Asn Leu Asp Leu Ser Pro Leu Gly Asp Gly Ser
        35                  40                  45

Ile Gln Leu Gln Ile Ser His Gln Leu Cys Asn Glu Ser Ser Arg Pro
    50                  55                  60

Met Val Ser Val Ile Val Ala Lys Glu Glu Pro Met Asn Pro Ser Ser
65                  70                  75                  80

Gln Val Val Cys Asp Asp Pro Lys Ser Ile Phe Ser Ser Val Phe
                85                  90                  95

Glu Glu Glu Pro Ile Val Leu Glu Lys His Ala Asn Gly Phe Leu Cys
            100                 105                 110

Asp Ala Thr Pro Val Gln Ser Val Asp Cys Lys Leu Gln Asp Lys Asp
        115                 120                 125

Glu Lys Ala Leu Val Leu Ala Gly Pro His Glu Leu Lys Ala Leu His
    130                 135                 140

Leu Leu Lys Gly Asp Leu Lys Arg Glu Val Val Phe Cys Met Ser Phe
145                 150                 155                 160

Val Gln Gly Asp Asp Ser Asp Asp Lys Ile Pro Val Thr Leu Gly Ile
                165                 170                 175

Lys Gly Lys Asn Leu Tyr Leu Ser Cys Val Met Lys Asp Asp Thr Pro
            180                 185                 190

Thr Leu Gln Leu Glu Asp Val Asp Pro Lys Ser Tyr Pro Lys Arg Asp
        195                 200                 205

Met Glu Lys Arg Phe Val Phe Tyr Lys Thr Glu Ile Lys Asn Arg Val
    210                 215                 220

Glu Phe Glu Ser Ala Leu Tyr Pro Asn Trp Tyr Ile Ser Thr Ser Gln
```

```
                225                 230                 235                 240
Ala Glu Gln Lys Pro Val Phe Leu Gly Asn Ser Lys Gly Arg Gln Asp
                245                 250                 255

Ile Thr Asp Phe Thr Met Glu Val Leu Ser Pro
                260                 265

<210> SEQ ID NO 58
<211> LENGTH: 266
<212> TYPE: PRT
<213> ORGANISM: Cavia porcellus

<400> SEQUENCE: 58

Met Ala Ala Val Pro Glu Leu Ser Ser Glu Val Thr Ala Tyr His Ser
  1               5                  10                  15

Asp Glu Asn Glu Leu Phe Phe Glu Val Asp Gly Pro Asn Lys Met Gln
                 20                  25                  30

Tyr Cys Phe Gln Asp Arg Asp Leu Cys Ser Leu Asp Glu Gly Ile Lys
             35                  40                  45

Leu Gln Ile Ser His Gln His Phe Asn Lys Ser Phe Arg Gln Thr Val
         50                  55                  60

Ser Leu Ile Val Ala Val Glu Lys Leu Arg Lys Leu Ala Pro Cys
 65                  70                  75                  80

Thr Trp Ala Phe Gln Asp Asp Leu Arg Pro Leu Pro Phe Ile
                 85                  90                  95

Phe Glu Glu Glu Pro Ile Val Cys Asp Thr Trp Asp Glu Glu Tyr Glu
                100                 105                 110

Ser Asp Thr Pro Val Pro Ser Arg Asn Cys Thr Leu His Asp Ile Gln
            115                 120                 125

His Lys Arg Leu Val Leu Ser Asp Pro Cys Glu Leu Lys Ala Leu His
        130                 135                 140

Leu Asn Gly Asp Asn Leu Asn Arg Gln Val Val Phe Ser Met Ser Phe
145                 150                 155                 160

Val Gln Gly Glu Arg Ser Asp Asn Lys Met Pro Val Ala Leu Gly Leu
                165                 170                 175

Lys Gly Lys Asn Leu Tyr Leu Ser Cys Val Met Lys Asp Gly Lys Pro
            180                 185                 190

Val Leu Gln Leu Glu Ser Val Asp Gly Lys Gln Tyr Pro Lys Lys Lys
        195                 200                 205

Met Glu Lys Arg Phe Val Phe Asn Lys Ile Thr Ser Lys Ser Thr Val
    210                 215                 220

Glu Phe Glu Ser Ala Gln Phe Pro Asn Trp Tyr Ile Ser Thr Ser Gln
225                 230                 235                 240

Ala Glu His Lys Pro Val Phe Leu Gly Asn Asn Asn Gly Gln Asp Ile
                245                 250                 255

Ile Asp Phe Lys Leu Glu Leu Val Ser Ser
                260                 265

<210> SEQ ID NO 59
<211> LENGTH: 266
<212> TYPE: PRT
<213> ORGANISM: Bos taurus

<400> SEQUENCE: 59

Met Ala Thr Val Pro Glu Pro Ile Asn Glu Met Met Ala Tyr Tyr Ser
  1               5                  10                  15

Asp Glu Asn Glu Leu Leu Phe Glu Ala Asp Asp Pro Lys Gln Met Lys
                 20                  25                  30
```

Ser Cys Ile Gln His Leu Asp Leu Gly Ser Met Gly Asp Gly Asn Ile
    35                  40                  45

Gln Leu Gln Ile Ser His Gln Phe Tyr Asn Lys Ser Phe Arg Gln Val
 50                  55                  60

Val Ser Val Ile Val Ala Met Glu Lys Leu Arg Asn Ser Ala Tyr Ala
65                   70                  75                  80

His Val Phe His Asp Asp Leu Arg Ser Ile Leu Ser Phe Ile Phe
                85                  90                  95

Glu Glu Glu Pro Val Ile Phe Glu Thr Ser Ser Asp Glu Phe Leu Cys
                100                 105                 110

Asp Ala Pro Val Gln Ser Ile Lys Cys Lys Leu Gln Asp Arg Glu Gln
            115                 120                 125

Lys Ser Leu Val Leu Ala Ser Pro Cys Val Leu Lys Ala Leu His Leu
        130                 135                 140

Leu Ser Gln Glu Met Asn Arg Glu Val Val Phe Cys Met Ser Phe Val
145                 150                 155                 160

Gln Gly Glu Glu Arg Asp Asn Lys Ile Pro Val Ala Leu Gly Ile Lys
                165                 170                 175

Asp Lys Asn Leu Tyr Leu Ser Cys Val Lys Lys Gly Asp Thr Pro Thr
            180                 185                 190

Leu Gln Leu Glu Val Asp Pro Lys Val Tyr Pro Lys Arg Asn Met
        195                 200                 205

Glu Lys Arg Phe Val Phe Tyr Lys Thr Glu Ile Lys Asn Thr Val Glu
        210                 215                 220

Phe Glu Ser Val Leu Tyr Pro Asn Trp Tyr Ile Ser Thr Ser Gln Ile
225                 230                 235                 240

Glu Glu Arg Pro Val Phe Leu Gly His Phe Arg Gly Gly Gln Asp Ile
                245                 250                 255

Thr Asp Phe Arg Met Glu Thr Leu Ser Pro
            260                 265

<210> SEQ ID NO 60
<211> LENGTH: 266
<212> TYPE: PRT
<213> ORGANISM: Ovis aries

<400> SEQUENCE: 60

Met Ala Thr Val Pro Glu Pro Ile Asn Glu Val Met Ala Tyr Tyr Ser
1               5                   10                  15

Asp Glu Asn Glu Leu Leu Phe Glu Val Asp Gly Pro Lys Gln Met Lys
                20                  25                  30

Ser Cys Thr Gln His Leu Asp Leu Gly Ser Met Gly Asp Gly Asn Ile
    35                  40                  45

Gln Leu Gln Ile Ser His Gln Leu Tyr Asn Lys Ser Phe Arg Gln Val
 50                  55                  60

Val Ser Val Ile Val Ala Met Glu Lys Leu Arg Ser Arg Ala Tyr Glu
65                   70                  75                  80

His Val Phe Arg Asp Asp Leu Arg Ser Ile Leu Ser Phe Ile Phe
                85                  90                  95

Glu Glu Glu Pro Val Ile Phe Glu Thr Ser Ser Asp Glu Leu Leu Cys
                100                 105                 110

Asp Ala Ala Val Gln Ser Val Lys Cys Lys Leu Gln Asp Arg Glu Gln
            115                 120                 125

Lys Ser Leu Val Leu Asp Ser Pro Cys Val Leu Lys Ala Leu His Leu
        130                 135                 140

```
Pro Ser Gln Glu Met Ser Arg Glu Val Val Phe Cys Met Ser Phe Val
145                 150                 155                 160

Gln Gly Glu Glu Arg Asp Asn Lys Ile Pro Val Ala Leu Gly Ile Arg
            165                 170                 175

Asp Lys Asn Leu Tyr Leu Ser Cys Val Lys Lys Gly Asp Thr Pro Thr
        180                 185                 190

Leu Gln Leu Glu Glu Val Asp Pro Lys Val Tyr Pro Lys Arg Asn Met
    195                 200                 205

Glu Lys Arg Phe Val Phe Tyr Lys Thr Glu Ile Lys Asn Thr Val Glu
210                 215                 220

Phe Glu Ser Val Leu Tyr Pro Asn Trp Tyr Ile Ser Thr Ser Gln Ile
225                 230                 235                 240

Glu Glu Lys Pro Val Phe Leu Gly Arg Phe Arg Gly Gly Gln Asp Ile
                245                 250                 255

Thr Asp Phe Arg Met Glu Thr Leu Ser Pro
            260                 265

<210> SEQ ID NO 61
<211> LENGTH: 267
<212> TYPE: PRT
<213> ORGANISM: Gallus gallus

<400> SEQUENCE: 61

Met Ala Phe Val Pro Asp Leu Asp Val Leu Glu Ser Ser Ser Leu Ser
1               5                   10                  15

Glu Glu Thr Phe Tyr Gly Pro Ser Cys Leu Cys Leu Gln Lys Lys Pro
            20                  25                  30

Arg Leu Asp Ser Glu His Thr Thr Val Asp Val Gln Val Thr Val Arg
        35                  40                  45

Lys Gly Arg Gly Ala Arg Ser Phe Arg Arg Ala Ala Val Leu Val Val
    50                  55                  60

Ala Met Thr Lys Leu Leu Arg Arg Pro Arg Ser Arg Asp Phe Ala Asp
65                  70                  75                  80

Ser Asp Leu Ser Ala Leu Leu Glu Glu Val Phe Glu Pro Val Thr Phe
                85                  90                  95

Gln Arg Leu Glu Ser Ser Tyr Ala Gly Ala Pro Ala Phe Arg Tyr Thr
            100                 105                 110

Arg Ser Gln Ser Phe Asp Ile Phe Asp Ile Asn Gln Lys Cys Phe Val
        115                 120                 125

Leu Glu Ser Pro Thr Gln Leu Val Ala Leu His Leu Gln Gly Pro Ser
    130                 135                 140

Ser Ser Gln Lys Val Arg Leu Asn Ile Ala Leu Tyr Arg Pro Arg Gly
145                 150                 155                 160

Pro Arg Gly Ser Ala Gly Thr Gly Gln Met Pro Val Ala Leu Gly Ile
                165                 170                 175

Lys Gly Tyr Lys Leu Tyr Met Ser Cys Val Met Ser Gly Thr Glu Pro
            180                 185                 190

Thr Leu Gln Leu Glu Glu Ala Asp Val Met Arg Asp Ile Asp Ser Val
        195                 200                 205

Glu Leu Thr Arg Phe Ile Phe Tyr Arg Leu Asp Ser Pro Thr Glu Gly
    210                 215                 220

Thr Thr Arg Phe Glu Ser Ala Ala Phe Pro Gly Trp Phe Ile Cys Thr
225                 230                 235                 240

Ser Leu Gln Pro Arg Gln Pro Val Gly Ile Thr Asn Gln Pro Asp Gln
                245                 250                 255
```

-continued

```
Val Asn Ile Ala Thr Tyr Lys Leu Ser Gly Arg
            260                 265

<210> SEQ ID NO 62
<211> LENGTH: 127
<212> TYPE: PRT
<213> ORGANISM: Canis familiaris

<400> SEQUENCE: 62

Gly Pro Gly Gly Ser Asn Val Lys Cys Cys Gln Asp Leu Asn His
1               5                   10                  15

Ser Ser Leu Val Asp Glu Gly Ile Gln Leu Gln Val Ser His Gln Leu
                20                  25                  30

Cys Asn Lys Ser Leu Arg His Phe Val Ser Val Ile Val Ala Leu Glu
            35                  40                  45

Lys Leu Lys Lys Pro Cys Pro Gln Val Leu Gln Glu Asp Asp Leu Lys
        50                  55                  60

Ser Ile Phe Cys Tyr Ile Phe Glu Glu Glu Pro Ile Ile Cys Lys Thr
65                  70                  75                  80

Asp Ala Asp Asn Phe Met Ser Asp Ala Ala Met Gln Ser Val Asp Cys
                85                  90                  95

Lys Leu Gln Asp Ile Ser His Lys Tyr Leu Val Leu Ser Asn Ser Tyr
            100                 105                 110

Glu Leu Arg Ala Leu His Leu Asn Gly Glu Asn Val Asn Lys Ala
        115                 120                 125

<210> SEQ ID NO 63
<211> LENGTH: 153
<212> TYPE: PRT
<213> ORGANISM: Homo sapiens

<400> SEQUENCE: 63

Leu Ser Asn Val Lys Tyr Asn Phe Met Arg Ile Ile Lys Tyr Glu Phe
1               5                   10                  15

Ile Leu Asn Asp Ala Leu Asn Gln Ser Ile Ile Arg Ala Asn Asp Gln
                20                  25                  30

Tyr Leu Thr Ala Ala Ala Leu His Asn Leu Asp Glu Ala Val Lys Phe
            35                  40                  45

Asp Met Gly Ala Tyr Lys Ser Ser Lys Asp Asp Ala Lys Ile Thr Val
        50                  55                  60

Ile Leu Arg Ile Ser Lys Thr Gln Leu Tyr Val Thr Ala Gln Asp Glu
65                  70                  75                  80

Asp Gln Pro Val Leu Leu Lys Glu Met Pro Glu Ile Pro Lys Thr Ile
                85                  90                  95

Thr Gly Ser Glu Thr Asn Leu Leu Phe Phe Trp Glu Thr His Gly Thr
            100                 105                 110

Lys Asn Tyr Phe Thr Ser Val Ala His Pro Asn Leu Phe Ile Ala Thr
        115                 120                 125

Lys Gln Asp Tyr Trp Val Cys Leu Ala Gly Gly Pro Pro Ser Ile Thr
    130                 135                 140

Asp Phe Gln Ile Leu Glu Asn Gln Ala
145                 150

<210> SEQ ID NO 64
<211> LENGTH: 153
<212> TYPE: PRT
<213> ORGANISM: Homo sapiens
```

<400> SEQUENCE: 64

```
Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
            100                 105                 110

Glu Ser Ala Gln Phe Pro Asn Trp Tyr Ile Ser Thr Ser Gln Ala Glu
        115                 120                 125

Asn Met Pro Val Phe Leu Gly Gly Thr Lys Gly Gly Gln Asp Ile Thr
    130                 135                 140

Asp Phe Thr Met Gln Phe Val Ser Ser
145                 150
```

```
<210> SEQ ID NO 65
<211> LENGTH: 183
<212> TYPE: PRT
<213> ORGANISM: Mus musculus
```

<400> SEQUENCE: 65

```
Met Asp Pro His His His His His Gly Ser Gly Asp Asp Asp Asp Asp
1               5                   10                  15

Lys Ala Leu Ala Pro Tyr Thr Tyr Gln Ser Asp Leu Arg Tyr Lys Leu
            20                  25                  30

Met Lys Leu Val Arg Gln Lys Phe Val Met Asn Asp Ser Leu Asn Gln
        35                  40                  45

Thr Ile Tyr Gln Asp Val Asp Lys His Tyr Leu Ser Thr Thr Trp Leu
    50                  55                  60

Asn Asp Leu Gln Gln Glu Val Lys Phe Asp Met Tyr Ala Tyr Ser Ser
65                  70                  75                  80

Gly Gly Asp Asp Ser Lys Tyr Pro Val Thr Leu Lys Ile Ser Asp Ser
                85                  90                  95

Gln Leu Phe Val Ser Ala Gln Gly Glu Asp Gln Pro Val Leu Leu Lys
            100                 105                 110

Glu Leu Pro Glu Thr Pro Lys Leu Ile Thr Gly Ser Glu Thr Asp Leu
        115                 120                 125

Ile Phe Phe Trp Lys Ser Ile Asn Ser Lys Asn Tyr Phe Thr Ser Ala
    130                 135                 140

Ala Tyr Pro Glu Leu Phe Ile Ala Thr Lys Glu Gln Ser Arg Val His
145                 150                 155                 160

Leu Ala Arg Gly Leu Pro Ser Met Thr Asp Phe Gln Ile Ser Leu Glu
                165                 170                 175

Gly Gly Gly Gly Gly Cys Gly
            180
```

```
<210> SEQ ID NO 66
<211> LENGTH: 180
<212> TYPE: PRT
```

<213> ORGANISM: Mus musculus

<400> SEQUENCE: 66

Met Asp Pro His His His His His Gly Ser Gly Asp Asp Asp Asp
1               5                   10                  15

Lys Ala Leu Ala Pro Ile Arg Gln Leu His Tyr Arg Leu Arg Asp Glu
            20                  25                  30

Gln Gln Lys Ser Leu Val Leu Ser Asp Pro Tyr Glu Leu Lys Ala Leu
        35                  40                  45

His Leu Asn Gly Gln Asn Ile Asn Gln Gln Val Ile Phe Ser Met Ser
    50                  55                  60

Phe Val Gln Gly Glu Pro Ser Asn Asp Lys Ile Pro Val Ala Leu Gly
65                  70                  75                  80

Leu Lys Gly Lys Asn Leu Tyr Leu Ser Cys Val Met Lys Asp Gly Thr
                85                  90                  95

Pro Thr Leu Gln Leu Glu Ser Val Asp Pro Lys Gln Tyr Pro Lys Lys
            100                 105                 110

Lys Met Glu Lys Arg Phe Val Phe Asn Lys Ile Glu Val Lys Ser Lys
        115                 120                 125

Val Glu Phe Glu Ser Ala Glu Phe Pro Asn Trp Tyr Ile Ser Thr Ser
130                 135                 140

Gln Ala Glu His Lys Pro Val Phe Leu Gly Asn Asn Ser Gly Gln Asp
145                 150                 155                 160

Ile Ile Asp Phe Thr Met Glu Ser Val Ser Ser Leu Glu Gly Gly Gly
                165                 170                 175

Gly Gly Cys Gly
            180

<210> SEQ ID NO 67
<211> LENGTH: 12
<212> TYPE: PRT
<213> ORGANISM: Homo sapiens

<400> SEQUENCE: 67

Met Arg Ile Ile Lys Tyr Glu Phe Ile Leu Asn Asp
1               5                   10

<210> SEQ ID NO 68
<211> LENGTH: 6
<212> TYPE: PRT
<213> ORGANISM: Homo sapiens

<400> SEQUENCE: 68

Arg Ile Ile Lys Tyr Glu
1               5

<210> SEQ ID NO 69
<211> LENGTH: 10
<212> TYPE: PRT
<213> ORGANISM: Homo sapiens

<400> SEQUENCE: 69

Tyr Glu Phe Ile Leu Asn Asp Ala Leu Asn
1               5                   10

<210> SEQ ID NO 70
<211> LENGTH: 12
<212> TYPE: PRT
<213> ORGANISM: Homo sapiens

<400> SEQUENCE: 70

Asn Asp Ala Leu Asn Gln Ser Ile Ile Arg Ala Asn
1               5                   10

<210> SEQ ID NO 71
<211> LENGTH: 10
<212> TYPE: PRT
<213> ORGANISM: Homo sapiens

<400> SEQUENCE: 71

Thr Ala Ala Ala Leu His Asn Leu Asp Glu
1               5                   10

<210> SEQ ID NO 72
<211> LENGTH: 12
<212> TYPE: PRT
<213> ORGANISM: Homo sapiens

<400> SEQUENCE: 72

Thr Ala Ala Ala Leu His Asn Leu Asp Glu Ala Val
1               5                   10

<210> SEQ ID NO 73
<211> LENGTH: 10
<212> TYPE: PRT
<213> ORGANISM: Homo sapiens

<400> SEQUENCE: 73

Ala Val Lys Phe Asp Met Gly Ala Tyr Lys
1               5                   10

<210> SEQ ID NO 74
<211> LENGTH: 11
<212> TYPE: PRT
<213> ORGANISM: Homo sapiens

<400> SEQUENCE: 74

Ala Tyr Lys Ser Ser Lys Asp Asp Ala Lys Ile
1               5                   10

<210> SEQ ID NO 75
<211> LENGTH: 31
<212> TYPE: PRT
<213> ORGANISM: Homo sapiens

<400> SEQUENCE: 75

Ser Ser Lys Asp Asp Ala Lys Ile Thr Val Ile Leu Arg Ile Ser Lys
1               5                   10                  15

Thr Gln Leu Tyr Val Thr Ala Gln Asp Glu Asp Gln Pro Val Leu
            20                  25                  30

<210> SEQ ID NO 76
<211> LENGTH: 13
<212> TYPE: PRT
<213> ORGANISM: Homo sapiens

<400> SEQUENCE: 76

Val Ile Leu Arg Ile Ser Lys Thr Gln Leu Tyr Val Thr
1               5                   10

<210> SEQ ID NO 77
<211> LENGTH: 22
<212> TYPE: PRT
<213> ORGANISM: Homo sapiens

<400> SEQUENCE: 77

Val Ile Leu Arg Ile Ser Lys Thr Gln Leu Tyr Val Thr Ala Gln Asp
1               5                   10                  15

Glu Asp Gln Pro Val Leu
            20

<210> SEQ ID NO 78
<211> LENGTH: 20
<212> TYPE: PRT
<213> ORGANISM: Homo sapiens

<400> SEQUENCE: 78

Thr Gln Leu Tyr Val Thr Ala Gln Asp Glu Asp Gln Pro Val Leu Leu
1               5                   10                  15

Lys Glu Met Pro
            20

<210> SEQ ID NO 79
<211> LENGTH: 21
<212> TYPE: PRT
<213> ORGANISM: Homo sapiens

<400> SEQUENCE: 79

Pro Val Leu Leu Lys Glu Met Pro Glu Ile Pro Lys Thr Ile Thr Gly
1               5                   10                  15

Ser Glu Thr Asn Leu
            20

<210> SEQ ID NO 80
<211> LENGTH: 14
<212> TYPE: PRT
<213> ORGANISM: Homo sapiens

<400> SEQUENCE: 80

Glu Met Pro Glu Ile Pro Lys Thr Ile Thr Gly Ser Glu Thr
1               5                   10

<210> SEQ ID NO 81
<211> LENGTH: 12
<212> TYPE: PRT
<213> ORGANISM: Homo sapiens

<400> SEQUENCE: 81

Lys Thr Ile Thr Gly Ser Glu Thr Asn Leu Leu Phe
1               5                   10

<210> SEQ ID NO 82
<211> LENGTH: 21
<212> TYPE: PRT
<213> ORGANISM: Homo sapiens

<400> SEQUENCE: 82

Pro Lys Thr Ile Thr Gly Ser Glu Thr Asn Leu Leu Phe Phe Trp Glu
1               5                   10                  15

Thr His Gly Thr Lys
            20

<210> SEQ ID NO 83
<211> LENGTH: 10
<212> TYPE: PRT
<213> ORGANISM: Homo sapiens

<400> SEQUENCE: 83

Gly Ser Glu Thr Asn Leu Leu Phe Phe Trp

-continued

```
1               5                   10
```

<210> SEQ ID NO 84
<211> LENGTH: 12
<212> TYPE: PRT
<213> ORGANISM: Homo sapiens

<400> SEQUENCE: 84

```
Leu Phe Ile Ala Thr Lys Gln Asp Tyr Trp Val Cys
1               5                   10
```

<210> SEQ ID NO 85
<211> LENGTH: 13
<212> TYPE: PRT
<213> ORGANISM: Homo sapiens

<400> SEQUENCE: 85

```
Phe Ile Ala Thr Lys Gln Asp Tyr Trp Val Cys Leu Ala
1               5                   10
```

<210> SEQ ID NO 86
<211> LENGTH: 18
<212> TYPE: PRT
<213> ORGANISM: Homo sapiens

<400> SEQUENCE: 86

```
Ile Ala Thr Lys Gln Asp Tyr Trp Val Cys Leu Ala Gly Gly Pro Pro
1               5                   10                  15

Ser Ile
```

<210> SEQ ID NO 87
<211> LENGTH: 5
<212> TYPE: PRT
<213> ORGANISM: Homo sapiens

<400> SEQUENCE: 87

```
Lys Gln Asp Tyr Trp
1               5
```

<210> SEQ ID NO 88
<211> LENGTH: 7
<212> TYPE: PRT
<213> ORGANISM: Homo sapiens

<400> SEQUENCE: 88

```
Gln Ile Leu Glu Asn Gln Ala
1               5
```

<210> SEQ ID NO 89
<211> LENGTH: 6
<212> TYPE: PRT
<213> ORGANISM: Homo sapiens

<400> SEQUENCE: 89

```
Ala Pro Val Arg Ser Leu
1               5
```

<210> SEQ ID NO 90
<211> LENGTH: 12
<212> TYPE: PRT
<213> ORGANISM: Homo sapiens

<400> SEQUENCE: 90

```
Ala Pro Val Arg Ser Leu Asn Cys Thr Leu Arg Asp
1               5                   10
```

```
<210> SEQ ID NO 91
<211> LENGTH: 10
<212> TYPE: PRT
<213> ORGANISM: Homo sapiens

<400> SEQUENCE: 91

Leu Asn Cys Thr Leu Arg Asp Ser Gln Gln
1               5                   10

<210> SEQ ID NO 92
<211> LENGTH: 12
<212> TYPE: PRT
<213> ORGANISM: Homo sapiens

<400> SEQUENCE: 92

Arg Asp Ser Gln Gln Lys Ser Leu Val Met Ser Gly
1               5                   10

<210> SEQ ID NO 93
<211> LENGTH: 12
<212> TYPE: PRT
<213> ORGANISM: Homo sapiens

<400> SEQUENCE: 93

Lys Ala Leu His Leu Gln Gly Gln Asp Met Glu Gln
1               5                   10

<210> SEQ ID NO 94
<211> LENGTH: 14
<212> TYPE: PRT
<213> ORGANISM: Homo sapiens

<400> SEQUENCE: 94

Lys Ala Leu His Leu Gln Gly Gln Asp Met Glu Gln Gln Val
1               5                   10

<210> SEQ ID NO 95
<211> LENGTH: 10
<212> TYPE: PRT
<213> ORGANISM: Homo sapiens

<400> SEQUENCE: 95

Gln Val Val Phe Ser Met Ser Phe Val Gln
1               5                   10

<210> SEQ ID NO 96
<211> LENGTH: 11
<212> TYPE: PRT
<213> ORGANISM: Homo sapiens

<400> SEQUENCE: 96

Phe Val Gln Gly Glu Glu Ser Asn Asp Lys Ile
1               5                   10

<210> SEQ ID NO 97
<211> LENGTH: 32
<212> TYPE: PRT
<213> ORGANISM: Homo sapiens

<400> SEQUENCE: 97

Gly Glu Glu Ser Asn Asp Lys Ile Pro Val Ala Leu Gly Leu Lys Glu
1               5                   10                  15

Lys Asn Leu Tyr Leu Ser Cys Val Leu Lys Asp Asp Lys Pro Thr Leu
            20                  25                  30
```

<210> SEQ ID NO 98
<211> LENGTH: 13
<212> TYPE: PRT
<213> ORGANISM: Homo sapiens

<400> SEQUENCE: 98

Val Ala Leu Gly Leu Lys Glu Lys Asn Leu Tyr Leu Ser
1               5                   10

<210> SEQ ID NO 99
<211> LENGTH: 23
<212> TYPE: PRT
<213> ORGANISM: Homo sapiens

<400> SEQUENCE: 99

Val Ala Leu Gly Leu Lys Glu Lys Asn Leu Tyr Leu Ser Cys Val Leu
1               5                   10                  15

Lys Asp Asp Lys Pro Thr Leu
            20

<210> SEQ ID NO 100
<211> LENGTH: 21
<212> TYPE: PRT
<213> ORGANISM: Homo sapiens

<400> SEQUENCE: 100

Lys Asn Leu Tyr Leu Ser Cys Val Leu Lys Asp Asp Lys Pro Thr Leu
1               5                   10                  15

Gln Leu Glu Ser Val
            20

<210> SEQ ID NO 101
<211> LENGTH: 20
<212> TYPE: PRT
<213> ORGANISM: Homo sapiens

<400> SEQUENCE: 101

Pro Thr Leu Gln Leu Glu Ser Val Asp Pro Lys Asn Tyr Pro Lys Lys
1               5                   10                  15

Lys Met Glu Lys
            20

<210> SEQ ID NO 102
<211> LENGTH: 13
<212> TYPE: PRT
<213> ORGANISM: Homo sapiens

<400> SEQUENCE: 102

Glu Ser Val Asp Pro Lys Asn Tyr Pro Lys Lys Lys Met
1               5                   10

<210> SEQ ID NO 103
<211> LENGTH: 12
<212> TYPE: PRT
<213> ORGANISM: Homo sapiens

<400> SEQUENCE: 103

Lys Asn Tyr Pro Lys Lys Lys Met Glu Lys Arg Phe
1               5                   10

<210> SEQ ID NO 104
<211> LENGTH: 10
<212> TYPE: PRT

<213> ORGANISM: Homo sapiens

<400> SEQUENCE: 104

Lys Lys Lys Met Glu Lys Arg Phe Val Phe
1               5                   10

<210> SEQ ID NO 105
<211> LENGTH: 18
<212> TYPE: PRT
<213> ORGANISM: Homo sapiens

<400> SEQUENCE: 105

Lys Lys Lys Met Glu Lys Arg Phe Val Phe Asn Lys Ile Glu Ile Asn
1               5                   10                  15

Asn Lys

<210> SEQ ID NO 106
<211> LENGTH: 14
<212> TYPE: PRT
<213> ORGANISM: Homo sapiens

<400> SEQUENCE: 106

Trp Tyr Ile Ser Thr Ser Gln Ala Glu Asn Met Pro Val Phe
1               5                   10

<210> SEQ ID NO 107
<211> LENGTH: 15
<212> TYPE: PRT
<213> ORGANISM: Homo sapiens

<400> SEQUENCE: 107

Tyr Ile Ser Thr Ser Gln Ala Glu Asn Met Pro Val Phe Leu Gly
1               5                   10                  15

<210> SEQ ID NO 108
<211> LENGTH: 22
<212> TYPE: PRT
<213> ORGANISM: Homo sapiens

<400> SEQUENCE: 108

Ile Ser Thr Ser Gln Ala Glu Asn Met Pro Val Phe Leu Gly Gly Thr
1               5                   10                  15

Lys Gly Gly Gln Asp Ile
            20

<210> SEQ ID NO 109
<211> LENGTH: 6
<212> TYPE: PRT
<213> ORGANISM: Homo sapiens

<400> SEQUENCE: 109

Gln Ala Glu Asn Met Pro
1               5

<210> SEQ ID NO 110
<211> LENGTH: 7
<212> TYPE: PRT
<213> ORGANISM: Homo sapiens

<400> SEQUENCE: 110

Thr Met Gln Phe Val Ser Ser
1               5

<210> SEQ ID NO 111

```
<211> LENGTH: 12
<212> TYPE: PRT
<213> ORGANISM: Mus musculus

<400> SEQUENCE: 111

Val Pro Ile Arg Gln Leu His Tyr Arg Leu Arg Asp
1               5                   10

<210> SEQ ID NO 112
<211> LENGTH: 14
<212> TYPE: PRT
<213> ORGANISM: Mus musculus

<400> SEQUENCE: 112

Lys Ala Leu His Leu Asn Gly Gln Asn Ile Asn Gln Gln Val
1               5                   10

<210> SEQ ID NO 113
<211> LENGTH: 15
<212> TYPE: PRT
<213> ORGANISM: Mus musculus

<400> SEQUENCE: 113

Tyr Ile Ser Thr Ser Gln Ala Glu His Lys Pro Val Phe Leu Gly
1               5                   10                  15

<210> SEQ ID NO 114
<211> LENGTH: 20
<212> TYPE: PRT
<213> ORGANISM: Rattus norvegicus

<400> SEQUENCE: 114

Asn Leu Tyr Leu Ser Cys Val Met Lys Asp Gly Thr Pro Thr Leu Gln
1               5                   10                  15

Leu Glu Ser Val
            20

<210> SEQ ID NO 115
<211> LENGTH: 20
<212> TYPE: PRT
<213> ORGANISM: Rattus norvegicus

<400> SEQUENCE: 115

Pro Thr Leu Gln Leu Glu Ser Val Asp Pro Lys Gln Tyr Pro Lys Lys
1               5                   10                  15

Lys Met Glu Lys
            20

<210> SEQ ID NO 116
<211> LENGTH: 22
<212> TYPE: PRT
<213> ORGANISM: Rattus norvegicus

<400> SEQUENCE: 116

Ile Ser Thr Ser Gln Ala Glu His Arg Pro Val Phe Leu Gly Asn Ser
1               5                   10                  15

Asn Gly Arg Asp Ile Val
            20

<210> SEQ ID NO 117
<211> LENGTH: 421
<212> TYPE: DNA
<213> ORGANISM: Artificial sequence
<220> FEATURE:
<223> OTHER INFORMATION: synthesized sequence
```

<400> SEQUENCE: 117

```
atggcaaata agccaatgca accgatcaca tctacagcaa ataaaattgt gtggtcggat      60
ccaactcgtt tatcaactac attttcagca agtctgttac gccaacgtgt taaagttggt     120
atagccgaac tgaataatgt ttcaggtcaa tatgtatctg tttataagcg tcctgcacct     180
aaaccggaag gttgtgcaga tgcctgtgtc attatgccga atgaaaacca atccattcgc     240
acagtgattt cagggtcagc cgaaaacttg gctaccttaa aagcagaatg ggaaactcac     300
aaacgtaacg ttgacacact cttcgcgagc ggcaacgccg gtttgggttt ccttgaccct     360
actgcggcta tcgtatcgtc tgatactact gcttaggggat ccggataatg catctaagct    420
t                                                                    421
```

<210> SEQ ID NO 118
<211> LENGTH: 421
<212> TYPE: DNA
<213> ORGANISM: Artificial sequence
<220> FEATURE:
<223> OTHER INFORMATION: synthesized sequence

<400> SEQUENCE: 118

```
atggcaaata agccaatgca accgatcaca tctacagcaa ataaaattgt gtggtcggat      60
ccaactcgtt tatcaactac attttcagca agtctgttac gccaacgtgt taaagttggt     120
atagccgaac tgaataatgt ttcaggtcaa tatgtatctg tttataagcg tcctgcacct     180
aaaccggaag gttgtgcaga tgcctgtgtc attatgccga atgaaaacca atccattcgc     240
acagtgattt cagggtcagc cgaaaacttg gctaccttaa aagcagaatg ggaaactcac     300
aaacgtaacg ttgacacact cttcgcgagc ggcaacgccg gtttgggttt ccttgaccct     360
actgcggcta tcgtatcgtc tgatactact gcttgaggat ccggataatg catctaagct     420
t                                                                    421
```

<210> SEQ ID NO 119
<211> LENGTH: 28
<212> TYPE: DNA
<213> ORGANISM: Artificial sequence
<220> FEATURE:
<223> OTHER INFORMATION: synthesized sequence
<220> FEATURE:
<221> NAME/KEY: misc_feature
<222> LOCATION: (1)..(2)
<223> OTHER INFORMATION: n is a, c, g, or t

<400> SEQUENCE: 119

```
nnccatggca aataagccaa tgcaaccg                                        28
```

<210> SEQ ID NO 120
<211> LENGTH: 52
<212> TYPE: DNA
<213> ORGANISM: Artificial sequence
<220> FEATURE:
<223> OTHER INFORMATION: synthesized sequence

<400> SEQUENCE: 120

```
gtaagcttag atgcattatc cggatcccta agcagtagta tcagacgata cg            52
```

<210> SEQ ID NO 121
<211> LENGTH: 52
<212> TYPE: DNA
<213> ORGANISM: Artificial sequence
<220> FEATURE:
<223> OTHER INFORMATION: synthesized sequence

<400> SEQUENCE: 121
gtaagcttag atgcattatc cggatcctca agcagtagta tcagacgata cg    52

<210> SEQ ID NO 122
<211> LENGTH: 25
<212> TYPE: DNA
<213> ORGANISM: Artificial sequence
<220> FEATURE:
<223> OTHER INFORMATION: synthesized sequence

<400> SEQUENCE: 122
ggtccggagc gctagcccct tacac    25

<210> SEQ ID NO 123
<211> LENGTH: 40
<212> TYPE: DNA
<213> ORGANISM: Artificial sequence
<220> FEATURE:
<223> OTHER INFORMATION: synthesized sequence

<400> SEQUENCE: 123
gtaagcttat gcattatgat atctggaagt ctgtcataga    40

<210> SEQ ID NO 124
<211> LENGTH: 36
<212> TYPE: DNA
<213> ORGANISM: Artificial sequence
<220> FEATURE:
<223> OTHER INFORMATION: synthesized sequence

<400> SEQUENCE: 124
atatatgata tccctgtacg atcactgaac tgcacg    36

<210> SEQ ID NO 125
<211> LENGTH: 37
<212> TYPE: DNA
<213> ORGANISM: Artificial sequence
<220> FEATURE:
<223> OTHER INFORMATION: synthesized sequence

<400> SEQUENCE: 125
atatatctcg agggaagaca caaattgcat ggtgaag    37

<210> SEQ ID NO 126
<211> LENGTH: 48
<212> TYPE: DNA
<213> ORGANISM: Artificial sequence
<220> FEATURE:
<223> OTHER INFORMATION: synthesized sequence

<400> SEQUENCE: 126
tatggatatc gaattcaagc ttctgcagct gctcgagtaa ttgattac    48

<210> SEQ ID NO 127
<211> LENGTH: 50
<212> TYPE: DNA
<213> ORGANISM: Artificial sequence
<220> FEATURE:
<223> OTHER INFORMATION: synthesized sequence

<400> SEQUENCE: 127
ctaggtaatc aattactcga gcagctgcag aagcttgaat tcgatatcca    50

<210> SEQ ID NO 128
<211> LENGTH: 52

-continued

```
<212> TYPE: DNA
<213> ORGANISM: Artificial sequence
<220> FEATURE:
<223> OTHER INFORMATION: synthesized sequence

<400> SEQUENCE: 128
tcgagcacca ccaccaccac cacggtggtt gctaataata attgattaat ac            52

<210> SEQ ID NO 129
<211> LENGTH: 52
<212> TYPE: DNA
<213> ORGANISM: Artificial sequence
<220> FEATURE:
<223> OTHER INFORMATION: synthesized sequence

<400> SEQUENCE: 129
ctaggtatta atcaattatt attagcaacc accgtggtgg tggtggtggt gc            52

<210> SEQ ID NO 130
<211> LENGTH: 166
<212> TYPE: PRT
<213> ORGANISM: Homo sapiens

<400> SEQUENCE: 130
```

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Asp Lys Ile Pro Val Ala Leu Gly Leu
    50                  55                  60

Lys Glu Lys Asn Leu Tyr Leu Ser Cys Val Leu Lys Asp Asp Lys Pro
65                  70                  75                  80

Thr Leu Gln Leu Glu Ser Val Asp Pro Lys Asn Tyr Pro Lys Lys Lys
                85                  90                  95

Met Glu Lys Arg Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Gln
        115                 120                 125

Ala Glu Asn Met Pro Val Phe Leu Gly Gly Thr Lys Gly Gly Gln Asp
    130                 135                 140

Ile Thr Asp Phe Thr Met Gln Phe Val Ser Ser Leu Glu His His His
145                 150                 155                 160

His His His Gly Gly Cys
                165

```
<210> SEQ ID NO 131
<211> LENGTH: 155
<212> TYPE: PRT
<213> ORGANISM: Homo sapiens

<400> SEQUENCE: 131
```

Met Asp Ile Pro Val Asp Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Asp Lys Ile Pro Val Ala Leu Gly Leu

```
                 50                  55                  60
Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Lys Lys Lys
                 85                  90                  95

Met Glu Lys Arg Phe Val Phe Asn Lys Ile Glu Ile Asn Asn Lys Leu
                100                 105                 110

Glu Phe Glu Ser Ala Gln Phe Pro Asn Trp Tyr Ile Ser Thr Ser Gln
                115                 120                 125

Ala Glu Asn Met Pro Val Phe Leu Gly Gly Thr Lys Gly Gly Gln Asp
                130                 135                 140

Ile Thr Asp Phe Thr Met Gln Phe Val Ser Ser
145                 150                 155

<210> SEQ ID NO 132
<211> LENGTH: 155
<212> TYPE: PRT
<213> ORGANISM: Homo sapiens

<400> SEQUENCE: 132

Met Asp Ile Pro Val Arg Ser Ala Asn Cys Thr Leu Arg Asp Ser Gln
  1               5                  10                  15

Gln Lys Ser Leu Val Met Ser Gly Pro Tyr Glu Leu Lys Ala Leu His
                 20                  25                  30

Leu Gln Gly Gln Asp Met Glu Gln Gln Val Val Phe Ser Met Ser Phe
                 35                  40                  45

Val Gln Gly Glu Glu Ser Asn Asp Lys Ile Pro Val Ala Leu Gly Leu
 50                  55                  60

Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Lys Lys Lys
                 85                  90                  95

Met Glu Lys Arg Phe Val Phe Asn Lys Ile Glu Ile Asn Asn Lys Leu
                100                 105                 110

Glu Phe Glu Ser Ala Gln Phe Pro Asn Trp Tyr Ile Ser Thr Ser Gln
                115                 120                 125

Ala Glu Asn Met Pro Val Phe Leu Gly Gly Thr Lys Gly Gly Gln Asp
                130                 135                 140

Ile Thr Asp Phe Thr Met Gln Phe Val Ser Ser
145                 150                 155

<210> SEQ ID NO 133
<211> LENGTH: 155
<212> TYPE: PRT
<213> ORGANISM: Homo sapiens

<400> SEQUENCE: 133

Met Asp Ile Pro Val Arg Ser Leu Asn Cys Gly Leu Arg Asp Ser Gln
  1               5                  10                  15

Gln Lys Ser Leu Val Met Ser Gly Pro Tyr Glu Leu Lys Ala Leu His
                 20                  25                  30

Leu Gln Gly Gln Asp Met Glu Gln Gln Val Val Phe Ser Met Ser Phe
                 35                  40                  45

Val Gln Gly Glu Glu Ser Asn Asp Lys Ile Pro Val Ala Leu Gly Leu
 50                  55                  60

Lys Glu Lys Asn Leu Tyr Leu Ser Cys Val Leu Lys Asp Asp Lys Pro
 65                  70                  75                  80
```

```
Thr Leu Gln Leu Glu Ser Val Asp Pro Lys Asn Tyr Pro Lys Lys Lys
                85                  90                  95

Met Glu Lys Arg Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Gln
        115                 120                 125

Ala Glu Asn Met Pro Val Phe Leu Gly Gly Thr Lys Gly Gly Gln Asp
    130                 135                 140

Ile Thr Asp Phe Thr Met Gln Phe Val Ser Ser
145                 150                 155

<210> SEQ ID NO 134
<211> LENGTH: 155
<212> TYPE: PRT
<213> ORGANISM: Homo sapiens

<400> SEQUENCE: 134

Met Asp Ile Pro Val Arg Ser Leu Asn Cys Thr Leu Gly Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Asp Lys Ile Pro Val Ala Leu Gly Leu
    50                  55                  60

Lys Glu Lys Asn Leu Tyr Leu Ser Cys Val Leu Lys Asp Asp Lys Pro
65                  70                  75                  80

Thr Leu Gln Leu Glu Ser Val Asp Pro Lys Asn Tyr Pro Lys Lys Lys
                85                  90                  95

Met Glu Lys Arg Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Gln
        115                 120                 125

Ala Glu Asn Met Pro Val Phe Leu Gly Gly Thr Lys Gly Gly Gln Asp
    130                 135                 140

Ile Thr Asp Phe Thr Met Gln Phe Val Ser Ser
145                 150                 155

<210> SEQ ID NO 135
<211> LENGTH: 155
<212> TYPE: PRT
<213> ORGANISM: Homo sapiens

<400> SEQUENCE: 135

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Arg Lys Ile Pro Val Ala Leu Gly Leu
    50                  55                  60

Lys Glu Lys Asn Leu Tyr Leu Ser Cys Val Leu Lys Asp Asp Lys Pro
65                  70                  75                  80

Thr Leu Gln Leu Glu Ser Val Asp Pro Lys Asn Tyr Pro Lys Lys Lys
                85                  90                  95
```

```
Met Glu Lys Arg Phe Val Phe Asn Lys Ile Glu Ile Asn Asn Lys Leu
                100                 105                 110

Glu Phe Glu Ser Ala Gln Phe Pro Asn Trp Tyr Ile Ser Thr Ser Gln
            115                 120                 125

Ala Glu Asn Met Pro Val Phe Leu Gly Gly Thr Lys Gly Gly Gln Asp
        130                 135                 140

Ile Thr Asp Phe Thr Met Gln Phe Val Ser Ser
145                 150                 155

<210> SEQ ID NO 136
<211> LENGTH: 155
<212> TYPE: PRT
<213> ORGANISM: Homo sapiens

<400> SEQUENCE: 136

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Asp Lys Ile Pro Val Ala Leu Gly Leu
    50                  55                  60

Lys Glu Lys Asn Leu Tyr Leu Ser Cys Val Leu Lys Asp Asp Lys Pro
65                  70                  75                  80

Thr Leu Gln Leu Glu Ser Val Asp Pro Lys Asn Tyr Pro Lys Lys Lys
                85                  90                  95

Met Glu Lys Arg Phe Val Phe Asn Lys Ile Glu Ile Asn Asn Lys Leu
                100                 105                 110

Glu Phe Glu Ser Ala Gln Phe Pro Asn Trp Tyr Ile Ser Thr Ser Gln
            115                 120                 125

Ala Glu Asn Met Pro Val Phe Leu Gly Gly Thr Lys Gly Gly Gln Asp
        130                 135                 140

Ile Thr Lys Phe Thr Met Gln Phe Val Ser Ser
145                 150                 155

<210> SEQ ID NO 137
<211> LENGTH: 153
<212> TYPE: PRT
<213> ORGANISM: Homo sapiens

<400> SEQUENCE: 137

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
```

```
                115                 120                 125
Asn Met Pro Val Phe Leu Gly Gly Thr Lys Gly Gly Gln Asp Ile Thr
        130                 135                 140

Asp Phe Thr Met Gln Phe Val Ser Ser
145                 150

<210> SEQ ID NO 138
<211> LENGTH: 152
<212> TYPE: PRT
<213> ORGANISM: Homo sapiens

<400> SEQUENCE: 138

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Lys Ile Pro Val Ala Leu Gly Leu Lys Glu Lys
    50                  55                  60

Asn Leu Tyr Leu Ser Cys Val Leu Lys Asp Asp Lys Pro Thr Leu Gln
65                  70                  75                  80

Leu Glu Ser Val Asp Pro Lys Asn Tyr Pro Lys Lys Met Glu Lys
                85                  90                  95

Arg Phe Val Phe Asn Lys Ile Glu Ile Asn Asn Lys Leu Glu Phe Glu
                100                 105                 110

Ser Ala Gln Phe Pro Asn Trp Tyr Ile Ser Thr Ser Gln Ala Glu Asn
            115                 120                 125

Met Pro Val Phe Leu Gly Gly Thr Lys Gly Gly Gln Asp Ile Thr Asp
        130                 135                 140

Phe Thr Met Gln Phe Val Ser Ser
145                 150

<210> SEQ ID NO 139
<211> LENGTH: 155
<212> TYPE: PRT
<213> ORGANISM: Homo sapiens

<400> SEQUENCE: 139

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Asp Lys Ile Pro Val Ala Leu Gly Leu
    50                  55                  60

Ser Glu Ser Asn Leu Tyr Leu Ser Cys Val Leu Lys Asp Asp Lys Pro
65                  70                  75                  80

Thr Leu Gln Leu Glu Ser Val Asp Pro Lys Asn Tyr Pro Lys Lys Lys
                85                  90                  95

Met Glu Lys Arg Phe Val Phe Asn Lys Ile Glu Ile Asn Asn Lys Leu
                100                 105                 110

Glu Phe Glu Ser Ala Gln Phe Pro Asn Trp Tyr Ile Ser Thr Ser Gln
            115                 120                 125

Ala Glu Asn Met Pro Val Phe Leu Gly Gly Thr Lys Gly Gly Gln Asp
        130                 135                 140
```

```
Ile Thr Asp Phe Thr Met Gln Phe Val Ser Ser
145                 150                 155

<210> SEQ ID NO 140
<211> LENGTH: 155
<212> TYPE: PRT
<213> ORGANISM: Homo sapiens

<400> SEQUENCE: 140

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
            20                  25                  30

Leu Gln Gly Gln Asp Met Glu Gln Gln Val Val Phe Ser Met Ser Phe
        35                  40                  45

Val Gln Gly Glu Glu Ser Asn Asp Lys Ile Pro Val Ala Leu Gly Leu
    50                  55                  60

Lys Glu Lys Asn Leu Tyr Leu Ser Cys Val Leu Lys Asp Asp Lys Pro
65                  70                  75                  80

Thr Leu Gln Leu Glu Ser Val Asp Pro Lys Asn Tyr Pro Lys Lys Lys
                85                  90                  95

Met Glu Lys Arg Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Ala
        115                 120                 125

Ala Ala Asn Met Pro Val Phe Leu Gly Gly Thr Lys Gly Gly Gln Asp
    130                 135                 140

Ile Thr Asp Phe Thr Met Gln Phe Val Ser Ser
145                 150                 155

<210> SEQ ID NO 141
<211> LENGTH: 39
<212> TYPE: DNA
<213> ORGANISM: Artificial sequence
<220> FEATURE:
<223> OTHER INFORMATION: synthesized sequence

<400> SEQUENCE: 141
atatatcata tgctgagcaa tgtgaaatac aactttatg                          39

<210> SEQ ID NO 142
<211> LENGTH: 37
<212> TYPE: DNA
<213> ORGANISM: Artificial sequence
<220> FEATURE:
<223> OTHER INFORMATION: synthesized sequence

<400> SEQUENCE: 142
atatatctcg agcgcctggt tttccagtat ctgaaag                            37

<210> SEQ ID NO 143
<211> LENGTH: 39
<212> TYPE: DNA
<213> ORGANISM: Artificial sequence
<220> FEATURE:
<223> OTHER INFORMATION: synthesized sequence

<400> SEQUENCE: 143
catatggata tccctgtaga ctcactgaac tgcacgctc                          39

<210> SEQ ID NO 144
```

```
<211> LENGTH: 39
<212> TYPE: DNA
<213> ORGANISM: Artificial sequence
<220> FEATURE:
<223> OTHER INFORMATION: synthesized sequence

<400> SEQUENCE: 144
gagcgtgcag ttcagtgagt ctacagggat atccatatg                                 39

<210> SEQ ID NO 145
<211> LENGTH: 39
<212> TYPE: DNA
<213> ORGANISM: Artificial sequence
<220> FEATURE:
<223> OTHER INFORMATION: synthesized sequence

<400> SEQUENCE: 145
gatatccctg tacgatcagc taactgcacg ctccgggac                                 39

<210> SEQ ID NO 146
<211> LENGTH: 39
<212> TYPE: DNA
<213> ORGANISM: Artificial sequence
<220> FEATURE:
<223> OTHER INFORMATION: synthesized sequence

<400> SEQUENCE: 146
gtcccggagc gtgcagttag ctgatcgtac agggatatc                                 39

<210> SEQ ID NO 147
<211> LENGTH: 37
<212> TYPE: DNA
<213> ORGANISM: Artificial sequence
<220> FEATURE:
<223> OTHER INFORMATION: synthesized sequence

<400> SEQUENCE: 147
gtacgatcac tgaactgcgg tctccgggac tcacagc                                   37

<210> SEQ ID NO 148
<211> LENGTH: 37
<212> TYPE: DNA
<213> ORGANISM: Artificial sequence
<220> FEATURE:
<223> OTHER INFORMATION: synthesized sequence

<400> SEQUENCE: 148
gctgtgagtc ccggagaccg cagttcagtg atcgtac                                   37

<210> SEQ ID NO 149
<211> LENGTH: 26
<212> TYPE: DNA
<213> ORGANISM: Artificial sequence
<220> FEATURE:
<223> OTHER INFORMATION: synthesized sequence

<400> SEQUENCE: 149
gaactgcacg ctcggggact cacagc                                               26

<210> SEQ ID NO 150
<211> LENGTH: 26
<212> TYPE: DNA
<213> ORGANISM: Artificial sequence
<220> FEATURE:
<223> OTHER INFORMATION: synthesized sequence

<400> SEQUENCE: 150
```
gctgtgagtc cccgagcgtg cagttc                                             26

<210> SEQ ID NO 151
<211> LENGTH: 39
<212> TYPE: DNA
<213> ORGANISM: Artificial sequence
<220> FEATURE:
<223> OTHER INFORMATION: synthesized sequence

<400> SEQUENCE: 151
caaggagaag aaagtaatcg caaaatacct gtggccttg                               39

<210> SEQ ID NO 152
<211> LENGTH: 39
<212> TYPE: DNA
<213> ORGANISM: Artificial sequence
<220> FEATURE:
<223> OTHER INFORMATION: synthesized sequence

<400> SEQUENCE: 152
caaggccaca ggtattttgc gattactttc ttctccttg                               39

<210> SEQ ID NO 153
<211> LENGTH: 40
<212> TYPE: DNA
<213> ORGANISM: Artificial sequence
<220> FEATURE:
<223> OTHER INFORMATION: synthesized sequence

<400> SEQUENCE: 153
catgtccttt gtacaaggaa gtaatgacaa aatacctgtg                              40

<210> SEQ ID NO 154
<211> LENGTH: 40
<212> TYPE: DNA
<213> ORGANISM: Artificial sequence
<220> FEATURE:
<223> OTHER INFORMATION: synthesized sequence

<400> SEQUENCE: 154
cacaggtatt ttgtcattac ttccttgtac aaaggacatg                              40

<210> SEQ ID NO 155
<211> LENGTH: 37
<212> TYPE: DNA
<213> ORGANISM: Artificial sequence
<220> FEATURE:
<223> OTHER INFORMATION: synthesized sequence

<400> SEQUENCE: 155
ctttgtacaa ggagaagaaa aaatacctgt ggccttg                                 37

<210> SEQ ID NO 156
<211> LENGTH: 37
<212> TYPE: DNA
<213> ORGANISM: Artificial sequence
<220> FEATURE:
<223> OTHER INFORMATION: synthesized sequence

<400> SEQUENCE: 156
caaggccaca ggtatttttt cttctccttg tacaaag                                 37

<210> SEQ ID NO 157
<211> LENGTH: 41
<212> TYPE: DNA
<213> ORGANISM: Artificial sequence
<220> FEATURE:

-continued

<223> OTHER INFORMATION: synthesized sequence

<400> SEQUENCE: 157
gtggccttgg gcctcagcga aagcaatctg tacctgtcct g  41

<210> SEQ ID NO 158
<211> LENGTH: 41
<212> TYPE: DNA
<213> ORGANISM: Artificial sequence
<220> FEATURE:
<223> OTHER INFORMATION: synthesized sequence

<400> SEQUENCE: 158
caggacaggt acagattgct ttcgctgagg cccaaggcca c  41

<210> SEQ ID NO 159
<211> LENGTH: 40
<212> TYPE: DNA
<213> ORGANISM: Artificial sequence
<220> FEATURE:
<223> OTHER INFORMATION: synthesized sequence

<400> SEQUENCE: 159
gtacatcagc acctctgcag cagcaaacat gcccgtcttc  40

<210> SEQ ID NO 160
<211> LENGTH: 40
<212> TYPE: DNA
<213> ORGANISM: Artificial sequence
<220> FEATURE:
<223> OTHER INFORMATION: synthesized sequence

<400> SEQUENCE: 160
gaagacgggc atgtttgctg ctgcagaggt gctgatgtac  40

<210> SEQ ID NO 161
<211> LENGTH: 40
<212> TYPE: DNA
<213> ORGANISM: Artificial sequence
<220> FEATURE:
<223> OTHER INFORMATION: synthesitzed sequence

<400> SEQUENCE: 161
gcggccagga tataactaaa ttcaccatgc aatttgtgtc  40

<210> SEQ ID NO 162
<211> LENGTH: 40
<212> TYPE: DNA
<213> ORGANISM: Artificial sequence
<220> FEATURE:
<223> OTHER INFORMATION: synthesized sequence

<400> SEQUENCE: 162
gacacaaatt gcatggtgaa tttagttata tcctggccgc  40

<210> SEQ ID NO 163
<211> LENGTH: 154
<212> TYPE: PRT
<213> ORGANISM: Mus musculus

<400> SEQUENCE: 163

Pro Tyr Thr Tyr Gln Ser Asp Leu Arg Tyr Lys Leu Met Lys Leu Val
1               5                   10                  15

Arg Gln Lys Phe Val Met Asn Asp Ser Leu Asn Gln Thr Ile Tyr Gln
            20                  25                  30

```
Asp Val Asp Lys His Tyr Leu Ser Thr Thr Trp Leu Asn Asp Leu Gln
             35                  40                  45

Gln Glu Val Lys Phe Asp Met Tyr Ala Tyr Ser Ser Gly Gly Asp Asp
 50                  55                  60

Ser Lys Tyr Pro Val Thr Leu Lys Ile Ser Asp Ser Gln Leu Phe Val
 65                  70                  75                  80

Ser Ala Gln Gly Glu Asp Gln Pro Val Leu Leu Lys Glu Leu Pro Glu
                 85                  90                  95

Thr Pro Lys Leu Ile Thr Gly Ser Glu Thr Asp Leu Ile Phe Phe Trp
            100                 105                 110

Lys Ser Ile Asn Ser Lys Asn Tyr Phe Thr Ser Ala Ala Tyr Pro Glu
        115                 120                 125

Leu Phe Ile Ala Thr Lys Glu Gln Ser Arg Val His Leu Ala Arg Gly
    130                 135                 140

Leu Pro Ser Met Thr Asp Phe Gln Ile Ser
145                 150

<210> SEQ ID NO 164
<211> LENGTH: 151
<212> TYPE: PRT
<213> ORGANISM: Mus musculus

<400> SEQUENCE: 164

Pro Ile Arg Gln Leu His Tyr Arg Leu Arg Asp Glu Gln Gln Lys Ser
 1               5                  10                  15

Leu Val Leu Ser Asp Pro Tyr Glu Leu Lys Ala Leu His Leu Asn Gly
             20                  25                  30

Gln Asn Ile Asn Gln Gln Val Ile Phe Ser Met Ser Phe Val Gln Gly
         35                  40                  45

Glu Pro Ser Asn Asp Lys Ile Pro Val Ala Leu Gly Leu Lys Gly Lys
 50                  55                  60

Asn Leu Tyr Leu Ser Cys Val Met Lys Asp Gly Thr Pro Thr Leu Gln
 65                  70                  75                  80

Leu Glu Ser Val Asp Pro Lys Gln Tyr Pro Lys Lys Met Glu Lys
                 85                  90                  95

Arg Phe Val Phe Asn Lys Ile Glu Val Lys Ser Lys Val Glu Phe Glu
            100                 105                 110

Ser Ala Glu Phe Pro Asn Trp Tyr Ile Ser Thr Ser Gln Ala Glu His
        115                 120                 125

Lys Pro Val Phe Leu Gly Asn Asn Ser Gly Gln Asp Ile Ile Asp Phe
    130                 135                 140

Thr Met Glu Ser Val Ser Ser
145                 150

<210> SEQ ID NO 165
<211> LENGTH: 155
<212> TYPE: PRT
<213> ORGANISM: Mus musculus

<400> SEQUENCE: 165

Met Asp Ile Pro Val Arg Ser Leu Asn Cys Thr Leu Arg Asp Ser Gln
 1               5                  10                  15

Gln Lys Ser Leu Val Met Ser Gly Pro Tyr Glu Leu Lys Ala Leu His
             20                  25                  30

Leu Gln Gly Gln Asp Met Glu Gln Gln Val Val Phe Ser Met Ser Phe
         35                  40                  45

Val Gln Gly Glu Glu Ser Asn Asp Lys Ile Pro Val Ala Leu Gly Leu
```

```
                50                 55                  60
Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Lys Lys Lys
                     85                  90                  95

Met Glu Lys Arg Phe Val Phe Asn Lys Ile Glu Ile Asn Asn Lys Leu
                    100                 105                 110

Glu Phe Glu Ser Ala Gln Phe Pro Asn Trp Tyr Ile Ser Thr Ser Gln
                115                 120                 125

Ala Glu Asn Met Pro Val Phe Leu Gly Gly Thr Lys Gly Gly Gln Asp
            130                 135                 140

Ile Thr Asp Phe Thr Met Gln Phe Val Ser Ser
145                 150                 155

<210> SEQ ID NO 166
<211> LENGTH: 569
<212> TYPE: PRT
<213> ORGANISM: Homo sapiens

<400> SEQUENCE: 166

Met Lys Val Leu Leu Arg Leu Ile Cys Phe Ile Ala Leu Leu Ile Ser
  1               5                  10                  15

Ser Leu Glu Ala Asp Lys Cys Lys Glu Arg Glu Glu Lys Ile Ile Leu
                 20                  25                  30

Val Ser Ser Ala Asn Glu Ile Asp Val Arg Pro Cys Pro Leu Asn Pro
             35                  40                  45

Asn Glu His Lys Gly Thr Ile Thr Trp Tyr Lys Asp Asp Ser Lys Thr
 50                  55                  60

Pro Val Ser Thr Glu Gln Ala Ser Arg Ile His Gln His Lys Glu Lys
 65                  70                  75                  80

Leu Trp Phe Val Pro Ala Lys Val Glu Asp Ser Gly His Tyr Tyr Cys
                 85                  90                  95

Val Val Arg Asn Ser Ser Tyr Cys Leu Arg Ile Lys Ile Ser Ala Lys
                100                 105                 110

Phe Val Glu Asn Glu Pro Asn Leu Cys Tyr Asn Ala Gln Ala Ile Phe
            115                 120                 125

Lys Gln Asn Leu Pro Val Ala Gly Asp Gly Gly Leu Val Cys Pro Tyr
130                 135                 140

Met Glu Phe Phe Lys Asn Glu Asn Asn Glu Leu Pro Lys Leu Gln Trp
145                 150                 155                 160

Tyr Lys Asp Cys Lys Pro Leu Leu Leu Asp Asn Ile His Phe Ser Gly
                165                 170                 175

Val Lys Asp Arg Leu Ile Val Met Asn Val Ala Glu Lys His Arg Gly
                180                 185                 190

Asn Tyr Thr Cys His Ala Ser Tyr Thr Tyr Leu Gly Lys Gln Tyr Pro
            195                 200                 205

Ile Thr Arg Val Ile Glu Phe Ile Thr Leu Glu Glu Asn Lys Pro Thr
            210                 215                 220

Arg Pro Val Ile Val Ser Pro Ala Asn Glu Thr Met Glu Val Asp Leu
225                 230                 235                 240

Gly Ser Gln Ile Gln Leu Ile Cys Asn Val Thr Gly Gln Leu Ser Asp
                245                 250                 255

Ile Ala Tyr Trp Lys Trp Asn Gly Ser Val Ile Asp Glu Asp Asp Pro
                260                 265                 270

Val Leu Gly Glu Asp Tyr Tyr Ser Val Glu Asn Pro Ala Asn Lys Arg
```

```
                275                 280                 285
Arg Ser Thr Leu Ile Thr Val Leu Asn Ile Ser Glu Ile Glu Ser Arg
        290                 295                 300

Phe Tyr Lys His Pro Phe Thr Cys Phe Ala Lys Asn Thr His Gly Ile
305                 310                 315                 320

Asp Ala Ala Tyr Ile Gln Leu Ile Tyr Pro Val Thr Asn Phe Gln Lys
                325                 330                 335

His Met Ile Gly Ile Cys Val Thr Leu Thr Val Ile Ile Val Cys Ser
            340                 345                 350

Val Phe Ile Tyr Lys Ile Phe Lys Ile Asp Ile Val Leu Trp Tyr Arg
        355                 360                 365

Asp Ser Cys Tyr Asp Phe Leu Pro Ile Lys Ala Ser Asp Gly Lys Thr
    370                 375                 380

Tyr Asp Ala Tyr Ile Leu Tyr Pro Lys Thr Val Gly Glu Gly Ser Thr
385                 390                 395                 400

Ser Asp Cys Asp Ile Phe Val Phe Lys Val Leu Pro Glu Val Leu Glu
                405                 410                 415

Lys Gln Cys Gly Tyr Lys Leu Phe Ile Tyr Gly Arg Asp Asp Tyr Val
            420                 425                 430

Gly Glu Asp Ile Val Glu Val Ile Asn Glu Asn Val Lys Lys Ser Arg
        435                 440                 445

Arg Leu Ile Ile Ile Leu Val Arg Glu Thr Ser Ser Phe Ser Trp Leu
    450                 455                 460

Gly Gly Ser Ser Glu Glu Gln Ile Ala Met Tyr Asn Ala Leu Val Gln
465                 470                 475                 480

Asp Gly Ile Lys Val Val Leu Glu Leu Glu Lys Ile Gln Asp Tyr
                485                 490                 495

Glu Lys Met Pro Glu Ser Ile Lys Phe Ile Lys Gln Lys His Gly Ala
            500                 505                 510

Ile Arg Trp Ser Gly Asp Phe Thr Gln Gly Pro Gln Ser Ala Lys Thr
        515                 520                 525

Arg Phe Trp Lys Asn Val Arg Tyr His Met Pro Val Gln Arg Arg Ser
    530                 535                 540

Pro Ser Ser Lys His Gln Leu Leu Ser Pro Ala Thr Lys Glu Lys Leu
545                 550                 555                 560

Gln Arg Glu Ala His Val Pro Leu Gly
                565

<210> SEQ ID NO 167
<211> LENGTH: 398
<212> TYPE: PRT
<213> ORGANISM: Homo sapiens

<400> SEQUENCE: 167

Met Leu Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
```

```
                    85                  90                  95
Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Trp Gly Ile
            340                 345                 350

Val Leu Ala Pro Leu Ser Leu Ala Phe Leu Val Leu Gly Gly Ile Trp
        355                 360                 365

Met His Arg Arg Cys Lys His Arg Thr Gly Lys Ala Asp Gly Leu Thr
    370                 375                 380

Val Leu Trp Pro His His Gln Asp Phe Gln Ser Tyr Pro Lys
385                 390                 395

<210> SEQ ID NO 168
<211> LENGTH: 576
<212> TYPE: PRT
<213> ORGANISM: Mus musculus

<400> SEQUENCE: 168

Met Glu Asn Met Lys Val Leu Leu Gly Leu Ile Cys Leu Met Val Pro
1               5                   10                  15

Leu Leu Ser Leu Glu Ile Asp Val Cys Thr Glu Tyr Pro Asn Gln Ile
            20                  25                  30

Val Leu Phe Leu Ser Val Asn Glu Ile Asp Ile Arg Lys Cys Pro Leu
        35                  40                  45

Thr Pro Asn Lys Met His Gly Asp Thr Ile Ile Trp Tyr Lys Asn Asp
    50                  55                  60

Ser Lys Thr Pro Ile Ser Ala Asp Arg Asp Ser Arg Ile His Gln Gln
```

-continued

```
              65                  70                  75                  80
         Asn Glu His Leu Trp Phe Val Pro Ala Lys Val Glu Asp Ser Gly Tyr
                              85                  90                  95

Tyr Tyr Cys Ile Val Arg Asn Ser Thr Tyr Cys Leu Lys Thr Lys Val
                             100                 105                 110

Thr Val Thr Val Leu Glu Asn Asp Pro Gly Leu Cys Tyr Ser Thr Gln
                             115                 120                 125

Ala Thr Phe Pro Gln Arg Leu His Ile Ala Gly Asp Gly Ser Leu Val
                             130                 135                 140

Cys Pro Tyr Val Ser Tyr Phe Lys Asp Glu Asn Asn Glu Leu Pro Glu
         145                 150                 155                 160

Val Gln Trp Tyr Lys Asn Cys Lys Pro Leu Leu Leu Asp Asn Val Ser
                             165                 170                 175

Phe Phe Gly Val Lys Asp Lys Leu Leu Val Arg Asn Val Ala Glu Glu
                             180                 185                 190

His Arg Gly Asp Tyr Ile Cys Arg Met Ser Tyr Thr Phe Arg Gly Lys
                             195                 200                 205

Gln Tyr Pro Val Thr Arg Val Ile Gln Phe Ile Thr Ile Asp Glu Asn
                             210                 215                 220

Lys Arg Asp Arg Pro Val Ile Leu Ser Pro Arg Asn Glu Thr Ile Glu
         225                 230                 235                 240

Ala Asp Pro Gly Ser Met Ile Gln Leu Ile Cys Asn Val Thr Gly Gln
                             245                 250                 255

Phe Ser Asp Leu Val Tyr Trp Lys Trp Asn Gly Ser Glu Ile Glu Trp
                             260                 265                 270

Asn Asp Pro Phe Leu Ala Glu Asp Tyr Gln Phe Val Glu His Pro Ser
                             275                 280                 285

Thr Lys Arg Lys Tyr Thr Leu Ile Thr Thr Leu Asn Ile Ser Glu Val
                             290                 295                 300

Lys Ser Gln Phe Tyr Arg Tyr Pro Phe Ile Cys Val Val Lys Asn Thr
         305                 310                 315                 320

Asn Ile Phe Glu Ser Ala His Val Gln Leu Ile Tyr Pro Val Pro Asp
                             325                 330                 335

Phe Lys Asn Tyr Leu Ile Gly Gly Phe Ile Ile Leu Thr Ala Thr Ile
                             340                 345                 350

Val Cys Cys Val Cys Ile Tyr Lys Val Phe Lys Val Asp Ile Val Leu
                             355                 360                 365

Trp Tyr Arg Asp Ser Cys Ser Gly Phe Leu Pro Ser Lys Ala Ser Asp
                             370                 375                 380

Gly Lys Thr Tyr Asp Ala Tyr Ile Leu Tyr Pro Lys Thr Leu Gly Glu
         385                 390                 395                 400

Gly Ser Phe Ser Asp Leu Asp Thr Phe Val Phe Lys Leu Leu Pro Glu
                             405                 410                 415

Val Leu Glu Gly Gln Phe Gly Tyr Lys Leu Phe Ile Tyr Gly Arg Asp
                             420                 425                 430

Asp Tyr Val Gly Glu Asp Thr Ile Glu Val Thr Asn Glu Asn Val Lys
                             435                 440                 445

Lys Ser Arg Arg Leu Ile Ile Ile Leu Val Arg Asp Met Gly Gly Phe
         450                 455                 460

Ser Trp Leu Gly Gln Ser Ser Glu Glu Gln Ile Ala Ile Tyr Asn Ala
                             470                 475                 480

Leu Ile Gln Glu Gly Ile Lys Ile Val Leu Leu Glu Leu Glu Lys Ile
                             485                 490                 495
```

-continued

Gln Asp Tyr Glu Lys Met Pro Asp Ser Ile Gln Phe Ile Lys Gln Lys
            500                 505                 510

His Gly Val Ile Cys Trp Ser Gly Asp Phe Gln Glu Arg Pro Gln Ser
        515                 520                 525

Ala Lys Thr Arg Phe Trp Lys Asn Leu Arg Tyr Gln Met Pro Ala Gln
530                 535                 540

Arg Arg Ser Pro Leu Ser Lys His Arg Leu Leu Thr Leu Asp Pro Val
545                 550                 555                 560

Arg Asp Thr Lys Glu Lys Leu Pro Ala Ala Thr His Leu Pro Leu Gly
                565                 570                 575

<210> SEQ ID NO 169
<211> LENGTH: 410
<212> TYPE: PRT
<213> ORGANISM: Mus musculus

<400> SEQUENCE: 169

Met Phe Ile Leu Leu Val Leu Val Thr Gly Val Ser Ala Phe Thr Thr
1               5                   10                  15

Pro Thr Val Val His Thr Gly Lys Val Ser Glu Ser Pro Ile Thr Ser
            20                  25                  30

Glu Lys Pro Thr Val His Gly Asp Asn Cys Gln Phe Arg Gly Arg Glu
        35                  40                  45

Phe Lys Ser Glu Leu Arg Leu Glu Gly Glu Pro Val Val Leu Arg Cys
    50                  55                  60

Pro Leu Ala Pro His Ser Asp Ile Ser Ser Ser His Ser Phe Leu
65                  70                  75                  80

Thr Trp Ser Lys Leu Asp Ser Ser Gln Leu Ile Pro Arg Asp Glu Pro
                85                  90                  95

Arg Met Trp Val Lys Gly Asn Ile Leu Trp Ile Leu Pro Ala Val Gln
            100                 105                 110

Gln Asp Ser Gly Thr Tyr Ile Cys Thr Phe Arg Asn Ala Ser His Cys
        115                 120                 125

Glu Gln Met Ser Val Glu Leu Lys Val Phe Lys Asn Thr Glu Ala Ser
130                 135                 140

Leu Pro His Val Ser Tyr Leu Gln Ile Ser Ala Leu Ser Thr Thr Gly
145                 150                 155                 160

Leu Leu Val Cys Pro Asp Leu Lys Glu Phe Ile Ser Ser Asn Ala Asp
                165                 170                 175

Gly Lys Ile Gln Trp Tyr Lys Gly Ala Ile Leu Leu Asp Lys Gly Asn
            180                 185                 190

Lys Glu Phe Leu Ser Ala Gly Asp Pro Thr Arg Leu Leu Ile Ser Asn
        195                 200                 205

Thr Ser Met Asp Asp Ala Gly Tyr Tyr Arg Cys Val Met Thr Phe Thr
210                 215                 220

Tyr Asn Gly Gln Glu Tyr Asn Ile Thr Arg Asn Ile Glu Leu Arg Val
225                 230                 235                 240

Lys Gly Thr Thr Thr Glu Pro Ile Pro Val Ile Ile Ser Pro Leu Glu
                245                 250                 255

Thr Ile Pro Ala Ser Leu Gly Ser Arg Leu Ile Val Pro Cys Lys Val
            260                 265                 270

Phe Leu Gly Thr Gly Thr Ser Ser Asn Thr Ile Val Trp Trp Leu Ala
        275                 280                 285

Asn Ser Thr Phe Ile Ser Ala Ala Tyr Pro Arg Gly Arg Val Thr Glu
    290                 295                 300

```
Gly Leu His His Gln Tyr Ser Glu Asn Asp Glu Asn Tyr Val Glu Val
305                 310                 315                 320

Ser Leu Ile Phe Asp Pro Val Thr Arg Glu Asp Leu His Thr Asp Phe
            325                 330                 335

Lys Cys Val Ala Ser Asn Pro Arg Ser Ser Gln Ser Leu His Thr Thr
        340                 345                 350

Val Lys Glu Val Ser Ser Thr Phe Ser Trp Ser Ile Ala Leu Ala Pro
    355                 360                 365

Leu Ser Leu Ile Ile Leu Val Val Gly Ala Ile Trp Met Arg Arg Arg
    370                 375                 380

Cys Lys Arg Arg Ala Gly Lys Thr Tyr Gly Leu Thr Lys Leu Arg Thr
385                 390                 395                 400

Asp Asn Gln Asp Phe Pro Ser Ser Pro Asn
                405                 410

<210> SEQ ID NO 170
<211> LENGTH: 5
<212> TYPE: PRT
<213> ORGANISM: Artificial sequence
<220> FEATURE:
<223> OTHER INFORMATION: synthesized sequence

<400> SEQUENCE: 170

Gly Gly Lys Gly Gly
1               5

<210> SEQ ID NO 171
<211> LENGTH: 3
<212> TYPE: PRT
<213> ORGANISM: Artificial sequence
<220> FEATURE:
<223> OTHER INFORMATION: synthesized sequence

<400> SEQUENCE: 171

Cys Gly Gly
1

<210> SEQ ID NO 172
<211> LENGTH: 10
<212> TYPE: PRT
<213> ORGANISM: Artificial sequence
<220> FEATURE:
<223> OTHER INFORMATION: synthesized sequence

<400> SEQUENCE: 172

Cys Gly Asp Lys Thr His Thr Ser Pro Pro
1               5                   10

<210> SEQ ID NO 173
<211> LENGTH: 17
<212> TYPE: PRT
<213> ORGANISM: Artificial sequence
<220> FEATURE:
<223> OTHER INFORMATION: synthesized sequence

<400> SEQUENCE: 173

Cys Gly Gly Pro Lys Pro Ser Thr Pro Pro Gly Ser Ser Gly Gly Ala
1               5                   10                  15

Pro

<210> SEQ ID NO 174
<211> LENGTH: 6
<212> TYPE: PRT
<213> ORGANISM: Artificial sequence
```

```
<220> FEATURE:
<223> OTHER INFORMATION: synthesized sequence

<400> SEQUENCE: 174

Gly Cys Gly Gly Gly Gly
1               5

<210> SEQ ID NO 175
<211> LENGTH: 18
<212> TYPE: PRT
<213> ORGANISM: Artificial sequence
<220> FEATURE:
<223> OTHER INFORMATION: synthesized sequence
<220> FEATURE:
<221> NAME/KEY: REPEAT
<222> LOCATION: (1)..(1)
<223> OTHER INFORMATION: occurs 0-5 times
<220> FEATURE:
<221> NAME/KEY: REPEAT
<222> LOCATION: (7)..(7)
<223> OTHER INFORMATION: occurs 0-12 times

<400> SEQUENCE: 175

Gly Gly Gly Gly Gly Cys Gly Gly Gly Gly Gly Gly Gly Gly Gly
1               5                   10                  15

Gly Gly

<210> SEQ ID NO 176
<211> LENGTH: 15
<212> TYPE: PRT
<213> ORGANISM: Artificial sequence
<220> FEATURE:
<223> OTHER INFORMATION: synthesized sequence
<220> FEATURE:
<221> NAME/KEY: REPEAT
<222> LOCATION: (1)..(5)
<223> OTHER INFORMATION: occurs 1-3 times

<400> SEQUENCE: 176

Gly Gly Gly Gly Ser Gly Gly Gly Gly Ser Gly Gly Gly Gly Ser
1               5                   10                  15

<210> SEQ ID NO 177
<211> LENGTH: 33
<212> TYPE: PRT
<213> ORGANISM: Artificial sequence
<220> FEATURE:
<223> OTHER INFORMATION: synthesized sequence
<220> FEATURE:
<221> NAME/KEY: REPEAT
<222> LOCATION: (1)..(1)
<223> OTHER INFORMATION: occurs 0-5 times
<220> FEATURE:
<221> NAME/KEY: REPEAT
<222> LOCATION: (7)..(7)
<223> OTHER INFORMATION: occurs 0-10 times
<220> FEATURE:
<221> NAME/KEY: REPEAT
<222> LOCATION: (17)..(17)
<223> OTHER INFORMATION: occurs 0-2 times
<220> FEATURE:
<221> NAME/KEY: REPEAT
<222> LOCATION: (19)..(23)
<223> OTHER INFORMATION: occurs 0-3 times

<400> SEQUENCE: 177

Gly Gly Gly Gly Gly Cys Gly Gly Gly Gly Gly Gly Gly Gly Gly
1               5                   10                  15

Ser Ser Gly Gly Gly Gly Ser Gly Gly Gly Gly Ser Gly Gly Gly Gly
            20                  25                  30
```

Ser

<210> SEQ ID NO 178
<211> LENGTH: 3
<212> TYPE: PRT
<213> ORGANISM: Artificial sequence
<220> FEATURE:
<223> OTHER INFORMATION: synthesized sequence

<400> SEQUENCE: 178

Gly Gly Cys
1

<210> SEQ ID NO 179
<211> LENGTH: 3
<212> TYPE: PRT
<213> ORGANISM: Artificial sequence
<220> FEATURE:
<223> OTHER INFORMATION: synthesized sequence
<220> FEATURE:
<221> NAME/KEY: MOD_RES
<222> LOCATION: (3)..(3)
<223> OTHER INFORMATION: NH2 (amidated)

<400> SEQUENCE: 179

Gly Gly Cys
1

<210> SEQ ID NO 180
<211> LENGTH: 10
<212> TYPE: PRT
<213> ORGANISM: Artificial sequence
<220> FEATURE:
<223> OTHER INFORMATION: synthesized sequence

<400> SEQUENCE: 180

Asp Lys Thr His Thr Ser Pro Pro Cys Gly
1               5                   10

<210> SEQ ID NO 181
<211> LENGTH: 18
<212> TYPE: PRT
<213> ORGANISM: Artificial sequence
<220> FEATURE:
<223> OTHER INFORMATION: synthesized sequence

<400> SEQUENCE: 181

Pro Lys Pro Ser Thr Pro Pro Gly Ser Ser Gly Gly Ala Pro Gly Gly
1               5                   10                  15

Cys Gly

<210> SEQ ID NO 182
<211> LENGTH: 6
<212> TYPE: PRT
<213> ORGANISM: Artificial sequence
<220> FEATURE:
<223> OTHER INFORMATION: synthesized sequence

<400> SEQUENCE: 182

Gly Gly Gly Gly Cys Gly
1               5

<210> SEQ ID NO 183
<211> LENGTH: 18
<212> TYPE: PRT
<213> ORGANISM: Artificial sequence
<220> FEATURE:
<223> OTHER INFORMATION: synthesized sequence

```
<220> FEATURE:
<221> NAME/KEY: REPEAT
<222> LOCATION: (1)..(1)
<223> OTHER INFORMATION: occurs 0-12 times
<220> FEATURE:
<221> NAME/KEY: REPEAT
<222> LOCATION: (14)..(14)
<223> OTHER INFORMATION: occurs 0-5 times

<400> SEQUENCE: 183

Gly Gly Gly Gly Gly Gly Gly Gly Gly Gly Gly Cys Gly Gly Gly
1               5                   10                  15

Gly Gly

<210> SEQ ID NO 184
<211> LENGTH: 15
<212> TYPE: PRT
<213> ORGANISM: Artificial sequence
<220> FEATURE:
<223> OTHER INFORMATION: synthesized sequence
<220> FEATURE:
<221> NAME/KEY: REPEAT
<222> LOCATION: (1)..(5)
<223> OTHER INFORMATION: ocurrs 1-3 times

<400> SEQUENCE: 184

Ser Gly Gly Gly Gly Ser Gly Gly Gly Ser Gly Gly Gly Gly
1               5                   10                  15

<210> SEQ ID NO 185
<211> LENGTH: 41
<212> TYPE: PRT
<213> ORGANISM: Artificial sequence
<220> FEATURE:
<223> OTHER INFORMATION: synthesized sequence
<220> FEATURE:
<221> NAME/KEY: REPEAT
<222> LOCATION: (1)..(1)
<223> OTHER INFORMATION: occurs 0-10 times
<220> FEATURE:
<221> NAME/KEY: REPEAT
<222> LOCATION: (11)..(11)
<223> OTHER INFORMATION: occurs 0-2 times
<220> FEATURE:
<221> NAME/KEY: REPEAT
<222> LOCATION: (13)..(17)
<223> OTHER INFORMATION: occurs 0-3 times
<220> FEATURE:
<221> NAME/KEY: REPEAT
<222> LOCATION: (28)..(28)
<223> OTHER INFORMATION: occurs 0-8 times
<220> FEATURE:
<221> NAME/KEY: REPEAT
<222> LOCATION: (37)..(37)
<223> OTHER INFORMATION: occurs 0-5 times

<400> SEQUENCE: 185

Gly Gly Gly Gly Gly Gly Gly Gly Gly Ser Ser Gly Gly Gly
1               5                   10                  15

Ser Gly Gly Gly Gly Ser Gly Gly Gly Ser Gly Gly Gly Gly
                20                  25                  30

Gly Gly Gly Cys Gly Gly Gly Gly Gly
        35                  40

<210> SEQ ID NO 186
<211> LENGTH: 6
<212> TYPE: PRT
<213> ORGANISM: Artificial sequence
<220> FEATURE:
<223> OTHER INFORMATION: synthesized sequence
```

```
<400> SEQUENCE: 186

Gly Gly Lys Lys Gly Cys
1               5

<210> SEQ ID NO 187
<211> LENGTH: 6
<212> TYPE: PRT
<213> ORGANISM: Artificial sequence
<220> FEATURE:
<223> OTHER INFORMATION: synthesized sequence

<400> SEQUENCE: 187

Cys Gly Lys Lys Gly Gly
1               5

<210> SEQ ID NO 188
<211> LENGTH: 4
<212> TYPE: PRT
<213> ORGANISM: Artificial sequence
<220> FEATURE:
<223> OTHER INFORMATION: synthesized sequence

<400> SEQUENCE: 188

Gly Gly Cys Gly
1

<210> SEQ ID NO 189
<211> LENGTH: 3
<212> TYPE: PRT
<213> ORGANISM: Artificial sequence
<220> FEATURE:
<223> OTHER INFORMATION: synthesized sequence

<400> SEQUENCE: 189

Gly Ser Gly
1

<210> SEQ ID NO 190
<211> LENGTH: 11
<212> TYPE: PRT
<213> ORGANISM: Artificial sequence
<220> FEATURE:
<223> OTHER INFORMATION: synthesized sequence

<400> SEQUENCE: 190

Leu Glu His His His His His His Gly Gly Cys
1               5                   10

<210> SEQ ID NO 191
<211> LENGTH: 21
<212> TYPE: PRT
<213> ORGANISM: Artificial sequence
<220> FEATURE:
<223> OTHER INFORMATION: synthesized sequence

<400> SEQUENCE: 191

Met Glu Val Gly Trp Tyr Arg Ser Pro Phe Ser Arg Val Val His Leu
1               5                   10                  15

Tyr Arg Asn Gly Lys
            20

<210> SEQ ID NO 192
<211> LENGTH: 31
<212> TYPE: DNA
<213> ORGANISM: Artificial sequence
<220> FEATURE:
<223> OTHER INFORMATION: synthesized sequence
```

<400> SEQUENCE: 192
gatccggagg tggtgtcccc attagacagc t　　　　　　　　　　　　　　　　31

<210> SEQ ID NO 193
<211> LENGTH: 27
<212> TYPE: DNA
<213> ORGANISM: Artificial sequence
<220> FEATURE:
<223> OTHER INFORMATION: synthesized sequence

<400> SEQUENCE: 193
gtaagcttag gaagacacag attccat　　　　　　　　　　　　　　　　　　　27

<210> SEQ ID NO 194
<211> LENGTH: 37
<212> TYPE: DNA
<213> ORGANISM: Artificial sequence
<220> FEATURE:
<223> OTHER INFORMATION: synthesized sequence

<400> SEQUENCE: 194
gatccggagg tggtgcccct gtacgatcac tgaactg　　　　　　　　　　　　37

<210> SEQ ID NO 195
<211> LENGTH: 37
<212> TYPE: DNA
<213> ORGANISM: Artificial sequence
<220> FEATURE:
<223> OTHER INFORMATION: synthesized sequence

<400> SEQUENCE: 195
gtatgcatta ggaagacaca aattgcatgg tgaagtc　　　　　　　　　　　　37

<210> SEQ ID NO 196
<211> LENGTH: 37
<212> TYPE: DNA
<213> ORGANISM: Artificial sequence
<220> FEATURE:
<223> OTHER INFORMATION: chemically synthesized

<400> SEQUENCE: 196
atatatcata tgtctgcccc ttacacctac cagagtg　　　　　　　　　　　　37

<210> SEQ ID NO 197
<211> LENGTH: 39
<212> TYPE: DNA
<213> ORGANISM: Artificial sequence
<220> FEATURE:
<223> OTHER INFORMATION: chemically synthesized

<400> SEQUENCE: 197
ggactgccct ctatgacaaa attccagata tcactcgag　　　　　　　　　　　39

<210> SEQ ID NO 198
<211> LENGTH: 39
<212> TYPE: DNA
<213> ORGANISM: Artificial sequence
<220> FEATURE:
<223> OTHER INFORMATION: chemically synthesized

<400> SEQUENCE: 198
ctcgagtgat atctggaatt ttgtcataga gggcagtcc　　　　　　　　　　　39

<210> SEQ ID NO 199
<211> LENGTH: 40

```
<212> TYPE: DNA
<213> ORGANISM: Artificial sequence
<220> FEATURE:
<223> OTHER INFORMATION: chemically synthesized

<400> SEQUENCE: 199
gggccaccct ctatcactaa atttcagata ctggaaaacc                              40

<210> SEQ ID NO 200
<211> LENGTH: 40
<212> TYPE: DNA
<213> ORGANISM: Artificial sequence
<220> FEATURE:
<223> OTHER INFORMATION: chemically synthesized

<400> SEQUENCE: 200
ggttttccag tatctgaaat ttagtgatag agggtggccc                              40

<210> SEQ ID NO 201
<211> LENGTH: 11
<212> TYPE: PRT
<213> ORGANISM: Artificial sequence
<220> FEATURE:
<223> OTHER INFORMATION: chemically synthesized

<400> SEQUENCE: 201

Leu Glu His His His His His His Gly Gly Cys
1               5                   10

<210> SEQ ID NO 202
<211> LENGTH: 157
<212> TYPE: PRT
<213> ORGANISM: Mus musculus

<400> SEQUENCE: 202

Met Ser Ala Pro Tyr Thr Tyr Gln Ser Asp Leu Arg Tyr Lys Leu Met
1               5                   10                  15

Lys Leu Val Arg Gln Lys Phe Val Met Asn Asp Ser Leu Asn Gln Thr
            20                  25                  30

Ile Tyr Gln Asp Val Asp Lys His Tyr Leu Ser Thr Thr Trp Leu Asn
        35                  40                  45

Asp Leu Gln Gln Glu Val Lys Phe Asp Met Tyr Ala Tyr Ser Ser Gly
    50                  55                  60

Gly Asp Asp Ser Lys Tyr Pro Val Thr Leu Lys Ile Ser Asp Ser Gln
65                  70                  75                  80

Leu Phe Val Ser Ala Gln Gly Glu Asp Gln Pro Val Leu Leu Lys Glu
                85                  90                  95

Leu Pro Glu Thr Pro Lys Leu Ile Thr Gly Ser Glu Thr Asp Leu Ile
            100                 105                 110

Phe Phe Trp Lys Ser Ile Asn Ser Lys Asn Tyr Phe Thr Ser Ala Ala
        115                 120                 125

Tyr Pro Glu Leu Phe Ile Ala Thr Lys Glu Gln Ser Arg Val His Leu
    130                 135                 140

Ala Arg Gly Leu Pro Ser Met Thr Asp Phe Gln Ile Ser
145                 150                 155

<210> SEQ ID NO 203
<211> LENGTH: 154
<212> TYPE: PRT
<213> ORGANISM: Homo sapiens

<400> SEQUENCE: 203
```

```
Met Leu Ser Asn Val Lys Tyr Asn Phe Met Arg Ile Ile Lys Tyr Glu
1               5                   10                  15

Phe Ile Leu Asn Asp Ala Leu Asn Gln Ser Ile Ile Arg Ala Asn Asp
                20                  25                  30

Gln Tyr Leu Thr Ala Ala Leu His Asn Leu Asp Glu Ala Val Lys
            35                  40                  45

Phe Asp Met Gly Ala Tyr Lys Ser Ser Lys Asp Asp Ala Lys Ile Thr
    50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Ile Thr Gly Ser Glu Thr Asn Leu Leu Phe Phe Trp Glu Thr His Gly
            100                 105                 110

Thr Lys Asn Tyr Phe Thr Ser Val Ala His Pro Asn Leu Phe Ile Ala
        115                 120                 125

Thr Lys Gln Asp Tyr Trp Val Cys Leu Ala Gly Gly Pro Pro Ser Ile
    130                 135                 140

Thr Asp Phe Gln Ile Leu Glu Asn Gln Ala
145                 150

<210> SEQ ID NO 204
<211> LENGTH: 157
<212> TYPE: PRT
<213> ORGANISM: Mus musculus

<400> SEQUENCE: 204

Met Ser Ala Pro Tyr Thr Tyr Gln Ser Asp Leu Arg Tyr Lys Leu Met
1               5                   10                  15

Lys Leu Val Arg Gln Lys Phe Val Met Asn Asp Ser Leu Asn Gln Thr
                20                  25                  30

Ile Tyr Gln Asp Val Asp Lys His Tyr Leu Ser Thr Thr Trp Leu Asn
            35                  40                  45

Asp Leu Gln Gln Glu Val Lys Phe Asp Met Tyr Ala Tyr Ser Ser Gly
    50                  55                  60

Gly Asp Asp Ser Lys Tyr Pro Val Thr Leu Lys Ile Ser Asp Ser Gln
65                  70                  75                  80

Leu Phe Val Ser Ala Gln Gly Glu Asp Gln Pro Val Leu Leu Lys Glu
                85                  90                  95

Leu Pro Glu Thr Pro Lys Leu Ile Thr Gly Ser Glu Thr Asp Leu Ile
            100                 105                 110

Phe Phe Trp Lys Ser Ile Asn Ser Lys Asn Tyr Phe Thr Ser Ala Ala
        115                 120                 125

Tyr Pro Glu Leu Phe Ile Ala Thr Lys Glu Gln Ser Arg Val His Leu
    130                 135                 140

Ala Arg Gly Leu Pro Ser Met Thr Lys Phe Gln Ile Ser
145                 150                 155

<210> SEQ ID NO 205
<211> LENGTH: 155
<212> TYPE: PRT
<213> ORGANISM: Homo sapiens

<400> SEQUENCE: 205

Met Asp Ile Pro Val Arg Ser Leu Asn Cys Thr Leu Arg Asp Ser Gln
1               5                   10                  15

Gln Lys Ser Leu Val Met Ser Gly Pro Tyr Glu Leu Lys Ala Leu His
```

```
                     20                  25                  30
Leu Gln Gly Gln Asp Met Glu Gln Gln Val Val Phe Ser Met Ser Phe
                 35                  40                  45

Val Gln Gly Glu Glu Ser Asn Asp Lys Ile Pro Val Ala Leu Gly Leu
             50                  55                  60

Lys Glu Lys Asn Leu Tyr Leu Ser Cys Val Leu Lys Asp Asp Lys Pro
 65                  70                  75                  80

Thr Leu Gln Leu Glu Ser Val Asp Pro Asn Asn Tyr Pro Lys Lys Lys
                 85                  90                  95

Met Glu Lys Arg Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Gln
            115                 120                 125

Ala Glu Asn Met Pro Val Phe Leu Gly Gly Thr Lys Gly Gly Gln Asp
            130                 135                 140

Ile Thr Asp Phe Thr Met Gln Phe Val Ser Ser
145                 150                 155

<210> SEQ ID NO 206
<211> LENGTH: 155
<212> TYPE: PRT
<213> ORGANISM: Homo sapiens

<400> SEQUENCE: 206

Met Asp Ile Pro Val Arg Ser Leu Asn Cys Thr Leu Arg Asp Ser Gln
 1               5                  10                  15

Gln Lys Ser Leu Val Met Ser Gly Pro Tyr Glu Leu Lys Ala Leu His
             20                  25                  30

Leu Gln Gly Gln Asp Met Glu Gln Gln Val Val Phe Ser Met Ser Phe
                 35                  40                  45

Val Gln Gly Glu Glu Ser Asn Asp Lys Ile Pro Val Ala Leu Gly Leu
             50                  55                  60

Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Lys Lys Lys
                 85                  90                  95

Met Glu Lys Gln Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Gln
            115                 120                 125

Ala Glu Asn Met Pro Val Phe Leu Gly Gly Thr Lys Gly Gly Gln Asp
            130                 135                 140

Ile Thr Asp Phe Thr Met Gln Phe Val Ser Ser
145                 150                 155

<210> SEQ ID NO 207
<211> LENGTH: 155
<212> TYPE: PRT
<213> ORGANISM: Homo sapiens

<400> SEQUENCE: 207

Met Asp Ile Pro Val Arg Ser Leu Asn Cys Thr Leu Arg Asp Ser Gln
 1               5                  10                  15

Gln Lys Ser Leu Val Met Ser Gly Pro Tyr Glu Leu Lys Ala Leu His
             20                  25                  30

Leu Gln Gly Gln Asp Met Glu Gln Gln Val Val Phe Ser Met Ser Phe
                 35                  40                  45
```

Val Gln Gly Glu Glu Ser Asn Asp Lys Ile Pro Val Ala Leu Gly Leu
 50                  55                  60

Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Lys Lys Lys
                 85                  90                  95

Met Glu Lys Arg Phe Val Phe Asn Leu Ile Glu Ile Asn Asn Lys Leu
                100                 105                 110

Glu Phe Glu Ser Ala Gln Phe Pro Asn Trp Tyr Ile Ser Thr Ser Gln
                115                 120                 125

Ala Glu Asn Met Pro Val Phe Leu Gly Gly Thr Lys Gly Gly Gln Asp
                130                 135                 140

Ile Thr Asp Phe Thr Met Gln Phe Val Ser Ser
145                 150                 155

<210> SEQ ID NO 208
<211> LENGTH: 152
<212> TYPE: PRT
<213> ORGANISM: Homo sapiens

<400> SEQUENCE: 208

Met Asp Ile Pro Val Arg Ser Leu Asn Cys Thr Leu Arg Asp Ser Gln
 1               5                  10                  15

Gln Lys Ser Leu Val Met Ser Gly Pro Tyr Glu Leu Lys Ala Leu His
                 20                  25                  30

Leu Gln Gly Gln Asp Met Glu Gln Gln Val Val Phe Ser Met Ser Phe
                 35                  40                  45

Val Gln Gly Glu Glu Ser Asn Asp Lys Ile Pro Val Ala Leu Gly Leu
 50                  55                  60

Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Met Glu Lys
                 85                  90                  95

Arg Phe Val Phe Asn Lys Ile Glu Ile Asn Asn Lys Leu Glu Phe Glu
                100                 105                 110

Ser Ala Gln Phe Pro Asn Trp Tyr Ile Ser Thr Ser Gln Ala Glu Asn
                115                 120                 125

Met Pro Val Phe Leu Gly Gly Thr Lys Gly Gly Gln Asp Ile Thr Asp
                130                 135                 140

Phe Thr Met Gln Phe Val Ser Ser
145                 150

<210> SEQ ID NO 209
<211> LENGTH: 155
<212> TYPE: PRT
<213> ORGANISM: Homo sapiens

<400> SEQUENCE: 209

Met Asp Ile Pro Val Arg Ser Leu Asn Cys Thr Asn Arg Asp Ser Gln
 1               5                  10                  15

Gln Lys Ser Leu Val Met Ser Gly Pro Tyr Glu Leu Lys Ala Leu His
                 20                  25                  30

Leu Gln Gly Gln Asp Met Glu Gln Gln Val Val Phe Ser Met Ser Phe
                 35                  40                  45

Val Gln Gly Glu Glu Ser Asn Asp Lys Ile Pro Val Ala Leu Gly Leu
 50                  55                  60

```
Lys Glu Lys Asn Leu Tyr Leu Ser Cys Val Leu Lys Asp Asp Lys Pro
 65                  70                  75                  80

Thr Leu Gln Leu Glu Ser Val Asp Pro Lys Asn Tyr Pro Lys Lys Lys
                 85                  90                  95

Met Glu Lys Arg Phe Val Phe Asn Lys Ile Glu Ile Asn Asn Lys Leu
            100                 105                 110

Glu Phe Glu Ser Ala Gln Phe Pro Asn Trp Tyr Ile Ser Thr Ser Gln
        115                 120                 125

Ala Glu Asn Met Pro Val Phe Leu Gly Gly Thr Lys Gly Gly Gln Asp
    130                 135                 140

Ile Thr Asp Phe Thr Met Gln Phe Val Ser Ser
145                 150                 155
```

<210> SEQ ID NO 210
<211> LENGTH: 154
<212> TYPE: PRT
<213> ORGANISM: Homo sapiens

<400> SEQUENCE: 210

```
Met Leu Ser Asn Val Lys Tyr Asn Phe Met Arg Ile Ile Lys Tyr Glu
  1               5                  10                  15

Phe Ile Leu Asn Asp Ala Leu Asn Gln Ser Ile Ile Arg Ala Asn Asp
                 20                  25                  30

Gln Tyr Leu Thr Ala Ala Ala Leu His Asn Leu Asp Glu Ala Val Lys
             35                  40                  45

Phe Asp Met Gly Ala Tyr Lys Ser Ser Lys Asp Ala Lys Ile Thr
         50                  55                  60

Val Ile Leu Arg Ile Ser Lys Thr Gln Leu Tyr Val Thr Ala Gln Asp
 65                  70                  75                  80

Glu Asp Gln Pro Val Leu Leu Lys Glu Met Pro Glu Ile Pro Lys Thr
                 85                  90                  95

Ile Thr Gly Ser Glu Thr Asn Leu Leu Phe Phe Trp Glu Thr His Gly
            100                 105                 110

Thr Lys Asn Tyr Phe Thr Ser Val Ala His Pro Asn Leu Phe Ile Ala
        115                 120                 125

Thr Lys Gln Asp Tyr Trp Val Cys Leu Ala Gly Gly Pro Pro Ser Ile
    130                 135                 140

Thr Lys Phe Gln Ile Leu Glu Asn Gln Ala
145                 150
```

<210> SEQ ID NO 211
<211> LENGTH: 154
<212> TYPE: PRT
<213> ORGANISM: Homo sapiens

<400> SEQUENCE: 211

```
Met Leu Ser Asn Val Lys Tyr Asn Phe Met Arg Ile Ile Lys Tyr Glu
  1               5                  10                  15

Phe Ile Lys Asn Asp Ala Leu Asn Gln Ser Ile Ile Arg Ala Asn Asp
                 20                  25                  30

Gln Tyr Leu Thr Ala Ala Ala Leu His Asn Leu Asp Glu Ala Val Lys
             35                  40                  45

Phe Asp Met Gly Ala Tyr Lys Ser Ser Lys Asp Ala Lys Ile Thr
         50                  55                  60

Val Ile Leu Arg Ile Ser Lys Thr Gln Leu Tyr Val Thr Ala Gln Asp
 65                  70                  75                  80

Glu Asp Gln Pro Val Leu Leu Lys Glu Met Pro Glu Ile Pro Lys Thr
```

```
                    85                  90                  95

Ile Thr Gly Ser Glu Thr Asn Leu Leu Phe Phe Trp Glu Thr His Gly
            100                 105                 110

Thr Lys Asn Tyr Phe Thr Ser Val Ala His Pro Asn Leu Phe Ile Ala
            115                 120                 125

Thr Lys Gln Asp Tyr Trp Val Cys Leu Ala Gly Gly Pro Pro Ser Ile
            130                 135                 140

Thr Asp Phe Gln Ile Leu Glu Asn Gln Ala
145                 150

<210> SEQ ID NO 212
<211> LENGTH: 154
<212> TYPE: PRT
<213> ORGANISM: Homo sapiens

<400> SEQUENCE: 212

Met Leu Ser Asn Val Lys Tyr Asn Phe Met Arg Ile Ile Lys Tyr Glu
1               5                   10                  15

Phe Ile Leu Asn Asp Ala Leu Asn Gln Ser Ile Ile Arg Ala Asn Asp
            20                  25                  30

Gln Tyr Leu Thr Ala Ala Ala Leu His Asn Leu Asp Glu Ala Val Lys
        35                  40                  45

Phe Asp Met Gly Ala Tyr Lys Ser Ser Lys Asp Ala Lys Ile Thr
    50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Ile Thr Gly Ser Glu Thr Asn Leu Leu Phe Phe Trp Glu Thr His Gly
            100                 105                 110

Thr Lys Asn Tyr Phe Thr Ser Val Ala His Pro Asn Leu Phe Ile Ala
            115                 120                 125

Thr Lys Gln Asp Tyr Trp Val Cys Leu Ala Gly Gly Pro Pro Ser Ile
            130                 135                 140

Thr Asp Asn Gln Ile Leu Glu Asn Gln Ala
145                 150

<210> SEQ ID NO 213
<211> LENGTH: 154
<212> TYPE: PRT
<213> ORGANISM: Homo sapiens

<400> SEQUENCE: 213

Met Leu Ser Asn Val Lys Tyr Asn Phe Met Ala Ile Ile Lys Tyr Glu
1               5                   10                  15

Phe Ile Leu Asn Asp Ala Leu Asn Gln Ser Ile Ile Arg Ala Asn Asp
            20                  25                  30

Gln Tyr Leu Thr Ala Ala Ala Leu His Asn Leu Asp Glu Ala Val Lys
        35                  40                  45

Phe Asp Met Gly Ala Tyr Lys Ser Ser Lys Asp Ala Lys Ile Thr
    50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Ile Thr Gly Ser Glu Thr Asn Leu Leu Phe Phe Trp Glu Thr His Gly
            100                 105                 110
```

Thr Lys Asn Tyr Phe Thr Ser Val Ala His Pro Asn Leu Phe Ile Ala
            115                 120                 125

Thr Lys Gln Asp Tyr Trp Val Cys Leu Ala Gly Gly Pro Pro Ser Ile
            130                 135                 140

Thr Asp Phe Gln Ile Leu Glu Asn Gln Ala
145                 150

<210> SEQ ID NO 214
<211> LENGTH: 154
<212> TYPE: PRT
<213> ORGANISM: Homo sapiens

<400> SEQUENCE: 214

Met Leu Ser Asn Val Lys Tyr Asn Phe Met Arg Ile Ile Lys Tyr Glu
1               5                   10                  15

Phe Ile Leu Asn Asp Ala Leu Asn Gln Ser Ile Ile Arg Ala Asn Asp
                20                  25                  30

Gln Tyr Leu Thr Ala Ala Ala Leu His Asn Leu Asp Glu Ala Val Lys
            35                  40                  45

Phe Asp Met Gly Ala Tyr Lys Ser Ser Lys Asp Ala Lys Ala Thr
    50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Ile Thr Gly Ser Glu Thr Asn Leu Leu Phe Phe Trp Glu Thr His Gly
            100                 105                 110

Thr Lys Asn Tyr Phe Thr Ser Val Ala His Pro Asn Leu Phe Ile Ala
            115                 120                 125

Thr Lys Gln Asp Tyr Trp Val Cys Leu Ala Gly Gly Pro Pro Ser Ile
            130                 135                 140

Thr Asp Phe Gln Ile Leu Glu Asn Gln Ala
145                 150

<210> SEQ ID NO 215
<211> LENGTH: 154
<212> TYPE: PRT
<213> ORGANISM: Homo sapiens

<400> SEQUENCE: 215

Met Leu Ser Asn Val Lys Tyr Asn Phe Met Arg Ile Ile Lys Tyr Glu
1               5                   10                  15

Phe Ile Leu Asn Asp Ala Leu Asn Gln Ser Ile Ile Arg Ala Asn Asp
                20                  25                  30

Gln Tyr Leu Thr Ala Ala Ala Leu His Asn Leu Asp Glu Ala Val Lys
            35                  40                  45

Phe Asp Met Gly Ala Tyr Lys Ser Ser Lys Asp Ala Lys Ile Thr
    50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Ile Thr Gly Ser Glu Thr Asn Leu Leu Phe Phe Glu Thr His Gly
            100                 105                 110

Thr Lys Asn Tyr Phe Thr Ser Val Ala His Pro Asn Leu Phe Ile Ala
            115                 120                 125

-continued

Thr Lys Gln Asp Tyr Trp Val Cys Leu Ala Gly Gly Pro Ser Ile
130                 135                 140

Thr Asp Phe Gln Ile Leu Glu Asn Gln Ala
145                 150

<210> SEQ ID NO 216
<211> LENGTH: 154
<212> TYPE: PRT
<213> ORGANISM: Homo sapiens

<400> SEQUENCE: 216

Met Leu Ser Asn Val Lys Tyr Asn Phe Met Arg Ile Ile Lys Tyr Glu
1               5                   10                  15

Phe Ile Leu Asn Val Ala Leu Asn Gln Ser Ile Ile Arg Ala Asn Asp
                20                  25                  30

Gln Tyr Leu Thr Ala Ala Ala Leu His Asn Leu Asp Glu Ala Val Lys
            35                  40                  45

Phe Asp Met Gly Ala Tyr Lys Ser Ser Lys Asp Ala Lys Ile Thr
        50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Ile Thr Gly Ser Glu Thr Asn Leu Leu Phe Phe Trp Glu Thr His Gly
            100                 105                 110

Thr Lys Asn Tyr Phe Thr Ser Val Ala His Pro Asn Leu Phe Ile Ala
        115                 120                 125

Thr Lys Gln Asp Tyr Trp Val Cys Leu Ala Gly Gly Pro Ser Ile
    130                 135                 140

Thr Asp Phe Gln Ile Leu Glu Asn Gln Ala
145                 150

<210> SEQ ID NO 217
<211> LENGTH: 151
<212> TYPE: PRT
<213> ORGANISM: Homo sapiens

<400> SEQUENCE: 217

Met Leu Ser Asn Val Lys Tyr Asn Phe Met Arg Ile Ile Lys Tyr Glu
1               5                   10                  15

Asn Asp Ala Leu Asn Gln Ser Ile Ile Arg Ala Asn Asp Gln Tyr Leu
                20                  25                  30

Thr Ala Ala Ala Leu His Asn Leu Asp Glu Ala Val Lys Phe Asp Met
            35                  40                  45

Gly Ala Tyr Lys Ser Ser Lys Asp Ala Lys Ile Thr Val Ile Leu
        50                  55                  60

Arg Ile Ser Lys Thr Gln Leu Tyr Val Thr Ala Gln Asp Glu Asp Gln
65                  70                  75                  80

Pro Val Leu Leu Lys Glu Met Pro Glu Ile Pro Lys Thr Ile Thr Gly
                85                  90                  95

Ser Glu Thr Asn Leu Leu Phe Phe Trp Glu Thr His Gly Thr Lys Asn
            100                 105                 110

Tyr Phe Thr Ser Val Ala His Pro Asn Leu Phe Ile Ala Thr Lys Gln
        115                 120                 125

Asp Tyr Trp Val Cys Leu Ala Gly Gly Pro Ser Ile Thr Asp Phe
    130                 135                 140

Gln Ile Leu Glu Asn Gln Ala

```
                      145                 150

<210> SEQ ID NO 218
<211> LENGTH: 150
<212> TYPE: PRT
<213> ORGANISM: Homo sapiens

<400> SEQUENCE: 218

Met Leu Ser Asn Val Lys Tyr Asn Phe Met Arg Ile Ile Lys Tyr Glu
1               5                  10                  15

Phe Ile Leu Asn Asp Ala Leu Asn Gln Ser Ile Ile Arg Ala Asn Asp
            20                  25                  30

Gln Tyr Leu Thr Ala Ala Ala Leu His Asn Leu Asp Glu Ala Val Lys
        35                  40                  45

Phe Asp Met Gly Ala Tyr Lys Ser Ser Lys Asp Asp Ala Lys Ile Thr
    50                  55                  60

Val Ile Leu Arg Ile Ser Lys Thr Gln Leu Tyr Val Thr Ala Gln Asp
65                  70                  75                  80

Glu Asp Gln Pro Val Leu Leu Lys Glu Met Pro Glu Ile Pro Lys Thr
                85                  90                  95

Glu Thr Asn Leu Leu Phe Phe Trp Glu Thr His Gly Thr Lys Asn Tyr
            100                 105                 110

Phe Thr Ser Val Ala His Pro Asn Leu Phe Ile Ala Thr Lys Gln Asp
        115                 120                 125

Tyr Trp Val Cys Leu Ala Gly Gly Pro Pro Ser Ile Thr Asp Phe Gln
    130                 135                 140

Ile Leu Glu Asn Gln Ala
145                 150
```